United States Patent
Imogai et al.

(10) Patent No.: US 8,841,323 B2
(45) Date of Patent: Sep. 23, 2014

(54) 1, 4-DISUBSTITUTED 3-CYANO-PYRIDONE DERIVATIVES AND THEIR USE AS POSITIVE ALLOSTERIC MODULATORS OF MGLUR2-RECEPTORS

(75) Inventors: Hassan Julien Imogai, Geneva (CH); Vincent Mutel, legal representative, Geneva (CH); Jose Maria Cid-Nunez, Toledo (ES); Jose Ignacio Andres-Gil, Toledo (ES); Andres Avelino Trabanco-Suarez, Toledo (ES); Julen Oyarzabal Santamarina, Toledo (ES); Frank Matthias Dautzenberg, Beerse (BE); Gregor James MacDonald, Beerse (BE); Shirley Elizabeth Pullan, Beerse (BE); Robert Johannes Lutjens, Geneva (CH); Guillaume Albert Jacques Duvey, Geneva (CH); Vanthea Nhem, Corsier (CH); Terry Patrick Finn, Geneva (CH); Gagik Melikyan, Manoukian (YE)

(73) Assignees: Janssen Pharmaceuticals, Inc., Titusville, NJ (US); Addex Pharma S.A., Geneva (CH)

( * ) Notice: Subject to any disclaimer, the term of this patent is extended or adjusted under 35 U.S.C. 154(b) by 935 days.

(21) Appl. No.: 12/282,663

(22) PCT Filed: Mar. 15, 2007

(86) PCT No.: PCT/EP2007/052442
§ 371 (c)(1),
(2), (4) Date: Dec. 9, 2009

(87) PCT Pub. No.: WO2007/104783
PCT Pub. Date: Sep. 20, 2007

(65) Prior Publication Data
US 2010/0166655 A1  Jul. 1, 2010

(30) Foreign Application Priority Data

Mar. 15, 2006 (EP) ..................... 06111215
Mar. 7, 2007 (EP) ..................... 07103654

(51) Int. Cl.
*A61K 31/4439* (2006.01)
*C07D 213/85* (2006.01)

(52) U.S. Cl.
USPC ......................... 514/316; 546/193

(58) Field of Classification Search
USPC ............................. 514/316; 546/193
See application file for complete search history.

(56) References Cited

U.S. PATENT DOCUMENTS

| | | |
|---|---|---|
| 4,051,244 A | 9/1977 | Mattioda et al. |
| 4,066,651 A | 1/1978 | Brittain et al. |
| 4,146,716 A | 3/1979 | Cox et al. |
| 4,196,207 A | 4/1980 | Webber |
| 4,256,738 A | 3/1981 | Woitun et al. |
| 4,358,453 A | 11/1982 | Bristol et al. |
| 4,550,166 A | 10/1985 | Moran et al. |
| 4,866,074 A | 9/1989 | Spada et al. |
| 4,898,654 A | 2/1990 | Toda et al. |
| 4,978,663 A | 12/1990 | Effland et al. |
| 5,032,602 A | 7/1991 | Fey et al. |
| 5,130,442 A | 7/1992 | Meisel et al. |
| 5,175,157 A | 12/1992 | Psiorz et al. |
| 5,204,198 A | 4/1993 | Bugner et al. |
| 5,236,917 A | 8/1993 | Dunlap et al. |
| 5,254,543 A | 10/1993 | Hanko et al. |
| 5,260,293 A | 11/1993 | Baker et al. |
| 5,280,026 A | 1/1994 | Brown et al. |

(Continued)

FOREIGN PATENT DOCUMENTS

| | | |
|---|---|---|
| BE | 841390 | 11/1976 |
| CA | 1019323 | 9/1977 |

(Continued)

OTHER PUBLICATIONS

Azume et al "Synthesis and reaction . . . " CA139:197340 (2003).*

(Continued)

*Primary Examiner* — Celia Chang
(74) *Attorney, Agent, or Firm* — Baker & Hostetler LLP

(57) ABSTRACT

The present invention relates to novel compounds, in particular novel pyridinone derivatives according to Formula (I)

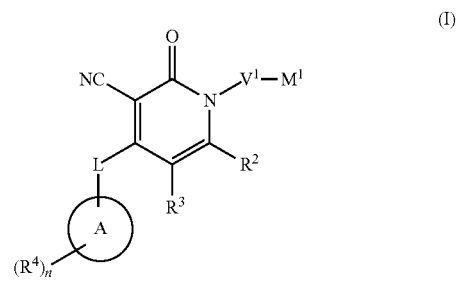

wherein all radicals are defined in the application and claims. The compounds according to the invention are positive allosteric modulators of metabotropic receptors-subtype 2 ("mGluR2") which are useful for the treatment or prevention of neurological and psychiatric disorders associated with glutamate dysfunction and diseases in which the mGluR2 subtype of metabotropic receptors is involved. In particular, such diseases are central nervous system disorders selected from the group of anxiety, schizophrenia, migraine, depression, and epilepsy. The invention is also directed to pharmaceutical compositions and processes to prepare such compounds and compositions, as well as to the use of such compounds for the prevention and treatment of such diseases in which mGluR2 is involved.

7 Claims, No Drawings

(56) References Cited

U.S. PATENT DOCUMENTS

| | | |
|---|---|---|
| 5,332,750 A | 7/1994 | Mederski et al. |
| 5,356,911 A | 10/1994 | Muller-Gliemann et al. |
| 5,366,981 A | 11/1994 | Vecchietti et al. |
| 5,371,074 A | 12/1994 | Dunlap et al. |
| 5,374,513 A | 12/1994 | Ohzeki et al. |
| 5,378,720 A | 1/1995 | Hlasta et al. |
| 5,407,948 A | 4/1995 | Fey et al. |
| 5,418,243 A | 5/1995 | Angerbauer et al. |
| 5,424,435 A | 6/1995 | Hani et al. |
| 5,473,077 A | 12/1995 | Monn et al. |
| 5,498,774 A | 3/1996 | Mitsudera et al. |
| 5,500,420 A | 3/1996 | Maiese |
| 5,512,576 A | 4/1996 | Desai et al. |
| 5,532,242 A | 7/1996 | Cliffe |
| 5,596,012 A | 1/1997 | Dunlap et al. |
| 5,602,145 A | 2/1997 | Samanen |
| 5,650,422 A | 7/1997 | Dunlap et al. |
| 5,654,307 A | 8/1997 | Bridges et al. |
| 5,675,013 A | 10/1997 | Hani et al. |
| 5,710,274 A | 1/1998 | Yuan et al. |
| 5,723,463 A | 3/1998 | Hofgen et al. |
| 5,741,798 A | 4/1998 | Lazer et al. |
| 5,801,179 A | 9/1998 | Van Lommen et al. |
| 5,814,645 A | 9/1998 | Kanellakopulos et al. |
| 5,855,654 A | 1/1999 | Willingham et al. |
| 5,859,020 A | 1/1999 | Preuss et al. |
| 5,869,428 A | 2/1999 | Morishima et al. |
| 5,874,432 A | 2/1999 | Dunlap et al. |
| 5,922,773 A | 7/1999 | Lipton et al. |
| 5,948,911 A | 9/1999 | Pamukcu et al. |
| 5,958,931 A | 9/1999 | Adam et al. |
| 6,013,672 A | 1/2000 | Ye et al. |
| 6,022,869 A | 2/2000 | Faull |
| 6,054,588 A | 4/2000 | Adam et al. |
| 6,093,718 A | 7/2000 | Waterson et al. |
| 6,100,268 A | 8/2000 | Van Lommen et al. |
| 6,103,475 A | 8/2000 | Burnett, Jr. et al. |
| 6,107,342 A | 8/2000 | Adam et al. |
| 6,110,920 A | 8/2000 | Rochus et al. |
| 6,121,278 A | 9/2000 | Jackson et al. |
| 6,130,217 A | 10/2000 | Arnold et al. |
| 6,133,271 A | 10/2000 | Pamukcu et al. |
| 6,136,861 A | 10/2000 | Chenard |
| 6,143,783 A | 11/2000 | Monn et al. |
| 6,162,804 A | 12/2000 | Bilodeau et al. |
| 6,169,091 B1 | 1/2001 | Cockerill et al. |
| 6,172,058 B1 | 1/2001 | Tercero et al. |
| 6,204,292 B1 | 3/2001 | Kozikowski et al. |
| 6,262,068 B1 | 7/2001 | Atwal et al. |
| 6,262,074 B1 | 7/2001 | Otten et al. |
| 6,284,759 B1 | 9/2001 | He |
| 6,313,127 B1 | 11/2001 | Waterson et al. |
| 6,316,498 B1 | 11/2001 | Nakazato et al. |
| 6,333,428 B1 | 12/2001 | Nakazato et al. |
| 6,358,975 B1 | 3/2002 | Eliasson et al. |
| 6,361,571 B1 | 3/2002 | Goettel et al. |
| 6,403,588 B1 | 6/2002 | Hayakawa et al. |
| 6,407,094 B1 | 6/2002 | Adam et al. |
| 6,432,958 B1 | 8/2002 | He |
| 6,433,014 B1 | 8/2002 | Acher et al. |
| 6,455,528 B1 | 9/2002 | Adachi et al. |
| 6,465,484 B1 | 10/2002 | Bilodeau et al. |
| 6,472,392 B1 | 10/2002 | Starck et al. |
| 6,479,436 B1 | 11/2002 | Otten et al. |
| 6,498,180 B1 | 12/2002 | Collado Cano et al. |
| 6,509,328 B1 | 1/2003 | Adam et al. |
| 6,569,863 B1 | 5/2003 | Gerritsma et al. |
| 6,586,441 B2 | 7/2003 | Borroni et al. |
| 6,607,563 B2 | 8/2003 | Ohashi et al. |
| 6,664,250 B2 | 12/2003 | Atwal et al. |
| 6,670,307 B2 | 12/2003 | Schnatterer et al. |
| 6,835,726 B2 | 12/2004 | Cushing et al. |
| 7,393,549 B2 | 7/2008 | Ebinuma |
| 7,456,289 B2 | 11/2008 | Hsieh et al. |
| 7,572,807 B2 | 8/2009 | Li |
| 7,579,360 B2 | 8/2009 | Li |
| 7,700,593 B2 | 4/2010 | Chakrabarti et al. |
| 7,879,837 B2 | 2/2011 | Hayashi et al. |
| 7,960,563 B2 | 6/2011 | Johnson et al. |
| 7,977,325 B2 * | 7/2011 | Schwede et al. ............... 514/183 |
| 2002/0009713 A1 | 1/2002 | Miller et al. |
| 2002/0022636 A1 | 2/2002 | Li et al. |
| 2002/0028813 A1 | 3/2002 | Jackson et al. |
| 2002/0041880 A1 | 4/2002 | DeFeo-Jones et al. |
| 2002/0137770 A1 | 9/2002 | Nara et al. |
| 2002/0147362 A1 | 10/2002 | Kozikowski et al. |
| 2002/0193367 A1 | 12/2002 | Adam et al. |
| 2002/0198197 A1 | 12/2002 | Adam et al. |
| 2003/0055085 A1 | 3/2003 | Wagenen et al. |
| 2003/0109504 A1 | 6/2003 | Brotchie et al. |
| 2003/0130264 A1 | 7/2003 | Jaen |
| 2003/0134902 A1 | 7/2003 | Nakazato et al. |
| 2003/0158155 A1 | 8/2003 | Hori et al. |
| 2003/0162802 A1 | 8/2003 | Guo et al. |
| 2003/0166639 A1 | 9/2003 | Adam et al. |
| 2003/0171380 A1 | 9/2003 | Arvanitis et al. |
| 2003/0199692 A1 | 10/2003 | Biediger et al. |
| 2003/0207882 A1 | 11/2003 | Stocker et al. |
| 2003/0207916 A1 | 11/2003 | Cheng et al. |
| 2004/0006114 A1 | 1/2004 | Coleman et al. |
| 2004/0034040 A1 | 2/2004 | Eggenweiler et al. |
| 2004/0043388 A1 | 3/2004 | Come et al. |
| 2004/0049032 A1 | 3/2004 | Charrier et al. |
| 2004/0053914 A1 | 3/2004 | Gharagozloo et al. |
| 2004/0063955 A1 | 4/2004 | Biediger et al. |
| 2004/0077599 A1 | 4/2004 | Curry |
| 2004/0097562 A1 | 5/2004 | Olesen et al. |
| 2004/0101833 A1 | 5/2004 | Lazdunski et al. |
| 2004/0102521 A1 | 5/2004 | Collado-Cano et al. |
| 2004/0106791 A1 | 6/2004 | Yoakim et al. |
| 2004/0116489 A1 | 6/2004 | Massey et al. |
| 2004/0127936 A1 | 7/2004 | Salahieh et al. |
| 2004/0132723 A1 | 7/2004 | Yoakim et al. |
| 2004/0138204 A1 | 7/2004 | Harrington, Jr. |
| 2004/0138238 A1 | 7/2004 | Dhanoa et al. |
| 2004/0167123 A1 | 8/2004 | Pratt et al. |
| 2004/0176385 A1 | 9/2004 | Nuss et al. |
| 2004/0204448 A1 | 10/2004 | Muller et al. |
| 2004/0220222 A1 | 11/2004 | Galley et al. |
| 2005/0004142 A1 | 1/2005 | Adams et al. |
| 2005/0026935 A1 | 2/2005 | Ford et al. |
| 2005/0054819 A1 | 3/2005 | Catalano et al. |
| 2005/0070538 A1 | 3/2005 | Cheng et al. |
| 2005/0113283 A1 | 5/2005 | Solow-Cordero et al. |
| 2005/0187227 A1 | 8/2005 | Himmelsbach et al. |
| 2005/0245530 A1 | 11/2005 | Borzilleri et al. |
| 2006/0083676 A1 | 4/2006 | Lesage et al. |
| 2006/0240501 A1 | 10/2006 | Ebinuma |
| 2007/0032469 A1 | 2/2007 | Isaac et al. |
| 2007/0066582 A1 | 3/2007 | Herold et al. |
| 2007/0213323 A1 | 9/2007 | Imogai et al. |
| 2007/0275984 A1 | 11/2007 | Imogai et al. |
| 2008/0221179 A1 | 9/2008 | Gaul et al. |
| 2008/0286265 A1 | 11/2008 | Gaul et al. |
| 2008/0306077 A1 | 12/2008 | Clayton et al. |
| 2009/0031422 A1 | 1/2009 | Aaron et al. |
| 2009/0111855 A1 | 4/2009 | Gaul et al. |
| 2009/0124609 A1 | 5/2009 | Albrecht et al. |
| 2009/0124612 A1 | 5/2009 | Albrecht et al. |
| 2009/0203668 A1 | 8/2009 | Li et al. |
| 2009/0275751 A1 | 11/2009 | Nagato et al. |
| 2009/0318436 A1 | 12/2009 | Albrecht et al. |
| 2010/0063054 A1 | 3/2010 | Bressi et al. |
| 2010/0063092 A1 | 3/2010 | Cid-Nunez et al. |
| 2010/0087487 A1 | 4/2010 | Cid-Nunez et al. |
| 2010/0099715 A1 | 4/2010 | Cid-Nunez et al. |
| 2010/0166655 A1 | 7/2010 | Imogai et al. |
| 2010/0240688 A1 | 9/2010 | Cid-Nunez et al. |
| 2010/0240706 A1 | 9/2010 | Cid-Nunez et al. |
| 2010/0286206 A1 | 11/2010 | Cid-Nunez et al. |
| 2010/0292241 A1 | 11/2010 | Brnardic et al. |
| 2011/0009441 A1 | 1/2011 | Trabanco-Suarez et al. |
| 2011/0245232 A1 | 10/2011 | Braje et al. |
| 2011/0275624 A1 | 11/2011 | Cid-Nunez et al. |

(56) References Cited

U.S. PATENT DOCUMENTS

| | | |
|---|---|---|
| 2011/0306642 A1 | 12/2011 | Cid-Nunez |
| 2012/0035167 A1 | 2/2012 | Cid-Nunez et al. |
| 2012/0135977 A1 | 5/2012 | Beshore et al. |

FOREIGN PATENT DOCUMENTS

| | | |
|---|---|---|
| CA | 2035144 | 7/1991 |
| CA | 2390948 | 12/2000 |
| CN | 1842532 | 10/2006 |
| CN | 102002040 | 4/2011 |
| DE | 19507522 | 9/1996 |
| EP | 82023 | 6/1983 |
| EP | 154190 | 9/1985 |
| EP | 292840 | 11/1988 |
| EP | 308020 | 3/1989 |
| EP | 365486 | 4/1990 |
| EP | 0373423 | 6/1990 |
| EP | 379806 | 8/1990 |
| EP | 0430385 | 6/1991 |
| EP | 441718 | 8/1991 |
| EP | 447118 | 9/1991 |
| EP | 447891 | 9/1991 |
| EP | 0452002 | 10/1991 |
| EP | 478195 | 4/1992 |
| EP | A10482939 | 4/1992 |
| EP | 530702 | 3/1993 |
| EP | 0542059 | 5/1993 |
| EP | 547708 | 6/1993 |
| EP | 548934 | 6/1993 |
| EP | 557016 | 8/1993 |
| EP | 612746 | 8/1994 |
| EP | 626378 | 11/1994 |
| EP | 728759 | 8/1996 |
| EP | 799826 | 10/1997 |
| EP | 838458 | 4/1998 |
| EP | 856255 | 8/1998 |
| EP | 903343 | 3/1999 |
| EP | 955301 | 11/1999 |
| EP | A1006112 | 6/2000 |
| EP | 1203766 | 5/2002 |
| EP | 1277726 | 1/2003 |
| EP | 1459765 | 9/2004 |
| EP | 1764099 | 3/2007 |
| EP | 1764367 | 3/2007 |
| EP | 2039687 | 3/2009 |
| GB | 1392849 | 4/1975 |
| GB | 1502312 | 3/1978 |
| JP | 50106981 | 8/1975 |
| JP | 53082783 | 7/1978 |
| JP | 57052334 | 11/1982 |
| JP | 6110557 | 1/1986 |
| JP | 2124871 | 5/1990 |
| JP | H02503317 | 10/1990 |
| JP | 2277044 | 11/1990 |
| JP | 5204071 | 8/1993 |
| JP | 6211797 | 8/1994 |
| JP | 6211798 | 8/1994 |
| JP | 7070018 | 3/1995 |
| JP | 7101861 | 4/1995 |
| JP | 10045750 | 2/1998 |
| JP | 1998029979 | 2/1998 |
| JP | 2000072731 | 3/2000 |
| JP | A2000072751 | 3/2000 |
| JP | 2001089367 | 4/2001 |
| JP | 2002003401 | 1/2002 |
| JP | 2002003401 | 3/2002 |
| JP | 2002/105085 | 4/2002 |
| JP | 2002308882 | 10/2002 |
| JP | 2003012653 | 1/2003 |
| JP | 2004/525192 | 8/2004 |
| JP | 2004339080 | 12/2004 |
| JP | 2005531501 | 6/2005 |
| JP | 2008509714 | 4/2008 |
| JP | 2008513414 | 11/2008 |
| RU | 1796625 | 2/1993 |
| RU | C12143433 | 12/1999 |
| SU | 509578 | 4/1976 |
| SU | 1509578 | 9/1989 |
| WO | 8400544 | 2/1984 |
| WO | 8400685 | 3/1984 |
| WO | 9109848 | 7/1991 |
| WO | 9218115 | 10/1992 |
| WO | 9301195 | 1/1993 |
| WO | 9315056 | 8/1993 |
| WO | 9419315 | 9/1994 |
| WO | 9504733 | 2/1995 |
| WO | 9506032 | 3/1995 |
| WO | 9511233 | 4/1995 |
| WO | 9517397 | 6/1995 |
| WO | 9524393 | 9/1995 |
| WO | 9535293 | 12/1995 |
| WO | 9605828 | 2/1996 |
| WO | 9606167 | 2/1996 |
| WO | 9615108 | 5/1996 |
| WO | 9622021 | 7/1996 |
| WO | 9633974 | 10/1996 |
| WO | 9637481 | 11/1996 |
| WO | 9641639 | 12/1996 |
| WO | 9710229 | 3/1997 |
| WO | 9710238 | 3/1997 |
| WO | 9721701 | 6/1997 |
| WO | 9746532 | 12/1997 |
| WO | 9748724 | 12/1997 |
| WO | 9806724 | 2/1998 |
| WO | 9811075 | 3/1998 |
| WO | 9817668 | 4/1998 |
| WO | 9824780 | 6/1998 |
| WO | 9832762 | 7/1998 |
| WO | 9838168 | 9/1998 |
| WO | 9850384 | 11/1998 |
| WO | 9906041 | 2/1999 |
| WO | 9911622 | 3/1999 |
| WO | 9911628 | 3/1999 |
| WO | 9911649 | 3/1999 |
| WO | 9912532 | 3/1999 |
| WO | 9916755 | 4/1999 |
| WO | 9918096 | 4/1999 |
| WO | 9921992 | 5/1999 |
| WO | 9931062 | 6/1999 |
| WO | 9931066 | 6/1999 |
| WO | 9932448 | 7/1999 |
| WO | 9933829 | 7/1999 |
| WO | 9936072 | 7/1999 |
| WO | 9952893 | 10/1999 |
| WO | 9953956 | 10/1999 |
| WO | 9962908 | 12/1999 |
| WO | 0003990 | 1/2000 |
| WO | 0012089 | 3/2000 |
| WO | 0021934 | 4/2000 |
| WO | 0034244 | 6/2000 |
| WO | 0053605 | 9/2000 |
| WO | 0061126 | 10/2000 |
| WO | 0069816 | 11/2000 |
| WO | 0073283 | 12/2000 |
| WO | 0110846 | 2/2001 |
| WO | 0129025 | 4/2001 |
| WO | 0132632 | 5/2001 |
| WO | 0132644 | 5/2001 |
| WO | 0146190 | 6/2001 |
| WO | WO 01/53288 | 7/2001 |
| WO | 0155132 | 8/2001 |
| WO | 0156990 | 8/2001 |
| WO | 0168097 | 9/2001 |
| WO | 0170731 | 9/2001 |
| WO | 0172712 | 10/2001 |
| WO | 0183481 | 11/2001 |
| WO | 0185716 | 11/2001 |
| WO | WO 01/83421 | 11/2001 |
| WO | WO 01/83431 | 11/2001 |
| WO | 0196308 | 12/2001 |
| WO | 0202568 | 1/2002 |
| WO | 0210807 | 2/2002 |
| WO | 0212236 | 2/2002 |

(56) References Cited

FOREIGN PATENT DOCUMENTS

| | | |
|---|---|---|
| WO | 0214282 | 2/2002 |
| WO | 0222598 | 3/2002 |
| WO | 0228837 | 4/2002 |
| WO | 02051849 | 7/2002 |
| WO | 02074025 | 9/2002 |
| WO | 02740025 | 9/2002 |
| WO | 02079498 | 10/2002 |
| WO | 02090333 | 11/2002 |
| WO | 02094264 | 11/2002 |
| WO | 02096318 | 12/2002 |
| WO | 02096363 | 12/2002 |
| WO | 02098869 | 12/2002 |
| WO | 02102807 | 12/2002 |
| WO | 03011293 | 2/2003 |
| WO | 03029209 | 4/2003 |
| WO | 03035639 | 5/2003 |
| WO | 03042989 | 5/2003 |
| WO | 03044021 | 5/2003 |
| WO | 03047577 | 6/2003 |
| WO | 03051481 | 6/2003 |
| WO | 03051841 | 6/2003 |
| WO | 03051842 | 6/2003 |
| WO | 03055878 | 7/2003 |
| WO | 03059871 | 7/2003 |
| WO | 03059884 | 7/2003 |
| WO | 03062392 | 7/2003 |
| WO | 03064428 | 8/2003 |
| WO | 03065994 | 8/2003 |
| WO | 03068230 | 8/2003 |
| WO | 03068750 | 8/2003 |
| WO | 03070712 | 8/2003 |
| WO | 03076405 | 9/2003 |
| WO | 03082191 | 10/2003 |
| WO | 03084610 | 10/2003 |
| WO | 03092595 | 11/2003 |
| WO | 03099808 | 12/2003 |
| WO | 03104217 | 12/2003 |
| WO | 03105846 | 12/2003 |
| WO | 04000846 | 12/2003 |
| WO | 2004004720 | 1/2004 |
| WO | 2004011441 | 2/2004 |
| WO | 2004014859 | 2/2004 |
| WO | 2004014920 | 2/2004 |
| WO | 2004017950 | 3/2004 |
| WO | 2004018386 | 3/2004 |
| WO | 2004019863 | 3/2004 |
| WO | 2004021984 | 3/2004 |
| WO | 2004024150 | 3/2004 |
| WO | 2004024936 | 3/2004 |
| WO | 2004029060 | 4/2004 |
| WO | 2004031189 | 4/2004 |
| WO | 2004041818 | 5/2004 |
| WO | 2004043927 | 5/2004 |
| WO | 2004054979 | 7/2004 |
| WO | 2004065380 | 8/2004 |
| WO | 2004067002 | 8/2004 |
| WO | 2004072025 | 8/2004 |
| WO | 2004076413 | 9/2004 |
| WO | 2004078175 | 9/2004 |
| WO | 2004078176 | 9/2004 |
| WO | 2004080891 | 9/2004 |
| WO | 2004080981 | 9/2004 |
| WO | 2004092123 | 10/2004 |
| WO | 2004092135 | 10/2004 |
| WO | 2005002585 | 1/2005 |
| WO | 2005007144 | 1/2005 |
| WO | 2005021552 | 3/2005 |
| WO | 2005028445 | 3/2005 |
| WO | 2005040337 | 5/2005 |
| WO | 2005080356 | 9/2005 |
| WO | 2005097052 | 10/2005 |
| WO | 2005100365 | 10/2005 |
| WO | 2005123703 | 12/2005 |
| WO | 2006012622 | 2/2006 |
| WO | 2006014918 | 2/2006 |
| WO | 2006015158 | 2/2006 |
| WO | 2006015737 | 2/2006 |
| WO | 2006018727 | 2/2006 |
| WO | 2006020879 | 2/2006 |
| WO | 2006030031 | 3/2006 |
| WO | 2006030032 | 3/2006 |
| WO | WO 2006/029980 | 3/2006 |
| WO | WO 2006/047237 | 5/2006 |
| WO | WO 2006/057860 | 6/2006 |
| WO | WO 2006/057869 | 6/2006 |
| WO | 2006074041 | 7/2006 |
| WO | WO 2006/071730 | 7/2006 |
| WO | WO 2006/091496 | 8/2006 |
| WO | WO 2006/099972 | 9/2006 |
| WO | WO 2006/109876 | 10/2006 |
| WO | 2006137350 | 12/2006 |
| WO | WO 2007/021308 | 2/2007 |
| WO | WO 2007/021309 | 2/2007 |
| WO | 2007031558 | 3/2007 |
| WO | 2007039439 | 4/2007 |
| WO | 2007059257 | 5/2007 |
| WO | WO 2007/078523 | 7/2007 |
| WO | 2007027669 | 8/2007 |
| WO | WO 2007/095024 | 8/2007 |
| WO | 2007103760 | 9/2007 |
| WO | 2007104783 | 9/2007 |
| WO | 2007113276 | 10/2007 |
| WO | 2007122258 | 11/2007 |
| WO | 2007135527 | 11/2007 |
| WO | 2007135529 | 11/2007 |
| WO | 2008006540 | 1/2008 |
| WO | 2008008539 | 1/2008 |
| WO | 2008012622 | 1/2008 |
| WO | WO 2008/012623 | 1/2008 |
| WO | WO 2008/032191 | 3/2008 |
| WO | 2008045393 | 4/2008 |
| WO | 2008051197 | 5/2008 |
| WO | 2008057855 | 5/2008 |
| WO | 2008076225 | 6/2008 |
| WO | 2008078091 | 7/2008 |
| WO | 2008078100 | 7/2008 |
| WO | WO 2008/100715 | 8/2008 |
| WO | 2008107125 | 9/2008 |
| WO | 2008107479 | 9/2008 |
| WO | 2008107480 | 9/2008 |
| WO | 2008107481 | 9/2008 |
| WO | WO 2008/112483 | 9/2008 |
| WO | 2008124085 | 10/2008 |
| WO | WO 2008/130853 | 10/2008 |
| WO | WO 2008/145616 | 12/2008 |
| WO | WO 2008/150232 | 12/2008 |
| WO | WO 2008/150233 | 12/2008 |
| WO | WO 2009/004430 | 1/2009 |
| WO | 2009033702 | 3/2009 |
| WO | 2009033703 | 3/2009 |
| WO | 2009033704 | 3/2009 |
| WO | 2009045753 | 4/2009 |
| WO | 2009062676 | 5/2009 |
| WO | 2009091374 | 7/2009 |
| WO | WO 2009/094265 | 7/2009 |
| WO | WO 2009/110901 | 9/2009 |
| WO | 2009124609 | 10/2009 |
| WO | WO 2009/140163 | 11/2009 |
| WO | WO 2009/140166 | 11/2009 |
| WO | WO 2009/148403 | 12/2009 |
| WO | WO 2010/009062 | 1/2010 |
| WO | 2010022076 | 2/2010 |
| WO | 2010022081 | 2/2010 |
| WO | 2010025890 | 3/2010 |
| WO | 2010043396 | 4/2010 |
| WO | 2010060589 | 6/2010 |
| WO | 2010063054 | 6/2010 |
| WO | 2010089303 | 8/2010 |
| WO | 2010117926 | 10/2010 |
| WO | WO 2010/114726 | 10/2010 |
| WO | 2010130422 | 11/2010 |
| WO | 2010130423 | 11/2010 |
| WO | 2010130424 | 11/2010 |
| WO | WO 2010/141360 | 12/2010 |

(56) References Cited

FOREIGN PATENT DOCUMENTS

| WO | WO 2011/022312 | 2/2011 |
|----|----|----|
| WO | WO 2011/034741 | 3/2011 |
| WO | WO 2011/034828 | 3/2011 |
| WO | WO 2011/034830 | 3/2011 |
| WO | WO 2011/034832 | 3/2011 |
| WO | WO 2011/051490 | 5/2011 |
| WO | WO 2011/109277 | 9/2011 |
| WO | WO 2011/116356 | 9/2011 |
| WO | WO 2011/136723 | 11/2011 |
| WO | WO 2011/137046 | 11/2011 |
| WO | WO 2011/156245 | 12/2011 |
| WO | WO 2012/021382 | 2/2012 |
| WO | 2012062750 | 5/2012 |
| WO | 2012062751 | 5/2012 |
| WO | 2012062752 | 5/2012 |
| WO | 2012062759 | 5/2012 |
| WO | WO 2012/151136 | 11/2012 |
| WO | WO 2012/151139 | 11/2012 |
| WO | WO 2012/151140 | 11/2012 |

OTHER PUBLICATIONS

Nell et al. "Preparation of . . . " CA149:32326 (2008).*
Chrostopoulos "Allosteric ginding . . . " Nature Rev. March, v.1, p. 198-201 (2002).*
Wikipedia "Allosteric . . . " p. 1-4 (2010).*
Benneyworth et al., "A Selective Positive Allosteric Modulator of Metabotropic Glutamate Receptor Subtype 2 Blocks a Hallucinogenic Drug Model of Psychosis," Mol. Pharmacol., 2007, 72, 477-484.
International Search Report and Combination Written Opinion of the International Searching Authority mailed Jul. 2, 2008 in re PCT/EP2008/052767, filed Mar. 7, 2008.
International Search Report and Combination Written Opinion of the International Searching Authority mailed Jun. 10, 2008 in re PCT/EP2008/052768, filed Mar. 7, 2008.
International Search Report and Combination Written Opinion of the International Searching Authority mailed Jun. 10, 2008 in re PCT/EP2008/052766, filed Mar. 7, 2008.
Eisa et al., "Synthesis of some novel tetrazole derivatives as potential antimicrobial agents," Pakistan J. of Scientific and Industrial Res, vol. 33, 1990, pp. 417-420.
Ruggero Galici, Carrie K. Jones, Kamondanai Hemstapat, Yi Nong, Nicholas G. Echemendia, Lilly C. Williams, Tomas de Paulis, and P. Jeffrey Conn, "Biphenyl-indanone A, a Positive Allosteric Modulator of the Metabotropic Glutamate Receptor Subtype 2, Has Antipsychotic- and Anxiolytic-Like Effects in Mice," JPET 318:173-185 2006.
The Synthesis of Perloline, 6-(3,4-Dimethoxyphenyl)-5-hydroxy-5,6-dihydrobenzo[c][2,7]napththyridin-4(3H)-one, Prager et al., Aust. J. Chem., 1983, 36, 1441-53.
A 'Biogenetic Like' Synthesis of Perloline, 6-(3,4-Dimethoxyphenyl)-5-hydroxy-5,6-dihydrobenzo[c][2,7]naphthyridin-4(3H)-one, Duong, et al., Aust. J. Chem., 1983, 36, 1431-40.
Ring Transformation of Uracils to 3-Pyridones. Hydrolysis of 6-(2-Dimethylaminovinyl) Uracils, Senda et al., Heterocycles, vol. 9, No. 6, 1978 (6 pages).
Synthese von 3-Cyan-6-methyl-4-pyridyl-und 3-cyan-4-methyl-6-pyridyl-pyrid-2(1H)-onen und -thionen, Hanfeld, et al., Pharmazie 43 (1988), H.11, 762-764.
Studies with Polyfunctionally Substituted Heteroaromatics: New Routes for the Synthesis of Polyfunctionally Substituted Pyridines and 1,2,4-Triazolo[1,5-a]pyridines, Al-Omran, et al., Heteratom. Chemistry, vol. 6, No. 6, 1995, 545-551.
Diels-Alder Reactions of the Heterodiene System in 2(1H)-Pyrazinones, Tutonda, et al., Tetrahedron Letters, vol. 27, No. 22, pp. 2509-2512, 1986.
Cycloadditions of Cyanoketenes to Cinnamylideneamines and Benzylideneamines. Synthetic Scope, Stereochemistry, and Mechanism, Moore, et al., J. Org. Chem, 1985, 50, 4231-4238.

Reactions of Some 4-Methylene-4H-pyran Derivatives with Primary and Secondary Amines, VanAllan, et al., Journal of Heterocyclic Chemistry, vol. 7, Jun. 1970, 495-507.
A One-Step Preparation of Functionalized 3-Cyano-2-Pyridones, Jain, et al., Tetrahedron Letters, vol. 36, No. 19, pp. 3307-3310, 1995.
A new Synthetic Approach to the C-D Ring Portion of Streptonigrin Analogues, Kilama, et al., Journal of Heterocyclic Chemistry, vol. 27, Jul.-Aug. 1990, 1437-1440.
A Convenient Method for the Preparation of 2-Pyridone Derivatives, Kambe et al., 1977, vol. 12, pp. 841-842.
Torp-Ziegler Cyclization in the Synthesis of 3-Amino-4-Cyanopyrrole Derivatives, Ryndina, et al., Chemistry of Heterocyclic Compounds, vol. 36, No. 12, 2000, pp. 1409-1420.
Derivatives of 2-Pyridone, Wenner, et al., Journal of Organic Chemistry, 1946, vol. 11, pp. 751-759.
Alkylations at the Methyl or alpha-Methylene Group of 6- or 4-Alkyl-3-cyano-2(1)-pyridones through Dianions, Boatman, et al., Journal of Organic Chemistry, 1965, vol. 30 Pt 11, pp. 3593-3597.
Chemical Abstract, Yalyaheva et al., Heterocycles, p. 687, vol. 107, 1987.
Chemical Abstracts, Ershov et al., 1985, vol. 103, Pt 21, pp. 678.
Therapeutic potential of non-competitive, subtype-selective metabotropic glutamate receptor ligands, V. Mutel, Expert Opin. Ther. Patents (2002), 12 (12) p. 1845-1852.
Regulation of Neurotransmitter Release by Metabotropic Glutamate Receptors, Cartmell et al., J. Neurochem., p. 889-907, vol. 75, No. 3, 2000.
The selective group mGlu2/3 receptor agonist LY379268 suppresses REM sleep and fast EEG in the rat, Feinberg et al., Pharmacology, Biochemistry and Behavior 73 (2002) 467-474.
A Selective Allosteric Potentiator of Metabotropic Glutamate (mGlu) 2 Receptors Has Effects Similar to an Orthosteric mGlu2/3 Receptor Agonist in Mouse Models Predictive of Antipsychotic Activity, Galici et al., J of Pharmacology and Experimental Therapeutics, p. 1181-1187, vol. 315, No. 3.
Activation of Group II Metabotropic Glutamate Receptors Inhibits Synaptic Excitation of the Subsantia Nigra Pars Reticulata, Bradley et al., J. of Neuroscience, May 1, 2000, 20(9):3085-3094.
Anxiolytic effects of a novel group II metabotropic glutamate receptor agonist (LY354740) in the fear-potentiated startle paradigm in humans, Grillon, et al., Psychopharmacology (2003) 168:446-454.
Anxiolytic and Side-Effect Profile of LY354740: A Potent, Highly Selective, Orally Active Agonist for Group II Metabotropic Glutamate Receptors, Helton et al., J. of Pharmacology and Experimental Therapeutics, p. 651-660, vol. 284, No. 2, 1997
Excited by Glutamate, Science, p. 1866-1868, vol. 300, Jun. 20, 2003.
Benzazoles as allosteric potentiators of metabotropic glutamate receptor 2 (mGluR2): Efficacy in an animal model for schizophrenia, Govek et al., Bioorg. Med. Chem Lett. 15 (2005) 4068-4072.
Metabotropic glutamate 2 receptor potentiators: receptor modulation, frequency-dependent synaptic activity, and efficacy in preclinical anxiety and psychosis model(s), Johnson et al., Psychopharmacology (2005) 179: 271-283.
Discovery of Allosteric Potentiators for the Metabotropic Glutamate 2 Receptor: Synthesis and Subtype Selectivity of N-(4-(2-Methoxyphenoxy)phenyl)-N-(2,2,2-trifluorethylsulfonyl)pyrid-3-ylmethyl-amine, Johnson et al., J. Med. Chem. 2003, 46, 3189-3192.
Effects of metabotropic glutamate2/3 receptor agonist (LY544344/LY354740) on panic anxiety induced by cholecystokinin tetrapeptide in health humans: preliminary results, Kellner et al., Psychopharmacology (2005) 179: 310-315.
Allosteric modulators of metabotropic glutamate receptors: lessons learnt from mGlu1, mGlu2 and mGlu5 potentiators and antagonists, Johnson et al., Biochemical Society Transactions (2004) vol. 32, part 5, 881-887.
Selective, Non-Amino Acid Allosteric mGlu2 Receptor Potentiators Inhibit Dural Plasma Protein Extravasation; A Potential Role in the Treatment of Migraine, Johnson et al., Abstracts/Neuropharmacology 43 (2002) 291.
Khimia Geterotsiklicheskikh Soedinenii, 1985, vol. 5, PT 1985, 646-649.

(56) References Cited

OTHER PUBLICATIONS

Glutamate receptors: brain function and signal transduction, Nakanishi, et al., Brain Research Reviews 26 (1998) 230-235.
Activation of Metabotropic Glutamate Receptor-1 Accelerates NMDA Receptor Trafficking, Lan et al., Abstracts/Neuropharmacology 43 (2002) 294.
Glutamate metabotropic receptors as targets for drug therapy in epilepsy, Moldrich et al., European Journal of Pharmacology 476 (2003) 3-16.
Metabotropic glutamate receptor 2 modulates excitatory synaptic transmission in the rat globus pallidus, Poisik, et al., Neuropharmacology 49 (2005) 57-69.
Pharmacological Characterization and Identification of Amino Acids Involved in the Positive Modulation of Metabotropic Glutamate Receptor Subtype 2, Schaffhauser et al., Mol. Pharmacol 64:798-810, 2003, vol. 64, No. 4.
The metabotropic glutamate receptor 5 antagonist MPEP and the mGluR2 agonist LY379268 modify disease progression in a transgenic mouse model of Huntington's disease, Schiefer, et al., Brain Research 1019 (2004) 246-254.
Phenyl-tetrazolyl Acetophenones: Discovery of Positive Allosteric Potentiators for the Metabotropic Glutamate 2 Receptor, Pinkerton, et al., J. Med. Chem 2004, 47, 4595-4599.
Pharmacological agents acting at subtypes of metabotropic glutamate receptors, Schoepp, Neuropharmacology 38 (1999) 1431-1476.
Group II mGluR receptor agonists are effective in persistent and neuropathic pain models in rats, Simmons, et al., Pharmacology, Biochemistry and Behavior 73 (2002) 419-427.
Preclinical Pharmacology of mGlu2/3 Receptor Agonists: Novel Agents for Schizophrenia?, Schoepp et al., CNS & Neurological Disorders, 2002, 1, 215-225.
Khimia Geterotsiklicheskikh Soedinenii, 1986, vol. 1986, PT 8, 1118-1123.
International Search Report for International Application No. PCT/EP2007/052442 dated Sep. 7, 2007.
Distribution of a metabotropic glutamate receptor, mGluR2, in the central nervous system of the rat and mouse: an immunohistochemical study with a monoclonal antibody, Ohishi, Neuroscience Research 30 (1998) 65-82.
Chemical Abstracts, Azimov et al. abstract No. 78798, vol. 105, No. 10, 1986.
CA Office Action (Requisition b Examiner) mailed Apr. 23, 2010 in re co-pending Canadian Application No. 2,581,144, filed Sep. 16, 2005.
"Notification on the necessity to present additional materials" from the Eurasian Patent Organization dated Dec. 17, 2008.
Rosowsky et al., "2, 4-Diaminothieno [2.3-d]dipyrimidines as Antifolates and Antimalaris 3. Synthesis of 5, 6-Disubstitued Derivatives and Related Tetracyclic Analogs", Journal of Medicinal Chemistry, vol. 16, No. 3, 1973 pp. 191-194.
Acta Chimica Slovencia, 2005, vol. 52, No. 4, pp. 391-397.
Bohme et al., "Darstellng and Umsetzungen von 3-Arylamino-2-halogencrotononitilen", Chem. Ber., 1976, 109, 2908-2913.
Braga et al. "Making Crystals from Crystals: A Green Route to Crystal Engineering and Polymorphism" Chem. Commun. 2005, 3635-3645.
Braish et al., "Construction of the (1x,5x,6x)-6-Amino-3-azabicyclo[3.1.0]hexane Ring System," Synlett, 1996, 1100-1102.
Brighty et al., "Synthesis of (1x,5x,6x)-6-Amino-3-azabicyclo[3.1.0]hexane, a Novel Achiral Diamine," Synlett, 1996, 1097-1099.
Clark et al., "Synthesis of Thieno[2,3-d]pyrimidines from 4,6-Dichloropyrimidine-5-carbaldehydes", Journal Heterocyclic Chem, 1993, vol. 30, 1065-1072.
Cook et al. "Diethylaminoalkyl Ester Hydrochlorides of N-Alkyl-4-carbostyrilcarboxylic Acids", J Am. Chem. Soc., 1952, 74, 543-554.
DiMichelle et al. "The Natural Course of Schizophrenia and Psychopathological Predictors of Outcome", (Mar.-Apr. 2004), 37(2), pp. 98-104 (abstract).

Erlenmeyer et al., "Uber einige Derivate des 2-Aminothiazols", Helvetica Chim Acta, 1949, 35-38.
Fuentes et al., "Synthesis of Heterocyclic Compounds; XL. Regioselective. synthesis of 4-subtituted 2-Amino-5-Cyano-6-methoxy-3-benzenesulfonylpyridines", Synthesis, 1984, pp. 768-770.
Ghammamy et al., "Cetyltrimethylammonium Bromochromate: A New and Efficient Oxidant for Organic Substrates", Synthetic Communications, 2007, 37, 599-605.
Hamaguchi et al., "Effects of Hetero Atom Substituents in the decomposition of Pyrazolines: Abnormal Behavior of Methoxy Group Compared with Arylthio of Arylseleno Group.", Heterocycles, 1986, vol. 24, 2111-2115.
Haper, "Agonist-Stimulated [35S]GTPyS Binding," Current Protocols in Pharmacology, 1998, Unit 2.6, 1-10.
Harriman et al. "Synthesis of 4-Substituted 4-Arylpiperidines", Tetrahedron Letters, 2000, 41, 8853-8856.
Hughes, "Progress in the Mitsunobu Reaction. A Review," Organic Preparations and Procedures International, 1996, 127-164.
Hughes, "The Mitsunobu Reaction", Organinc Reactions, 1992, vol. 42, 335-656.
International Search Report dated Oct. 26, 2009 for international application No. PCT/EP2009/006326.
Kiselyov et al., "A one pot synthesis of polysubstituted inidazo[1,2-a]pyridines", Tetrahedron Letters, 2006, 47, 2941-2944.
Kitano et al., "Synthesis and antifouling activity of 3-isocyanotheonellin and its analogues", Jour Chem Soc Perkin Trans, 2002, 2251-2255, The Royal Society of Chemistry.
Klemm et al. "Chemistry of Thienopyridines. VIII. Substitution Products Derived from Thieno[2,3-b] pyridine 7-Oxide (1)", Journal of Heterocyclic Chemistry, 1970, 7(1), 81-89.
Larock, "Comprehensive Organic Transformations", VCH Publishers, 1989, 595-596.
Lee et al., "Benzylic Bromination of Alkylbenzenes with Sodium Bromate-Bromotrimethylsilane", Bull. Korean Chem. Soc, 1995, vol. 16, pp. 371-374.
Malames et al. "N-Substituted Spirosuccinimide, Spiropyridazine, Spiroazetidine, and Acetic Acid Aidose Reductase Inhibitiors Derived From Isoquinoline-1,3-dinoes. 2", J Med Chem., 1994, 37(13), 2059-2070.
McElvain et al. "Piperidine Derivatives. XXX. 1,4-Dialkyl-4-arylpiperidines", J. Am. Chem. Soc, 1958, 80, 3915-3923.
Mongin et al. "Advances in the directed metallation of azines and diazines (pyridines, pyrimidines, pyrazines, pyridazines, quinolines, benzodiazines and carbolines). Part 1: Metallation of Pyridines, quinolines and carbolines", Tetrahedron, 2001, 57(19), 4059-4090.
Morrill et al., "Synthesis of 4-Arylpiperidines from 1-Benzyl-4piperidone: Application of the Sharpiro Reaction and Alkenylsilane Cross-coupling," Organic Letters, 2007, vol. 9, pp. 1505-1508.
Mutel et al., "Characterization of (2S,2'R,3'R)-2-(2',3'[3H]-Dicarboxycyclopropyl)glycine Binding in Rat Brain," J Neurochemistry, 71(6), 1998, 2558-2564.
Nakamura et al., "An Efficient Synthesis of Platelet-Activating Factor (PAF) J'IJ I-Qalkyl-2-~-(3-Isoxazolyl)-SN_Glycero-3-Phosphocholine, A New PAF Agonist. Utilization of the 3-Isoxazolyloxy Group as a Protected Hydroxyl." Tetrahedron Letters, 1990, vol. 31, 699-702.
Nakano et al. "1-Alkyl-3-phenylpyridinium 1-Alkyl-2(1H)-pyridone 3-Phenyl 5-Phenyl", Annual Report of Tohoku College of Pharmacy, 1998, 45, 145-148.
Ojima et al., "Hydroformation of Fluoro Olefins, RfCH=CH2, Catalyzed by Group VIII Transition-Metal Catalysts. Crucial Factors for Extremly High Regioselectivity", Journal of American Chemical Society, 1987, 109, 7714-7720.
Pin et al., "New perspectives for the development of selective metabotropic glutamate receptor ligands," European J of Pharmacology, 1999, 375, 277-294.
Potts et al. "1,2,4-Triazoles. XII. Derivatives of the s-Triazolo[4,3-a]pyridine Ring System", Journal of Organic Chemistry, 1966, 251-260.
Potts et al. "1,2,4-Trizoles. XXV. The Effect of Pyridine Substitution on the Isomerization of s-Triazolo [4,3-a] pyridines into s-Triazolo [1,5-a] pyridines (1)", J. Heterocycl. Chem., 1970, 7, 1019-1027.

(56) References Cited

OTHER PUBLICATIONS

Rani et al. "Thiazoline Analogues of Epiderstatin, New Inhibitiors of Cell Cycle of TsFT-210 Cells", Journal of Antibiotics, 1995, 48(10), 1179-1181.
Roma et al., "1,8-Naphthyridines VII. New substituted 5-amino[1,2,4]triazolo[4,3-a] [1,8]naphthyridine-6-carboxamides and their isosteric analogues, exhibiting notable anti-inflammatory and/or analgesic activities, but no acute gastrolesivity", European Journal of Medical Chemistry. 2008, 43, 1665-1680.
Schaffhauser et al., "In Vitro Binding Characteristics of a New Selective Group II Metabotropic Glutamate Receptor Radioligand, [3H]LY354740, in Rat Brain," Mol Pharmacology, 53, 228-233, 1998/.
Seddon "Pseudopolymorph: A Polemic" Crystal Growth & Design, 4(6), 1087, 2004.
Shiba et al. "Synthesis and binding affinities of methylvesamicol analogs for the acetylcholine transporter and sigma receptor", Bioorganic and Medicinal Chemistry, 2006, 14, 2620-2626.
SIPO Office Action Jun. 30, 2010.
Stewart et al. "Discovery of Inhibitors of Cell Adhesion Molecule Expression in Human Endothelial Cell. 1. Selective Inhibition of ICAM-1 and E-Selectin Expression", J Med Chem, 2001, 44, 998-1002.
Turck et al. "Advances in the directed metallation of azines and diazines (pyridines, pyrimidines, pyrazines, pyridazines, quinolines, benzodiazines and carbolines). Part 2: Metallation of pyrimidines, pyrazines, pyridazines and benzodiazines", Tetrahedron, 2001, 57(21), 4489-4505.
Vilsmaier et al., "Diastereoselective Syntheses of N-Protected Derivatives of la,5a,6fi-6-Amino-3-azabicyclo [3.101] hexane; A Route to Trovafloxacin 6fl-Diastereomer," Synthesis, 1998, 739-744.
Vippagunta et al., Crystalline Solids, Adv. Drug Deily. Rev., 2001, 48, pp. 3-26.
Wang et al. "A simple and efficient automatable one step synthesis of triazolopyridines form carboxylic acids", Tetrahedron Letters, 2007, 48, 2237-2240.
Watanbe et al. "Pd/P(t-Bu)3-Catalyzed Synthesis of Aromatic Amines", Journal of TOSOH Research, 1999, vol. 43, 38-50.
West Anthony R. Solid State Chemistry and Its Applications, Wiley, New York, 1988 pp. 358 & 365.
Wikipedia, "Allosteric Regulation", 2010, 1-4.
Azume et al., "Synthesis and reactions of 4-choloro-1, 2-dihydro-6-methyl-2-oxo-3-pyridinecarbonitrile", CA139:197340 (2003).
Chrostopoulos., "Allosteric Binding Sites on Cell-Sturcture Receptors: Novel Targets for Drug Discovery", Nature Rev., Mar. 2002, 1, 198-210.
Nell et al., "Preparation of 4-amino-3,5-dicyano-2-thiopyridines as cardiovascular agents", CA149:32326 (2008).
Schoepp, "Unveiling the Functions of Presynaptic Metabotropic Glutamate Receptors in the Central Nervous System", The Journal of Pharmacology and Experimental Therapeutics, 2001, vol. 299, No. 1.
Antuono, "Decreased glutamate 1 glutamine in Alzheimer's disease detected in vivo with 1H-MRS at 0.5 T", Neurology, 2001, 56:737-742.
Chen, "The chemical biology of clinically tolerated NMDA receptor antagonists", Journal of Neurochemistry, 2006, 97, 1611-1626.
Cummings, "Behavioral effects of memantine in Alzheimer disease patients receiving donepezil treatment" Neurology 2006;67:57-63.
FDA Center for Drug Evaluation and Research, "Introduction and Drug History", 2003, NDA 21-487, Pharmacology Reviews, p. ix.
Forstl, "Clinical Features of Alzheimer's disease", Eur Arch Psychiatry Clin Neurosci, 1999, 249: 288-290.
Herminghaus, "Brain metabolism in Alzheimer disease and vascular dementia assessed by in vivo proton magnetic resonance spectroscopy", Psychiatry Research: Neuroimaging 123, 2003, 183-190.
Lipton, "Excitatory Amino Acids as a Final Common Pathway for Neurologic Disorders", Mechanisms of Disease, The New England Journal of Medicine, 1994, vol. 330 No. 9., pp. 613-622.
Metman, "Huntington's disease A randomized, controlled trial using the NMDA-antagonist amantadine", Neurology, 2002; 59:694-699.
Atlante, "Glutamate neurotoxicity, oxidative stress and mitochondria", FEBS Letters 497, 2001, 1-5.
Arundine, "Molecular mechanisms of glutamate-dependent neurodegeneration in ischemia and traumatic brain injury", Cellular and Molecular Life Sciences, 61, 2004, pp. 657-668.
Copani, "Activation of Metabotropic Glutamate Receptors Protects Cultured Neurons Against Apoptosis Induced by—Amyloid Peptide", Molecular Pharmacology, 1995, 47:890-897.
Harich, "Stimulation of the metabotropic glutamate 2/3 receptor attenuates social novelty discrimination deficits induced by neonatal phencyclidine treatment", Psychopharmacology, 2007, 192, pp. 511-519.
Higgins, "Pharmacological manipulation of mGlu2 receptors influences cognitive performance in the rodent", Neuropharmacology, 46, 2004, pp. 907-917.
Hovelso, "Therapeutic Potential of Metabotropic Glutamate Receptor Modulators", Current Neuropharmacology, 2012, 10, pp. 12-48.
Huntington Study Group, "Dosage effects of riluzole in Huntington's disease: A multicenter placebo-controlled study", Neurology, 2003, 61, pp. 1551-1556.
Kenny, "The ups and downs of addiction: role of metabotropic glutamate receptors", TRENDS in Pharmacological Sciences, 2004, vol. 25 No. 5, pp. 265-272.
Landwehrmeyer, "Riluzole in Huntington's Disease: A 3-Year, Randomized Controlled Study", Ann Neurol, 2007, 62, pp. 262-272.
Matrisciano, "Metabotropic glutamate receptors and neuroadaptation to antidepressants: imipramine-induced down-regulation of b-adrenergic receptors in mice treated with metabotropic glutamate 2/3 receptor ligands", Journal of Neurochemistry, 2005, 93, pp. 1345-1352.
Matrisciano, "Synergism between fluoxetine and the mGlu2/3 receptor agonist, LY379268, in an in vitro model for antidepressant drug-induced neurogenesis", Neuropharmacology, 54, 2008, pp. 428-437.
Orlando, "The Role of Group I and Group II Metabotropic Glutamate Receptors in Modulation of Striatal NMDA and Quinolinic Acid Toxicity", Experimental Neurology, 2001, 167, 196-204.
O'Suilleabhain, "A Randomized Trial of Amantadine in Huntington Disease", Arch Neurol, 2003, 60, 996-998.
Pinkerton, "Allosteric potentiators of the metabotropic glutamate receptor 2 (mGlu2). Part 3: Identification and biological activity of indanone containing mGlu2 receptor potentiators", Bioorganic & Medicinal Chemistry Letters 15, 2005, 1565-1571.
Lee, "The role of metabotropic glutamate receptors in Alzheimer's disease", Acta Neurobiol Exp, 2004, 64: 89-98.
Bruno, "Metabotropic Glutamate Receptor Subtypes as Targets for Neuroprotective Drugs", Journal of Cerebral Blood Flow and Metabolism, 2001, 21:1013-1033.
Zarate, "A randomized trial of an N-methyl-D-aspartate antagonist in treatment-resistant major depression," Arch. Gen. Psychiatry, 63(8):856-64 (Aug. 2006).
Zhang, Jie et al. "Neuroprotective Effects of Poly(ADP-ribose) Polymerase Inhibition on Focal Cerebral Ischemia" Portland Press Proceedings, 1998, vol. 15 (Biology of Nitric Oxide, Part 6), pp. 125.
European Search Report dated May 8, 2009 for EP 08 16 6832.
Office Action for Israeli Application No. 192868 dated Dec. 21, 2011.
Office Action for Australian application No. 2007224431 dated Mar. 19, 2010.
Office Action for Chinese application No. 200780009210.5 dated Jun. 19, 2012.
Office Action for South Korean application No. 2010-053694958 dated Nov. 25, 2012.
Office Action for European application No. 07726932.2-2117 dated Sep. 8, 2009.
Office Action for Chilean application No. 681-2007 dated Jan. 11, 2011.
Office Action for Taiwanese application No. 096108666.
Office Action for European application No. 11181481.1-2117 dated Dec. 6, 2012.
Office Action for Japanese application No. 2008558820 dated Aug. 28, 2012.
Office Action for Eurasian application No. 20080193428 dated May 13, 2010.

(56) References Cited

OTHER PUBLICATIONS

Examiner's Report for Australian Application 2008297877 dated Oct. 31, 2012.
Examiner's Report for Australian Application 2008223796 dated Nov. 3, 2010.
Office Action for Chilean Application No. 671-2008 dated Oct. 29, 2010.
Official Communication for European Application No. 08717515.4-2117 dated May 3, 2010.
Office Action for Mexican Application MX 2009009422 dated Jun. 28, 2011.
Office Action for Australian application No. 2005284098 dated Oct. 11, 2010.
Office Action for European Application No. 08717514.7-2117 dated Jun. 28, 2010.
Office Action for Australian Application No. 2008223795 dated May 29, 2012.
Office Action for Eurasian application No. 200901116228 dated Apr. 18, 2011.
Office Action for European Application No. 05787278.0-2101 dated May 11, 2012.
Office Action for Taiwanese application No. 094132375 dated Aug. 25, 2011.
Office Action for Japanese Application No. 2007531759 dated Jun. 27, 2011.
Office Action for Japanese Application No. 2009552215 dated Dec. 18, 2012.
Office Action for Canadian application No. 2581144 dated May 13, 2009.
Office Action for U.S. Appl. No. 12/677,618 dated Jun. 24, 2013.
Putt et al. "An enzymatic assay for poly(ADP-ribose) polymerase-1 (PARP-1) via the chemical quantitation of NAD+: application to the high-throughput screening of small molecules as potential inhibitors." Analytical Biochemistry. vol. 326. 2004. 78-86.
Redondo et al. "Selective Heteronuclear NOE Enhancements in Benzoheterocycles. Effect of Ring Size on Indirect Three-Spin Effects." Magnetic Resonance in Chemistry. vol. 26. 1988. 511-7.
Rehwald et al. "3-Amino-2(1H)-Quinolones by Cyclization of N-Acylated Anthranilic Acid Derivatives." Heterocycles. vol. 45 (3). 1997. 483-92.
Reis et al. "Reactions of Tricarbonyl(vinylketene)iron(0) Complexes with Imines." Organometallics. vol. 14. 1995. 1586-91.
Renslo et al., "Synthesis of Aza-, Oxa-, and Thiabicyclo[3.1.0]hexane Heterocycles from a Common Synthetic Intermediate," Organic Letters, 2005, vol. 7, No. 13, 2627-2630, American Chemical Society, USA.
Ried et al. "Reactions with Cyclobutenediones, IX. 3-Hydroxypyridones-(2) from Phenylcyclobutenedione and Enamines." Liebigs Ann. Chem. vol. 725. 1969. 230-3.
Sakamoto et al. "Condensed Heteroaromatic Ring Systems. VIII. Synthesis 3-Substituted Isocoumarins from o-Halobenzoic Acid Derivatives." Chem. Pharm. Bull. vol. 34 (7). 1986. 2754-9.
Semple et al. "3-Aryl Pyridone Derivatives. Potent and Selective Kappa Opioid Receptor Agonists." Bioorganic and Medicinal Chemistry Letters. vol. 12. 2002. 197-200.
Smalley et al. "Pyrolysis of Aryle Azides in Acetic Anhydride." 1963. 5571-2.
Steinpreis. "The behavioral and neurochemical effects of phencyclidine in humans and animals: some implications for modeling psychosis." Behavioral Brain Research. vol. 74. 1996. 45-55.
Stella et al. "4. Prodrugs: the contrul of drug delivery via bioreversible chemical modification." Drug Delivery Systems: Characteristics and Biomedical Applications. New York: Oxford University Press, 1980. 67 pgs.
Stella et al. "Prodrugs: Do They Have Advantages in Clinical Practice?" Drugs. vol. 29. 1985. 455-73.
Stogryn et al. "5-Hetarylmethylene-2,4-diaminopyrimidines (1)." vol. 11. Apr. 1974. 251-3.
Suh et al. "Hypoglycemic Neuronal Death and Cognitive Impairment Are Prevented by Poly(ADP-Ribose) Polymerase Inhibitors Administered after Hypoglycemia." The Journal of Neuroscience. vol. 23 (33). Nov. 2003. 10681-90.
Suzuki et al. "Synthesis of the Selective 5-Hydroxytryptamine 4 (5-HT4) Receptor Agonist (+)-(S)-2-Chloro-5-methoxy-4[5-(2-piperidylmethyl)-1,2,4-oxadiazol-3-yl]aniline." Chem. Pharm. Bull. vol. 47 (1). 1999. 120-2.
Takahashi et al. "Post-treatment with an inhibitor of poly(ADP-ribose) polymerase attenuates cerebral damage in focal ischemia." Brain Research. vol. 829. 1999. 46-54.
Teran et al. "Regioselective Oxidation of 3-Substituted Pyridinium Salts." Molecules. vol. 5. 2000. 1175-81.
Tsiveriotis et al. "Nickel(II) and cobalt(II) complexes of 2,4-diaminothieno[2,3-d]-pyrimidines." Transition Metal Chemistry. vol. 19. 1994. 335-9.
Vaughan et al. "Reactivity of 3-Alkyl-4-arylazomethylene-3,4-dihydro-1,2,3-benzotriazines in Protic Solvents: 1,4-Addition Reactions and Dimroth Rearrangement." Journal of Heterocyclic Chemistry. vol. 28. Nov. 1991. 1709-13.
Wiley et al. "2-Pyrones. XVIII. 5-Aroyl-2-pyridones." vol. 78. Jun. 1956. 2393-98.
Yakovidis et al. Copper(II) Complexes of Thieno[2,3-d] pyrimidine Derivatives. Inorganica Chimica Acta. vol. 151. 1988. 165-7.
Yousif et al. "Studies on Tertiary Amine Oxides. LXXV. Reactions of Aromatic N-oxides with Meldrum's Acid in the Presence of Acetic Anhydride." Chem. Pharm. Bull. vol. 30 (5). 1982. 1680-91.
Yui et al. "Studies of Amphetamine or Methamphetamine Psychosis in Japan: Relation of Methamphetamine Psychosis to Schizophrenia." Annals New York Academy of Sciences. 1-12, 2000.
Zhang et al. "Neuroprotective Effects of Poly(ADP-ribose) Polymerase Inhibition on Focal Cerebral Ischemia." 125, 1997.
Structures. Chemical Abstracts. May 13, 2009. 23 pgs.
Office Action for Chilean application No. 2745-2008 dated Apr. 15, 2011.
Office Action for Chinese application No. 200880107135.0 dated Jul. 4, 2012.
Office Action for Japanese application No. 2010-524405 dated Jun. 5, 2012.
Office Action for U.S. Appl. No. 12/282,663 dated Jan. 13, 2012.
Office Action for U.S. Appl. No. 12/282,663 dated Aug. 9, 2012.
Office Action for U.S. Appl. No. 12/529,632 dated Dec. 16, 2011.
Office Action for U.S. Appl. No. 12/529,632 dated May 18, 2012.
Office Action for Japanese application No. 2008-558820 dated Aug. 28, 2012.
Office Action for Eurasian application No. 200801934/28 dated May 13, 2010.
Adams, "A long-term, phase 2, multicenter, randomized, open-label, comparative safety study of pomaglumetad methionil (LY2140023 monohydrate) versus atypical antipsychotic standard of care in patients with schizophrenia," BMC Psychiatry 13(143): 1-9 (2013).
Backstrom, "Suppression of alcohol self-administration and cue-induced reinstatement of alcohol seeking by the mGlu2/3 receptor agonist LY379268 and the mGlu8 receptor agonist (S)-3,4-DCPG" Eur. J. Pharmacol. 528:110-118 (2005).
Borowitz et al. "Organophosphorus Chemistry. III. The Reactions of Triphenylphosphine with Secondary a-Bromo Ketones and with 2-Bromodimedone." Journal of Organic Chemistry, Dec. 1966. 4031-7.
Calabresi, "Antiepileptic drugs in migraine: from clinical aspects to cellular mechanisms," TRENDS in Pharmacological Sci. 28(4): 188-195 (2007).
Cartmell et al. "Regulation of Neurotransmitter Release by Metabotropic Glutamate Receptors", J. Neurochem., p. 889-907, vol. 75, No. 3, 2000.
Chakrasali et al. "Reaction of Acylketene S,N-Acetals with Malonyl Chloride: Synthesis of Novel 1,5-Substituted 4-Hydroxy-6-methylthio-2 (1H)-pyridones and 6,8-Substituted 4-Hydroxy-7-methylthio-2,5-dioxo-5,6-dihydro-2H-pyrano[3,2-c] pyridines." Synthesis, Jan. 1988. 87-9.
Clarke, "Tripartite model of anxiety and depression: psychometric evidence and taxonomic implications" J. Abnormal Psych. 100(3):316-336 (1991).

(56) References Cited

OTHER PUBLICATIONS

Corti, "The use of knock-out mice unravels distinct roles for mGlu2 and mGlu3 metabotropic glutamate receptors in mechanisms of neurodegeneration/neuroprotection," J. Neurosci. 27(31): 8297-8308 (2007).
Cymbalta® Highlights of Prescribing Information (2004).
Dunayevich, "Efficacy and tolerability of an mGlu2/3 agonist in the treatment of generalized anxiety disorder," Neuropsychopharmacol. 33: 1603-1610 (2008).
During, "Extracellular hippocampal glutamate and spontaneous seizure in the conscious human brain" Lancet 341:1607-1610 (1993).
Galici et al., A Selective Allosteric Potentiator of Metabotropic Glutamate (mGlu) 2 Receptors Has Effects Similar to an Orthosteric mGlu2/3 Receptor Agonist in Mouse Models Predictive of Antipsychotic Activity, J of Pharmacology and Experimental Therapeutics, p. 1181-1187, vol. 315, No. 3, 2005.
Gewald et al. "Heterocyclen aus CH-aciden Nitrilen, VIII. 2-Aminothiophene aus methylenaktiven Nitrilen Carbonylverbindungen und Schwefel." Chemische Berichte vol. 99. 1966. 94-100.
Gewald. "Heterocyclen aus CH-aciden Nitrilen, VII. 2-Aminothiophene aus a-Oxo-mercaptanen und methylenaktiven Nitrilen." Chemische Berichte vol. 98. 1965. 3571-7.
Herdeis et al. "A Facile Entry to the 2-Azabicyclo[2.2.2]octane-6-one Skeleton via [4+2]-Cycloaddition." Synthesis, Jan. 1988. 76-8.
Hickinbottom. "Reactions of organic compounds." Gonti: Moscow 1939. 360-2. (Russian with English translation).
Insel, Thomas et al. "Research Domain Criteria (RDoC): Toward a New Classification Framework for Research on Mental Disorders" Am. J. Psychiatry 167(7) Jul. 2010, 748-751.
Kambe et al "A Convenient Method for the Preparation of 2-Pyridone Derivatives", 1977, Synthesis, vol. 12, pp. 841-842.
Kinon, "A multicenter, inpatient, phase 2, double-blind, placebo-controlled dose-ranging study of LY2140023 monohydrate in patients with DSM-IV Schizophrenia" J. Clin. Psychopharmacology, 31(3):349-355 (2011).
Krohnke et al. "Methylketon-Addukte der Chinolinium-und Isochinolinium-Reihe." Justus Liebigs Annalen der Chemie 1956; p. 211-28.
Krystal, "N-methyl-D-aspartate glutamate receptors and alcoholism: reward, dependence, treatment, and vulnerability," Pharmacol. & Therapeutics 99: 79-94 (2003).
Lamotrigine Highlights of Prescribing Information, 2012.
Landmark, "Antiepileptic drugs in non-epilepsy disorders," CNS Drugs 22(1) 27-47 (2008).
Large, "The potential role of lamotrigine in schizophrenia," Psychopharmacol., 181: 415-436 (2005).
Levine et al. Abstracts/Neuropharmacology, 2002, 43, 294-295.
Linden, "Anxiolytic-like activity of the mGLU2/3 receptor agonist LY354740 in the elevated plus maze test is disrupted in metabotropic glutamate receptor 2 and 3 knock-out mice," Psychopharmacol. 179: 284-291(2005).
Litman, "AZD8529, A positive allosteric modulator at the mGluR2 receptor, does not improve symptoms in schizophrenia: a proof of principle study" NCDEU: An Annual Meeting Sponsored by Am Soc. of Clin. Psychopharmacology, Poster and Abstract, 2013.
Maeng, "Cellular mechanisms underlying the antidepressant effects of ketamine: role of alpha-amino-3-hydroxy-5-methylisoxazole-4-propionic acid receptors," Biol. Psychiatry 63: 349-352 (2008).
Mason, "Acamprosate in the treatment of alcohol dependence," Expert Opin. Pharmacother. 6(12): 2103-2115. (2005).
Mayo Clinic "Mental illness" p. 1-13 (2012).
Mcelroy, "A 52-week, open-label continuation study of lamotrigine in the treatment of bipolar depression," J. Clin. Psychiatry p. 204-210 (Feb. 2004).
Michelson, "Clinical studies with mGluR2/3 agonists: LY354740 compared with placebo in patients with generalized anxiety disorder," Abstracts Neuropharmacol. 49: 257 (2005).
Moghaddam, "Targeting metabotropic glutamate receptors for treatment of the cognitive symptoms of schizophrenia," Psychopharmacology 174:39-44 (2004).

Nestler, "Common Molecular and Cellular Substrates of Addiction and Memory," Neurobiol. of Learning and Memory 78:637-647 (2002).
Office Action for CA Application No. 2,581,144 dated Dec. 4, 2012 with CAS structures.
Patil, "Activation of mGlu2/3 receptors as a new approach to treat schizophrenia: a randomized Phase 2 clinical trial," Nature Medicine, 13(9): 1102-1107 (2007).
Petroff, "Glutamate-glutamine cycling in the epileptic human hippocampus," Epilepsia 43(7) 703-710 (2002).
Schoepp et al., "Preclinical Pharmacology of mGlu2/3 Receptor Agonists: Novel Agents for Schizophrenia?", CNS & Neurological Disorders, 2002, 1, 215-225.
Seroquel XR® Highlights of Prescribing Information (2013).
Shalev, "Neurobiology of Relapse to Heroin and Cocaine Seeking: A Review," Pharmacol. Rev. 54(1): 1-42. (2002).
Smalley et al. "Pyrolysis of Aryle Azides in Acetic Anhydride." J. Chem. Soc., 1963. 5571-2.
Stogryn et al. "5-Hetarylmethylene-2,4-diaminopyrimidines (1)." J. Heterocyclic Chem. vol. 11. Apr. 1974. 251-3.
Theberge, "Glutamate and glutamine in the anterior cingulate and thalamus of medicated patients with chronic schizophrenia and healthy comparison subjects measured with 4.0-T proton MRS," Am. J. Psychiatry 160: 2231-2233 (2003).
Theberge, "Glutamate and glutamine measured with 4.0T proton MRS in never-treated patients with schizophrenia and healthy volunteers," Am. J. Psychiatry 159: 1944-1946 (2002).
Tsai, "Glutamatergic mechanisms in schizophrenia," Ann. Rev. Pharmacol. Toxicol. 42: 165-179 (2002).
Tuominen, "Glutamatergic drugs for schizophrenia: a systematic review and meta-analysis," Schiz. Res. 72: 225-234 (2005).
Valproate Information available from http://www.fda.gov/Drugs/DrugSafety/PostmarketDrugSafetyInformationforPatientsandProviders/ucm192645.htm (2011).
Wenner et al, "Derivatives of 2-Pyridone", Journal of Organic Chemistry, 1946, vol. 11, pp. 751-759.
Wiley et al. "2-Pyrones. XVIII. 5-Aroyl-2-pyridones." J. Am. Chem. Soc., vol. 78. Jun. 1956. 2393-98.
Yui, Kunio et al. "Studies of Amphetamine or Methamphetamine Psychosis in Japan: Relation of Methamphetamine Psychosis to Schizophrenia" Annals New York Academy of Sciences. 2000, vol. 914, pp. 1-12.
Office Action for U.S. Appl. No. 12/529,632 dated Jul. 26, 2012.
Office Action for U.S. Appl. No. 12/529,632 dated Aug. 27, 2012.
Office Action for U.S. Appl. No. 12/677,691 dated Mar. 9, 2012.
Office Action for U.S. Appl. No. 12/529,568 dated Jul. 16, 2012.
Office Action for U.S. Appl. No. 11/575,433 dated May 25, 2012.
Office Action for U.S. Appl. No. 12/677,618 dated Oct. 11, 2012.
Office Action for U.S. Appl. No. 12/677,691 dated Dec. 14, 2011.
Office Action for U.S. Appl. No. 13/123,984 dated Sep. 25, 2012.
Office Action for U.S. Appl. No. 13/131,360 dated Sep. 26, 2012.
Office Action for U.S. Appl. No. 11/575,432 dated Jul. 22, 2010.
Office Action for U.S. Appl. No. 11/575,432 dated Mar. 28, 2011.
Office Action for U.S. Appl. No. 11/575,433 dated Dec. 9, 2010.
Office Action for U.S. Appl. No. 11/575,433 dated Aug. 18, 2011.
Office Action for U.S. Appl. No. 12/529,555 dated Jan. 10, 2012.
Office Action for U.S. Appl. No. 12/529,568 dated Feb. 7, 2012.
Office Action for U.S. Appl. No. 12/677,618 dated May 16, 2012.
Office Action for U.S. Appl. No. 12/677,618 dated Mar. 6, 2013.
Office Action for U.S. Appl. No. 12/677,691 dated Jan. 19, 2011.
Office Action for U.S. Appl. No. 12/742,638 dated Nov. 23, 2012.
Office Action for U.S. Appl. No. 13/061,183 dated May 16, 2013.
Office Action for U.S. Appl. No. 13/123,984 dated Jun. 28, 2012.
Office Action for U.S. Appl. No. 13/131,360 dated Jun. 28, 2012.
Office Action for U.S. Appl. No. 13/556,547 dated Jan. 15, 2013.
Office Action for U.S. Appl. No. 13/319,568 dated Jul. 1, 2013.
International Search Report for PCT/EP2011/069640 dated Dec. 23, 2011.
International Search Report for PCT/EP2011/069641 dated Dec. 23, 2011.
International Search Report for PCT/EP2011/069643 dated Dec. 27, 2011.

(56) References Cited

OTHER PUBLICATIONS

International Search Report for PCT/EP2011/069654 dated Dec. 23, 2011.
Adam, Octavian R. "Symptomatic Treatment of Huntington Disease" Neurotherapuetics: The Journal of the American Society for Experimental NeuroTherapeutics Apr. 2008, vol. 5, 181-197.
Hook, V. Y.H. "Neuroproteases in Peptide Neurotransmission and Nuerodegenerative Diseases Applications to Drug Discovery Research" Biodrugs 2006, 105-119.
Conn, P.J. "Activation of meabotropic glutamate receptors as a novel approach for the treatment of schizophrenia." Trends in Pharmacological Sciences 2008 vol. 30 No. 1 25-31.
Eric R. Marcotte "Animal models of schizophrenia: a critical review" Psychiatry Neurosci 2001;26(5):395-410.
Abshire et al., "Injection of L-Allylglycine Into the Posterior Hypothalamus in Rats Causes Decreases in Local GABA Which Correlate with Increases in Heart Rate", Neuropharmacology, 1988, 27(11), 1171-1177.
Adams et al., "Effect of Clozapine, Haloperidol, or M100907 on Phencyclidine-Activated Glutamate Efflux in the Prefrontal Cortex", Biol. Psychiatry 2001, 50(10), 750-757.
Addex Partner Completes ADX71149 Phase I Program, Press release Aug. 25, 2010, http://www.addextherapeutics.com/investors/press-releases/news-details/?tx_ttnews%5Btt_news%5D%20=103&cHash=91fade38b1d3dc85979989357b1a9281, retrieved on Aug. 22, 2013.
Addex Partner Doses First Patient in Phase 2 Clinical Study of ADX71149 for the Treatment of Major Depressive Disorder Patients with Anxiety Symptoms, Press Release Sep. 17, 2012, http://www.addextherapeutics.com/investors/press-releases/news-details/?tx_ttnews%5Btt_news%5D%20=214&cHash=12a9cc5ffefdb63c27d5b87a673f74eb , retrieved on Aug. 22, 2013.
Addex Partner to Initiate Phase 2 Clinical Trial of ADX71149 for the Treatment of Major Depressive Disorder with Anxiety Symptoms, Press Release Jun. 5, 2012 http://www.addextherapeutics.com/investors/press-releases/news-details/?tx_ttnews%5Btt_news%5D%20=204&cHash=1865c3b31d0b9042f84c017bb2b5f32c, retrieved on Aug. 22, 2013.
Addex Reports Top-line Data from a Successful Phase 2a Clinical Study with ADX71149 in Schizophrenia Patients, Press Release Nov. 5, 2012, http://www.addextherapeutics.com/investors/press-releases/news-details/?tx_ttnews%5Btt_news%5D%20=225&cHash=9e5e13cb042971e6135f8ac786ce7453 retrieved on Aug. 22, 2013.
Addington et al., "A depression rating scale for schizophrenics", Schizophr Res. 1990, 3(4), 247-251.
Ader et al., "Effects of Chlorpromazine on the Acquisition and Extinction of an Avoidance Response in the Rat", J. Pharmacol. Exp. Ther., 1957, 131, 144-148.
Agari et al., "Intrapallidal Metabotropic Glutamate Receptor Activation in a Rat Model of Parkinson's Disease: Behavioral and Histological Analyses", Brain Res., 2008, 1203, 189-196.
Aghajanian et al., "Serotonin model of schizophrenia: Emerging role of glutamate Mechanisms", Brain Research Reviews, 2000, 31, 302-312.
Aghajanian, "Modeling 'Psychosis' in Vitro by Inducing Disordered Neuronal Network Activity in Cortical Brain Slices", Psychopharmacology 2009, 206(4), 575-585.
Agid et al., "How Can Drug Discovery for Psychiatric Disorders Be Improved?" Nature Reviews Drug Discovery, 2007, 6, 189-201.
Ago et al., "Activation of Metabotropic Glutamate 2/3 Receptors Attenuates Methamphetamine-Induced Hyperlocomotion and Increase in Prefrontal Serotonergic Neurotransmission", Psychopharmacology, 2011, 217, 443-452.
Ahnaou et al., "Modulation of Group II Metabotropic Glutamate Receptor (Mglu2) Elicits Common Changes in Rat and Mice Sleep-Wake Architecture", European Journal of Pharmacology, 2009, 603, 62-72.
Ainslie et al., "Practical Drug Evaluation Method", Arch Gen Psychiat, 1965, 12, 368-373.
Alagarsamy et al., "Coordinate Regulation of Metabotropic Glutamate Receptors", Current Opinion in Neurobiology, 2001, 11(3), 357-362.
Albasanz et al., "Internalization of Metabotropic Glutamate Receptor in C6 Cells Through Clathrin-Coated Vesicles", Molecular Brain Research, 2002, 99, 54-66.
Alderson et al., "Purification and Characterization of a Soluble Cyclic Nucleotide-Independent Ca2+-Calmodulin-Sensitive Protein Kinase from Rat Brain", J. Neurochem., 1986, 46, 594-603.
Aleppo et al., "Metabotropic Glutamate Receptors and Neuronal Toxicity", Advances in Experimental Medicine & Biology, 1992, 318, 137-145.
Alexander et al., "Metabotropic Glutamate Receptors as a Strategic Target for the Treatment of Epilepsy", Epilepsy Res., 2006, 71(1), 1-22.
Allen et al., "Group II Metabotropic Glutamate Receptor Activation Attenuates Traumatic Neuronal Injury and Improves Neurological Recovery After Traumatic Brain Injury", J Pharmacol. Exp. Ther., 1999, 290(1), 112-120.
Alley et al., "Memantine Lowers Amyloid-Beta Peptide Levels in Neuronal Cultures and in APP/PS1 Transgenic Mice", J Neurosci Res, 2010, 88, 143-154.
Al-Shamma et al., "Nelotanserin, a Novel Selective Human 5-Hydroxytryptamine2a Inverse Agonist for the Treatment of Insomnia", J Pharmacol Exp Ther, 2010, 332, 281-290.
Altamura et al., "Designing Outcome Studies to Determine Efficacy and Safety of Antipsychotics for 'Real World' Treatment of Schizophrenia", Int J Neuropsychopharmacol, 2010;13(7):971-973.
Altamura et al., "Plasma and Platelet Exctitatory Amino Acids in Psychiatric Disorders", Am J Psychiatry, 1993, 150(11), 1731-1733.
Altamura et al., "Plasma Concentrations of Excitatory Amino Acids Serine, Glycine, Taurine and Histidine in Major Depression", Eur Neuropsychopharmacol, 1995; 5(Suppl), 71-75.
Amiri et al., "A Role for Leu118 of Loop E in Agonist Binding to the α7 Nicotinic Acetylcholine Receptor" Mol Pharmacol, 2008, 73, 1659-1667.
Amitai et al., "Effects of Metabotropic Glutamate Receptor 2/3 Agonism and Antagonism on Schizophrenia-Like Cognitive Deficits Induced by Phencyclidine in Rats", European Journal of Pharmacology, 2010, 639, 67-80.
Andreescu et al., "Comorbid Anxiety and Depression: Bête Noire or Quick Fix?", British Journal of Psychiatry 2012, 200:179-181.
Andreescu et al., "Effect of Comorbid Anxiety on Treatment Response and Relapse Risk in Late-Life Depression: Controlled Study", The British Journal of Psychiatry, 2007, 190, 344-349.
Andreescu et al., "The Default Mode Network in Late-Life Anxious Depression", Am J Geriatr Psychiatry, Nov. 2011, 19(11), 5 pages.
Andres et al., "2-(Dimethylaminomethyl)-Tetrahydroisoxazolopyridobenzazepine Derivatives. Synthesis of a New 5-HT2C Antagonist with Potential Anxiolytic Properties", Bioorganic & Medicinal Chemistry Letters, 2002, 12, 3573-3577.
Andres et al., "Synthesis, Evaluation, and Radiolabeling of New Potent Positive Allosteric Modulators of the Metabotropic Glutamate Receptor 2 As Potential Tracers for Positron Emission Tomography Imaging", J Med Chem, 2012, 55, 8685-8699.
Angenstein et al., "Activation of Metabotropic Glutamate Receptors Increases Endogenous Protein Kinase C Substrate Phosphorylation in Adult Hippocampal Slices", Brain Research, 1997, 745(1-2), 46-54.
Angers et al., "Dimerization: An Emerging Concept for G Protein-Coupled Receptor Ontogeny and Function", Annu. Rev. Pharmacol. Toxicol., 2002, 42, 409-435.
Anwyl "Metabotropic Glutamate Receptor-Dependent Long-Term Potentiation", Neuropharmacology, 2009, 56, 735-740.
Anwyl "Metabotropic Glutamate Receptors: Electrophysiological Properties and Role in Plasticity", Brain Res. Brain Res., 1999, 29, 83-120.
Aparicio-Legarza et al., "Deficits of [3h]D-Aspartate Binding to Glutamate Uptake Sites in Striatal and Accumbens Tissue in Patients with Schizophrenia", Neuroscience Letters, 1997, 232(1), 13-16.

(56) References Cited

OTHER PUBLICATIONS

Aparicio-Legarza et al., "Increased Density of Glutamate/N-Methyl-D-Aspartate Receptors in Putamen From Schizophrenic Patients", Neuroscience Letters,1998, 241(2-3), 143-146.

Arnt, "Pharmacological Specificity of Conditioned Avoidance Response Inhibition in Rats: Inhibition by Neuroleptics and Correlation to Dopamine Receptor Blockade", Acta Pharmacol. Toxicol., 1982, 51, 321-329.

Aronica et al., "Metabotropic Glutamate Receptors in Cultured Cerebellar Granule Cells: Developmental Profile", Journal of Neurochemistry, 1993, 60(2), 559-565.

Aronica et al., "Pharmacological Characterization of Metabotropic Glutamate Receptors in Cultured Cerebellar Granule Cells", Neurochemical Research, 1993, 18(5), 605-612.

Aronica et al., "Status Epilepticus-Induced Alterations in Metabotropic Glutamate Receptor Expression in Young and Adult Rats", J. Neurosci., 1997, 17(21), 8588-8595.

Aronson et al., "Triiodothyronine Augmentation in the Treatment of Refractory Depression. A Meta-Analysis", Arch Gen Psychiatry, 1996, 53, 842-848.

Arriza et al., "Functional Comparisons of Three Glutamate Transporter Subtypes Cloned From Human Motor Cortex", J. Neurosci., 1994, 14(9), 5559-5569.

Attwell et al., "Anticonvulsant and Glutamate Release-Inhibiting Properties of the Highly Potent Metabotropic Glutamate Receptor Agonist (2s,2'r, 3'r)-2-(2',3'- Dicarboxycyclopropyl)Glycine (Dcg-Iv)", Brain Res., 1998, 805(1-2), 138-143.

Auer et al., "Reduced Glutamate in the Anterior Cingulate Cortex in Depression: An in Vivo Proton Magnetic Resonance Spectroscopy Study", Biol Psychiatry, 2000, 47(4), 305-313.

Auerbach et al., "Mutations Causing Syndromic Autism Define an Axis of Synaptic Pathophysiology", Nature, 2011, 480, 63-68.

Aultman et al., "Distinct Contributions of Glutamate and Dopamine Receptors to Temporal Aspects of Rodent Working Memory Using a Clinically Relevant Task", Psychopharmacology (Berl), 2001, 153(3), 353-364.

Austin et al., "Symptomatic and Neuroprotective Effects Following Activation of Nigral Group III Metabotropic Glutamate Receptors in Rodent Models of Parkinson's Disease", British Journal of Pharmacology, 2010, 160, 1741-1753.

Awouters et al., "Astemizole: Effects on General Behavior and Interactions with the Central Nervous System", Jap. Pharmacol. & Therapeutics, 1991, 19, 73-89.

Ayalew et al., "Convergent Functional Genomics of Schizophrenia: From Comprehensive Understanding to Genetic Risk Prediction", Molecular Psychiatry 2012, 1-19.

Ayan-Oshodi et al., "Adverse Events in Healthy Subjects Exposed to Single and Multiple Doses of Ly2140023 Monohydrate", J Clin Psychopharmacol, 2012, 32, 408-411.

Badawy et al., "Epilepsy: Ever-Changing States of Cortical Excitability" Neuroscience, 2012, 22, 89-99.

Baffa et al., "Norepinephrine and Serotonin Transporter Genes: Impact on Treatment Response in Depression", Neuropsychobiology, 2010, 62, 121-131.

Bagby et al., "Psychosocial and Clinical Predictors of Response to Pharmacotherapy for Depression" J Psychiatry Neurosci, 2002, 27(4), 250-7.

Bakker et al., "Activation of the Metabotropic Glutamate Receptor 2 (Mglu2) by Orthosteric and Allosteric Ligands", Poster 642.6/E30 Presented at the 40$^{th}$ Annual Meeting of Society for Neuroscience 2010, 1 page.

Bakker et al., "Reduction of Hippocampal Hyperactivity Improves Cognition in Amnestic Mild Cognitive Impairment", Neuron, 2012, 74(3), 467-474.

Balastrieri et al., "Assessing Mixed Anxiety-Depressive Disorder. A National Primary Care Survey", Psychiatry Research, 2010, 176, 197-201.

Balazs et al., "Metabotropic Glutamate Receptor Agonists Potentiate Cyclic Amp Formation Induced by Forskolin or Beta-Adrenergic Receptor Activation in Cerebral Cortical Astrocytes in Culture", Journal of Neurochemistry, 1998, 70(6), 2446-2458.

Bandelow et al., "Adjunct Quetiapine XR in Patients with Major Depressive Disorder: A Pooled Analysis of Data From Patients with Anxious Depression", Abstracts of the 19th European Congress of Psychiatry, Mar. 2011, 1 page.

Barda et al., "Sar Study of A Subtype Selective Allosteric Potentiator of Metabotropic Glutamate 2 Receptor, N-(4-Phenoxyphenyl)-N-(3-Pyridinylmethyl)Ethanesulfonamide", Bioorganic & Medicinal Chemistry Letters, 2004, 14, 3099-3102.

Barker et al., "A Temporally Distinct Role for Group I and Group II Metabotropic Glutamate Receptors in Object Recognition Memory", Learn. Mem., 2006, 13(2), 178-186.

Barnes et al., "A Review of Central 5-Ht Receptors and their Function", Neuropharmacology, 1999, 38, 1083-1152.

Bar-Peled et al., "Distribution of Glutamate Transporter Subtypes During Human Brain Development", J Neurochem., 1997, 69(6), 2571-2580.

Barrett, "Mglur2-Positive Allosteric Modulators: Therapeutic Potential for Treating Cocaine Abuse?", Neuropsychopharmacology, 2010, 35, 2007-2008.

Bartha et al., "Measurement of Glutamate and Glutamine in the Medial Prefrontal Cortex of Never-Treated Schizophrenic Patients and Healthy Controls by Proton Magnetic Resonance Spectroscopy", Archives of General Psychiatry, 1997, 54(10), 959-965.

Barton et al., "Comparison of the Effect of Glutamate Receptor Modulators in the 6 Hz and Maximal Electroshock Seizure Models", Epilepsy Research, 2003, 56, 17-26.

Basan et al., "Valproate for Schizophrenia", Cochrane Collaboration, Cochrane Database Syst Rev., 2008, 2, 38 pages.

Batchelor et al., "Novel Synaptic Potentials in Cerebellar Purkinje Cells: Probable Mediation by Metabotropic Glutamate Receptors", Neuropharmacology, 1993, 32(1), 11-20.

Battaglia et al., "Selective Activation of Group-II Metabotropic Glutamate Receptors Is Protective Against Excitotoxic Neuronal Death," European Journal of Pharmacology, 1998, 356(2-3), 271-274.

Bauer et al., "Extended Release Quetiapine as Adjunct to an Antidepressant in Patients with Major Depressive Disorder: Results of a Randomized, Placebo-Controlled, Double-Blind Study", J Clin Psychiatry 2009, 70(4), 540-549.

Bauzo et al., "Interactions Between the Mglur2/3 Agonist, Ly379268, and Cocaine on in Vivo Neurochemistry and Behavior in Squirrel Monkeys", Pharmacol. Biochem. Behav., 2009, 94(1), 204-210.

Bech et al., "Quantitative Rating of Depressive States", Acta Psychiatr Scand, 1975, 51(3), 161-170.

Bech, "Dose-Response Relationship of Pregabalin in Patients with Generalized Anxiety Disorder. A Pooled Analysis of Four Placebo-Controlled Trials", Pharmacopsychiatry, 2007, 40, 163-168.

Bech, "The Bech-Rafaelsen Melancholia Scale (Mes) in of Therapies in Depressive Disorders: A 20-Year Review of Its Use As Outcome Measure", Acta Psychiatr Scand, 2002, 106(4), 252-264.

Beesdo, "Incidence and Risk Patterns of Anxiety and Depressive Disorders and Categorization of Generalized Anxiety Disorder", Arch Gen Psychiatry, 2010, 67(1), 47-57.

Behrens et al., "Ketamine-Induced Loss of Phenotype of Fast-Spiking Interneurons is Mediated by Nadph-Oxidase", Science, 2007, 318, 1645-1647.

Belenikin et al., "Comparative Analysis of the Ligand-Binding Sites of the Metabotropic Glutamate Receptors Mglurl-Mglur8", Doklady Biochemistry & Biophysics., 2002, 386, 251-256.

Bell et al., "Altered Synaptic Function in Alzheimer's Disease", European Journal of Pharmacology, 2006, 545(1), 11-21.

Bellani et al., "Brain Anatomy of Major Depression II. Focus on Amygdala", Epidemiology and Psychiatric, Sciences, 2011, 20(1), 33-36.

Bellesi et al., "The Mglur2/3 Agonist Ly379268 Blocks the Effects of Glt-I Upregulation on Prepulse Inhibition of the Startle Reflex in Adult Rats", Neuropsychopharmacology, 2010, 1-8.

Bellesi et al., "The Mglur2/3 Agonist Ly379268 Blocks the Effects of Glt-1 Upregulation on Prepulse Inhibition of the Startle Reflex in Adult Rats", Neuropsychopharmacology, 2010, 35(6), 1253-1260.

(56) References Cited

OTHER PUBLICATIONS

Belousov et al., "Non-Cholinergic Excitation in Neurons After a Chronic Glutamate Receptor Blockade", Neuroreport, 2004, 15(1), 113-117.
Benarroch, "Metabotropic Glutamate Receptors: Synaptic Modulators and Therapeutic Targets for Neurologic Disease", Neurology, 2008, 70(12), 964-968.
Benca et al., "Sleep and Psychiatric Disorders. A Meta-Analysis", Arch Gen Psychiatry, 1992, 49, 651-670.
Beneyto et al., "Abnormal Glutamate Receptor Expression in the Medial Temporal Lobe in Schizophernia and Mood Disorders", Neuropsychopharmacology, 2007, 32(9), 1888-1902.
Benilova et al., "The Toxic Aβ Oligomer and Alzheimer's Disease: An Emperor in Need of Clothes", Nature Neuroscience, 2012, 15(3), 349-357.
Benneyworth et al., "Chronic Phenethylamine Hallucinogen Treatment Alters Behavioral Sensitivity to a Metabotropic Glutamate 2/3 Receptor Agonist", Neuropsychopharmacology, 2008, 33(9), 2206-2216.
Benquet et al., "Two Distinct Signaling Pathways Upregulate Nmda Receptor Responses Via Two Distinct Metabotropic Glutamate Receptor Subtypes", Journal of Neuroscience, 2002, 22(22), 9679-9686.
Benson et al., "A Comparison of Observational Studies and Randomized, Controlled Studies", N Engl J Med., 2000, 342(25), 1878-1886.
Bergink et al., "Metabotropic Glutamate II Receptor Agonists in Panic Disorder: A Double Blind Clinical Trial with Ly354740", International Clinical Psychopharmacology, 2005, 20, 291-293.
Berman et al., "The Efficacy and Safety of Aripiprazole as Adjunctive Therapy in Major Depressive Disorder: A Multicenter, Randomized, Double-Blind, Placebo-Controlled Study", J Clin Psychiatry, 2007, 68, 843-853.
Bermudo-Soriano, "New Perspectives in Glutamate and Anxiety", Pharmacol Biochem Behav, 2011, Epub, No Page Numbers, Doi:10.1016/J.Pbb.2011.04.010.
Berthele et al., "Distribution and Developmental Changes in Metabotropic Glutamate Receptor Messenger RNA Expression in the Rat Lumbar Spinal Cord", Developmental Brain Research, 1999, 112(1), 39-53.
Berthele et al., "Expression of Metabotropic Glutamate Receptor Subtype MRNA (Mglur1-8) in Human Cerebellum", Neuroreport, 1999, 10(18), 3861-3867.
Bertrand et al., "Common and Selective Molecular Determinants Involved in Metabotopic Glutamate Receptor Agonist Activity", J. Med. Chem., 2002, 45(15), 3171-3183.
Bespalov et al., "Behavioral Characterization of the Mglu Group II/III Receptor Antagonist, Ly-341495, in Animal Models of Anxiety and Depression", European Journal of Pharmacology 2008, 592, 96-102.
Bespalov et al., "Habituation Deficits Induced by Metabotropic Glutamate Receptors 2/3 Receptor Blockade in Mice: Reversal by Antipsychotic Drugs", Journal of Pharmacology & Experimental Therapeutics, 2007, 320(2), 944-950.
Bessho et al., "Glutamate and Quisqualate Regulate Expression of Metabotropic Glutamate Receptor MRNA in Cultured Cerebellar Granule Cells", Journal of Neurochemistry, 1993, 60(1), 253-259.
Bessis et al., "Metabotropic Glutamate Receptors: Exciting Possibilities in Excitatory Transmission", Celltransmissions, 2000, 17, 3-10.
Bijl et al., "Current and Residual Functional Disability Associated with Psychopathology: Findings from the Netherlands Mental Health Survey and Incidence Study (Nemesis)", Psychological Medicine, May 2000, 657-668.
Bilkei-Gorzo et al., "MCPP-Induced Anxiety in the Light-Dark Box in Rats—A New Method for Screening Anxiolytic Activity", Psychopharmacology (Berl), 1998, 136(3), 291-298.
Binder et al., "Association of Polymorphisms in Genes Regulating the Corticotropin-Releasing Factor System with Antidepressant Treatment Response", Arc Gen Psychiatry, 2010, 67(4), 369-370.

Black et al., "Compound A, A Novel, Potent and Selective Mglur2 Positive Allosteric Modulator: II. Effects in Models Predictive of Therapeutic Activity Against Cognitive Impairment Associated with Schizophrenia", Poster 767.7 Presented at the 40th Annual Meeting of Society for Neuroscience, Nov. 2010, 1 page.
Blaha et al., "Stimulation of the Ventral Subiculum of the Hippocampus Evokes Glutamate Receptor-Mediated Changes in Dopamine Efflux in the Rat Nucleus Accumbens", European Journal of Neuroscience, 1997, 9(5), 902-911.
Blanco et al., "Changes in the Prevalence of Non-Medical Prescription Drug Use and Drug Use Disorders in the United States: 1991-1992 and 2001-2002", Drug and Alcohol Dependence, 2007, 90, 252-260.
Bockaert et al., "Metabotropic Glutamate Receptors: An Original Family of G Protein-Coupled Receptors", Fundamental & Clinical Pharmacology, 1993, 7(9), 473-485.
Bockaert et al., "Molecular Tinkering of G Protein-Coupled Receptors: An Evolutionary Success", Embo Journal, 1999, 18(7), 1723-1729.
Bodick et al., "Protocols to Demonstrate Slowing of Alzheimer Disease Progression. Position Paper on the International Working Group on Harmonization of Dementia Drug Guidelines", Alzheimer Disease and Associated Disorders, 1997, 11(Suppl 3), 50-53.
Boldyrev et al., "Homocysteine and its Derivatives as Possible Modulators of Neuronal and Non-Neuronal Cell Glutamate Receptors in Alzheimer's Disease", J Alzheimers. Dis, 2007, 11(2), 219-228.
Bolton et al., "Exploring the Correlates of Suicide Attempts Among Individuals with Major Depressive Disorder: Findings from the National Epidemiologic Survey on Alcohol and Related Conditions", J Clin Psychiatry, 2008, 69, 1139-1149.
Bonanno et al., "Chronic Antidepressants Reduce Depolarization-Evoked Glutamate Release and Protein Interactions Favoring Formation of Snare Complex in Hippocampus", J Neurosci 2005, 25, 3270-3279.
Bond et al., "Neuroprotective Effects of Ly379268, A Selective Mglu2/3 Receptor Agonist: Investigations Into Possible Mechanism of Action in Vivo", J Pharmacol. Exp. Ther., 2000, 294(3), 800-809.
Bond et al., "Pharmacology of Metabotropic Glutamate Receptor-Mediated Enhancement of Responses to Excitatory and Inhibitory Amino Acids on Rat Spinal Neurones in Vivo", Neuropharmacology, 1995, 34(8), 1015-1023.
Bonnefous et al., "Biphenyl-Indanones: Allosteric Potentiators of Metabotropic Glutamate Subtype 2 Receptor", Bioorg Med Chem Lett, 2005, 15, 4354-4358.
Boris-Moller et al., "Changes in the Extracellular Levels of Glutamate and Aspartate During Ischemia and Hypoglycemia. Effects of Hypothermia", Experimental Brain Research, 1998, 121(3), 277-284.
Bortolotto et al., "Roles of Metabotropic Glutamate Receptors in LTP and LTD in the Hippocampus", Current Opinion in Neurobiology, 1999, 9(3), 299-304.
Boules et al., "Neurotensin Agonists: Potential in the Treatment of Schizophrenia", CNS Drugs, 2007, 21(1), 13-23.
Bouvrais-Veret et al., "Microtubule-Associated Stop Protein Deletion Triggers Restricted Changes in Dopaminergic Neurotransmission", J. Neurochem., 2008, 104, 745-756.
Boyette et al., "Factor Structure of the Yale-Brown Obsessive-Compulsive Scale (Y-Bocs) in a Large Sample of Patients with Schizophrenia or Related Disorders and Comorbid Obsessive-Compulsive Symptoms", Psychiatry Res., 2011, 409-413.
Brabet et al., "Comparative Effect of L-CCG-I, DCG-IV and Gamma-Carboxy-L-Glutamate on all Cloned Metabotropic Glutamate Receptor Subtypes", Neuropharmacology, 1998, 37, 1043-1051.
Braff et al., "Human Studies of Prepulse Inhibition of Startle: Normal Subjects, Patient Groups, and Pharmacological Studies", Psychopharmacology, 2001, 156, 234-258.
Brauner-Osborne et al., "A New Highly Selective Metabotropic Excitatory Amino Acid Agonist: 2-Amino-4-(3-Hydroxy-5-Methylisoxazol-4-YI)Butyric Acid", Journal of Medicinal Chemistry, 1996, 39(16), 3188-3194.

(56) References Cited

OTHER PUBLICATIONS

Brauner-Osborne et al., "Interaction of CPCCOET with a Chimeric Mglu1b and Calcium Sensing Receptor", Neuroreport, 1999, 10(18), 3923-3925.

Brauner-Osborne et al., "Molecular Pharmacology of 4-Substituted Glutamic Acid Analogues at Ionotropic and Metabotropic Excitatory Amino Acid Receptors", European Journal of Pharmacology, 1997, 335(2-3), R1-R3.

Brauner-Osborne et al., "Pharmacology of (S)-Homoquisqualic Acid and (S)-2-Amino-5-Phosphonopentanoic Acid [(S)-Ap5] at Cloned Metabotropic Glutamate Receptors", British Journal of Pharmacology, 1998, 123(2), 269-274.

Brauner-Osborne, "Structure, Pharmacology and Therapeutic Prospects of Family C G-Protein Coupled Receptors", Current Drug Targets, 2007, 8, 169-184.

Breier et al., "Association of Ketamine-Induced Psychosis with Focal Activation of the Prefrontal Cortex in Healthy Volunteers", Am J Psychiatry, 1997, 154, 805-811.

Bremner et al., "Development and Preliminary Psychometric Properties of an Instrument for the Measurement of Childhood Trauma: The Early Trauma Inventory", Depress Anxiety, 2000, 12(1), 1-12.

Bremner et al., "Psychometric Properties of the Early Trauma Inventory-Self Report", J Nerv Ment Dis, 2007, 195(3), 211-218.

Brnardic et al., "3-Aryl-5-Phenoxymethyl-1,3-Oxazolidin-2-Ones As Positive Allosteric Modulators of Mglur2 for the Treatment of Schizophrenia: Hit-To-Lead Efforts", Bioorg Med Chem Lett, 2010, 20, 3129-3133.

Broekkamp et al., "Major Tranquillizers can be Distinguished From Minor Tranquillizers on the Basis of Effects on Marble Burying and Swim-Induced Grooming in Mice", Eur. J. Pharmacol., 1986, 126, 223-229.

Bruno et al., "Activation of Class II or III Metabotropic Glutamate Receptors Protects Cultured Cortical Neurons Against Excitotoxic Degeneration", European Journal of Neuroscience, 1995, 7(9), 1906-1913.

Bruno et al., "Activation of Metabotropic Glutamate Receptors Coupled to Inositol Phospholipid Hydrolysis Amplifies NMDA-Induced Neuronal Degeneration in Cultured Cortical Cells", Neuropharmacology, 1995, 34(8), 1089-1098.

Bruno et al., "Excitatory Amino Acids and Neurotoxicity", Functional Neurology 1993, 8(4), 279-292.

Bruno et al., "Metabotropic Glutamate Receptors and Neurodegeneration", Progress in Brain Research, 1998, 116, 209-221.

Bruno et al., "Metabotropic Glutamate Receptors and Neuronal Degeneration in Culture", Advances in Neurology, 1996, 71, 47-52.

Bruno et al., "Molecular Dynamics Simulation of the Heterodimeric Mglur2/5ht(2a) Complex. An Atomistic Resolution Study of a Potential New Target in Psychiatric Conditions", J. Chem. Inf. Model., 2009, 49(6), 1602-1616.

Bruno et al., "Neuroprotection by Glial Metabotropic Glutamate Receptors is Mediated by Transforming Growth Factor-Beta", J. Neurosci., 1998, 18(23), 9594-9600.

Bruno et al., "The Neuroprotective Activity of Group-II Metabotropic Glutamate Receptors Requires New Protein Synthesis and Involves a Glial-Neuronal Signaling", J. Neurosci., 1997, 17(6), 1891-1897.

Buisson et al., "The Inhibitory Mglur Agonist, S-4-Carboxy-3-Hydroxy-Phenylglycine Selectively Attenuates NMDA Neurotoxicity and Oxygen-Glucose Deprivation-Induced Neuronal Death", Neuropharmacology, 1995, 34(8), 1081-1087.

Bunch et al., "Excitatory Amino Acid Transporters as Potential Drug Targets", Expert Opin Ther Targets, 2009, 13(60), 719-731.

Bunney et al., "Norepinephrine in Depression Reactions. A Review", Arch Gen Psychiatry, 1965, 13(6), 483-494.

Burford et al., "Strategies for the Identification of Allosteric Modulators of G-Protein-Coupled Receptors", Biochem Pharmacol, 2011, 1-12.

Bushell et al., "Pharmacological Antagonism of the Actions of Group II and III Mglur Agonists in the Lateral Perforant Path of Rat Hippocampal Slices", Br. J Pharmacol., 1996, 117(7), 1457-1462.

Bustillo et al., "1H-MRS At 4 Tesla in Minimally Treated Early Schizophrenia", Mol Psychiatry, 2010, 15(6), 629-636.

Butterfield et al., "The Glutamatergic System and Alzheimer's Disease: Therapeutic Implications" CNS Drugs, 2003, 17(9), 641-652.

Byrnes et al., "Metabotropic Glutamate Receptors as Targets for Multipotential Treatment of Neurological Disorders", Neurotherapeutics, 2009, 6(1), 94-107.

Cacabelos et al., "The Glutamatergic System and Neurodegeneration in Dementia: Preventive Strategies in Alzheimer's Disease", International Journal of Geriatric Psychiatry, 1999, 14(1), 3-47.

Cai et al., "Local Potentiation of Excitatory Synapses by Serotonin and its Alteration in Rodent Models of Depression", Nature Neuroscience, 2013, 16(4), 464-472.

Campbell et al., "An Update on Regional Brain Volume Differences Associated with Mood Disorders", Curr Opin Psychiatry, 2006, 19(1), 25-33.

Caraci et al., "Metabotropic Glutamate Receptors in Neurodegeneration/Neuroprotection: Still a Hot Topic?", Neurochemistry Intl, 2012, 61(4), 559-565.

Caraci et al., "Targeting Group II Metabotropic Glutamate (MGLU) Receptors for the Treatment of Psychosis Associated with Alzheimer's Disease: Selective Activation of Mglu2 Receptors Amplifies B-Amyloid Toxicity in Cultured Neurons, Whereas Dual Activation of Mglu2 and Mglu3 Receptors is Neuroprotective", Mol Pharmacol, 2011, 79, 618-626.

Carlsson et al., "Neurotransmitter Aberrations in Schizophrenia: New Perspectives and Therapeutic Implications", Life Sciences, 1997, 61(2), 75-94.

Carlsson, "The Neurochemical Circuitry of Schizophrenia", Pharmacopsychiatry, 2006, 39, S10-S14.

Carter, "Schizophrenia Susceptibility Genes Converge on Interlinked Pathways Related to Glutamatergic Transmission and Long-Term Potentiation, Oxidative Stress and Oligodendrocyte Viability", Schizophr. Res., 2006, 86(1-3), 1-14.

Cartmell et al., "Acute Increases in Monoamine Release in the Rat Prefrontal Cortex by the Mglu2/3 Agonist Ly379268 are Similar in Profile to Risperidone, Not Locally Mediated, and Can Be Elicited in the Presence of Uptake Blockade", Neuropharmacology, 2001, 40(7), 847-855.

Cartmell et al., "Attenuation of Specific Pcp-Evoked Behaviors by the Potent Mglu2/3 Receptor Agonist, Ly379268 and Comparison with the Atypical Antipsychotic, Clozapine", Psychopharmacology, 2000, 148, 423-429.

Cartmell et al., "Dopamine and 5-Ht Turnover are Increased by the Mglu2/3 Receptor Agonist Ly379268 in Rat Medial Prefrontal Cortex, Nucleus Accumbens and Striatum", Brain Res., 2000, 887(2), 378-384.

Cartmell et al., "Effect of Metabotropic Glutamate Receptor Activation on Receptor-Mediated Cyclic Amp Responses in Primary Cultures of Rat Striatal Neurones", Brain Res., 1998, 791(1-2), 191-199.

Cartmell et al., "The Metabotropic Glutamate 2/3 Receptor Agonists Ly354740 and Ly379268 Selectively Attenuate Phencyclidine Versus D-Amphetamine Motor Behavior in Rats", J Pharmacol Exp Ther, 1999, 291, 161-170.

Cartmell et al., "The Mglu(2/3) Receptor Agonist Ly379268 Selectively Blocks Amphetamine Ambulations and Rearing", Eur. J Pharmacol., 2000, 400(2-3), 221-224.

Cartmell et al., "The Potent, Selective Mglu2/3 Receptor Agonist Ly379268 Increases Extracellular Levels of Dopamine, 3,4-Dihydroxyphenylacetic Acid, Homovanillic Acid, and 5-Hydroxyindole-3-Acetic Acid in the Medial Prefrontal Cortex of the Freely Moving Rat", J Neurochem., 2000, 75(3), 1147-1154.

Cartmell et al., "Tolerance to the Motor Impairment, But Not the Reversal of PCP-Induced Motor Activities by Oral Administration of the Mglu2/3 Receptor Agonist, Ly379268", Naunyn Schmiedebergs Arch Pharmacol, 2000, 361, 39-46.

Casado et al., "GPCR Homomers and Heteromers: A Better Choice as Targets for Drug Development Than GPCR Monomers?", Pharmacology & Therapeutics, 2009, 124, 248-257.

(56) References Cited

OTHER PUBLICATIONS

Castagne et al., "Preclinical Behavioral Models for Predicting Antipsychotic Activity", Adv. Pharmacol., 2009, 57, 381-418.
Catania et al., "Desensitization of Metabotropic Glutamate Receptors in Neuronal Cultures", Journal of Neurochemistry, 1991, 56(4), 1329-1335.
Catania et al., "Group I Metabotropic Glutamate Receptors: A Role in Neurodevelopmental Disorders?", Mol Neurobiol, 2007, 35, 298-307.
Catania et al., "Homologous Desensitization of Metabolotropic Glutamate Receptors in Neuronal Cultures", Pharmacological Research, 1990, 22(Suppl 1), 79-80.
Catania et al., "Metabotropic Glutamate Receptor Heterogeneity in Rat Brain", Molecular Pharmacology, 1994, 45(4), 626-636.
Catania et al., "Metabotropic Glutamate Receptors are Differentially Regulated During Development", Neuroscience, 1994, 61(3), 481-495.
Catterall, "Structure and Function of Neuronal Ca2+ Channels and Their Role in Neurotransmitter Release", Cell Calcium, 1998, 24(5-6), 307-323.
Cavalli et al., "Multi-Target-Directed Ligands to Combat Neurodegenerative Diseases", J. Med. Chem., 2007-2008, 26 pages.
Cavanni et al., "Pharmacological Analysis of Carboxyphenylglycines at Metabotropic Glutamate Receptors", European Journal of Pharmacology, 1994, 269(1), 9-15.
Celanire et al., "Recent Advances in the Drug Discovery of Metabotropic Glutamate Receptor 4 (mGluR4) Activators for the Treatment of CNS and Non-CNS Disorders", Expert Opin. Drug Discovery, 2012, 7(3), 261-280.
Chaki "Group II Metabotropic Glutamate Receptor Agonists as a Potential Drug for Schizophrenia", European Journal of Pharmacology, 2010, 639, 59-66.
Chaki et al, "Anxiolytic- and Antidepressant-Like Profile of a New Crf1 Receptor Antagonist, R278995/Cra0450", Eur J Pharmacol, 2004, 485, 145-158.
Chaki et al., "Mglu2/3 and Mglu5 Receptors: Potential Targets for Novel Antidepressants", Neuropharmacology, 2013, 66, 40-52.
Chaki et al., "Targeting of Metabotropic Glutamate Receptors for the Treatment of Schizophrenia", Current Pharmaceutical Design, 2011, 17, 94-102.
Chakos et al., "Baseline Use of Concomitant Psychotropic Medications to Treat Schizophrenia in the Catie Trial", Psychiatr Serv., 2006, 57(8), 1094-1101.
Chakrabarty et al., "Glutamatergic Dysfunction in OCD", Neuropsychopharmacology, 2005, 30(9), 1735-1740.
Charney et al., "Increased Anxiogenic Effects of Caffeine in Panic Disorders", Arch Gen Psychiatry, 1985, 42, 233-243.
Charney et al., "Life Stress, Genes, and Depression: Multiple Pathways Lead to Increased Risk and New Opportunities for Intervention", Science's Stke, 2004, (225), Re5, 12 pages.
Charney et al., "Noradrenergic Function in Panic Anxiety. Effects of Yohimbine in Healthy Subjects and Patients with Agoraphobia and Panic Disorder", Arch. Gen. Psychiatry, 1984, 41, 751-763.
Chaudhari et al., "A Metabotropic Glutamate Receptor Variant Functions as a Taste Receptor", Nature Neuroscience, 2000, 3, 113-119.
Chavez-Noriega et al., "Metabotropic Glutamate Receptors: Potential Drug Targets for the Treatment of Schizophrenia", Current Drug Targets—CNS & Neurological Disorders, 2002, 1(3), 261-281.
Chavis et al., "Facilitatory Coupling Between a Glutamate Metabotropic Receptor and Dihydropyridine-Sensitive Calcium Channels in Cultured Cerebellar Granule Cells", J. Neurosci., 1995, 15(1), 135-143.
Chavis et al., "Modulation of Calcium Channels by Metabotropic Glutamate Receptors in Cerebellar Granule Cells", Neuropharmacology, 1995, 34(8), 929-937.
Chen et al., "Second-Generation Antipsychotics in Major Depressive Disorder: Update and Clinical Perspective", Curr Opin Psychiatry, 2011, 24, 19-17.
Chiechio et al., "Epigenetic Modulation of Mglu2 Receptors by Histone Deacetylase Inhibitors in the Treatment of Inflammatory Pain", Mol. Pharmacol., 2009, 75(5), 1014-1020.
Chiechio et al., "Metabotropic Glutamate Receptors and the Control of Chronic Pain", Curr Opin Pharmacol, 2012, 12, 28-34.
Chiechio et al., "Transcriptional Regulation of Type-2 Metabotropic Glutamate Receptors: An Epigenetic Path to Novel Treatments for Chronic Pain", Trends in Pharmacological Sciences, 2010, 31(4), 153-160.
Chin et al., "Amyloid Beta Protein Modulates Glutamate-Mediated Neurotransmission in the Rat Basal Forebrain: Involvement of Presynaptic Neuronal Nicotinic Acetylcholine and Metabotropic Glutamate Receptors", J. Neurosci., 2007, 27(35), 9262-9269.
Chin et al., "Awake Rat Pharmacological Magnetic Resonance Imaging as a Translational Pharmacodynamic Biomarker: Metabotropic Glutamate 2/3 Agonist Modulation of Ketamine-Induced Blood Oxygenation Level Dependence Signals", Jpet, 2011, 336, 709-715.
Chin et al., "Awake Rat Pharmacological MRI as a Translational Pharmacodynamic Biomarker: Mglur2/3 Agonist Modulation of Ketamine-Induced Bold Signals", Jpet, 2010, 22 pages.
Choi, "Methods for Antagonizing Glutamate Neurotoxicity", Cerebrovascular & Brain Metabolism Reviews, 1990, 2(2), 105-147.
Chojnacka-Wojcik et al., "Glutamate Receptor Ligands as Anxiolytics", Current Opinion in Investigational Drugs, 2001, 2(8), 1112-1119.
Christopolous et al., "G Protein-Coupled Receptor Allosterism and Complexing", Pharmacol Rev, 2002, 54, 323-374.
Cid et al., "Discovery of 1,4-Disubstituted 3-Cyano-2-Pyridones: A New Class of Positive Allosteric Modulators of the Metabotropic Glutamate 2 Receptor", J Med Chem, 2012, 55, 2388-2405.
Cid et al., "Discovery of 1,5-Disubstituted Pyridones: A New Class of Positive Allosteric Modulators of the Metabotropic Glutamate 2 Receptor", ACS Chem Neurosci, 2010, 1, 788-795.
Cid et al., "Discovery of 3-Cyclopropylmethyl-7-(4-Phenylpiperidin-1-Yl)-8-Trifluoromethyl[1,2,4]Triazolo[4,3-A]Pyridine (Jnj-42153605): A Positive Allosteric Modulator of the Metabotropic Glutamate 2 Receptor", J Med Chem, 2012, 55, 8770-8789.
Cid, "Discovery of a Potent and Orally Bioavailable Positive Allosteric Modulator of Mglur2 for the Treatment of CNS Disorders", Presentation Slides, 16th SCI/RSC Medicinal Chemistry Symposium, Cambridge, Sep. 2011, 26 pages.
Cid, "JNJ-42153605: A Novel Positive Allosteric Modulator of Mglur2 for the Treatment of CNS Disorders" Presentation Slides, RICT 2012—48th International Conference on Medicinal Chemistry, Poitiers 2012, 28 pages.
Citrome, "Adjunctive Aripiprazole, Olanzapine, or Quetiapine for Major Depressive Disorder: An Analysis of Number Needed to Treat, Number Needed to Harm, and Likelihood to Be Helped or Harmed", Postgraduate Medicine, 2010, 122(4), 39-48.
Clark et al., "Effects of the Mglu2/3 Receptor Agonist Ly379268 on Motor Activity in Phencyclidine-Sensitized Rats", Pharmacol. Biochem. Behav., 2002, 73(2), 339-346.
Clayton et al., "Follow-Up and Family Study of Anxious Depression" Am J Psychiatry, 1991, 148, 1512-1517.
Cleary et al., "Factor Analysis of the Hamilton Depression Scale" Drugs Exptl Clin Res, 1977, 1(1-2), 115-120.
Clements et al., "The Time Course of Glutamate in the Synaptic Cleft", Science, 1992, 258(5087), 1498-1501.
Cleve et al., "Positive Allosteric Modulators of Type 5 Metabotropic Glutamate Receptors (mGluR5) and their Therapeutic Potential for the Treatment of CNS Disorders", Molecules, 2011, 16, 2097-2106.
Clinical Trials, "A Dose-Ranging Study of JNJ-40411813 in Healthy Male Volunteers", Available from http://clinicaltrials.gov/show/NCT01358006, retrieved on Aug. 1, 2013.
Clinical Trials, "A Study of [11C]JNJ-42491293, a Possible PET Ligand for the mGlu2 Receptor, in Healthy Adult Volunteers", Available from http://clinicaltrials.gov/show/NCT01359852, retrieved on Aug. 1, 2013.
Clinical Trials, "A Study of JNJ-40411813 as Supplementary Treatment to an Antidepressant in Adults with Depression and Anxiety Symptoms", Available from: http://clinicaltrials.gov/show/NCT01582815, retrieved on Aug. 1, 2013.

(56) References Cited

OTHER PUBLICATIONS

Clinical Trials, "AZD8529 Single Ascending Dose Study (Sad)", Clinicaltrials.Gov. No. NCT00755378, Available From: Http://Clinicaltrials.Gov/Show/Nct00755378, retrieved on Aug. 22, 2013.
Clinical Trials, "First-In-Patient Study to Assess the Safety and Tolerability and to Explore the Potential Therapeutic Efficacy of a Novel Glutamate Modulator as Monotherapy and as Add-On Therapy in Patients with Schizophrenia", Available From: Https://Www.Clinicaltrialsregister.Eu—Eudract No. 2010-023369-23, retrieved on Aug. 1, 2013.
Clinical Trials, "Investigation of the Safety, Tolerability and Potential Therapeutic Effects of JNJ-40411813 in Patients with Schizophrenia", Clinicaltrials Gov. No. NCT01323205, Available From: Http://Clinicaltrials.Gov/Show/NCT01323205, Retrieved Aug. 1, 2013.
Clinical Trials, "Ketamine Challenge Study with JNJ-40411813", Clinical Trials. Gov No. NCT01101659, Available From: Http://Clinicaltrials.Gov/Ct2/Show/Nct01101659, 2010, 3 pages.
Clinical Trials, "Study to Assess the Efficacy, Safety, and Tolerability of AZD8529 in Adult Schizophrenia Patients", Clinicaltrials.Gov. No. NCT00921804, Available From: Http://Clinicaltrials.Gov/Show/Nct00921804, retrieved on Aug. 23, 2013, 3 pages.
Clinical Trials, "The Effects Azd8529 on Cognition and Negative Symptoms in Schizophrenics", Clinicaltrials.Gov. No. NCT00986531, Available From: Http://Clinicaltrials.Gov/Show/Nct00986531, retrieved on Aug. 23, 2013, 2 pages.
Cloninger et al., "The Empirical Structure of Psychiatric Comorbidity and its Theoretical Significance", Comorbidity of Mood and Anxiety Disorders, 1990, 439-462.
Cohen et al., "A Global Measure of Perceived Stress", J Health Soc Behav, 1983 24(4), 385-396.
Colangelo et al., "Differential Effects of Acute Administration of Clozapine or Haloperidol on Local Cerebral Glucose Utilization in the Rat", Brain Research, 1997, 768, 273-278.
Collingridge et al., "Excitatory Amino Acid Receptors and Synaptic Plasticity", Trends in Pharmacological Sciences, 1990, 11(7), 290-296.
Collins et al., "Arachidonic Acid Metabolites and the Synaptic Potentiation Evoked by Activation of Metabotropic Glutamate Receptors", European Journal of Pharmacology, 1998, 342(2-3), 213-216.
Collins et al., "From Ligand Binding to Gene Expression: New Insights into the Regulation of G-Protein-Coupled Receptors", Trends in Biochemical Sciences, 1992, 17(1), 37-39.
Colpaert et al., "A Critical Study on Ro-4-1284 Antagonism in Mice", Arch. Int. Pharmacodyn., 1975, 215, 40-90.
Colzi et al., "Monoamine Oxidase-A Inhibitors and Dopamine Metabolism in Rat Caudatus: Evidence that an Increased Cytosolic Level of Dopamine Displaces Reversible Monoamine Oxidase-A Inhibitors in Vivo", J. Pharmacol. Exper. Therapeutics, 1993, 265, 103-111.
Committee for Proprietary Medicinal Products (CPMP), European Agency for the Evaluation of Medicinal Products; Meeting Feb. 26, 1998, London (UK): Note for Guidance on the Clinical Investigation of Medicinal Products in the Treatment of Schizophrenia, 10.
Conigrave et al., "Allosteric Activation of Plasma Membrane Receptors—Physiological Implications and Structural Origins", Progress in Biophysics & Molecular Biology, 2003, 81(3), 219-40.
Conn et al., "Allosteric Modulators of Gpers: A Novel Approach for the Treatment of CNS Disorders", Nature Reviews Drug Discovery, 2009, 8, 41-54.
Conn et al., "Metabotropic Glutamate Receptors in the Basal Ganglia Motor Circuit", Nature Reviews Neuroscience, 2005, 6, 787-798.
Conn et al., "Pharmacology and Functions of Metabotropic Glutamate Receptors", Annu Rev Pharmacol Toxicol, 1997, 37, 205-237.
Conn, "Physiological Roles and Therapeutic Potential of Metabotropic Glutamate Receptors", Annals of the New York Academy of Sciences, 2003, 1003, 12-21.
Connolly et al., "If At First You Don't Succeed: A Review of the Evidence for Antidepressant Augmentation, Combination and Switching Strategies", Drugs, 2011, 71(1), 43-64.
Cook et al., "Behavioral Effects of Some Psychopharmacological Agent", Ann. Ny Acad. Sci., 1957, 66, 740-752.
Cook et al., "Effects of Drugs on Avoidance and Escape Behavior", Fed. Proc. 23, 1964, 818-835.
Copeland et al., "Positive Allosteric Modulation Reveals a Specific Role for Mglu2 Receptors in Sensory Processing in the Thalamus", J Physiol, 2012, 590.4, 937-951.
Corlett et al., "Glutamatergic Model Psychoses: Prediction Error, Learning, and Inference", Neuropsychopharmacology, 2011, 36(1), 294-315.
Coryell et al., "Effects of Anxiety on the Long-Term Course of Depressive Disorders", The British Journal of Psychiatry, 2012, 200, 210-215.
Coyle, "The Gaba-Glutamate Connection in Schizophrenia: Which is the Proximate Cause?", Biochem. Pharmacol., 2004, 68(8), 1507-1514.
Cozzi et al., "Type 2 Metabotropic Glutamate (Mglu) Receptors Tonically Inhibit Transmitter Release in Rat Caudate Nucleus: in Vivo Studies with (2s,1's,2's,3'r)-2-(2'-Carboxy-3'-Phenylcyclopropyl)Glycine, A New Potent and Selective Antagonist", European Journal of Neuroscience, 1997, 9(7), 1350-1355.
Craddock et al., "The Genetics of Schizophrenia and Bipolar Disorder: Dissecting Psychosis", J Med Genet, 2005, 42, 193-204.
Cropley et al., "Molecular Imaging of the Dopaminergic System and its Association with Human Cognitive Function", Biol.Psychiatry, 2006, 59, 898-907.
Cube et al., "3-(2-Ethoxy-4-{4-[3-Hydroxy-2-Methyl-4-(3-Methylbutanoyl)-Phenoxy]Butoxy}Phenyl)Propanoic Acid: A Brain Penetrant Allosteric Potentiator at the Metabotropic Glutamate Receptor 2 (Mglur2)", Bioorganic & Medicinal Chemistry Letters, 2005, 15, 2389-2393.
D'Alessandro et al., "The Identification of Structurally Novel, Selective, Orally Bioavailable Positive Allosteric Modulators of Mglur2", Bioorg Med Chem Lett, 2010, 20, 759-762.
D'Antoni et al., "Metabotropic Glutamate Receptors in Glial Cells", Neurochem. Res., 2008, 33(12), 2436-2443.
Dale et al., "Mechanisms of Metabotropic Glutamate Receptor Desensitization: Role in the Patterning of Effector Enzyme Activation", Neurochemistry Intl, 2002, 41, 319-326.
Dale et al., "Spatial-Temporal Patterning of Metabotropic Glutamate Receptor-Mediated Inositol 1,4,5-Triphosphate, Calcium, and Protein Kinase C Oscillations: Protein Kinase C-Dependent Receptor Phosphorylation Is Not Required", J. Biol. Chem., 2001, 276(38), 35900-35908.
Danner et al., "Integrating Patients' Views Into Health Technology Assessment: Analytic Hierarchy Process (Ahp) as a Method to Elicit Patient Preferences", Intl Journal of Technology Assessment in Health Care, 2011, 27(4), 369-375.
D'Ascenzo et al., "Mglur5 Stimulates Gliotransmission in the Nucleus Accumbens", Proc. Natl. Acad. Sci., 2007, 104(6), 1995-2000.
Dash et al., "Long-Term Homeostasis of Extracellular Glutamate in the Rat Cerebral Cortex Across Sleep and Waking States", J Neurosci, 2009, 29, 620-629.
Datta et al., "Microinjection of Glutamate into the Pedunculopontine Tegmentum Induces Rem Sleep and Wakefulness in the Rat", Am J Physiol., Regul Integr Comp Physiol, 2001, 280, R752-R759.
Davidson et al., "Achieving Remission with Venlafaxine and Fluoxetine in Major Depression: Its Relationship to Anxiety Symptoms", Depression and Anxiety, 2002, 16, 4-13.
Davidson et al., "Differential Effects of Neuroleptic and Other Psychotropic Agents on Acquisition of Avoidance in Rats", Life Sci., 1976, 18, 1279-1284.
Davis, "Diazepam and Flurazepam: Effects on Conditioned Fear as Measured with the Potentiated Startle Paradigm", Psychopharmacology, 1979, 62, 1-7.
Davis, "Pharmacological and Anatomical Analysis of Fear Conditioning Using the Fear-Potentiated Startle Paradigm", Behavioral Neuroscience, 1986, 100, 814-824.
Dawson et al., "Novel Analysis for Improved Validity in Semi-Quantitative 2-Deoxyglucose Autoradiographic Imaging", Journal of Neuroscience Methods, 2008, 175, 25-35.

(56) References Cited

OTHER PUBLICATIONS

De Blasi et al., "Molecular Determinants of Metabotropic Glutamate Receptor Signaling", Trends in Pharmacological Sciences, 2001, 22(3), 114-120.
De Boer et al., "Characterization of the Clinical Effect of a Positive Allosteric Modulator of the Metabotropic Glutamate Receptor-2", Society of Biological Psychiatry 67th Annual Scientific Convention, May 2012, 2 pages.
De Montis et al., "Selective Adenylate Cyclase Increase in the Limbic Area of Long-Term Imipramine-Treated Rats", European Journal of Pharmacology, 1990, 180(1), 169-174.
De Novellis et al., "Type I and II Metabotropic Glutamate Receptors Modulate Periaqueductal Grey Glycine Release: Interaction Between Mglu2/3 and A1 Adenosine Receptors", Neuropharmacology, 2002, 43(7), 1061-1069.
Dean, "The Cortical Serotonin2a Receptor and the Pathology of Schizophrenia: A Likely Accomplice", J. Neurochem., 2003, 85, 1-13.
Dedeurwaerdere et al., "Memantine-Induced Brain Activation as a Model for the Rapid Screening of Potential Novel Antipsychotic Compounds: Exemplified by Activity of an Mglu2/3 Receptor Agonist", Psychopharmacology, 2011, 214, 505-514.
Del Rio et al., "Differential Coupling of G-Protein-Linked Receptors to Ca2+ Mobilization Through Inositol(1,4,5)Trisphosphate or Ryanodine Receptors in Cerebellar Granule Cells in Primary Culture", European Journal of Neuroscience, 1999, 11(9), 3015-3022.
Del'guidice et al., "Messing Up with Traffic: Different Effects of Antipsychotic Agents on Glutamate Receptor Complexes in Vivo", Mol. Pharmacol., 2008, 73(5), 1339-1342.
Delille et al., "Heterocomplex Formation of 5-HT2A-Mglu2 and its Relevance for Cellular Signaling Cascades", Neuropharmacology, 2012, 1-8.
Delille et al., "The Two Faces of the Pharmacological Interaction of Mglu2 and 5-Ht2a—Relevance of Receptor Heterocomplexes and Interaction Through Functional Brain Pathways", Neuropharmacology, 2013, 70, 296-305.
Derks et al., "Kreapelin Was Right: A Latent Class Analysis of Symptom Dimensions in Patients and Controls", Schizophrenia Bull., 2012, 38(3), 495-505.
Desseilles et al., "Assessing the Adequacy of Past Antidepressant Trials: A Clinician's Guide to the Antidepressant Treatment Response Questionnaire", J Clin Psychiatry, 2011, 72(8), 1152-1154.
Dhami et al., "G Protein-Coupled Receptor Kinase 2 Regulator of G Protein Signaling Homology Domain Binds to Both Metabotropic Glutamate Receptor 1a and Galphaq to Attenuate Signaling", Journal of Biological Chemistry, 2004, 279(16), 16614-16620.
Dhami et al., "Regulation of Metabotropic Glutamate Receptor Signaling, Desensitization and Endocytosis", Pharmacol. Ther., 2006, 111(1), 260-271.
Dhanya et al., "Design and Synthesis of an Orally Active Metabotropic Glutamate Receptor Subtype-2 (Mglur2) Positive Allosteric Modulator (Pam) That Decreases Cocaine Self-Administration in Rats", J Med Chem, 2011, 54, 342-353.
Dhonnchadha et al., "Anxiolytic-Like Effects of 5-Ht2 Ligands on Three Mouse Models of Anxiety", Behavioural Brain Research, 2003, 140, 203-214.
Di Liberto et al., "Group II Metabotropic Glutamate Receptor Activation by Agonist Ly379268 Treatment Increases the Expression of Brain Derived Neurotrophic Factor in the Mouse Brain", Neuroscience, 2010, 165, 863-873.
Dingledine et al., "Excitatory Amino Acid Receptors in Epilepsy", Trends in Pharmacological Sciences, 1990, 11(8), 334-338.
Dingledine et al., "Peripheral Glutamate Receptors: Molecular Biology and Role in Taste Sensation", J Nutr, 2000, 130(4s Suppl):1039s-1042s.
Doherty et al., "Functional Interactions Between Cannabinoid and Metabotropic Glutamate Receptors in the Central Nervous System", Current Opinion in Pharmacology, 2003, 3(1), 46-53.
Doherty et al., "Rapid Internalization and Surface Expression of a Functional, Fluorescently Tagged G-Protein-Coupled Glutamate Receptor", Biochemical Journal, 1999, 341(Pt 2), 415-422.
Domschke et al., "Anxious Versus Non-Anxious Depression: Difference in Treatment Outcome", J Psychopharmacol, 2010, 24, 621-622.
D'onofrio et al., "Neuroprotection Mediated by Glial Group-II Metabotropic Glutamate Receptors Requires the Activation of the Map Kinase and the Phosphatidylinositol-3-Kinase Pathways", Journal of Neurochemistry, 2001, 78(3), 435-445.
Doreulee et al., "The Role of the Mglur Allosteric Modulation in the Nmda-Hypofunction Model of Schizophrenia", Georgian Medical News, 2009, 177, 59-65.
Doumazene et al., "A New Approach to Analyze Cell Surface Protein Complexes Reveals Specific Heterodimeric Metabotropic Glutamate Receptors", Faseb, 2011, 25, 66-77.
Doumazene, "Illuminating the Activation Mechanisms and Allosteric Properties of Metabotropic Glutamate Receptors", PNAS, 2013, 1-10.
Downey et al., "Ecdysone-Based System for Controlled Inducible Expression of Metabotropic Glutamate Receptor Subtypes 2,5, and 8", Journal of Biomolecular Screening, 2005, 10(8), 841-848.
Doyle et al., "Quantifying the Attenuation of the Ketamine Phmri Response in Humans: a Validation Using Antipsychotic and Glutamatergic Agents", Jpet Fast Forward, Jan. 31, 2013, 42 pages.
Drevets et al., "Functional Anatomical Correlates of Antidepressant Drug Treatment Assessed Using Pet Measures of Regional Glucose Metabolism", European Neuropsychopharmacology, 2002, 12, 527-544.
Drew et al., "Multiple Metabotropic Glutamate Receptor Subtypes Modulate Gabaergic Neurotransmission in Rat Periaqueductal Grey Neurons in Vitro", Neuropharmacology, 2004, 46(7), 927-934.
Duncan et al., "Comparison of the Effects of Clozapine, Risperidone, and Olanzapine on Ketamine-Induced Alterations in Regional Brain Metabolism", Jpet, 2000, 293, 8-14.
Duncan et al., "Differential Effects of Clozapine and Haloperidol on Ketamine-Induced Brain Metabolic Activation", Brain Res, 1998, 812, 65-75.
Duncan et al., "Metabolic Mapping of the Rat Brain After Subanesthetic Doses of Ketamine: Potential Relevance to Schizophrenia", Brain Research, 1998, 787, 181-190.
Duncan et al., "Topographic Patterns of Brain Activity in Response to Swim Stress: Assessment by 2-Deoxyglucose Uptake and Expression of Fos-Like Immunoreactivity", J Neurosci, 1993, 13, 3932-3943.
Dunlop, "Glutamate-Based Therapeutic Approaches: Targeting the Glutamate Transport System", Current Opinion in Pharmacology, 2006, 6 (1), 103-107.
Duplantier et al., "3-Benzyl-1,3-Oxazolidin-2-Ones as Mglur2 Positive Allosteric Modulators: Hit to Lead and Lead Optimization", Bioorg Med Chem Lett, 2009, 19, 2524-2529.
Durand et al., "Role of Metabotropic Glutamate Receptors in the Control of Neuroendocrine Function", Neuropharmacology, 2008, 55(4), 577-583.
Dutar et al., "Pharmacological Characterization of an Unusual Mglur-Evoked Neuronal Hyperpolarization Mediated by Activation of Girk Channels", Neuropharmacology, 1999, 38(4), 467-475.
Egan et al., "Neurobiology of Schizophrenia", Current Opinion in Neurobiology, 1997, 7(5), 701-707.
Egashira et al., "Impaired Social Interaction and Reduced Anxiety-Related Behavior in Vasopressin V1a Receptor Knockout Mice", Behav Brain Res, 2007, 5 pages.
Ehlert, "Analysis of Allosterism in Functional Assays", J Pharmacol. Exp. Ther., 2005, 315(2), 740-754.
Eintrei et al., "Effects of Diazepam and Ketamine Administered Individually or in Combination on Regional Rates of Glucose Utilization in Rat Brain", Br J Anaesth, 1999, 82, 596-602.
Elia et al., "Genome-Wide Copy Number Variation Study Associates Metabotropic Glutamate Receptor Gene Networks with Attention Deficit Hyperactivity Disorder", Nature Genetics, 2011, 9 pages.
Ellenbroek et al., "Animal Models with Construct Validity for Schizophrenia", Behavioural Pharmacology, 1990, 1, 469-490.

(56) References Cited

OTHER PUBLICATIONS

Emmitte, "Recent Advances in the Design and Development of Novel Negative Allosteric Modulators of Mglu5", Chem. Neurosci., 2011, 2, 411-432.
Engin et al., "The Effects of Intra-Cerebral Drug Infusions on Animals' Unconditioned Fear Reactions: A Systematic Review", Prog Neuropsychopharmacol Biol Psychiatry, 2008, 32, 1399-1419.
Enomoto et al., "Phencyclidine and Genetic Animal Models of Schizophrenia Developed in Relation to the Glutamate Hypothesis", Methods Find. Exp. Clin Pharmacol., 2007, 29(4), 291-301.
Ermolinsky et al., "Differential Changes in Mglu2 and Mglu3 Gene Expression Following Pilocarpine-Induced Status Epilepticus: A Comparative Real-Time Pcr Analysis", Brain Research, 2008, 1226, 173-180.
Esposito et al., "Patterns of Benzodiazepine Use in a Canadian Population Sample", Epidemiol Psichiatr Soc., 2009, 18(3), 248-254.
Etkin et al., "Common Abnormalities and Disorder-Specific Compensation During Implicit Regulation of Emotional Processing in Generalized Anxiety and Major Depressive Disorders", Am J Psychiatry, 2011, 168, 968-978.
Etkin, "Neurobiology of Anxiety: From Neural Circuits to Novel Solutions?", Depression and Anxiety, 2012, 29, 355-358.
Ezquerra et al., "Efficient Reagents for the Synthesis of 5-, 7-, and 5,7-Substituted Indoles Starting from Aromatic Amines: Scopes and Limitations", J Org Chem, 1996, 61, 5804-5812.
Fagni et al., "Identification and Functional Roles of Metabotropic Glutamate Receptor-Interacting Proteins", Seminars in Cell & Developmental Biology, 2004, 15(3), 289-298.
Farabaugh et al., "Anxious Depression and Early Changes in the Hamd-17 Anxietysomatization Factor Items and Antidepressant Treatment Outcome", Int Clin Psychopharmacol., Jul. 2010, 25(4), 214-217.
Faries et al., "The Double-Blind Variable Placebo Lead-in Period: Results from Two Antidepressant Clinical Trials", Journal of Clinical Psychopharmacology, 2001, 21, 561-568.
Fava et al., "Anxiety Disorders in Major Depression" Comprehensive Psychiatry 2000, 41(2), 97-102.
Fava et al., "Clinical Correlates and Symptom Patterns of Anxious Depression Among Patients with Major Depressive Disorder in Star*D", Psychological Medicine, 2004, 34, 1299-1308.
Fava et al., "Difference in Treatment Outcome in Outpatients with Anxious Versus Nonanxious Depression: A Star*D Report", Am J Psychiatry, 2008, 165, 342-351.
Fava et al., "Major Depressive Subtypes and Treatment Response", Biol. Psychiatry, 1997, 42, 568-576.
Fava et al., "Reliability and Validity of the Massachusetts General Hospital Cognitive and Physical Functioning Questionnaire", Psychother Psychosom, 2009, 78(2), 91-97.
Fava et al., "The Efficacy and Tolerability of Duloxetine in the Treatment of Anxious Versus Non-Anxious Depression: A Post-Hoc Analysis of an Open-Label Outpatient Study", Annals of Clinical Psychiatry, 2007, 19(3), 187-195.
Fava et al., "The Problem of the Placebo Response in Clinical Trials for Psychiatric Disorders: Culprits, Possible Remedies, and a Novel Study Design Approach", Psychother Psychosom, 2003, 72, 115-127.
Fava et al., "What Clinical and Symptom Features and Comorbid Disorders Characterize Outpatients with Anxious Major Depressive Disorder: A Replication and Extension", Can J Psychiatry, Nov. 2006, 51(13), 823-835.
Fawcett et al., "Anxiety Syndromes and Their Relationship to Depressive Illness", J Clin Psychiatry, Aug. 1983, 44(8 Pt 2), 8-11.
Fawcett et al., "The Detection and Consequences of Anxiety in Clinical Depression", J Clin Psychiatry, 1997, 58(Suppl 8), 35-40.
Fawcett, "Treating Impulsivity and Anxiety in the Suicidal Patient", Ann NY Acad Sci., Apr. 2001, 932, 94-102.
Feeley et al., "Mglurs: A Target for Pharmacotherapy in Parkinson Disease", Experimental Neurology, 2003, 184(Suppl-6), S30-S36.
Feenstra et al., "Local Activation of Metabotropic Glutamate Receptors Inhibits the Handling-Induced Increased Release of Dopamine in the Nucleus Accumbens But Not That of Dopamine or Noradrenaline in the Prefrontal Cortex: Comparison with Inhibition of Ionotropic Receptors", Journal of Neurochemistry, 1998, 70(3), 1104-1113.
Feinberg et al., "The Metabotropic Glutamate (Mglu)2/3 Receptor Antagonist Ly341495 [2s-2-Amino-2-(1s,2s-2-Carboxycyclopropyl-1-Yl)-3-(Xanth-9-Yl)Propanoic Acid] Stimulates Waking and Fast Electroencephalogram Power and Blocks the Effects of the Mglu2/3 Receptor Agonist Ly379268 [(−)-2-Oxa-4-Aminobicyclo[3.1.0]Hexane-4,6-Dicarboxylate] in Rats", Jpet, 2005, 312, 826-833.
Fell et al., "Activation of Metabotropic Glutamate (Mglu)2 Receptors Suppresses Histamine Release in Limbic Brain Regions Following Acute Ketamine Challenge", Neuropharmacology, 2010, 58, 632-639.
Fell et al., "Evidence for the Role of Mglu2 Not Mglu3 Receptors in the Preclinical Antipsychotic Pharmacology of the Mglu2/3 Receptor Agonist Ly404039", Journal of Pharmacology & Experimental Therapeutics, 2008, 326, 209-217.
Fell et al., "Group II Metabotropic Glutamate Receptor Agonists and Positive Allosteric Modulators as Novel Treatments for Schizophrenia", Neuropharmacology 2012, 62, 1473-1483.
Fell et al., "In Vitro and In Vivo Evidence for a Lack of Interaction with Dopamine D2 Receptors by the Metabotropic Glutamate 2/3 Receptor Agonists 1s,2s,5r,6s-2-Aminobicyclo[3.1.0]Hexane-2,6-Bicaroxylate Monohydrate (Ly354740) and (−)-2-Oxa-4-Aminobicyclo[3.1.0] Hexane-4,6-Dicarboxylic Acid (Ly379268)", Jpet, 2009, 331, 1126-1136.
Fell et al., "N-(4-((2-(Trifluoromethyl)-3-Hydroxy-4-(Isobutyryl)Phenoxy)Methyl)Benzyl)-1-Methyl-1h-Imidazole-4-Carboxamide (Thiic), A Novel Metabotropic Glutamate 2 Potentiator with Potential Anxiolytic/Antidepressant Properties: in Vivo Profiling Suggests a Link Between Behavioral and Central Nervous System Neurochemical Changes", Jpet, 2011, 336, 165-177.
Fendt et al., "Metabotropic Glutamate Receptors are Involved in Amygdaloid Plasticity", European Journal of Neuroscience, 2002, 15(9), 1535-1541.
Fenton et al., "The Role of a Prescription in Anxiety Medication Use, Abuse, and Dependence", Am J Psychiatry, 2010, 167, 1247-1253.
Ferraguti et al., "Activation of the Extracellular Signal-Regulated Kinase 2 by Metabotropic Glutamate Receptors", European Journal of Neuroscience, 1999, 11(6), 2073-2082.
Ferraguti et al., "Metabotropic Glutamate 1 Receptor: Current Concepts and Perspectives", Pharmacol Rev, 2008, 60, 536-581.
Ferraguti et al., "Metabotropic Glutamate Receptors", Cell Tissue Res, 2006, 326, 483-504.
Ferris et al., "Interactions Between Ly354740, A Group II Metabotropic Agonist and the Gabaa-Benzodiazepine Receptor Complex in the Rat Elevated Plus-Maze", J Psychopharmacol, 2001, 15, 76-82.
Feyissa et al., "Elevated Level of Metabotropic Glutamate Receptor 2/3 in the Prefrontal Cortex in Major Depression", Prog. Neuropsychopharmacol. Biol. Psychiatry, 2010, 34(2), 279-283.
File, "The Use of Social Interaction as a Method for Detecting Anxiolytic Activity of Chlordiazepoxide-Like Drugs", Journal of Neuroscience Methods, 1980, 2(3), 219-38.
Filinger, "Effect of a Reserpine-Like Agent on the Release and Metabolism of [3h]Na in Cell Bodies and Terminals", Gen. Pharmac., 1994, 25, 1039-1043.
Fiorella et al., "The Role of the 5-Ht2a and 5-Ht2c Receptors in the Stimulus Effects of Hallucinogenic Drugs I: Antagonist Correlation Analysis", Psychopharmacology, 1995, 121, 347-356.
Fisher et al., "Antinociceptive Effects Following Intrathecal Pretreatment with Selective Metabotropic Glutamate Receptor Compounds in a Rat Model of Neuropathic Pain", Pharmacology, Biochemistry and Behavior, 2002, 73, 411-418.
Fisher et al., "Intrathecal Administration of the Mglur Compound, (S)-4cpg, Attenuates Hyperalgesia and Allodynia Associated with Sciatic Nerve Constriction Injury in Rats", Pain, 1998, 77(1), 59-66.
Fisher et al., "The Contribution of Metabotropic Glutamate Receptors (Mglurs) to Formalin-Induced Nociception", Pain, 1996, 68(2-3), 255-263.

(56) References Cited

OTHER PUBLICATIONS

Flint et al., "Anxious Depression in Elderly Patients: Response to Antidepressant Treatment", Am J Geriatr Psychiatry, 1997, 5(2), 107-115.
Flor et al., "Molecular Cloning, Functional Expression and Pharmacological Characterization of the Human Metabotropic Glutamate Receptor Type 2", Eur J Neurosci, 1995, 7, 622-629.
Fonnum et al., "Role of Glutamate and Glutamate Receptors in Memory Function and Alzheimer's Disease", Annals of the New York Academy of Sciences, 1995, 757, 475-486.
Fraley, "Positive Allosteric Modulators of the Metabotropic Glutamate Receptor 2 for the Treatment of Schizophrenia", Expert Opin. Ther. Patents, 2009, 19(9), 1259-1275.
Franco et al., "Novel Pharmacological Targets Based on Receptor Heteromers", Brain Research Reviews, 2008, 58, 475-482.
Franco et al., "The Two-State Dimer Receptor Model: A General Model for Receptor Dimers", Molecular Pharmacology, 2006, 69, 1906-1912.
Frank et al., "Depression and Health-Related Quality of Life for Low-Income African-American Women in the U.S.", Quality of Life Research, 2005, 14, 2293-2301.
Frauli et al., "Among the Twenty Classical L-Amino Acids, Only Glutamate Directly Activates Metabotropic Glutamate Receptors", Neuropharmacology, 2006, 50(2), 245-253.
Freedman et al., "Desensitization of G Protein-Coupled Receptors", Recent Progress in Hormone Research, 1996, 51, 319-351.
Freedman, "Schizophrenia", N. Engl. J. Med., 2003, 349, 1738-1749.
French et al., Subfield-Specific Immediate Early Gene Expression Associated with Hippocampal Long-Term Potentiation in Vivo. European Journal of Neuroscience 2001, 13 (5), 968-976.
Fribourg et al., "Decoding the Signaling of A Gpcr Heteromeric Complex Reveals a Unifying Mechanism of Action of Antipsychotic Drugs", Cell, 2011, 147, 1011-1023.
Fricker et al., "Effects of N-Acetylaspartylglutamate (Naag) At Group II Mglurs and Nmdar", Neuropharmacology, 2009, 56(6-7), 1060-1067.
Fujii et al., "A Chemical LTP Induced by Co-Activation of Metabotropic and N-Methyl-D-Aspartate Glutamate Receptors in Hippocampal Cal Neurons", Brain Research, 2004, 999(1), 20-28.
Fujimoto et al., "Motor and Cognitive Function Evaluation Following Experimental Traumatic Brain Injury", Neurosci. and Biobehav. Rev., 2004, 28, 365-378.
Furukawa et al., "Antidepressants Plus Benzodiazepines for Major Depression", The Cochrane Collaboration, 2009, 31 pages.
Fuxe et al., "Integrated Signaling in Heterodimers and Receptor Mosaics of Different Types of GPCRS of the Forebrain: Relevance for Schizophrenia", J Neural Transm, 2009, 116(8), 923-939.
Galimberti et al., "Long-Term Rearrangements of Hippocampal Mossy Fiber Terminal Connectivity in the Adult Regulated by Experience", Neuron 2006, 50, 749-763.
Gama et al., "Heterodimerization of Calcium Sensing Receptors with Metabotropic Glutamate Receptors in Neurons", J. Biol. Chem., 2001, 276(42), 39053-39059.
Garbaccio et al., "Discovery of Oxazolobenzimidazoles as Positive Allosteric Modulators for the Mglur2 Receptor", Acs Med Chem Lett, 2010, 1, 406-410.
Garrido-Sanabria et al., "Impaired Expression and Function of Group II Metabotropic Glutamate Receptors in Pilocarpine-Treated Chronically Epileptic Rats", Brain Res., 2008, 1240, 165-176.
Garriock et al., "Genetic Studies of Drug Response and Side Effects in the Star*D Study, Part 1", J Clin Psychiatry, 2009, 70(8), 1186-1187.
Gasparini et al., "Allosteric Modulators for Mglu Receptors", Curr Neuropharmacol, 2007, 5, 187-194.
Gerber et al., "Metabotropic Glutamate Receptors: Intracellular Signaling Pathways", Current Opinion in Pharmacology, 2007, 7(1), 56-61.
Gerwitz et al., "Behavioral Evidence for Interactions Between a Hallucinogenic Drug and Group II Metabotropic Glutamate Receptors", Neuropsychopharmacology, 2000, 23, 569-576.
Geyer, "Are Cross-Species Measures of Sensorimotor Gating Useful for the Discovery of Procognitive Cotreatments for Schizophrenia?", Dialogues Clin Neurosci., 2006, 8(1), 9-16.
Ghose et al., "Differential Expression of Metabotropic Glutamate Receptors 2 and 3 in Schizophrenia: A Mechanism for Antipsychotic Drug Action?", Am J Psychiatry, 2009, 166, 812-820.
Gill et al., "Immunochemical Localization of the Metabotropic Glutamate Receptors in the Rat Heart", Brain Research Bulletin, 1999, 48(2), 143-146.
Gilling et al., "Potency, Voltage-Dependency, Agonist Concentration-Dependency, Blocking Kinetics and Partial Untrapping of the Uncompetitive N-Methyl-D-Aspartate (NMDA) Channel Blocker Memantine at Human Nmda (Glun1/Glun2a) Receptors", Neuropharmacology 2009, 56, 866-875.
Gilmour et al., "Diverse and Often Opposite Behavioural Effects of NMDA Receptor Antagonists in Rats: Implications for NMDA Antagonist Modelling of Schizophrenia", Psychopharmacology, 2009, 205, 203-216.
Girardi et al., "Differential Expression of Cerebellar Metabotropic Glutamate Receptors Mglur2/3 and Mglur4a After the Administration of a Convulsant Drug and the Adenosine Analogue Cyclopentyladenosine", Neurochem. Res., 2007, 32(7), 1120-1128.
Gjoni et al., "Receptor Activation Involving Positive Allosteric Modulation, Unlike Full Agonism, Does Not Result in Gabab Receptor Desensitization", Neuropharmacology, 2008, 55, 1293-1299.
Gleeson, "Generation of a Set of Simple, Interpretable Admet Rules of Thumb", J Med Chem, 2008, 51, 817-834.
Glick et al., "A Double-Blind Randomized Trial of Mood Stabilizer Augmentation Using Lamotrigine and Valproate for Patients with Schizophrenia Who Are Stabilized and Partially Responsive", J Clin Psychopharmacol, 2009, 29(3), 267-271.
Glick et al., "Concomitant Medications May Not Improve Outcome of Antipsychotic Monotherapy for Stabilized Patients with Non-Acute Schizophrenia", J Clin Psychiatry, 2006, 67(8), 1261-1265.
Glin et al., "The Intermediate Stage of Sleep in Mice", Physiology & Behavior, 1991, 50, 951-953.
Goff et al., "Lamotrigine As Add-On Therapy in Schizophrenia: Results of 2 Placebo-Controlled Trials", J Clin Psychopharmacol., 2007, 27(6), 582-589.
Goldberg et al., "Novel Non-Benzodiazepine Anxiolytics", Neuropharmacology, 1983, 22, 1499-1504.
Gonzalez-Maeso et al., "Identification of a Serotonin/Glutamate Receptor Complex Implicated in Psychosis", Nature, 2008, 452, 93-97.
Gonzalez-Maeso et al., "Psychedelics and Schizophrenia", Trends Neurosci., 2009, 32(4), 225-232.
Gonzalez-Maeso, "Hallucinogens Recruit Specific Cortical 5-Ht2a Receptor-Mediated Signaling Pathways to Affect Behavior", Neuron, 2007, 53, 439-452.
Gonzalez-Maeso, "Transcriptome Fingerprints Distinguish Hallucinogenic and Nonhallucinogenic 5-Hydroxytryptamine 2a Receptor Agonist Effects in Mouse Somatosensory Cortex", J. Neurosci., 2003, 23, 8836-8843.
Goodman et al., "The Yale-Brown Obsessive Compulsive Scale: I. Development, Use, and Reliability", Arch Gen Psychiatry, 1989, 46(11), 1006-1011.
Goodwin et al., "Advantages and Disadvantages of Combination Treatment with Antipsychotics", Nice. Eur Neuropsychoparmacol., 2009, 19(7), 520-532.
Gorcs et al., "Immunohistochemical Visualization of a Metabotropic Glutamate Receptor", Neuroreport, 1993, 4(3), 283-286.
Gorman et al., "A Hypothesized Role for Dendritic Remodeling in the Etiology of Mood and Anxiety Disorders", J Neuropsychiatry Clin Neurosci, 2010, 22(3), 256-264.
Gorman et al., "Anxiogenic Effects of Co2 and Hyperventilation in Patients with Panic Disorder", Am J Psychiatry, 1994, 151, 547-553.
Gorman, "Comorbid Depression and Anxiety Spectrum Disorders", Depression and Anxiety, 1996/1997, 4, 160-168.
Goudet et al., "Asymmetric Functioning of Dimeric Metabotropic Glutamate Receptors Disclosed by Positive Allosteric Modulators", J. Biol. Chem., 2005, 280(26), 24380-24385.
Goudet et al., "Metabotropic Receptors for Glutamate and Gaba in Pain", Brain Res. Rev., 2009, 60(1), 43-56.

(56) References Cited

OTHER PUBLICATIONS

Gouzoulis-Mayfrank, "Inhibition of Return in the Human 5ht2a Agonist and Nmda Antagonist Model of Psychosis", Neuropsychopharmacology, 2006, 31, 431-441.
Gouzoulis-Mayfrank, "Psychological Effects of (S)-Ketamine and N,N-Dimethyltryptamine (Dmt): A Double-Blind, Cross-Over Study in Healthy Volunteers", Pharmacopsychiatry, 2005, 38, 301-311.
Gozzi et al., "Differential Effects of Antipsychotic and Glutamatergic Agents on the Phmri Response to Phencyclidine", Neuropsychopharmacology, 2008, 33, 1690-1703.
Gregory et al., "Allosteric Modulation of Metabotropic Glutamate Receptors: Structural Insights and Therapeutic Potential", Neuropharmacology, 2011, 60, 66-81.
Gregory et al., "Overview of Receptor Allosterism", Current Protocols in Pharmacology, 2010, 1.21.1-1.21.34.
Gregory et al., "Prefrontal Group II Metabotropic Glutamate Receptor Activation Decreases Performance on a Working Memory Task", Ann N Y. Acad. Sci., 2003, 1003, 405-409.
Groebe, "Screening for Positive Allosteric Modulators of Biological Targets", Drug Discov. Today, 2006, 11(13-14), 632-639.
Grueter et al., "Group II and III Metabotropic Glutamate Receptors Suppress Excitatory Synaptic Transmission in the Dorsolateral Bed Nucleus of the Stria Terminalis", Neuropsychopharmacology, 2005, 30(7), 1302-1311.
Gu et al., "Distribution of Metabotropic Glutamate 2 and 3 Receptors in the Rat Forebrain: Implications in Emotional Responses and Central Disinhibition", Brain Res, 2008, 1197, 47-62.
Gu et al., "Expression of Functional Metabotropic Glutamate Receptors in Primary Cultured Rat Osteoblasts. Cross-Talk with N-Methyl-D-Aspartate Receptors", J. Biol. Chem., 2000, 275(44), 34252-34259.
Guerineau et al., "G-Protein-Mediated Desensitization of Metabotropic Glutamatergic and Muscarinic Responses in Ca3 Cells in Rat Hippocampus", Journal of Physiology, 1997, 500(Pt 2), 487-496.
Guerineau et al., Activation of a Nonselective Cationic Conductance by Metabotropic Glutamatergic and Muscarinic Agonists in Ca3 Pyramidal Neurons of the Rat Hippocampus, J. Neurosci., 1995, 15(6), 4395-4407.
Guimaraes et al., "Ritanserin Facilitates Anxiety in a Simulated Public-Speaking Paradigm", Journal of Psychopharmacology, 1997, 11(3), 225-231.
Gunduz-Bruce, "The Acute Effects of Nmda Antagonism: from the Rodent to the Human Brain", Brain Res Rev, 2009, 60, 279-286.
Gupta et al., "Metabotropic Glutamate Receptor Protein Expression in the Prefrontal Cortex and Striatum in Schizophrenia", Synapse, 2005, 57(3), 123-131.
Gurevich et al., "Alterations in the Cortical Serotonergic System in Schizophrenia: A Postmortem Study", Biol. Psychiatry, 1997, 42, 529-545.
Haak et al., "Metabotropic Glutamate Receptor Activation Modulates Kainate and Serotonin Calcium Response in Astrocytes", J. Neurosci., 1997, 17(5), 1825-1837.
Hackler et al., "Selective Potentiation of the Metabotropic Glutamate Receptor Subtype 2 Blocks Phencyclidine-Induced Hyperlocomotion and Brain Activation", Neuroscience, 2010, 168(1), 209-218.
Hamilton, "A Rating Scale for Depression", J Neurol Neurosurg Psychiatry, 1960, 23, 56-62.
Hamilton, "Diagnosis and Rating of Anxiety, in Studies of Anxiety", MM Lader, Ed., Meedley Bros., Kent, 1969, 76-79.
Hamilton, "Standardised Assessment and Recording of Depressive Symptoms", Psychiatr Neurol Neurochir, 1969, 72(2), 201-205.
Hamilton, "The Assessment of Anxiety States by Rating", Br J Med Psycho!, 1959, 32(1), 50-55.
Hampson et al., "Characterization of Two Alternatively Spliced Forms of a Metabotropic Glutamate Receptor in the Central Nervous System of the Rat", Neuroscience, 1994, 60(2), 325-336.
Handley et al., "Effects of Alpha-Adrenoceptor Agonists and Antagonists in a Maze-Exploration Model of Fear-Motivated Behavior", Naunyn-Schmied. Arch. Pharmacol., 327, 1-5, 1984.

Hanna et al., "Differentiating the Roles of Mglu2 and Mglu3 Receptors Using Ly541850, an Mglu2 Agonist/Mglu3 Antagonist", Neuropharmacology, 2012, 1-8.
Hannah et al., "Heterocomplex Formation of 5-Ht2a-Mglu2 and Its Relevance for Cellular Signaling Cascades", Neuropharmacology, 2012, 62, 2184-2191.
Hansen et al., "Glutamate Joins the Ranks of Immunomodulators", Nature Medicine, 2010, 16(8), 856-858.
Happe et al., "Agonist-Stimulated [35s]Gtpgammas Autoradiograph: Optimization for High Sensitivity", Eur J Pharmacol, 2001, 422, 1-13.
Harald et al., "Meta-Review of Depressive Subtyping Models", Journal of Affective Disorders, 2012, 139, 126-140.
Hero et al., "The Clinical Global Impression-Schizophrenia Scale: A Simple Instrument to Measure the Diversity of Symptoms Present in Schizophrenia", Acta Psychiatr Scand Suppl., 2003, 416, 16-23.
Harrison et al., "The Group II Metabotropic Glutamate Receptor 3 (Mglur3, Mglu3, Grm3): Expression, Function and Involvement in Schizophrenia", J. Psychopharmacol., 2008, 22(3), 308-322.
Harrison, "Metabotropic Glutamate Receptor Agonists for Schizophrenia", The British Journal of Psychiatry, 2008, 192, 86-87.
Hartveit et al., "Expression of the Mrna of Seven Metabotropic Glutamate Receptors (Mglurl to 7) in the Rat Retina. An in Situ Hybridization Study on Tissue Sections and Isolated Cells", Eur. J Neurosci., 1995, 7(7), 1472-1483.
Hascup et al., "An Allosteric Modulator of Metabotropic Glutamate Receptors (Mglur2), (+)-Tfmpip, Inhibits Retraint Stress-Induced Phasic Glutamate Release in Rat Prefrontal Cortex", Journal of Neurochemistry, 2012, 122, 619-627.
Hashimoto et al., "Increased Levels of Glutamate in Brains from Patients with Mood Disorders", Biol Psychiatry, 2007, 62(11), 1310-1316.
Hashimoto, "Emerging Role of Glutamate in the Pathophysiology of Major Depressive Disorder", Brain Research Reviews, 2009, 61, 105-123.
Hasin et al., "Epidemiology of Major Depressive Disorder. Results from the National Epidemiologic Survey On Alcoholism and Related Conditions", Arch Gen Psychiatry, 2005, 62, 1097-1106.
Hasler et al., "Reduced Prefrontal Glutamate/Glutamine and Gamma-Aminobutyric Acid Levels in Major Depression Determined Using Proton Magnetic Resonance Spectroscopy", Arch Gen Psychiatry, 2007, 64(2), 193-200.
Hawgood et al., "Anxiety Disorders and Suicidal Behavior: An Update", Current Opinion in Psychiatry, 2008, 21, 51-64.
Helton et al., "Ly354740: A Metabotropic Glutamate Receptor Agonist Which Ameliorates Symptoms of Nicotine Withdrawal in Rats", Neuropharmacology, 1997, 36(11/12), 1511-1516.
Hemstapat et al., "A Novel Family of Potent Negative Allosteric Modulators of Group II Metabotropic Glutamate Receptors", Jpet, 2007, 322, 254-264.
Henley et al., "Characterization of the Allosteric Modulatory Protein Associated with Non-Nmda Receptors", Biochemical Society Transactions, 1993, 21(1), 89-93.
Henry et al., "The MglurS Antagonist Mpep, But Not the Mglur2/3 Agonist Ly314582, Augments Pcp Effects on Prepulse Inhibition and Locomotor Activity", Neuropharmacology, 2002, 43(8), 1199-209.
Heresco-Levy, "Glutamatergic Neurotransmission Modulators as Emerging New Drugs for Schizophrenia", Expert Opin Emerging Drugs, 2005, 10(4), 827-844.
Hermann et al., "Human Eeg Gamma Oscillations in Neuropsychiatric Disorders", Clinical Neurophysiology, 2005, 116, 2719-2733.
Hermans et al., "Structural, Signalling and Regulatory Properties of the Group I Metabotropic Glutamate Receptors: Prototypic Family C G-Protein-Coupled Receptors", Biochem. J., 2001, 359, 465-484.
Herrero et al., "Functional Switch from Facilitation to Inhibition in the Control of Glutamate Release by Metabotropic Glutamate Receptors", J. Biol. Chem., 1998, 273(4), 1951-1958.
Herrero et al., "Positive Feedback of Glutamate Exocytosis by Metabotropic Presynaptic Receptor Stimulation", Nature, 1992, 360(6400), 163-166.

(56) References Cited

OTHER PUBLICATIONS

Herrero et al., "Rapid Desensitization of the Metabotropic Glutamate Receptor that Facilitates Glutamate Release in Rat Cerebrocortical Nerve Terminals", European Journal of Neuroscience, 1994, 6(1), 115-120.

Hettema "The Nosologic Relationship Between Generalized Anxiety Disorder and Major Depression", Depression and Anxiety, 2008, 25, 300-316.

Hetzenauer et al., "Individual Contribution of Metabotropic Glutamate Receptor (Mglu) 2 and 3 to C Expression Pattern Evoked by Mglu2/3 Antagonism", Psychopharmacology, 2008, 201, 1-13.

Higashida et al., "Subtype-Specific Coupling with Adp-Ribosyl Cyclase of Metabotropic Glutamate Receptors in Retina, Cervical Superior Ganglion and Ng108-15 Cells", Journal of Neurochemistry, 2003, 85, 1148-1158.

Hijzen et al., "Predictive Validity of the Potentiated Startle Response As a Behavioral Model for Anxiolytic Drugs", Psychopharmacology, 1995, 118, 150-154.

Hlavackova et al., "Evidence for a Single Heptahelical Domain Being Turned on Upon Activation of a Dimeric GPCR", Embo, 2005, 24, 499-509.

Hoang et al., "Expression of Metabotropic Glutamate Receptors in Nodose Ganglia and the Nucleus of the Solitary Tract", Am J Physiol Heart Circ Physiol, 2001, 281, 457-462.

Hoeben et al., "Prediction of Serotonin 2a Receptor (5-Ht$_{2a}$r) Occupancy in Man From Nonclinical Pharmacology Data. Exposure Vs. 5-Ht$_{2a}$r Occupancy Modeling Used to Help Design a Positron Emission Tomography (Pet) Study in Healthy Male Subjects", Abstract, 2013 Annual Meeting of the Population Approach Group in Europe, 2 pages.

Hoffman et al., "Human and Economic Burden of Generalized Anxiety Disorder", Depression and Anxiety, 2008, 25, 72-90.

Hofmeijer-Sevink et al., "Clinical Relevance of Comorbidity in Anxiety Disorders: A Report From the Netherlands Study of Depression and Anxiety (NESDA)", Journal of Affective Disorders, 2012, 137, 106-112.

Hohnadel et al., "Effect of Repeated Nicotine Exposure on High-Affinity Nicotinic Acetylcholine Receptor Density in Spontaneously Hypertensive Rats", Neuroscience Letters, 2005, 382, 158-163.

Holcomb et al., "Effects of Noncompetitive Nmda Receptor Blockade on Anterior Cingulate Cerebral Blood Flow in Volunteers with Schizophrenia", Neuropsychopharmacology, 2005, 30, 2275-2282.

Holloway et al., "Prenatal Stress Induces Schizophrenia-Like Alterations of Serotonin 2a and Metabotropic Glutamate 2 Receptors in the Adult Offspring: Role of Maternal Immune System", J. Neurosci., 2013, 33(3), 1088-1098.

Holscher et al., "Metabotropic Glutamate Receptor Activation and Blockade: Their Role in Long-Term Potentiation, Learning and Neurotoxicity", Neuroscience & Biobehavioral Reviews, 1999, 23(3), 399-410.

Homayoun et al., "Activation of Metabotropic Glutamate 2/3 Receptors Reverses the Effects of Nmda Receptor Hypofunction on Prefrontal Cortex Unit Activity in Awake Rats", J. Neurophysiol., 2005, 93(4), 1989-2001.

Homayoun et al., "Group 5 Metabotropic Glutamate Receptors: Role in Modulating Cortical Activity and Relevance to Cognition", European Journal of Pharmacology, 2010, 639, 33-39.

Homayoun et al., "Orbitofrontal Cortex Neurons as a Common Target for Classic and Glutamatergic Antipsychotic Drugs", Proc. Natl. Acad. Sci. USA, 2008, 105(46), 18041-18046.

Honer et al., "Clozapine Alone Versus Clozapine and Risperidone with Refractory Schizophrenia", N Engl J Med., 2006, 354(5), 472-482.

Hopkins "Is There a Path Forward for Mglu2 Positive Allosteric Modulators for the Treatment of Schizophrenia?", ACS Chem. Neurosci., 2013, 4, 211-213.

Horiguchi et al., "Interaction of Mglu2/3 Agonism with Clozapine and Lurasidone to Restore Novel Object Recognition in Subchronic Phencyclidine-Treated Rats", Psychopharmacology, 2011, 217, 13-24.

Horiguchi et al., "Interactions Among the Atypical Antipsychotic Drug (APD), Lurasidone, 5-HT1A and Metabotropic Glutamate Receptor 2/3 (Mglur2/3) Agonism, and 5-HT2A Antagonism, to Attenuate Phencyclidine (PCP)-Induced Deficit in Rat Novel Object Recognition (NOR)" Poster 610.12 Presented At the 40$^{th}$ Annual Meeting of Society for Neuroscience, 2010, 1 page.

Hostetler, "PET Tracer Discovery for Subtype-Specific Mglur Allosteric Modulators: Challenges and Insights" Presentation Slides 7th International Meeting on Metabotropic Glutamate Receptors, Merck, Oct. 2011, 8 pages.

Houamed et al., "Cloning, Expression, and Gene Structure of a G Protein-Coupled Glutamate Receptor from Rat Brain", Science, 1991, 252(5010), 1318-1321.

Hsia et al., "Evidence Against a Role for Metabotropic Glutamate Receptors in Mossy Fiber Ltp: the Use of Mutant Mice and Pharmacological Antagonists", Neuropharmacology, 1995, 34, 1567-1572.

Hu et al., "Altered Profile of Gene Expression in Rat Hearts Induced by Chronic Nicotine Consumption", Biochemical and Biophysical Research Communications, 2002, 297, 729-736.

Hu et al., "Emotion Enhances Learning Via Norepinephrine Regulation of Ampa-Receptor Trafficking", Cells, 2007, 131, 160-173.

Hu et al., "Glutamate Receptors in Preclinical Research on Alzheimer's Disease: Update on Recent Advances", Pharmacology, Biochemistry and Behavior, 2012, 100, 855-862.

Hu et al., "Identification of Glutamate Receptors and Transporters in Mouse and Human Sperm", Journal of Andrology, 2004, 25(1), 140-6.

Hu et al., "Pyrimidine Methyl Anilines: Selective Potentiators for the Metabotropic Glutamate 2 Receptor", Bioorganic & Medicinal Chemistry Letters, 2004, 14, 5071-5074.

Hu et al., "The Regulation of Dopamine Transmission by Metabotropic Glutamate Receptors", J. Pharmacol. Exp. Ther., 1999, 289(1), 412-416.

Huang et al., "Alzheimer Mechanisms and Therapeutic Strategies", Cell, 2012, 148, 1204-1222.

Huang et al., "Inhibition of Microtubule Formation by Metabotropic Glutamate Receptors", Journal of Neurochemistry, 2000, 74(1), 104-113.

Huang et al., "Interdomain Movements in Metabotropic Glutamate Receptor Activation", Proc Natl Acad Sci USA, 2011, 108, 15480-15485.

Huang et al., "Potentiation of the Novel Atypical Antipsychotic Drug Lurasidone-Induced Dopamine Efflux in Rat Medial Prefrontal Cortex and Hippocampus by DA D1 and Mglur2/3 Agonism but not D3 Receptor Antagonism" Poster 610.13 Presented at the 40$^{th}$ Annual Meeting of Society for Neuroscience, Nov. 2010, 1 page.

Huang et al., "Prevalence, Correlates, and Comorbidity of Nonmedical Prescription Drug Use and Drug Use Disorders in the United States: Results of the National Epidemiologic Survey on Alcohol and Related Conditions", J Clin Psychiatry, 2006, 67, 1062-1073.

Hucho et al., "Epac Mediates a Camp-To-Pkc Signaling in Inflammatory Pain: An Isolectin B4(+) Neuron-Specific Mechanism", Journal of Neuroscience, 2005, 25(26), 6119-6126.

Hucho et al., "Estrogen Controls Pkce-Dependent Mechanical Hyperalgesia Through Direct Action on Nociceptive Neurons", European Journal of Neuroscience, 2006, 24, 527-534.

Huey et al., "Development of Subtle Psychotic Symptoms with Memantine: A Case Report", J Clin Psychiatry, 2005, 66, 658-659.

Iacovelli et al., "Regulation of Group II Metabotropic Glutamate Receptors by G Protein-Coupled Receptor Kinases: Mglu2 Receptors are Resistant to Homologous Desensitization", Mol Pharmacol., 2009, 75(4), 991-1003.

Iglesias et al., "Metabotropic Glutamate Receptor/Phospholipase C System in Female Rat Heart", Brain Res., 2007, 1153, 1-11.

Imre et al., "Dose-Response Characteristics of Ketamine Effect on Locomotion, Cognitive Function and Central Neuronal Activity", Brain Res. Bull, 2006, 69(3), 338-345.

Imre et al., "Effects of the Mglur2/3 Agonist Ly379268 on Ketamine-Evoked Behaviours and Neurochemical Changes in the Dentate Gyrus of the Rat", Pharmacology, Biochemistry and Behavior, 2006, 84, 392-399.

(56) References Cited

OTHER PUBLICATIONS

Imre et al., "Subchronic Administration of Ly354740 Does Not Modify Ketamine-Evoked Behavior and Neuronal Activity in Rats", Eur. J Pharmacol., 2006, 544(1-3), 77-81.
Imre, "The Preclinical Properties of a Novel Group II Metabotropic Glutamate Receptor Agonist Ly379268", CNS Drug Reviews, 2007, 13(4), 444-464.
Inta et al., "Mice with Genetically Altered Glutamate Receptors as Models of Schizophrenia: A Comprehensive Review", Neuroscience & Biobehavioral Reviews, 2010, 34(3), 285-94.
Ionescu et al., "Defining Anxious Depression: A Review of the Literature", CNS Spectrums, 2013, 1-9.
Iovieno et al., "Does the Presence of an Open-Label Antidepressant Treatment Period Influence Study Outcome in Clinical Trials Examining Augmentation/Combination Strategies in Treatment Partial Responders/Nonresponders with Major Depressive Disorder?", J Clin Psychiatry, 2012, 8 pages.
Irifune et al., "Riluzole, A Glutamate Release Inhibitor, Induces Loss of Righting Reflex, Antinociception, and Immobility in Response to Noxious Stimulation in Mice", Anesthesia & Analgesia, 2007, 104(6), 1415-1421.
Jablensky et al., "Polymorphisms Associated with Normal Memory Variation Also Affect Memory Impairment in Schizophrenia", Genes, Brain nd Behavior, 2011, 10, 410-417.
Jane et al., "Potent Antagonists at the L-AP4- and (1s,3s)-ACPD-Sensitive Presynaptic Metabotropic Glutamate Receptors in the Neonatal Rat Spinal Cord", Neuropharmacology, 1996, 35(8), 1029-1035.
Janssens et al., "Glutamate Receptor Subunit Expression in Primary Neuronal and Secondary Glial Cultures", J Neurochem, 2001, 77, 1457-1474.
Japanese Patent Application No. 2010-553485: Office Action dated Jul. 11, 2013, 3 pages.
Javitt, "Glutamatergic Theories of Schizophrenia", ISR J Psychiatry Relat Sci, 2010, 47(1), 4-16.
Javitt et al., "Recent Advances in the Phenylcyclidine Model of Schizophrenia", Am J Psychiatry, 1991, 148, 1301-1308.
Jenkins et al., "Disturbances in Social Interaction Occur Along with Pathophysiological Deficits Following Sub-Chronic Phencyclidine Administration in the Rat", Behavioural Brain Research, 2008, 194, 230-235.
Jensen et al., "Allosteric Modulation of the Calcium-Sensing Receptor", Current Neuropharmacology, 2007, 5, 180-186.
Jin et al., "The Mglur2 Positive Allosteric Modulator Bina Decreases Cocaine Self-Administration and Cue-Induced Cocaine-Seeking and Counteracts Cocaine-Induced Enhancement of Brain Reward Function in Rats", Neuropsych., 2010, 35(10), 2021-2036.
Jingami et al., "Structure of the Metabotropic Glutamate Receptor", Current Opinion in Neurobiology, 2003, 13(3), 271-278.
Joffe et al., "Anxious and Nonanxious Depression", Am J Psychiatry, 1993, 150, 1257-1258.
Joffe et al., "Lifetime History of Depression and Anxiety Disorders as a Predictor of Quality of Life in Midlife Women in the Absence of Current Illness Episodes", Arch Gen Psychiatry, 2012, 69(5), 484-492.
Johansen et al., "Excitatory Amino Acid Receptor Ligands: Resolution, Absolute Stereochemistry, and Enantiopharmacology of 2-Amino-3-(4-Butyl-3-Hydroxyisoxazol-5-Yl)Propionic Acid", J of Medicinal Chem, 1998, 41(6), 930-939.
John et al., "Rapid Changes in Glutamate Levels in the Posterior Hypothalamus Across Sleep-Wake States in Freely Behaving Rats", American Journal of Physiology—Regulatory Integrative & Comparative Physiology, 2008, 295(6), R2041-2049.
Johnson et al., "Activation of Group II Metabotropic Glutamate Receptors Induces Long-Term Depression of Excitatory Synaptic Transmission in the Substantia Nigra Pars Reticulate", Neuroscience Letters, 2011, 504, 102-106.
Johnson et al., "Disruption of Gabaergic Tone in the Dorsomedial Hypothalamus Attenuates Responses in A Subset of Serotonergic Neurons in the Dorsal Raphe Nucleus Following Lactate-Induced Panic", J Psychopharmacol, 2008, 22, 642-652.
Johnson et al., "Glutamate Receptors as Therapeutic Targets for Parkinson's Disease", CNS Neurol Disord Drug Targets, 2009, 8, 475-491.
Johnson et al., "Group II Metabotropic Glutamate Receptor Type 2 Allosteric Potentiators Prevent Sodium Lactate-Induced Panic Like Response in Panic-Vulnerable Rats", J Psychopharmacol, 2013, 27, 152-161.
Johnson et al., "Species Variations in Transmembrane Region V of the 5-Hydroxytryptamine Type 2a Receptor Alter the Structure-Activity Relationship of Certain Ergolines and Tryptamines", Molecular Pharmacology, 1994, 45, 277-286.
Jones et al., "A Rotarod Suitable for Quantitative Measurements of Motor Incoordination in Naïve Mice", Naunyn Schmiedebergs Arch. Exper. Pathol. Pharmacol., 1968, 259, 211.
Jones et al., "Analgesic Effects of the Selective Group II (Mglu2/3) Metabotropic Glutamate Receptor Agonists Ly379268 and Ly389795 in Persistent and Inflammatory Pain Models After Acute and Repeated Dosing", Neuropharmacology, 2005, 49, 206-218.
Jones et al., "Discovery, Synthesis, and Structure—Activity Relationship Development of a Series of N-4-(2,5-Dioxopyrrolidin-1-Yl)Phenylpicolinamides (Vu0400195, Ml182): Characterization of a Novel Positive Allosteric Modulator of the Metabotropic Glutamate Receptor 4 (Mglu4) with Oral Efficacy in an Antiparkinsonian Animal Model", J Med Chem, 2011, 54, 7639-7647.
Jones et al., "The Mglur2/3 Agonist Ly379268 Reverses Post-Weaning Social Isolation-Induced Recognition Memory Deficits in the Rat", Psychopharmacology, 2011, 214, 269-283.
Julio-Pieper et al., "Exciting Times Beyond the Brain: Metabotropic Glutamate Receptors in Peripheral and Non-Neural Tissues", Pharmacological Review, 2011, 63, 35-58.
Kagaya et al., "Heterologous Supersensitization Between Serotonin2 and Alpha 2-Adrenergic Receptor-Mediated Intracellular Calcium Mobilization in Human Platelets", Journal of Neural Transmission, 1992, 88(1), 25-36.
Kahn et al., "Group 2 Metabotropic Glutamate Receptors Induced Long Term Depression in Mouse Striatal Slices", Neurosci. Lett., 2001, 316(3), 178-182.
Kalivas et al., "Repeated Cocaine Administration Alters Extracellular Glutamate in the Ventral Tegmental Area", Journal of Neurochemistry, 1998, 70(4), 1497-1502.
Kapur et al., "From Dopamine to Salience to Psychosis—Linking Biology, Pharmacology and Phenomenology of Psychosis", Schizophr.Res., 2005, 79, 59-68.
Karlsson et al., "Loss of Glial Glutamate and Aspartate Transporter (Excitatory Amino Acid Transporter 1) Causes Locomotor Hyperactivity and Exaggerated Responses to Psychotomimetics: Rescue by Haloperidol and Metabotropic Glutamate 2/3 Agonist", Biol. Psychiatry, 2008, 64(9), 810-814.
Kato "Molecular Genetics of Bipolar Disorder and Depression" Psychiatry and Clinical Neurosciences 2007, 61, 3-19.
Katon et al., "Major Depression: The Importance of Clinical Characteristics and Treatment Response to Prognosis", Depression and Anxiety, 2010, 27, 19-26.
Kaupmann et al., "Expression Cloning of Gaba(B) Receptors Uncovers Similarity to Metabotropic Glutamate Receptors", Nature, 1997, 386(6622), 239-246.
Kawabata et al., "Diversity of Calcium Signaling by Metabotropic Glutamate Receptors", J. Biol. Chem., 1998, 273(28), 17381-17385.
Kearney et al., "Intrasubthalamic Nucleus Metabotropic Glutamate Receptor Activation: A Behavioral, FOS Immunohistochemical and [14c]2-Deoxyglucose Autoradiographic Study", Neuroscience, 2000, 95(2), 409-416.
Kearney et al., "Metabotropic Glutamate Agonist-Induced Rotation: A Pharmacological, FOS Immunohistochemical, and [14c]-2-Deoxyglucose Autoradiographic Study", J Neurosci., 1997, 17(11), 4415-4425.
Kehne et al., "Anxiolytic Effects of Buspirone and Gepirone in the Fear-Potentiated Startle Paradigm", Psychopharmacology, 1988, 94, 8-13.
Keller et al., "Anxiety Symptom Relief in Depression Treatment Outcomes", J Clin Psychiatry, 1995, 56(Suppl 6), 22-29.

(56) References Cited

OTHER PUBLICATIONS

Kenakin et al., "Seven Transmembrane Receptors as Shapeshifting Proteins: The Impact of Allosteric Modulation and Functional Selectivity on New Drug Discovery", Pharmacological Reviews, 2010, 62(2), 265-304.
Kenakin et al., "Signalling Bias in New Drug Discovery: Detection, Quantification and Therapeutic Impact", Nature Reviews Drug Discovery, 2013, 12, 205-216.
Kenakin, "A Holistic View of GPCR Signaling", Nature Biotechnology, 2010, 28, 928-929.
Kenakin, "Allosteric Agonist Modulators", Journal of Receptors and Signal Transduction, 2007, 27(4), 247-259.
Kenakin, "Allosteric Modulators: The New Generation of Receptor Antagonist", Molecular Interventions, Aug. 2004, 4(4), 222-229.
Kenakin, "Collateral Efficacy in Drug Discovery: Taking Advantage of the Good (Allosteric) Nature of 7tm Receptors", Trends Pharmacol. Sci., 2007, 28(8), 407-415.
Kenakin, "Seven Transmembrane Receptors As Nature's Prototype Allosteric Protein: De-Emphasizing the Geography of Binding" Molecular Pharmacology 2008, 74, 541-543.
Kendler et al., "Major Depression and Generalized Anxiety Disorder: Same Genes, (Partly) Different Environments?", Arch Gen Psychiatry, 1992, 49, 716-722.
Kendler, "The Nosologic Validity of Paranoia (Simple Delusional Disorder)", Arch Gen Psychiatry, 1980, 37, 699-706.
Kennett et al., "Evidence That 5-Ht2c Receptor Antagonists are Anxiolytic in the Rat Geller-Seifter Model of Anxiety", Psychopharmacology, 1994, 114, 90-96.
Kenny et al., "Group II Metabotropic and Alpha-Amino-3-Hydroxy-5-Methyl-4-Isoxazole Propionate (Ampa)/Kainate Glutamate Receptors Regulate the Deficit in Brain Reward Function Associated with Nicotine Withdrawal in Rats", J Pharmacol. Exp. Ther., 2003, 306(3), 1068-1076.
Kent, "Safety, Tolerability and Potential Therapeutic Efficacy of a Novel Glutamate Modulator as Adjunctive Treatment in Patients with Schizophrenia", Abstract No. 3160, American Psychiatric Association Annual Meeting, 2013, 1 page.
Kessler et al., "Comorbid Major Depression and Generalized Anxiety Disorders in the National Comorbidity Survey Follow-Up", Psycho! Med., Mar. 2008, 38(3), 365-374.
Kessler et al., "Epidemiology of Anxiety Disorders", Current Topics in Behavioral Neurosciences, 2010, 2, 21-35.
Kessler et al., "Impairment in Pure and Comorbid Generalized Anxiety Disorder and Major Depression at 12 Months in Two National Surveys", American Journal of Psychiatry, 1999, 156(12), 1915-1923.
Kessler et al., "Lifetime and 12-Month Prevalence of DSM-III-R Psychiatric Disorders in the United States: Results From the National Comorbidity Survey", Arch Gen Psych, 1994, 51, 8-19.
Kessler et al., "Rethinking the Duration Requirement for Generalized Anxiety Disorder: Evidence from the National Comorbidity Survey Replication", Psychological Medicine, 2005, 7, 1073-1082.
Kessler et al., "The Epidemiology of Co-Ocurring Addictive and Mental Disorders: Implications for Prevention and Service Utilization", American Journal of Orthopsychiatry, 1996, 66(1), 17-31.
Kessler et al., "The Epidemiology of Major Depressive Disorder: Results from the National Comorbidity Survey Replication (NCS-R)", JAMA, 2003, 289(23), 3095-3105.
Kew et al., "Activity-Dependent Presynaptic Autoinhibition by Group II Metabotropic Glutamate Receptors at the Perforant Path Inputs to the Dentate Gyrus and Ca1", Neuropharmacology, 2001, 40, 20-27.
Kew et al., "Differential Regulation of Synaptic Transmission by Mglu2 and Mglu3 at the Perforant Path Inputs to the Dentate Gyrus and Ca1 Revealed in Mglu2 −/− Mice", Neuropharmacology, 2002, 43, 215-221.
Kew et al., "Ionotropic and Metabotropic Glutamate Receptor Structure and Pharmacology", Psychopharmacology, 2005, 179, 4-29.
Kew, "Positive and Negative Allosteric Modulation of Metabotropic Glutamate Receptors: Emerging Therapeutic Potential", Pharmacology & Therapeutics, 2004, 104, 233-244.
Kilbride et al., "Presynaptic Group II Mglur Inhibition of Short-Term Depression in the Medial Perforant Path of the Dentate Gyrus in Vitro", Neurophysiol, 2001, 85, 2509-2515.
Kilbride et al., "Presynaptic Inhibitory Action of the Group II Metabotropic Glutamate Receptor Agonists, Ly354740 and DCG-IV", European Journal of Pharmacology, 1998, 356, 149-157.
Kim et al., "Activation of Metabotropic Glutamate Receptors in the Rat Nucleus Accumbens Increases Locomotor Activity in A Dopamine-Dependent Manner", Journal of Pharmacology & Experimental Therapeutics, 1997, 283(2), 962-968.
Kim et al., "Group II Metabotropic Glutamate Receptor Stimulation Triggers Production and Release of Alzheimer's Amyloid B42 From Isolated Intact Nerve Terminals", Journal of Neuroscience, 2010, 30(11), 3870-3875.
Kim et al., "Metabotropic Glutamate Receptors in the Rat Nucleus Accumbens Contribute to Amphetamine-Induced Locomotion", Journal of Pharmacology & Experimental Therapeutics, 1998, 284(1), 317-322.
Kim et al., "Metabotropic Glutamate Receptors, Phosphorylation and Receptor Signaling", Journal of Neuroscience Research, 2008, 86, 1-10.
Kim et al., "Neurofilament-M Interacts with the D1 Dopamine Receptor to Regulate Cell Surface Expression and Desensitization", Journal of Neuroscience, 2002, 22(14), 5920-5930.
Kim et al., "Predictors of 12-Week Remission in a Nationwide Cohort of People with Depressive Disorders: The Crescend Study", Hum. Psychopharmacol Clin Exp, 2011, 26, 41-50.
Kingston et al., "Ly341495 is a Nanomolar Potent and Selective Antagonist of Group II Metabotropic Glutamate Receptors", Neuropharmacology, 1998, 37, 1-12.
Kingston et al., "Neuroprotection by Metabotropic Glutamate Receptor Agonists: Ly354740, Ly379268 and Ly389795", European Journal of Pharmacology, 1999, 377, 155-165.
Kingston et al., "Neuroprotective Actions of Novel and Potent Ligands of Group I and Group II Metabotropic Glutamate Receptors", Annals New York Academy of Sciences, 1999, 890, 438-449.
Kilts, "The Changing Roles and Targets for Animal Models of Schizophrenia", Biol. Psychiatr., 2001, 50, 845-855.
Klein "Mixed Anxiety Depression. For and Against", L'encéphale, 1993, 493-495.
Klein et al., "Glutamatergic Activation of Hippocampal Phospholipase D: Postnatal Fading and Receptor Desensitization", Journal of Neurochemistry, 1998, 70(4), 1679-1685.
Klodzinska et al., "Group II Mglu Receptor Agonists Inhibit Behavioural and Electrophysiological Effects of Doi in Mice", Pharmacology, Biochemistry and Behavior, 2002, 73(2), 327-332.
Klodzinska et al., "Roles of Group II Metabotropic Glutamate Receptors in Modulation of Seizure Activity", Naunyn Schmiedebergs Arch Pharmacol, 2000, 361, 283-288.
Klodzinska et al., "Selective Group II Glutamate Metabotropic Receptor Agonist Ly354740 Attenuates Pentetrazole- and Picrotoxin-Induced Seizures", Pol J Pharmacol, 1999, 51, 543-545.
Knesevich, "Validity of Hamilton Rating-Scale for Depression", Br J Psychiatry, 1977, 131, 49-52.
Kniazeff et al., "Closed State of Both Binding Domains of Homodimeric Mglu Receptors is Required for Full Activity", Nat Struct Mol Biol, 2004, 11, 706-713.
Knight et al., "Pharmacological Characterization of the Agonist Radioligand Binding Site of 5-Ht2a, 5-Ht2b and 5-Ht2c Receptors", Naunyn-Schmiedeberg's Arch Pharmacol, 2004, 370, 114-123.
Knoflach et al., "R1315, A Potent Orally Active Non-Competitive Group II Metabotropic Glutamate Receptor Antagonist with Cognitive Enhancing Properties", 5th International Meeting on Metabotropic Glutamate Receptors, Taormina Sicily—Italy, Sep. 2005, 1 page.
Kodama et al., "Enhanced Glutamate Release During Rem Sleep in the Rostromedial Medulla As Measured by in Vivo Microdialysis", Brain Res, 1998, 780, 178-181.

(56) References Cited

OTHER PUBLICATIONS

Koh et al., "Deficits in Social Behavior and Sensorimotor Gating in Mice Lacking Phospholipase Cb1", Genes, Brain and Behavior, 2008, 7, 120-128.
Koh et al., "Non-NMDA Receptor-Mediated Neurotoxicity in Cortical Culture", J. Neurosci., 1990, 10(2), 693-705.
Koh et al., "Treatment Strategies Targeting Excess Hippocampal Activity Benefit Aged Rats with Cognitive Impairment", Neuropsychopharmacology, 2010, 35, 1016-1025.
Komossa et al., "Second-Generation Antipsychotics for Major Depressive Disorder and Dysthymia (Review)", The Cochrane Collaboration, 2012, 222 pages.
Konarski et al., "Volumetric Neuroimaging Investigations in Mood Disorders: Bipolar Disorder Versus Major Depressive Disorder", Bipolar Disord, 2008, 10(1), 1-37.
Konieczny et al., "Ly354740, A Group II Metabotropic Glutamate Receptor Agonist with Potential Antiparkinsonian Properties in Rats", Naunyn Schmiedebergs Arch. Pharmacol., 1998, 358(4), 500-502.
Konstantakopoulos et al., "Lamotrigine Associated Exacerbation of Positive Symptoms in Paranoid Schizophrenia", Schizophr Res., 2008, 98(1-3), 325-326.
Koolschijn et al., "Brain Volume Abnormalities in Major Depressive Disorder: A Meta-Analysis of Magenetic Resonance Imaging Studies", Hum Brain Mapp, 2009, 30(11), 3719-3735.
Koroshetz et al., "Emerging Treatments for Stroke in Humans", Trends in Pharmacological Sciences, 1996, 17(6), 227-233.
Kostrzewa et al., "Supersensitized D1 Receptors Mediate Enhanced Oral Activity After Neonatal 6-Ohda. Pharmacology", Biochemistry & Behavior, 1991, 39(3), 677-682.
Kotlinska et al., "The Role of Group I Mglu Receptors in the Expression of Ethanol-Induced Conditioned Place Preference and Ethanol Withdrawal Seizures in Rats", European Journal of Pharmacology, 2011, 670, 154-161.
Koulen et al., "Group II and Group III Metabotropic Glutamate Receptors in the Rat Retina: Distributions and Developmental Expression Patterns", European Journal of Neuroscience, 1996, 8(10), 2177-2187.
Kowal et al., "A [35s]Gtpgammas Binding Assessment of Metabotropic Glutamate Receptor Standards in Chinese Hamster Ovary Cell Lines Expressing the Human Metabotropic Receptor Subtypes 2 and 4", Neuropharmacology, 1998, 37(2), 179-187.
Kowal et al., "Functional Calcium Coupling with the Human Metabotropic Glutamate Receptor Subtypes 2 and 4 by Stable Co-Expression with a Calcium Pathway Facilitating G-Protein Chimera in Chinese Hamster Ovary Cells", Biochemical Pharmacology, 2003, 66(5), 785-790.
Krieger, "The Plasma Level of Cortisol as a Predictor of Suicide", Diseases of the Nervous System, 1974, 35(5), 237-240.
Krishnan et al., "The Molecular Neurobiology of Depression", Nature, 2008, 455, 894-902.
Krivoy et al., "The Possible Involvement of Metabotropic Glutamate Receptors in Schizophrenia", European Neuropsychopharmacology, 2008, 18, 395-405.
Krystal et al., "Comparative and Interactive Human Psychopharmacologic Effects of Ketamine and Amphetamine: Implications for Glutamatergic and Dopaminergic Model Psychoses and Cognitive Function", Archives of General Psychiatry, 2005, 62(9), 985-994.
Krystal et al., "Neuroplasticity as a Target for the Pharmacotherapy of Anxiety Disorders, Mood Disorders, and Schizophrenia", Drug Discov. Today, 2009, 14(13-14), 690-697.
Krystal et al., "NMDA Receptor Antagonist Effects, Cortical Glutamatergic Function, and Schizophrenia: Toward a Paradigm Shift in Medication Development", Psychopharmacology, 2003, 169(3-4), 215-33.
Krystal et al., "Potential Psychiatric Applications of Metabotropic Glutamate Receptor Agonists and Antagonists", CNS Drugs, 2010, 24(8), 669-693.
Krystal et al., "Preliminary Evidence of Attenuation of the Disruptive Effects of the Nmda Glutamate Receptor Antagonist, Ketamine, on Working Memory by Pretreatment with the Group II Metabotropic Glutamate Receptor Agonist, Ly354740, in Healthy Human Subjects", Psychopharmacology (Berl)., 2005, 179(1), 303-309.
Krystal et al., "Subanesthetic Effects of the Noncompetitive NMDA Antagonist, Ketamine, in Humans. Psychotomimetic, Perceptual, Cognitive, and Neuroendocrine Responses", Arch Gen Psychiatry, 1994, 51(3), 199-214.
Kubo et al., "Structural Basis for a Ca2+-Sensing Function of the Metabotropic Glutamate Receptors", Science, 1998, 279(5357), 1722-1725.
Kubokawa et al., "Cloning and Characterization of a Bifunctional Metabotropic Receptor Activated by Both Extracellular Calcium and Glutamate", Febs Letters, 1996, 392(1), 71-76.
Kucukibrahimoglu et al., "The Change in Plasma Gaba, Glutamine and Glutamate Levels in Fluoxetine- or S-Citalopram-Treated Female Patients with Major Depression", Eur J Clin Pharmacol, 2009, 65(6), 571-577.
Kufahl et al., "Enhanced Sensitivity to Attenuation of Conditioned Reinstatement by the Mglur2/3 Agonist Ly379268 and Increased Functional Activity of Mglur2/3 in Rats with a History of Ethanol Dependence", Neuropsychopharmacology, 2011, 1-12.
Kugaya et al., "Beyond Monoamines: Glutamatergic Function in Mood Disorders", CNS Spectr, 2005, 10, 808-819.
Kullmann et al., "Extrasynaptic Glutamate Spillover in the Hippocampus: Evidence and Implications", Trends Neurosci., 1998, 21(1), 8-14.
Kunishima et al., "Structural Basis of Glutamate Recognition by a Dimeric Metabotropic Glutamate Receptor", Nature, 2000, 407, 971-977.
Kuo, "Allosteric Cofactor-Mediated Enzyme Cooperativity: A Theoretical Treatment", Proc. Natl. Acad. Sci. USA, Sep. 1983, 80, 5243-5247.
Kurita et al., "Hdac2 Regulates Atypical Antipsychotic Responses through the Modulation of Mglu2 Promoter Activity", Nature Neuroscience, 2012, 15(9), 1245-1254.
Kurumaji et al., "Effects of Mk-801 Upon Local Cerebral Glucose Utilization in Conscious Rats and in Rats Anaesthetized with Halothane",J Cereb Blood Flow Metab, 1989, 9, 786-794.
Lahti et al., "Ketamine Activates Psychosis and Alters Limbic Blood Flow in Schizophrenia", Neuroreport, 1995, 6(6), 869-872.
Lam et al., "Effects of the Selective Metabotropic Glutamate Agonist Ly354740 in a Rat Model of Permanent Ischaemia", Neuroscience Letters, 1998, 254(2), 121-123.
Lambeng et al., "Selective Mglur2 Negative Allosteric Modulators Reverse the Scopolamine-Induced Memory Deficit in the Novel Object Recognition Test", Society for Neuroscience 40th Annual Meeting, Nov. 2010, 1 page.
Lambert et al., "Current Issues in Schizophrenia: Overview of Patient Acceptability, Functioning Capacity and Quality of Life", CNS Drugs, 2004,18(Suppl 2), 5-17.
Lamers et al., "Comorbidity Patterns of Anxiety and Depressive Disorders in a Large Cohort Study: the Netherlands Study of Depression and Anxiety (Nesda)", J Clin Psychiatry, 2011, 72(3), 341-348.
Landen et al., "A Randomized, Double-Blind, Placebo-Controlled Trial of Buspirone in Combination with an Ssri in Patients with Treatment-Refractory Depression", J Clin Psychiatry, 1998, 59, 664-668.
Landin et al., "The Impact of Restrictive Entry Criterion During the Placebo Lead-in Period", Biometrics, 2000, 56, 271-278.
Lane et al., "Bridging the Gap: Bitopic Ligands of G-Protein-Coupled Receptors", Trends in Pharmacological Sciences, Jan. 2013, 34(1), 59-66.
Lang et al., "Molecular Mechanisms of Depression Perspective on New Treatment Strategies", Cell Physiol Biochem, 2013, 31, 761-777.
Lang et al., "Molecular Mechanisms of Schizophrenia", Cell Physiol Biochem., 2007, 20(6), 687-702.
Langmead, "Ligand Properties and Behaviours in an Allosteric Age", Trends Pharmacol Sci, 2012, 33, 621-622.

(56) References Cited

OTHER PUBLICATIONS

Langmead, "Screening for Positive Allosteric Modulators: Assessment of Modulator Concentration-Response Curves as a Screening Paradigm", Journal of Biomolecular Screening, 2007, 668-676.
Large, "Do NMDA Receptor Antagonist Models of Schizophrenia Predict the Clinical Efficacy of Antipsychotic Drugs?", J Psychopharmacol, 2007, 21, 283-301.
Larsson et al., "Neurochemical and Behavioral Studies on Ethanol and Nicotine Interactions", Neuroscience and Biobehavioral Reviews, 2004, 27, 713-720.
Laruelle et al., "Glutamate, Dopamine, and Schizophrenia: From Pathophysiology to Treatment", Ann Ny Acad Sci, 2003, 1003, 138-158.
Laruelle et al., "Relationships Between Radiotracer Properties and Image Quality in Molecular Imaging of the Brain with Positron Emission Tomography", Mol Imaging Biol, 2003, 5, 363-375.
Larzabal et al., "Distribution of the Grlup II Metabotropic Glutamate Receptors (Mglur2/3) in the Enteric Nervous System of the Rat", Neuroscience Letters, 1999, 276, 91-94.
Laughren et al., "Food and Drug Administration Perspective on Negative Symptoms in Schizophrenia as a Target for a Drug Treatment Claim", Schizophr Bull., 2006, 32(2), 220-222.
Laughren, "The Scientific and Ethical Basis for Placebo-Controlled Trials in Depression and Schizophrenia: An Fda Perspective", Eur Psychiatry, 2001, 16, 418-423.
Lavreysen et al., "[$^3$h]R214127: A Novel High-Affinity Radioligand for the Mglu1 Receptor Reveals a Common Binding Site Shared by Multiple Allosteric Antagonists", Mol Pharmacol, 2003, 63, 1082-1093.
Lavreysen et al., "A Study on the Molecular Interaction Between Mglu2 Receptor Agonists and Positive Allosteric Modulators", International Meeting on Metabotropic Glutamate Receptors, Poster, Sep. 2008, 1 page.
Lavreysen et al., "A Study on the Molecular Interaction Between Mglu2 Receptor Agonists and Positive Allosteric Modulators" Poster, Society for Neuroscience Annual Meeting, 2009, 1 page.
Lavreysen et al., "JNJ16259685, A Highly Potent, Selective and Systemically Active Mglu1 Receptor Antagonist" Neuropharmacology 2004, 47, 961-972.
Lavreysen et al., "JNJ-40068782: A Novel Potent, Selective and Systemically Active Positive Allosteric Modulator of the Mglu2 Receptor" Abstract, Society for Neuroscience Annual Meeting, 2010, 1 page.
Lavreysen et al., "Pharmacological Characterization of JNJ-40068782, A New Potent, Selective, and Systemically Active Positive Allosteric Modulator of the Mglu2 Receptor and Its Radioligand [3h]Jnj-40068782", J Pharmacol Exp Ther, Sep. 2013, 346, 514-527.
Lavreysen et al., "Therapeutic Potential of Group III Metabotropic Glutamate Receptors", Current Medicinal Chemistry, 2008, 15, 671-684.
Lavreysen, "The Development of Mglu2 Pams: Identification of JNJ-40068782 as a Novel Tool Compound", Allosteric Modulator Drug Discovery Congress, Nov. 2010, 34 pages.
Leach et al., "Allosteric Gpcr Modulators: Taking Advantage of Permissive Receptor Pharmacology", Trends in Pharmacological Sciences, 2007, 28(8), 382-389.
Leach et al., "Quantification of Allosteric Interactions Unit 1.22 at G Protein-Coupled Receptors Using Radioligand Binding Assays", Current Protocols in Pharmacology, Mar. 2011, 1.22.1-1.22.41.
Leber, "Observations and Suggestions on Antidementia Drug Development", Alzheimer Disease and Associated Disorders, 1996, 10 (Suppl 1), 31-35.
Lebois, "Neither Typical Nor Atypical: Ly404039 Provides Proof of Concept That Selective Targeting of Mglur2/3 Receptors is a Valid Mechanism for Obtaining Antipsychotic Efficacy", Curr. Top. Med. Chem., 2008, 8(16), 1480-1481.
Lecci et al., "Pharmacological Validation of a Novel Animal Model of Anticipatory Anxiety in Mice", Psychopharmacology, 1990, 101, 255-261.
Lee et al., "Amyloid Precursor Protein Processing is Stimulated by Metabotropic Glutamate Receptors", National Academy of Sciences USA, 1995, 92(17), 8083-8087.
Lee et al., "Characterization of the Inward Current Induced by Metabotropic Glutamate Receptor Stimulation in Rat Ventromedial Hypothalamic Neurones", Journal of Physiology, 1997, 504(Pt 3), 649-663.
Lee et al., "Glutamategic Afferent Projections to the Dorsal Raphe Nucleus of the Rat", Brain Res, 2003, 963, 57-71.
Lee et al., "Low Doses of Cannabinoids Enhance the Antinociceptive Effects of Intracisternally Administered Mglurs Groups II and III Agonists in Formalin-Induced Tmj Nociception in Rats", Pain, 2008, 139(2), 367-375.
Lee et al., "The Effect of Mglur2 Activation on Signal Transduction Pathways and Neuronal Cell Survival", Brain Res., 2009, 1249, 244-250.
Lee et al., "The Mglu2/3 Receptor Agonist Ly354740 Suppresses Immobilization Stress-Induced Increase in Rat Prefrontal Cortical Bdnf Mrna Expression", Neuroscience Letters, 2006, 398, 328-332.
Leeson et al., "The Influence of Drug-Like Concepts on Decision-Making in Medicinal Chemistry", Nat Rev Drug Discovery, 2007, 6, 881-890.
Leever et al., "Identification of a Site in Glur1 and Glur2 That is Important for Modulation of Deactivation and Desensitization", Mol Pharmacol, 2003, 64(1), 5.
Lennon et al., "Metabotropic Glutamate Receptor Mglu2 is Resistant to Homologous Agonist-Induced Desensitization But Undergoes Protein Kinase C-Mediated Heterologous Desensitization", Eur J Phamacol, 2010, 649, 29-37.
Lenox et al., "Mechanism of Action of Antidepressants and Mood Stabilizers" Neuropsychopharmacology: Tthe Fifth Generation of Progress, American College of Neuropsychopharmacology, 2002, 1139-1163.
Leo et al., "The Application of Nuclear Magnetic Resonance-Based Metabonomics to the Dominant-Submissive Rat Behavioral Model", Analytical Biochemistry, 2005, 339, 174-178.
Lerner et al., "The Work Limitations Questionnaire", Med Care, 2001, 39(1), 72-85.
Leucht et al., "Second-Generation Versus First-Generation Antipsychotic Drugs for Schizophrenia: A Meta-Analysis", Lancet, 2009, 373(9657), 31-41.
Levitt et al., "Optical Control of Metabotropic Glutamate Receptors", Nature Neuroscience, 2013, 16(4), 507-516.
Lewis et al., "Cognitive Dysfunction in Schizophrenia: Convergence of Gamma-Aminobutyric Acid and Glutamate Alterations", Arch. Neurol., 2006, 63(10), 1372-1376.
Lewis, "The Molecular Choreography of a Store-Operated Calcium Channel", Nature, 2007, 446, 284-287.
Leysen et al., "[3h]Ketanserin (R 41 468), A Selective 3h-Ligand for Serotonin2 Receptor Binding Sites. Binding Properties, Brain Distribution, and Functional Role", Molecular Pharmacology, 1982, 21(2), 301-314.
Leysen et al., "Receptor Interactions of New Antipsychotics: Relation to Pharmacodynamics and Clinical Effects", Intl Journal of Psychiatry in Clinical Practice, 1998, 2, S3-S17.
Li et al., "Design and Synthesis of 4-Arylpiperidinyl Amide and N-Arylpiperdin-3-Yl-Cyclopropane Carboxamide Derivatives As Novel Melatonin Receptor Ligands", Bioorganic & Medicinal Chemistry Letters, 2011, 21, 1236-1242.
Li et al., "Evaluation of the Motor Initiation Hypothesis of Apd-Induced Conditioned Avoidance Decreases", Pharmacol. Biochem. Behav., 2004, 78, 811-819.
Lieberman et al., "A Randomized, Placebo-Controlled Study of Memantine as Adjunctive Treatment in Patients with Schizophrenia", Neuropsychopharmacology, 2009, 34, 1322-1329.
Lieberman et al., "Antipsychotic Drugs: Comparison in Animal Models of Efficacy, Neurotransmitter Regulation, and Neuroprotection", Pharmacol. Rev, 2008, 60(3), 358-403.
Lieberman et al., "Effectiveness of Antipsychotic Drugs in Patients with Chronic Schizophrenia", N Engl J Med., 2005, 353(12), 1209-1223.
Lieberman, "Serotonergic Basis of Antipsychotic Drug Effects in Schizophrenia", Biol. Psychiatry, 1998, 44, 1099-1117.

(56) References Cited

OTHER PUBLICATIONS

Liebowitz et al., "Biological Accompaniments of Lactate-Induced Panic", Psychopharmacology Bulletin, 1984, 20(1), 43-44.
Liebowitz et al., "Lactate Provocation of Panic Attacks. I. Clinical and Behavioral Findings", Archives of General Psychiatry, 1984, 41(8), 764-70.
Liechti et al., "Interactive Effects of the Mglu5 Receptor Angatonist Mpep and the Mglu2/3 Receptor Antagonist Ly341495 on Nicotine Self-Administration and Reward Deficits Associated with Nicotine Withdrawal in Rats", European Journal of Pharmacology, 2007, 554, 164-174.
Liechti et al., "Metabotropic Glutamate 2/3 Receptor Activation Induced Reward Deficits But Did Not Aggravate Brain Reward Deficits Associated with Spontaneous Nicotine Withdrawal in Rats", Biochemical Pharmacology, 2007, 74, 1299-1307.
Liechti et al., "Metabotropic Glutamate 2/3 Receptors in the Ventral Tegmental Area and the Nucleus Accumbens Shell are Involved in Behaviors Relating to Nicotine Dependence", Journal of Neuroscience, 2007, 27(34), 9077-9085.
Liechti et al., "Role of the Glutamatergic System in Nicotine Dependence Implications for the Discovery and Development of New Pharmacological Smoking Cessation Therapies", CNS Drugs, 2008, 22(9), 705-724.
Lilly, "Stops Phase III Development of Pomaglumetad Methionil for the Treatment of Schizophrenia Based on Efficacy Results", Press Release, Aug. 29, 2012, 1 page.
Lin et al., "A Meta-Analytic Review of Double-Blind, Placebo-Controlled Trials of Antidepressant Efficacy of Omega-3 Fatty Acids", J Clin Psychiatry, 2007, 68(7), 1056-1061.
Lindemann et al., "Ctep: A Novel, Potent, Long-Acting, and Orally Bioavailable Metabotropic Glutamate Receptor 5 Inhibitor", Jpet, 2011, 339, 474-486.
Linden et al., "Anxiolytic Activity of the Mglu2/3 Receptor Agonist Ly354740 on the Elevated Plus Maze is Associated with the Suppression of Stress-Induced C-Fos in the Hippocampus and Increases in C-Fos Induction in Several Other Stress-Sensitive Brain Regions", Neuropsychopharmacology, 2004, 29, 502-513.
Linden et al., "Comparison of C-Fos Induction in the Brain by the Mglu2/3 Receptor Antagonist Ly341495 and Agonist Ly354740: Evidence for Widespread Endogenous Tone at Brain Mglu2/3 Receptors In Vivo", Neuropharmacology, 2005, 49(Suppl 1), 120-134.
Linden et al., "Effects of Mglu2 or Mglu3 Receptor Deletions on Mglu2/3 Receptor Agonist (Ly354740)-Induced Brain C-Fos Expression: Specific Roles for Mglu2 in the Amygdala and Subcortical Nuclei, and Mglu3 in the Hippocampus", Neuropharmacology, 2006, 51, 213-228.
Linden et al., "Use of Mglur2 and Mglur3 Knockout Mice to Explore In Vivo Receptor Specificity of the Mglur2/3 Selective Agonist Ly341495", Neuropharmacology, 2009, 57, 172-182.
Lindsley et al., "Progress Towards Validating the NMDA Receptor Hypofunction Hypothesis of Schizophrenia", Current Topics in Medicinal Chemistry, 2006, 6, 771-785.
Linn et al., "Activation of Metabotropic Glutamate Receptors Modulates the Voltage-Gated Sustained Calcium Current in a Teleost Horizontal Cell", Journal of Neurophysiology, 1999, 81(2), 425-434.
Lissin et al., "An Immunocytochemical Assay for Activity-Dependent Redistribution of Glutamate Receptors from the Postsynaptic Plasma Membrane", Annals of the New York Academy of Sciences, 1999, 868, 550-553.
Liu et al., "A Unified Theory of Two-Stage Adaptive Designs", Theory and Methods, 2002, 97, 1034-1041.
Liu et al., "Doubly Randomized Delayed-Start Design for Enrichment Studies with Responders or Nonresponders", Journal of Biopharmaceutical Statistics, 2012, 22(4), 737-757.
Liu et al., "Ischemic Insults Direct Glutamate Receptor Subunit 2-Lacking AMPA Receptors to Synaptic Sites", Journal of Neuroscience, May 17, 2006, 26(20), 5309-5319.
Liu et al., "Pharmacogenetic Analysis of the Mglu2/3 Agonist Ly2140023 Monohydrate in the Treatment of Schizophrenia", Pharmacogenomics Journal, 2010, 1-9.

Lopez-Rodriguez et al., "Changes in Extracellular Glutamate Levels in Rat Orbitofrontal Cortext During Sleep and Wakefulness", Arch Med Res, 2007, 38, 52-55.
Lorenzetti et al., "Structural Brain Abnormalities in Major Depressive Disorder: A Selective Review of Recent MRI Studies", J Affect Disord, 2009, 117(1-2), 1-17.
Lorrain et al., "Group II Mglu Receptor Activation Suppresses Norepinephrine Release in the Ventral Hippocampus and Locomotor Responses to Acute Ketamine Challenge", Neuropsychopharmacology, 2003, 28, 1622-1632.
Lou et al., "Allosteric Modulation of the Presynaptic Ca2+ Sensor for Vesicle Fusion", Nature, 2005, 435, 497-501.
Lourenco et al., "Differential Distribution of Metabotropic Glutamate Receptor Subtype MRNAS in the Thalamus of the Rat", Brain Research, 2000, 854(1-2), 93-105.
Lowe et al., "Effects of a Novel Mglu2/3 Receptor Agonist Prodrug, Ly2140023 Monohydrate, on Central Monoamine Turnover as Determined in Human and Rat Cerebrospinal Fluid", Psychopharmacology, 2011, 1-12.
Lowry et al., "Serotonergic Systems, Anxiety, and Affective Disorder: Focus on the Dorsomedial Part of the Dorsal Raphe Nucleus", Annals of the New York Academy of Sciences, 2008, 1148, 86-94.
Lujan et al., "Glutamate and Gaba Receptor Signalling in the Developing Brain", Neuroscience, 2005, 130, 567-580.
Luscher et al., "Group I Mglur-Dependent Synaptic Long-Term Depression: Mechanisms and Implications for Circuitry and Disease", Neuron, 2010, 65, 445-459.
Lyon et al., "Altered Hippocampal Expression of Glutamate Receptors and Transporters in Grm2 and Grm3 Knockout Mice", Synapse, 2008, 62, 842-850.
Lyon et al., "Fractionation of Spatial Memory in Grm2/3 (Mglu2/Mglu3) Double Knockout Mice Reveals a Role for Group II Metabotropic Glutamate Receptors at the Interface Between Arousal and Cognition", Neuropsychopharmacology, 2011, 1-13.
Macchiarulo et al., "The Role of Electrostatic Interaction in the Molecular Recognition of Selective Agonists to Metabotropic Glutamate Receptors", Proteins, 2003, 50(4), 609-619.
Macdonald "The Design of Allosteric Modulators for the Treatment of CNS Disorders", $11^{th}$ Advances and Progress in Drug Design, Feb. 2012, 36 pages.
Macdonald, "The Design of Mglur Modulators for the Treatment of CNS Disorders" Presentation Slides, $6^{th}$ Anglo-Swedish Medicinal Chemistry Symposium, Stockholm, Jun. 19, 2013.
Macdonald, "Positive Allosteric Modulation of Mglur2 Receptors in the Treatment of CNS Disorders", $3^{rd}$ Symposium on GPCRS in Medicinal Chemistry, Oss, Sep. 2010, 29 pages.
Macek et al., "Differential Involvement of Group II and Group III Mglurs as Autoreceptors at Lateral and Medial Perforant Path Synapses", J Neurophysiol, 1996, 76(6), 3798-3806.
Macek et al., "Protein Kinase C and A3 Adenosine Receptor Activation Inhibit Presynaptic Metabotropic Glutamate Receptor (Mglur) Function and Uncouple Mglurs from Gtp-Binding Proteins", J. Neurosci., 1998, 18(16), 6138-6146.
Mackrill, "Protein-Protein Interactions in Intracellular Ca2+-Release Channel Function", Biochemical Journal, 1999, 337(Pt 3), 345-361.
Maeda et al., "Different Roles of Group I and Group II Metabotropic Glutamate Receptors on Phencyclidine-Induced Dopamine Release in the Rat Prefrontal Cortex", Neuroscience Letters, 2003, 336 (3), 171-174.
Maione et al., "Characterisation of Mglurs Which Modulate Nociception in the Pag of the Mouse", Neuropharmacology,1998, 37(12), 1475-1483.
Makoff et al., "Molecular Characterization and Localization of Human Metabotropic Glutamate Receptor Type 3", Molecular Brain Research, 1996, 40(1), 55-63.
Malatynska et al., "Assessing Activity Onset Time and Efficacy for Clinically Effective Antidepressant and Antimanic Drugs in Animal Models Based on Dominant-Submissive Relationships", Neuroscience and Biobehavioral Reviews, 2007, 31, 904-919.
Malatynska et al., "Dominant-Submissive Behavior As Models of Mania and Depression", Neuroscience and Biobehavioral Reviews, 2005, 29(4-5), 715-37.

(56) References Cited

OTHER PUBLICATIONS

Malatynska et al., "Levels of Mrna for A-, B-, and Γ-Synuclein in the Brains of Newborn, Juvenile, and Adult Rats", J Mol Neurosci., 2006, 29(3), 269-77.

Malatynska et al., "Reduction of Dominant or Submissive Behaviors as Models for Antimanic or Antidepressant Drug Testing: Technical Considerations", J Neurosci Methods, 2007, 165(2), 175-182.

Malatynska et al., "Submissive Behavior in Mice as a Test for Antidepressant Drug Activity", Pharmacol Biochem Behavior, 2005, 82, 306-313.

Malenka et al., "Ltp and Ltd: An Embarrassment of Riches", Neuron, 2004, 44, 5-21.

Malherbe et al., "Identification of Essential Residues Involved in the Glutamate Binding Pocket of the Group II Metabotropic Glutamate Receptor", Molecular Pharmacology., 2001, 60 (5), 944-954.

Malherbe et al., "Opposite Effects of Zn on the In Vitro Binding of [3h]Ly354740 to Recombinant and Native Metabotropic Glutamate 2 and 3 Receptors", J Neurochem., 2005, 94(1), 150-160.

Malhi et al., "Recognizing the Anxious Face of Depression", Journal of Nervous and Mental Disease, 2002, 190(6), 366-73.

Malhotra et al., "NMDA Receptor Function and Human Cognition: The Effects of Ketamine in Healthy Volunteers", Neuropsychopharmacology, May 1996, 14(5), 301-307.

Mansbach et al., "Blockade of Potentiated Startle Responding in Rats by 5-Hydroxytryptamine1a Receptor Ligands", Eur. J. Pharmacology, 1988, 156, 375-383.

Marcus et al., "The Efficacy and Safety of Aripiprazole as Adjunctive Therapy in Major Depressive Disorder: A Second Multicenter, Randomized, Double-Blind, Placebo-Controlled Study", Journal of Clinical Psychopharmacology, 2008, 28(2), 156-165.

Marek, "Metabotropic Glutamate2/3 (Mglu2/3) Receptors, Schizophrenia and Cognition", European Journal of Pharmacology, 2010, 639, 81-90.

Marek et al., "5-Hydroxytryptamine2a (5-Ht2a) Receptor Regulation in Rat Prefrontal Cortex: Interaction of a Phenethylamine Hallucinogen and the Metabotropic Glutamate2/3 Receptor Agonist Ly354740", Neuroscience Letters, 2006, 403(3), 256-260.

Marek et al., "Glutamatergic (N-Methyl-D-Aspartate Receptor) Hypofrontality in Schizophrenia: Too Little Juice or a Miswired Brain?", Molecular Pharmacology, 2010, 77(3), 317-326.

Marek et al., "Physiological Antagonism Between 5-Hydroxytryptamine2a and Group II Metabotropic Glutamate Receptors in Prefrontal Cortex", J. Pharm. Exper. Therapeut., 2000, 292, 76-87.

Marek et al., "The Electrophysiology of Prefrontal Serotonin Systems: Therapeutic Implications for Mood and Psychosis", Biol Psychiatry, 1998, 44, 1118-1127.

Marek, "Metabotropic Glutamate 2/3 Receptors as Drug Targets", Curr. Opin. Pharmacol., 2004, 4, 18-22.

Markou, "The Role of Metabotropic Glutamate Receptors in Drug Reward, Motivation and Dependence", Drug News Perspect, 2007, 20(2), 103-108.

Martella et al., "Enhanced Sensitivity to Group II Mglu Receptor Activation at Corticostriatal Synapses in Mice Lacking the Familial Parkinsonism-Linked Genes Pink1 or Parkin.", Exp. Neurol., 2009, 215(2), 388-396.

Martin et al., "Cellular Localization of a Metabotropic Glutamate Receptor in Rat Brain", Neuron, 1992, 9(2), 259-270.

Martin et al., "Cross-Talk Between Beta-Adrenergic and Metabotropic Glutamate Receptors in Rat C6 Glioma Cells", Biochimica Et Biophysica Acta, 1998, 1393(1), 186-192.

Masu et al., "Sequence and Expression of a Metabotropic Glutamate Receptor", Nature, 1991, 349(6312), 760-765.

Matrisciano et al., "Activation of Group-II Metabotropic Glutamate Receptors Promotes DNA Demethylation in the Mouse Brain", Molecular Pharmacology, Apr. 2011, 52 pages.

Matrisciano et al., "Defective Group-II Metaboropic Glutamate Receptors in the Hippocampus of Spontaneously Depressed Rats", Neuropharmacology, 2008, 55(4), 525-531.

Matrisciano et al., "Group-II Metabotropic Glutamate Receptor Ligands as Adjunctive Drugs in the Treatment of Depression: A New Strategy to Shorten the Latency of Antidepressant Medication?", Molecular Psychiatry, 2007, 12, 704-706.

Matrisciano et al., "Imipramine Treatment Up-Regulates the Expression and Function of Mglu2/3 Metabotropic Glutamate Receptors in the Rat Hippocampus", Neuropharmacology, 2002, 42(8), 1008-1015.

Maurel et al., "Cell-Surface Protein-Protein Interaction Analysis with Time-Resolved Fret and Snap-Tag Technologies: Application to Gpcr Oligomerization", Nat Methods, 2008, 5(6), 561-567.

Maxwell et al., "Ketamine Produces Lasting Disruptions in Encoding of Sensory Stimuli", J Pharmacol Exp Ther, 2006, 316, 315-324.

May et al., "Allosteric Modulation of G Protein-Coupled Receptors", Annu Rev Pharmacol Toxicol, 2007, 47, 14.1-14.51.

May et al., "Regional Serotonin Receptor Studies: Chronic Methysergide Treatment Induces a Selective and Dose-Dependent Decrease in Serotonin-2 Receptors in Mouse Cerebral Cortex", Life Sciences, 1986, 38(19), 1741-1747.

Mayers et al., "Antidepressants and Their Effect on Sleep", Hum Psychopharmacol., 2005, 20, 5333-559.

McClintock et al., "Assessing Anxious Features in Depressed Outpatients" Int. J. Methods Psychiatr. Res., 2011, 20(4), E69-E82.

McDermott et al., "Design and Analysis of Two-Period Studies of Potentially Disease-Modifying Treatments", Controlled Clinical Trials, 2002, 23, 635-649.

McEvoy et al., "Effectiveness of Clozapine Versus Olanzapine, Quetiapine, and Risperidone in Patients with Chronic Schizophrenia Who Did Not Respond to Prior Atypical Antipsychotic Treatment", Am J Psychiatry, 2006, 163(4), 600-610.

McIntyre et al., "Quetiapine Adjunct to Selective Serotonin Reuptake Inhibitors or Venlafaxine in Patients with Major Depression, Comorbid Anxiety, and Residual Depressive Symptoms: A Randomized, Placebo-Controlled Pilot Study", Depression and Anxiety, 2007, 24, 487-494.

Meador-Woodruff et al., "Glutamate Receptor Expression in Schizophrenic Brain", Brain Res., 2000, 31(2-3), 288-294.

Melancon et al., "Allosteric Modulation of 7 Transmembrane Spanning Receptors: Theory, Practice and Opportunities for CNS Drug Discovery", J Med Chem, 2012, 55(4), 1445-1464.

Melartin et al., "Current Comorbidity of Psychiatric Disorders Among DSM-IV Major Depressive Disorder Patients in Psychiatric Care in the Vantaa Depression Study", J Clin Psychiatry, 2002, 63, 126-134.

Meldrum et al., "Excitatory Amino Acid Neurotoxicity and Neurodegenerative Disease", Trends in Pharmacological Sciences, 1990, 11(9), 379-387.

Meldrum et al. "Glutamate Receptors and Trasnporters in Genetic and Acquired Models of Epilepsy", Epilepsy Res, 1999, 36, 189-204.

Meltzer et al., "Serotonin Receptors: Their Key Role in Drugs to Treat Schizophrenia", Prog. Neuropsychopharmacol. Biol. Psychiatry, 2003, 27(7), 1159-1172.

Meltzer, "Illuminating the Molecular Basis for Some Antipsychotic Drug-Induced Metabolic Burden", Proc. Natl. Acad. Sci. USA, 2007, 104(9), 3019-3020.

Merikangas et al., "Longitudinal Trajectories of Depression and Anxiety in a Prospective Community Study", Arch Gen Psychiatry, 2003, 60, 993-1000.

Mezler et al., "Ly2140023, A Prodrug of the Group II Metabotropic Glutamate Receptor Agonist Ly-404039 for the Potential Treatment of Schizophrenia", Current Opinion in Investigational Drugs, 2010, 11(7), 833-845.

Michael et al., "Metabolic Changes Within the Left Dorsolateral Prefrontal Cortex Occurring with Electroconvulsive Therapy in Patients with Treatment Resistant Unipolar Depression", Psychol Med, 2003, 33(7), 1277-1284.

Michael et al., "Neurotrophic Effects of Eletroconvulsive Therapy: A Proton Magnetic Resonance Study of the Left Amygdalar Region in Patients with Treatment-Resistant Depression", Neuropsychopharmacology, 2003, 28(4), 720-725.

Miller, "Mechanisms of Action of Antipsychotic Drugs of Different Classes, Refractoriness to Therapeutic Effects of Classical

(56) References Cited

OTHER PUBLICATIONS

Neuroleptics, and Individual Variation in Sensitivity to Their Actions: Part I", Current Neuropharmacology, 2009, 7, 302-314.
Miller et al., "Roles of Metabotropic Glutamate Receptors in Brain Plasticity and Pathology", Annals of the New York Academy of Sciences, 1995, 757, 460-474.
Mills et al., "Epidemiology and Reporting of Randomized Trials Employing Re-Randomization of Patient Groups: A Systematic Survey", Contemporary Clinical Trials, 2007, 28, 268-275.
Mitchell et al., "An Update on the Role of Glutamate in the Pathophysiology of Depression", Acta Psychiatrica Scandinavica, 2010, 122(3), 192-210.
Mitri et al., "Divergent Evolution in Metabotropic Glutamate Receptors. A New Receptor Activated by an Endogenous Ligand Different from Glutamate in Insects", Journal of Biological Chemistry, 2004, 279(10), 9313-9320.
Mittal et al., "Impact of Comorbid Anxiety Disorders on Health-Related Quality of Live Among Patients with Major Depressive Disorder", Psychiatric Services, 2006, 57(12), 1731-1737.
Miuller et al., "The Immunological Basis of Glutamatergic Disturbance in Schizophrenia: Towards an Integrated View", J Neural Transm, 2007, 72, 269-280.
Miyamoto et al., "Effects of Ketamine, Mk-801, and Amphetamine on Regional Brain 2-Deoxyglucose Uptake in Freely Moving Mice", Neuropsychopharmacology, 2000, 22, 400-412.
Miyamoto et al., "Treatments for Schizophrenia: A Critical Review of Pharmacology and Mechanisms of Action of Antipsychotic Drugs", Mol. Psychiatry, 2005, 10, 79-104.
Modafferi "Morphine Withdrawal Increases Metabotropic Glutamate 2/3 Receptors Expression in Nucleus Accumbens", Neurochemistry, 2008, 19(9), 911-914.
Moffitt et al., "Depression and Generalized Anxiety Disorder", Arch. Gen. Psychiatry, 2007, 64, 651-660.
Moghaddam et al., "Activation of Glutamatergic Neurotransmission by Ketamine: A Novel Step in the Pathway from NMDA Receptor Blockade to Dopaminergic and Cognitive Disruptions Associated with the Prefrontal Cortex", J Neurosci. 1997, 17(8), 2921-2927.
Moghaddam et al., "From Revolution to Evolution: the Glutamate Hypothesis of Schizophrenia and Its Implication for Treatment", Neuropsychopharmacology, 2012, 37, 4-15.
Moghaddam et al., "Reversal of Phencyclidine Effects by a Group II Metabotropic Glutamate Receptor Agonist in Rats", Science, 1998, 281, 1349-1352.
Moldrich et al., "Anti-Epileptic Activity of Group II Metabotropic Glutamate Receptor Agonists (−)-2-Oxa-4-Aminobicyclo[3.1.0]Hexane-4,6-Dicarboxylate (Ly379268) and (−)-2-Thia-4-Aminobicyclo[3.1.0]Hexane-4,6-Dicarboxylate (Ly389795)", Neuropharmacology, 2001, 41, 8-18.
Moldrich et al., "Astrocyte Mglu(2/3)-Mediated Camp Potentiation is Calcium Sensitive: Studies in Murine Neuronal and Astrocyte Cultures", Neuropharmacology, 2002, 43(2), 189-203.
Moldrich et al., "Emerging Signalling and Protein Interactions Mediated Via Metabotropic Glutamate Receptors", Curr. Drug Targets. CNS Neurol. Disord., 2003, 2(2), 109-122.
Molina et al., "Polymorphic Variation at the Serotonin 1-A Receptor Gene is Associated with Comorbid Depression and Generalized Anxiety", Psychiatry Genetics, 2011, 21, 195-201.
Molinaro et al., "Activation of Mglu2/3 Metabotropic Glutamate Receptors Negatively Regulates the Stimulation of Inositol Phospholipid Hydrolysis Mediated by 5-Hydroxytryptamine2a Serotonin Receptors in the Frontal Cortex of Living Mice", Mol. Pharmacol., 2009, 76(2), 379-387.
Monn et al., "Design, Synthesis, and Pharmacological Characterization of (+)-2-Aminobicyclo[3.1.0]Hexane-2,6-Dicarboxylic Acid (Ly354740): A Potent, Selective, and Orally Active Group 2 Metabotropic Glutamate Receptor Agonist Possessing Anticonvulsant and Anxiolytic Properties", J Med Chem, 1997, 40, 528-537.
Monn et al., "Synthesis and Metabotropic Glutamate Receptor Activity of S-Oxidized Variants of (−)-4-Amino-2-Thiabicyclo-[3.1.0]Hexane-4,6-Dicarboxylate: Identification of Potent, Selective, and Orally Bioavailable Agonists for Mglu2/3 Receptors", J. Med. Chem., 2007, 50, 233-240.
Monti et al., "Conventional and Power Spectrum Analysis of the Effects of Zolpidem on Sleep Eeg in Patients with Chronic Primary Insomnia", Sleep, 2000, 23, 1075-1084.
Mora et al., "Role of 5-Ht2a and 5-Ht2c Receptor Subtypes in the Two Types of Fear Generated by the Elevated T-Maze", Pharmacology Biochemistry and Behavior, 1997, 58, 1051-1057.
Moreno et al., "Group II Metabotropic Glutamate Receptors and Schizophrenia", Cell Mol. Life Sci., 2009, 66(23), 3777-3785.
Moreno et al., "Maternal Influenza Viral Infection Causes Schizophrenia-Like Alterations of 5-Ht2a and Mglu2 Receptors in the Adult Offspring", Journal of Neuroscience, 2011, 31(5), 1863-1872.
Moreno et al., "Metabotropic Glutamate Mglu2 Receptor is Necessary for the Pharmacological and Behavioral Effects Induced by Hallucinogenic 5-Ht2a Receptor Agonists", Neurosci. Lett., 2011, 493, 76-79.
Moreno et al., "Pindolol Augmentation of Treatment-Resistant Depressed Patients" J Clin Psychiatry 1997, 58, 437-439.
Morgan et al., "Is Persistent Ketamine Use a Valid Model of the Cognitive and Oculomotor Deficits in Schizophrenia?", Biol. Psychiatry, 2009, 65(12), 1099-1102.
Morikawa et al., "Two Intracellular Pathways Mediate Metabotropic Glutamate Receptor-Induced Ca2+ Mobilization in Dopamine Neurons", Journal of Neuroscience, 2003, 23(1), 149-157.
Morishima et al., "Enhanced Cocaine Responsiveness and Impaired Motor Coordination in Metabotropic Glutamate Receptor Subtype 2 Knockout Mice", Proc. Natl. Acad. Sci., 2005, 102(11), 4170-4175.
Morishita, "Clonazepam as a Therapeutic Adjunct to Improve the Management of Depression: A Brief Review", Hum Psychopharmacol Clin Exp, 2009, 24, 191-198.
Morpurgo et al., "Drug-Induced Modifications of Discriminated Avoidance Behavior in Rats", Psychopharmacol., 1965, 8, 91-99.
Morrison et al., "Schizophrenia: More Evidence for Less Glutamate", Expert Rev Neurother., 2007, 7 (1), 29-31.
Moussawi et al., "Group II Metabotropic Glutamate Receptors (Mglu2/3) in Drug Addiction", European Journal of Pharmacology, 2010, 639, 115-122.
Mudge et al., "Genomic Convergence Analysis of Schizophrenia: Mrna Sequencing Reveals Altered Synaptic Vesicular Transport in Post-Mortem Cerebellum", Plos One, 2008, 3(11) 1-24.
Mukhin et al., "Mglur Modulation of Post-Traumatic Neuronal Death: Role of NMDA Receptors", Neuroreport, 1997, 8(11), 2561-2566.
Muller, "Inflammation and the Glutamate System in Schizophrenia: Implications for Therapeutic Targets and Drug Development", Expert Opin. Ther. Targets, 2008, 12(12), 1497-1507.
Muly et al., "Group II Metabotropic Glutamate Receptors in Anxiety Circuitry: Correspondence of Physiological Response and Subcellular Distribution", J Comp Neurol., 2007, 505(6), 682-700.
Muntasir et al., "Inverse Agonist Activity of Sarpogrelate, A Selective 5-Ht2a-Receptor Antagonist, at the Constitutively Active Human 5-Ht2a Receptor", Journal of Pharmacological Sciences, 2006, 102(2), 189-195.
Murck et al., "State Markers of Depression in Sleep Eeg: Dependency on Drug and Gender in Patients Treated with Tianepine or Paroxetine", Neuropsychopharmacol. 2003, 28, 348-358.
Muto et al., "Structures of the Extracellular Regions of the Group II/III Metabotropic Glutamate Receptors", Proc. Natl. Acad. Sci. USA, 2007, 104(10), 3759-3764.
Nabeshima et al., "Animal Model of Schizophrenia. Dysfunction of Nmda Receptor-Signaling in Mice Following Withdrawal from Repeated Administration of Phencyclidine", Ann. N.Y. Acad. Sci., 2006, 1086, 160-168.
Naimoli et al., "Compound A, A Novel Potent and Selective Mglur2 Positive Allosteric Modulator: III. Effects in Clinically Relevant Translational Cognition Models That Could be Used as Biomarkers" Poster 767.1 Presented at the 40th Annual Meeting of Society for Neuroscience, Nov. 2010, 1 page.
Nasca et al., "L-Acetylcarnitine Causes Rapid Antidepressant Effects Through the Epigenetic Induction of Mglu2 Receptors", Proceedings of the Nat. Acad. of Sci. of US, 2013, 110(12), 4804-4809.

(56) References Cited

OTHER PUBLICATIONS

Neale, "The Neurotransmitter N-Acetylaspartylglutamate in Models of Pain, Als, Diabetic Neuropathy CNS Injury and Schizophrenia", Trends in Pharmacological Sciences 2005, 26(9), 477-484.
Neki et al., "Metabotropic Glutamate Receptors Mglur2 and Mglur5 are Expressed in Two Non-Overlapping Populations of Golgi Cells in the Rat Cerebellum", Neuroscience, 1996, 75(3), 815-826.
Neki et al., "Pre- and Postsynaptic Localization of a Metabotropic Glutamate Receptor, Mglur2, in the Rat Brain: An Immunohistochemical Study with a Monoclonal Antibody", Neurosci. Lett., 1996, 202(3), 197-200.
Nelson, "Anxiety Does Not Predict Response to Duloxetine in Major Depression: Results of a Pooled Analysis of Individual Patient Data From 11 Placebo-Controlled Trials", Depression and Anxiety, 2010, 27, 12-18.
Nelson et al., "Anxiety Does Not Predict Response to Antidepressant Treatment in Late Life Depression: Results of a Meta-Analysis", Int J Geriatr Psychiatry, 2009, 24, 539-544.
Nelson et al., "Species Differences in the Pharmacology of the 5-Hydroxytrayptamine2 Receptor: Structurally Specific Differentiation by Ergolines and Tryptamines", Jpet, 1993, 265, 1272-1279.
Nelson, "Anxious Depression and Response to Treatment", Am J Psychiatry, 2008, 165(3), 297-299.
Neubig et al., "Specificity of Receptor-G Protein Coupling: Protein Structure and Cellular Determinants", Seminars in Neuroscience, 1998, 9, 189-197.
Neugebauer et al., "Groups II and III Metabotropic Glutamate Receptors Differentially Modulate Brief and Prolonged Nociception in Primate Stt Cells", J Neurophysiol, 2000, 84, 2998-3009.
Neugebauer et al., "Peripheral Metabotropic Glutamate Receptors as Drug Targets for Pain Relief", Expert Opinion on Therapeutic Targets, 2002, 6(3), 349-361.
Neugebauer et al., "Requirement of Metabotropic Glutamate Receptors for the Generation of Inflammation-Evoked Hyperexcitability in Rat Spinal Cord Neurons", European Journal of Neuroscience, 1994, 6(7), 1179-1186.
Neugebauer, "Metabotropic Glutamate Receptors—Important Modulators of Nociception and Pain Behavior", Pain, 2002, 98, 1-8.
"Neuroprotection As Initial Therapy in Acute Stroke", Third Report of an Ad Hoc Consensus Group Meeting, European Ad Hoc Consensus Group, Cerebrovascular Diseases 1998, 8(1), 59-72.
Ngomba et al., "Metabotropic Glutamate Receptors in the Thalamocortical Network: Strategic Targets for the Treatment of Absence Epilepsy", Epilepsia, 2011, 52(7), 1211-1222.
Ngomba et al., "The Preferential Mglu2/3 Receptor Antagonist, Ly341495, Reduces the Frequency of Spike-Wave Discharges in the Wag/Rij Rat Model of Absence Epilepsy", Neuropharmacology, 2005, 49, 89-103.
Nguyen et al., "An in Vivo Biosensor for Neurotransmitter Release and In Situ Receptor Activity", Nature Neuroscience, 2010, 13(1), 127-32.
Nicholls et al., "Mglur2 Acts Through Inhibitory G? Subunits to Regulate Transmission and Long-Term Plasticity at Hippocampal Mossy Fiber-Ca3 Synapses", Proc. Natl. Acad. Sci. USA, 2006, 103(16), 6380-6385.
Nicholls et al., "The Release and Uptake of Excitatory Amino Acids", Trends in Pharmacological Sciences, 1990, 11(11), 462-468.
Nicolas et al., "A Combined Marble Buyring-Locomotor Activity Test in Mice: A Practical Screening Test with Sensitivity to Different Classes of Anxiolytics and Antidepressants", Eur J Pharmacol., 2006, 547(1-3), 106-115.
Nicoletti et al., "Lesions of Putative Glutamatergic Pathways Potentiate the Increase of Inositol Phospholipid Hydrolysis Elicited by Excitatory Amino Acids", Brain Research, 1987, 436(1), 103-112.
Nicoletti et al., "Metabotropic Glutamate Receptors: Beyond the Regulation of Synaptic Transmission", Psychoneuroendocrinology, 2007, 32(Suppl 1), S40-S45.
Nicoletti et al., "Metabotropic Glutamate Receptors: from the Workbench to the Bedside", Neuropharmacology, 2011, 60, 1017-1041.
Nicoletti et al., "Metabotropic Glutamate Receptors: New Targets for the Control of Tumor Growth", Trends in Pharmacological Sciences, 2007, 206-213.
Nicoletti et al., "Pertussis Toxin Inhibits Signal Transduction at a Specific Metabolotropic Glutamate Receptor in Primary Cultures of Cerebellar Granule Cells", Neuropharmacology, 1988, 27(6), 551-556.
Niemegeers et al., "Direct Measurement of the Ph in the Stomach of the Conscious Rat, Using a Special Electrode", Experentia, 1979, 35, 1538-1539.
Niemegeers et al., "Interaction of Drugs with Apomorphine, Tryptamine, and Norepinephrine. A New 'in Vivo' Approach: the Atn-Test in Rats", Arch. Int. Pharmacodyn., 1977, 227, 238-253.
Niemegeers et al., "Protection of Rats from Compound 48/80-Induced Lethality. A Simple Test for Inhibitors of Mast Cell-Mediated Shock", Arch. Int. Pharmacodyn., 1978, 234,164-176.
Nierenberg et al., "Lithium Augmentation of Nortriptyline for Subject Resistant to Multiple Antidepressants", J Clin Psychopharmacol, 2003, 23, 92-95.
Nijholt et al., "Neuronal Akap150 Coordinates Pka and Epac-Mediated Pkb/Akt Phosphorylation", Cellular Signaling, 2008, 20, 1715-1724.
Nikiforuk et al., "Effects of a Positive Allosteric Modulator of Group II Metabotropic Glutamate Receptors, Ly487379, on Cognitive Flexibility and Impulsive-Like Responding in Rats", Jpet, 2010, 335, 665-673.
Niswender et al., "Metabotropic Glutamate Receptors: Physiology, Pharmacology, and Disease", Annu Rev Pharmacol Toxicol, 2010, 50, 295-322.
Nofzinger et al., "Changes in Forebrain Function from Waking to Rem Sleep in Depression: Preliminary Analyses of [18f]Fdg Pet Studies", Psychiatry Res, 1999, 91, 59-78.
Nordquist, "Metabotropic Glutamate Receptor Modulation, Translational Methods, and Biomarkers: Relationships with Anxiety", Psychopharmacology, 2008, 199, 389-402.
O'Brien et al., "Molecular Mechanisms of Glutamate Receptor Clustering at Excitatory Synapses", Current Opinion in Neurobiology, 1998, 8(3), 364-369.
O'Connor et al., "Metabotropic Glutamate Receptor 7: At the Interface of Cognition and Emotion", European Journal of Pharmacology, 2010, 639, 123-131.
O'Neill et al., "Effects of Ischaemic Conditions on Uptake of Glutamate, Aspartate, and Noradrenaline by Cell Lines Derived from the Human Nervous System", Journal of Neurochemistry, 1994, 63(2), 603-611.
O'Neill et al., "Recent Developments in Metabotropic Glutamate Receptors as Novel Drug Targets", Drugs of the Future, 2010, 35, 307-324.
Odagaki et al., "Functional Coupling Between Metabotropic Glutamate Receptors and G-Proteins in Rat Cerebral Cortex Assessed by Guanosine-5'-O-(3-[35s]Thio)Triphosphate ([35s]Gtpys) Binding Assay", Basic & Clinical Pharmacology & Toxicology, 2011, 44 pages.
Odagaki et al., "Group II Metabotropic Glutamate Receptor-Mediated Activation of G-Proteins in Rat Hippocampal and Striatal Membranes", Neuroscience Letters, 2013, 24 pages.
Oehlrich, "Positive Allosteric Modulation of Mglur2 Receptors in the Treatment of CNS Disorders", Neuroscience Med Chem, 2012, 31 pages.
Ohishi et al., "Distribution of the Messenger Rna for Metabotropic Glutamate Receptor, Mglu2, in the Central Nervous System of the Rat", Neuroscience, 1993, 53, 1009-1018.
Olbrich et al., "Frontolimbic Glutamate Alterations in First Episode Schizophrenia: Evidence From a Magnetic Resonance Spectroscopy Study", World J Biol Psychiatry, 2008, 9(1), 59-63.
Oldenziel et al., "In Vivo Monitoring of Extracellular Glutamate in the Brain with a Microsensor", Brain Res., 2006, 1118(1), 34-42.
Olive, "Cognitive Effects of Group I Metabotropic Glutamate Receptor Ligands in the Context of Drug Addiction", European Journal of Pharmacology, 2010, 639, 47-58.
Olive, Metabotropic Glutamate Receptor Ligands as Potential Therapeutics for Addiction. Curr. Drug Abuse Rev 2009, 2 (1), 83-98.

(56) References Cited

OTHER PUBLICATIONS

Olivier et al., "Stress-Induced Hyperthermia and Anxiety: Pharmacological Validation", Eur J Pharmacol, 2003, 463, 117-132.
Olney et al., "NMDA Receptor Hypofunction Model of Schizophrenia", Journal of Psychiatric Research, 1999, 33, 523-533.
Olszewski et al., "Naag Peptidase Inhibition Reduces Locomotor Activity and Some Stereotypes in the Pcp Model of Schizophrenia Via Group II Mglur", J. Neurochem., 2004, 89(4), 876-885.
Olszewski et al., "Phencyclidine and Dizocilpine Induced Behaviors Reduced by N-Acetylaspartylglutamate Peptidase Inhibition Via Metabotropic Glutamate Receptors", Biol. Psychiatry, 2008, 63(1), 86-91.
Ong et al., "Localisation of Glutamate Receptors in the Substantia Nigra Pars Compacta of the Monkey", Journal Fur Hirnforschung, 1997, 38(3), 291-298.
Oquendo et al., "A Computer Algorithm for Calculating the Adequacy of Antidepressant Treatment in Unipolar and Bipolar Depression", J Clin Psychiatry, 2003, 64(7), 825-833.
Orlowski et al., "D- and L-Stereoisomers of Allylglycine: Convulsive Action and Inhibition of Brain L-Glutamate Decarboxylase", J Neurochem, 1977, 28, 349-353.
Orrenius et al., "Calcium Ions and Oxidative Cell Injury", Annals of Neurology, 1992, 32 (Supp)-42), S33-S42.
Osikowicz et al., "Glutamate Receptor Ligands Attenuate Allodynia and Hyperalgesia and Potentiate Morphine Effects in a Mouse Model of Neuropathic Pain", Pain, 2008, 139, 117-126.
Ossowska et al., "The Role of Glutamate Receptors in Antipsychotic Drug Action", Amino. Acids, 2000, 19(1), 87-94.
Ossowska et al., "The Striatum as a Target for Anti-Rigor Effects of an Antagonist of Mglur1, But Not an Agonist of Group II Metabotropic Glutamate Receptors", Brain Research, 2002, 950, 88-94.
Othmer et al., "Brain Functions and Psychiatric Disorders: A Clinical View", Diagnostic Dilemmas, Part I, the Psychiatryc Clinics of N.A., Sep. 1998, 21(3), 517-566.
Ottersen et al., "Organization of Glutamate Receptors at the Synapse", European Journal of Neuroscience, 1997, 9(11), 2219-2224.
Overstreet et al., "A 5-Ht1a Agonist and a 5-Ht2c Antagonist Reduce Social Interaction Deficit Induced by Multiple Ethanol Withdrawals in Rats", Psychopharmacology, 2003, 167, 344-352.
Ozawa et al., "Glutamate Receptors in the Mammalian Central Nervous System", Progress in Neurobiology, 1998, 54(5), 581-618.
Page et al., "Metabotropic Glutamate Receptors Inhibit Mechanosensitivity in Vagal Sensory Neurons", Gastroenterology, 2005, 128(2), 402-410.
Pajer et al., "Discovery of Blood Transcriptomic Markers for Depression in Animal Models and Pilot Validation in Subjects with Early-Onset Major Depression", Transl Psychiatry, 2012, 2(E101), 10 pages.
Pajonk et al., "Comparing the Efficacy of Atypical Antipsychotics in Open Uncontrolled Versus Double-Blind Controlled Trials in Schizophrenia", Psychopharmacology (Berl.), 2002, 162(1), 29-36.
Palazzo et al., "Metabotropic and Nmda Glutamate Receptors Participate in the Cannabinoid-Induced Antinociception", Neuropharmacology, 2001, 40(3), 319-326.
Palop et al., "Amyloid-B—Induced Neuronal Dysfunction in Alzheimer's Disease: From Synapses Toward Neural Networks", Nature Neuroscience, 2010, 13(7), 812-818.
Palucha et al., "Chronic Imipramine Treatment Reduces Inhibitory Properties of Group II Mglu Receptors Without Affecting Their Density or Affinity", Pharmacol. Rep., 2007, 59(5), 525-530.
Palucha et al., "Metabotropic Glutamate Receptor Ligands as Possible Anxiolytic and Antidepressant Drugs", Pharmacology & Therapeutics, 2007, 115, 116-147.
Palucha et al., "The Involvement of Glutamate in the Pathophysiology of Depression", Drug News Perspect, 2005, 18(4), 262-268.
Palucha, "Are Compounds Acting at Metabotropic Glutamate Receptors the Answer to Treating Depression?", Expert Opin. Investig. Drugs, 2006, 15(12), 1545-1553.
Palucha-Poniewiera et al., "On the Mechanism of the Antidepressant-Like Action of Group II Mglu Receptor Antagonist, Mgs0039", Psychopharmacology, 2010, 212, 523-535.
Panzer, "Are SSRIs Really More Effective for Anxious Depression?", Annals of Clinical Psychiatry, 2005, 17(1), 23-29.
Papakostas et al., "Augmentation of Antidepressants with Atypical Antipsychotic Medications for Treatment-Resistant Major Depressive Disorder: A Meta-Analysis", J Clin Psychiatry 2007, 68(6), 826-831.
Papakostas et al., "Efficacy of Bupropion and the Selective Serotonin Reuptake Inhibitors in the Treatment of Major Depressive Disorder with High Levels of Anxiety (Anxious Depression): A Pooled Analysis of 10 Studies", J Clin Psychiatry, 2008, 69(8), 1287-1292.
Papakostas et al., "Fluxetine-Clonazepam Cotherapy for Anxious Depression: An Exploratory, Post-Hoc Analysis of a Randomized, Double Blind Study", International Clinical Psychopharmacology, 2010, 25, 17-21.
Papakostas et al., "Predictors, Moderators, and Mediators (Correlates) of Treatment Outcome in Major Depressive Disorder", Dialogues Clin Neurosci., 2008, 10, 439-451.
Papakostas et al., "Severe and Anxious Depression: Combining Definitions of Clinical Sub-Types to Identify Patients Differentially Responsive to Selective Serotonin Reuptake Inhibitors", European Neuropsychopharmacology, 2012, 22, 347-355.
Papakostas et al., "Testing Anxious Depression as a Predictor and Moderator of Symptom Improvement in Major Depressive Disorder During Treatment with Escitalopram", Eur Arch Psychiatry Clin Neurosci, 2011, 261, 147-156.
Parmentier et al., "A Model for the Functioning of Family 3 Gpcrs", Trends in Pharmacological Sciences, 2002, 23(6), 268-274.
Parnot et al., "Toward Understanding Gpcr Dimers", Nature Structural & Molecular Biology, 2004, 11(8), 691-692.
Parsons et al., "Memantine: A NMDA Receptor Antagonist That Improves Memory by Restoration of Homeostasis in the Glutamatergic System—Too Little Activation Is Bad, Too Much Is Even Worse", Neuropharmacology, 2007, 53, 699-723.
Passchier et al., "Measuring Drug-Related Receptor Occupancy with Positron Emission Tomography", Methods, 2002, 27, 278-286.
Pastorino et al., "Pin1 Protects Against Alzheimer's Disease: One Goal, Multiple Mechanisms", Intech, 2013, 36 pages.
Patil, "Activation of Mglu2/3 Receptors as a New Approach to Treat Schizophrenia: A Randomized Phase 2 Clinical Trial", Nature Medicine, 2007, 13(9), 1102-1107.
Paykel et al., "Response to Phenelzine and Amitriptyline in Subtypes of Outpatient Depression", Arch Gen Psychiatry, 1982, 39, 1041-1049.
Pehrson et al., "Impact of Metabotropic Glutamate 2/3 Receptor Stimulation on Activated Dopamine Release and Locomotion", Psychopharmacology, 2010, 211, 443-455.
Pellicciari et al., "Metabotropic Glutamate Receptors: Structure and New Subtype-Selective Ligands", II Farmaco, 2001, 56(1-2), 91-94.
Pellicciari et al., "Metabotropic G-Protein-Coupled Glutamate Receptors As Therapeutic Targets", Current Opinion in Chemical Biology, 1999, 3(4), 433-440.
Pellicciari et al., "Modulation of Glutamate Receptor Pathways in the Search for New Neuroprotective Agents", Farmaco, 1998, 53(4), 255-261.
Penninx et al., "Two-Year Course of Depressive and Anxiety Disorders: Results from the Netherlands Study of Depression and Anxiety (Nesda)", Journal of Affective Disorders, 2011, 133, 76-85.
Pereira et al., "Study Pharmacologic of the Gabaergic and Glutamatergic Drugs on Seizures and Status Epilepticus Induced by Pilocarpine in Adult Wistar Rats", Neuroscience Letters, 2007, 419, 253-257.
Perkins et al., "Pharmacokinetics, Metabolism, and Excretion of the Intestinal Peptide Transporter 1 (Slc15a1)-Targeted Prodrug (1s,2s,5r,6s)-2-[(2's)-(2-Amino)Propionyl]Aminobicyclo[3.1.0]Hexen-2,6-Dicarboxylic Acid (Ly544344) in Rats and Dogs: Assessment of First-Pass Bioactivation and Dose Linearity", Drug Metabolism and Disposition, 2007, 35, 1903-1909.
Perroy et al., "The C Terminus of the Metabotropic Glutamate Receptor Subtypes 2 and 7 Specifies the Receptor Signaling Pathways", Journal of Biological Chemistry, 2001, 276(49), 45800-45805.

(56) References Cited

OTHER PUBLICATIONS

Pettmann et al., "Neuronal Cell Death", Neuron, 1998, 20(4), 633-647.
Pfeiffer et al., "Benzodiazepines and Adequacy of Initial Antidepressant Treatment for Depression", J Clin Psychopharmacol, 2011, 31, 360-364.
Piccinin et al., "Interaction Between Ephrins and Mglu5 Metabotropic Glutamate Receptors in the Induction of Long-Term Synaptic Depression in the Hippocampus", Journal of Neuroscience, 2010, 30(8), 2835-2843.
Pietraszek et al., "The Role of Group I Metabotropic Glutamate Receptors in Schizophrenia", Amino Acids, 2006, 7 pages.
Pike, "Pet Radiotracers: Crossing the Blood-Brain Barrier and Surviving Metabolism", Trends Pharmacol Sci, 2009, 30, 431-440.
Pilc et al., "Mood Disorders: Regulation by Metabotropic Glutamate Receptors", Biochemical Pharmacology, 2008, 75, 997-1006.
Pin et al., "Evolution, Structure, and Activation Mechanism of Family 3/C G-Protein-Coupled Receptors", Pharmacology & Therapeutics, 2003, 98, 325-354.
Pin et al., "Get Receptive to Metabotropic Glutamate Receptors", Current Opinion in Neurobiology, 1995, 5(3), 342-349.
Pin et al., "Positive Allosteric Modulators for—Aminobutyric Acidb Receptors Open New Routes for the Development of Drugs Targeting Family 3 G-Protein-Coupled Receptors" Mol Pharmacol 2001, 60, 881-884.
Pin et al., "Release of Endogenous Amino Acids From Striatal Neurons in Primary Culture", Journal of Neurochemistry, 1986, 47(2), 594-603.
Pin et al., "The Metabotropic Glutamate Receptors: Structure and Functions", Neuropharmacology, 1995, 34(1), 1-26.
Pin et al., "Alternative Splicing Generates Metabotropic Glutamate Receptors Inducing Different Patterns of Calcium Release in Xenopus Oocytes", Proceedings of the National Academy of Sciences of the USA, 1992, 89(21), 10331-10335.
Pinhasov et al., "Reduction of Submissive Behavior Model for Antidepressant Drug Activity Testing: Study Using a Video-Tracking System", Behav Pharmacol, 2005, 16, 657-664.
Pinheiro et al., "Presynaptic Glutamate Receptors: Physiological Functions and Mechanisms of Action", Nat. Rev Neurosci., 2008, 9(6), 423-436.
Pinkerton et al., "Allosteric Potentiators of the Metabotropic Glutamate Receptor 2 (Mglu2). Part 1: Identification and Synthesis of Phenyl-Tetrazolyl Acetophenones", Bioorganic & Medicinal Chemistry Letters, 2004, 14, 5329-5332.
Pinkerton et al., "Allosteric Potentiators of the Metabotropic Glutamate Receptor 2 (Mglu2). Part 2: 4-Thiopyridyl Acetophenones as Non-Tetrazole Containing Mglu2 Receptor Potentiators", Bioorganic & Medicinal Chemistry Letters, 2004, 14, 5867-5872.
Pinkerton et al., "Substituted Acetophenones as Selective and Potent Allosteric Potentiators of the Metabotropic Glutamate Receptor 2 (Mglur2)", 229th ACS National Meeting, Mar. 2005, 1 page.
Pittenger et al., "Stress, Depression, and Neuroplasticity: A Convergence of Mechanisms", Neuropsychopharmacology, 2008, 33(1), 88-109.
Pitts et al., "Lactate Metabolism in Anxiety Neurosis",New England Journal of Medicine, 1967, 277, 1329-1336.
Pizzi et al., "Activation of Multiple Metabotropic Glutamate Receptor Subtypes Prevents NMDA-Induced Excitotoxicity in Rat Hippocampal Slices", European Journal of Neuroscience, 1996, 8(7), 1516-1521.
Popik et al., "Selective Agonist of Group II Glutamate Metabotropic Receptors, Ly354740, Inhibits Tolerance to Analgesic Effects of Morphine in Mice", British Journal of Pharmacology, 2000, 130, 1425-1431.
Porsolt et al., "Behavioural Despair in Mice: A Primary Screening Test for Antidepressants", Arch. Int. Pharmacodyn., 1977, 229, 327-336.
Porsolt et al., "Behavioural Despair in Rats: A New Model Sensitive to Antidepressant Treatments", Eur. J. Pharmacol., 1978, 47(4), 379-391.
Porter et al., "(S)-Homoquisqualate: A Potent Agonist at the Glutamate Metabotropic Receptor", British Journal of Pharmacology, 1992, 106(3), 509-510.
Posluns, "An Analysis of Chlorpromazine-Induced Suppression of the Avoidance Response.", Psychopharmacol. 3: 361-373 (1962).
Posner et al., "Columbia Classification Algorithm of Suicide Assessment (C-Casa): Classification of Suicidal Events in the FDA's Pediatric Suicidal Risk Analysis of Antidepressants", American Journal of Psychiatry, 2007, 164, 1035-1043.
Poyurovsky et al., "Lamotrigine Augmentation in Schizophrenia and Schizoaffective Patients with Obsessive-Compulsive Symptoms", J Psychopharmacol., 2010, 24(6), 861-866.
Prabakaran et al., "2-D Dige Analysis of Liver and Red Blood Cells Provides Further Evidence for Oxidative Stress in Schizophrenia", Journal of Proteome Research, 2007, 6, 141-149.
Pralong et al., "Cellular Perspectives on the Glutamate-Monoamine Interactions in Limbic Lobe Structures and Their Relevance for Some Psychiatric Disorders", Progress in Neurobiology, 2002, 67, 173-202.
Prezeau et al., "Functional Crosstalk Between Gpcrs: With or Without Oligomerization", Current Opinion in Pharmacology, 2010, 10, 6-13.
Prezeau et al., "Pharmacological Characterization of Metabotropic Glutamate Receptors in Several Types of Brain Cells in Primary Cultures", Mol Pharmacol, 1993, 45(4), 570-577.
Prina et al., "Co-occurrence of Anxiety and Depression Amongst Older Adults in Low and Middle Income Countries: Findings From the 10/66 Study", Psychological Medicine, Oct. 2011, 41(10), 2047-2056.
Priolo et al., "Panic-Like Attack Induced by Microinfusion Into the Locus Coeruleus of Antagonists and Inverse Agonists at Gabaa-Receptors in Rodents", Funct Neurol, 1991, 6, 393-403.
Profaci et al., "Group II Mglur Agonist Ly354740 and Naag Peptidase Inhibitor Effects on Prepulse Inhibition in Pcp and D-Amphetamine Models of Schizophrenia", Psychopharmacology, 2011, 216, 235-243.
Prous Science Integrity 2007—Chemical Structure Ly-404039.
Prous Science Integrity 2007—Chemical Synthesis Ly-2140023.
Pszczolkowski et al., "Effect of Metabotropic Glutamate Receptor Agonists and Signal Transduction Modulators on Feeding by a Caterpillar", Pharmacology, Biochemistry and Behavior, 2005, 82, 678-685.
Putt et al., "An Enzymatic Assay for Poly(Adp-Ribose) Polymerase-1 (Parp-1) Via the Chemical Quantitation of Nad+: Application to the High-Throughput Screening of Small Molecules as Potential Inhibitors", Analytical Biochemistry, 2004, 326, 78-86.
Quitkin et al., "Placebo Run-in Period in Studies of Depressive Disorders: Clinical, Heuristic and Research Implications", British Journal of Psychiatry, 1998, 173, 242-248.
Raffray et al., "Apoptosis and Necrosis in Toxicology: A Continuum or Distinct Modes of Cell Death?", Pharmacology & Therapeutics, 1997, 75(3), 153-177.
Rao et al., "Anxious Depression: Clinical Features and Treatment", Current Psychiatry Reports, 2009, 11, 429-436.
Raskin et al., "Differential Response to Chlorpromazine, Imipramine, and Placebo. A Study of Subgroups of Hospitalized Depressed Patients", Arch Gen Psychiat, 1970, 23, 164-173.
Ravaris et al., "Phenelzine and Amitriptyline in the Treatment of Depression: A Comparison of Present and Past Studies", Arch Gen Psychiatry, 1980, 37, 1075-1080.
Recasens et al., "Metabotropic Glutamate Receptors as Drug Targets", Current Drug Targets, 2007, 8(5), 651-681.
Regier et al., "Comorbidity of Mental Disorders with Alcohol and Other Drug Abuse. Results From the Epidemiologic Catchment Area (Eca) Study", Jama, 1990, 264, 2511-2518.
Reiner et al., "Bdnf May Play a Differential Role in the Protective Effect of the Mglur2/3 Agonist Ly379258 on Striatal Projection Neurons in R6/2 Huntington's Disease Mice", Brain Research, 2012, 1473, 161-172.
Reynolds et al., "New Approaches to the Drug Treatment of Schizophrenia", Adv. Pharmacol., 1995, 32, 461-503.
Reynolds et al., "Sleep Research in Affective Illness: State of the Art Circa", Sleep, 1987, 10, 199-215.

(56) References Cited

OTHER PUBLICATIONS

Rhebergen et al., "The 7-Year Course of Depression and Anxiety in the General Population", Acta Psychiatr Scand, 2011, 123, 297-306.
Ribeiro et al., "Group I Metabotropic Glutamate Receptor Signaling and Its Implication in Neurological Disease", CNS & Neurological Disorders—Drug Targets, 2010, 9, 574-595.
Ribeiro et al., "Metabotropic Glutamate Receptor-Mediated Cell Signaling Pathways are Altered in a Mouse Model of Huntington's Disease", Journal of Neuroscience, 2010, 30(1), 316-324.
Richards et al., "Distribution and Abundance of Metabotropic Glutamate Receptor Subtype 2 in Rat Brain Revealed by [3h]Ly354740 Binding in Vitro and Quantitative Radioautography: Correlation with the Sites of Synthesis, Expression, and Agonist Stimulation of [35s]Gtps Binding", J Comp Neurology, 2005, 487, 15-27.
Richardson-Burns et al., Metabotropic Glutamate Receptor Mrna Expression in the Schizophrenic Thalamus, Biol. Psychiatry, 2000, 47(1), 22-28.
Rickels et al., "Efficacy of Extended-Release Venlafaxine in Nondepressed Outpatients with Generalized Anxiety Disorder", Am J Psychiatry, 2000, 157, 968-974.
Rickels et al., "Long-Term Diazepam Therapy and Clinical Outcome", Jama, 1983, 250, 767-771.
Riedel et al., "Glutamate Receptor Function in Learning and Memory", Behavioural Brain Research, 2003, 140(1-2), 1-47.
Riederer et al., "Pharmacotoxic Psychosis After Memantine in Parkinson's Disease", Lancet, 1991, 338, 1022-1023.
Ritzen et al., "Molecular Pharmacology and Therapeutic Prospects of Metabotropic Glutamate Receptor Allosteric Modulators", Basic Clin Pharmacol Toxicol, 2005, 97, 202-213.
Robbe et al., "Role of P/Q-Ca2+ Channels in Metabotropic Glutamate Receptor 2/3-Dependent Presynaptic Long-Term Depression at Nucleus Accumbens Synapses", J Neurosci., 2002, 22(11), 4346-4356.
Robbe et al., "Metabotropic Glutamate Receptor 2 3-Dependent Long-Term Depression in the Nucleus Accumbens is Blocked in Morphine Withdrawn Mice", Eur. J Neurosci., 2002, 16(11), 2231-2235.
Robbins et al., "The Neuropsychopharmacology of Fronto-Executive Function: Monoaminergic Modulation", Annu Rev Neurosci, 2009, 32, 267-287.
Roberts et al., "Pharmacological Tools for the Investigation of Metabotropic Glutamate Receptors (Mglurs): Phenylglycine Derivatives and Other Selective Antagonists—An Update", Neuropharmacology, 1995, 34(8), 813-819.
Robins et al., "Establishment of Diagnostic Validity in Psychiatric Illness: Its Application to Schizophrenia", Amer J Psychiat, 1970, 126(7), 107-111.
Robison et al., "The Rearrangement of Isoquinoline-N-Oxides", J Org Chem, 1957, 21, 1337-1341.
Rodd et al., "The Metabotropic Glutamate 2/3 Receptor Agonist Ly404039 Reduces Alcohol-Seeking But Not Alcohol Self-Administration in Alcohol-Preferring (P) Rats", Behavioural Brain Research, 2006, 171, 207-215.
Rodriguez et al., "Attenuation of Ketamine-Induced Hyperactivity Responses in Rats Following Administration of a Novel Metabotropic Glutamate Receptor 2 Selective Positive Modulator",Annual Meeting of the Society for Neuroscience, Oct. 2004, Abstract No. 798.8, 2 pages.
Rodriguez et al., "Relationships Among Psychosocial Functioning, Diagnostic Comorbidity, and the Recurrence of Generalized Anxiety Disorder, Panic Disorder, and Major Depression", Anxiety Disorders, 2005, 19, 752-766.
Rodriguez-Moreno et al., "Kainate Receptors with a Metabotropic Modus Operandi", Trends Neurosci., 2007, 30(12), 630-637.
Rondard et al., "Coupling of Agonist Binding to Effector Domain Activation in Metabotropic Glutamate-Like Receptors", J Biol. Chem., 2006, 281(34), 24653-24661.
Rorick-Kehn et al., "Improved Bioavailability of the Mglu2/3 Receptor Agonist Ly354740 Using a Prodrug Strategy: In Vivo Pharmacology of Ly544344", J. Pharmacol. Exper. Therapeut., 2006, 316, 905-913.
Rorick-Kehn et al., "In Vivo Pharmacological Characterization of the Structurally Novel, Potent, Selective Mglu2/3 Receptor Agonist Ly404039 in Animal Models of Psychiatric Disorders", Psychopharmacology, 2007, 193, 121-136.
Rorick-Kehn et al., "Pharmacological and Pharmacokinetic Properties of a Structurally Novel, Potent, and Selective Metabotropic Glutamate 2/3 Receptor Agonist: in Vitro Characterization of Agonist (−)-(1r,4s,5s,6s)-4-Amino-2-Sulfonylbicyclo[3.1.0]-Hexane-4,6-Dicarboxylic Acid (Ly404039)" J. Pharmacol. Exper. Therapeut., 2007, 321, 308-317.
Rorick-Kehn et al., "Pharmacological Characterization of Stress-Induced Hyperthermia in Dba/2 Mice Using Metabotropic and Ionotropic Glutamate Receptor Ligands", Psychopharmacology (Berl)., 2005, 183(2), 226-40.
Ross et al., "Expression of Functional Metabotropic and Ionotropic Glutamate Receptors in Baculovirus-lnfected Insect Cells", Neuroscience Letters, 1994, 173(1-2), 139-142.
Roth et al., "G Protein-Coupled Receptor (Gpcr) Trafficking in the Central Nervous System: Relevance for Drugs of Abuse", Drug & Alcohol Dependence, 1998, 51(1-2), 73-85.
Roth et al., "Synthesis of Small Molecule Inhibitors of the Orphan Nuclear Receptor Steroidogenic Factor-1 (Nr5a1) Based on Isoquinolinone Scaffolds", Bioorg Med Chem Lett, 2008, 18, 2628-2632.
Rothman et al., "Excitatory and the NMDA Receptor", Trends in Neurosciences, 1987, 10(7), 299-302.
Rovira et al., "Modeling the Binding and Function of Metabotropic Glutamate Receptors", Jpet, 2008, 325, 443-456.
Rowe et al., "Transposition of Three Amino Acids Transforms the Human Metabotropic Glutamate Receptor (Mglur)-3 Positive Allosteric Modulation Site to Mglur2, and Additional Characterization of the Mglur2 Positive Allosteric Modulation Site", J. Pharmacol. Exper. Therapeut., 2008, 326, 240-251.
Roy et al., "A Twin Study of Generalized Anxiety Disorder and Major Depression" Psychological Medicine, 1995, 5, 1037-1049.
Roychowdhury et al., "G Protein Alpha Subunits Activate Tubulin Gtpase and Modulate Microtubule Polymerization Dynamics", J. Biol. Chem., 1999, 274(19), 13485-13490.
Roychowdhury et al., "G Protein Beta1gamma2 Subunits Promote Microtubule Assembly", J. Biol. Chem., 1997, 272(50), 31576-31581.
Rozenfeld et al., "Receptor Heteromerization and Drug Discovery", Trends in Pharmacological Sciences, 2010, 31(3), 124-130.
Rudd et al., "Positive Allosteric Modulators of the Metabotropic Glutamate Receptor Subtype 2 (Mglur2)", Current Topics in Medicinal Chemistry, 2005, 5, 869-884.
Rush et al., "Comorbid Psychiatric Disorders in Depressed Outpatients: Demographic and Clinical Features", Journal of Affective Disorders, 2005, 87, 43-55.
Rush et al., "Response in Relation to Baseline Anxiety Levels in Major Depressive Disorder Treated with Bupropion Sustained Release or Sertraline", Neuropsychopharmacology, 2001, 25(1), 131-138.
Rush et al., "Sequenced Treatment Alternatives to Relieve Depression (Star*D): Rationale and Design", Controlled Clinical Trials, 2004, 25, 119-142.
Rush et al., "The Inventory for Depressive Symptomatology (Ids): Preliminary Findings", Psychiatry Res, May 1986, 18(1), 65-87.
Rush et al., "The Inventory of Depressive Symptomatology (Ids)—Preliminary Findings", Psychopharmacology Bulletin, 1986, 22(3), 985-990.
Rush et al., "The Inventory of Depressive Symptomatology (Ids): Psychometric Properties", Psychol Med, May 1996, 26(3), 477-486.
Russell et al., "Amyloid-Β Acts as a Regulator of Neurotransmitter Release Disrupting the Interaction Between Synaptophysin and Vamp2", Plos One, 2012, 7(8), E43201, 1-14.
Sackheim et al., "The Impact of Medication Resistance and Continuation Pharmacotherapy on Relapse Following Response to

(56) References Cited

OTHER PUBLICATIONS

Electroconvulsive Therapy in Major Depression", J Clin Psychpharmacol, Apr. 1990, 10(2), 96-104.
Sagara et al., "The Activation of Metabotropic Glutamate Receptors Protects Nerve Cells from Oxidative Stress", J. Neurosci., 1998, 18(17), 6662-6671.
Sahara et al., "Cellular Localization of Metabotropic Glutamate Receptors Mglur1, 2/3, 5 and 7 in the Main and Accessory Olfactory Bulb of the Rat", Neuroscience Letters, 2001, 312(2), 59-62.
Sahni et al., "Compound A, A Novel, Potent and Selective Metabotropic Glutamate Receptor 2 (Mglur2) Positive Allosteric Modulator: I. Pharmacological Characterization" Poster 767.6 Presented at the 40th Annual Meeting of Society for Neuroscience, Nov. 2010, 1 page.
Sajdyk et al., "Measurement of Panic-Like Responses Unit 9.17 Following Intravenous Infusion of Sodium Lactate in Panic-Prone Rats", Current Protocols in Neuroscience, 2003, 9.17.1-9.17.19.
Sakharkar et al., "Druggability of Human Disease Genes", Int J Biochem. Cell Biol., 2007, 39(6), 1156-1164.
Salinska et al., "Metabotropic Glutamate Receptors (Mglurs) are Involved in Early Phase of Memory Formation: Possible Role of Modulation of Glutamate Release", Neurochemistry Intl, 2003, 43, 469-474.
Samadi et al., "Basal Ganglia Group II Metabotropic Glutamate Receptors Specific Binding in Non-Human Primate Model of L-Dopa-Induced Dyskinesias", Neuropharmacology, 2008, 54(2), 258-268.
Samadi et al., "Metabotropic Glutamate Receptor II in the Brains of Parkinsonian Patients", J. Neuropathol. Exp. Neurol., 2009, 68(4), 374-382.
Sanacora et al., "Subtype-Specific Alterations of Gamma-Aminobutyric Acid and Glutamate in Patients with Major Depression", Arch Gen Psychiatry, 2004, 61, 705-713.
Sanacora et al., "Targeting the Glutamatergic System to Develop Novel, Improved Therapeutics for Mood Disorders", Nat Rev Drug Discov, May 2008, 7(5), 426-437.
Sanacora et al., "Towards a Glutamate Hypothesis of Depression: An Emerging Frontier of Neuropsychopharmacology for Mood Disorders", Neuropharmacology, 2012, 62, 63-77.
Sanders et al., "Regulation of Anxiety by Gabaa Receptors in the Rat Amygdala", Pharmacology, Biochemistry and Behavior, 1995, 52(4), 701-706.
Sanderson et al., "Syndrome Comorbidity in Patients with Major Depression or Dysthymia: Prevalence and Temporal Relationships", Am J Psychiatry, Aug. 1990, 147(8), 1025-1028.
Sanger et al., "Pharmacological Profiling of Native Group II Metabotropic Glutamate Receptors in Primary Cortical Neuronal Cultures Using a Flipr", Neuropharmacology 2012, 1-10.
Santi et al., "Temporal and Depolarization-Induced Changes in the Absolute Amounts of Mrnas Encoding Metabotropic Glutamate Receptors in Cerebellar Granule Neurons in Vitro", Journal of Neurochemistry, 1994, 63(4), 1207-1217.
Sareen et al., "Anxiety Disorders and Risk for Suicidal Ideation and Suicide Attempts", Arch Gen Psychiatry, 2005, 62, 1249-1257.
Sarichelou et al., "Metabotropic Glutamate Receptors Regulate Differentiation of Embryonic Stem Cells Into Gabaergic Neurons", Cell Death. Differ., 2008, 15(4), 700-707.
Sarter et al., "Cortical Cholinergic Transmission and Cortical Information Processing in Schizophrenia", Schizophr. Bull, 2005, 31(1), 117-138.
Satow et al., "Pharmacological Effects of the Metabotropic Glutamate Receptor 1 Antagonist Compared with Those of the Metabotropic Glutamate Receptor 5 Antagonist and Metabotropic Glutamate Receptor 2/3 Agonist in Rodents: Detailed Investigations with a Selective Allosteric Metabotropic Glutamate Receptor 1 Antagonist, Ftidc [4-[1-(2-Fluoropyridine-3-Yl)-5-Methyl-1h-1,2,3-Triazol-4-Yl]-Nisopropyl-N-Methyl-3,6-Dihydropyridine-1(2h)-Carboxamide]", J. Pharmacol. Exper. Therapeut., 2008, 326, 577-586.
Saugstad et al., "Cloning and Expression of a New Member of the L-2-Amino-4-Phosphonobutyric Acid-Sensitive Class of Metabotropic Glutamate Receptors", Mol Pharmacol, 1994, 45, 367-372.
Saugstad et al., "Metabotropic Glutamate Receptors Activate G-Protein-Coupled Inwardly Rectifying Potassium Channels in Xenopus Oocytes", J. Neurosci., 1996, 16(19), 5979-5985.
Sawamoto et al., "Cognitive Slowing in Parkinson Disease is Accompanied by Hypofunctioning of the Striatum", Neurology, 2007, 68, 1062-1068.
Sawamoto et al., "Cognitive Slowing in Parkinson's Disease: A Behavioral Evaluation Independent of Motor Slowing", J.Neurosci., 2002, 22, 5198-5203.
Scaccianoce et al., "Endogenous Activation of Group-II Metabotropic Glutamate Receptors Inhibits the Hypothalamic-Pituitary-Adrenocortical Axis", Neuropharmacology, 2003, 44, 555-561.
Scanziani et al., "Use-Dependent Increases in Glutamate Concentration Active Presynaptic Metabotropic Glutamate Receptors", Nature, 1997, 385, 630-634.
Schaffhauser et al., "Camp-Dependent Protein Kinase Inhibits Mglur2 Coupling to G-Proteins by Direct Receptor Phosphorylation", J Neurosci., 2000, 20(15), 5663-5670.
Schaffhauser et al., "In Vitro Characterization of N-(4'-(2-Methoxyphenoxy)Phenyl-N-(2,2,2-Trifluoroethylsulfonyl)Pyrid-3-Ylmethylamine (Ly487379) a Selective Mglu2 Receptor Positive Modulator", Neuropharmacology, 2002, 43, 307.
Schaffhauser et al., "Multiple Pathways for Regulation of the Kcl-Induced [3h]-Gaba Release by Metabotropic Glutamate Receptors, in Primary Rat Cortical Cultures", Brain Res., 1998, 782(1-2), 91-104.
Schaffhauser et al., "Pharmacological Characterization of Metabotropic Glutamate Receptors Linked to the Inhibition of Adenylate Cyclase Activity in Rat Striatal Slices", Neuropharmacology, 1997, 36(7), 933-940.
Schapira, "Science, Medicine, and the Future: Parkinson's Disease", Brit.Med.J., 1999, 318, 311-314.
Scheer et al., "Constitutively Active G Protein-Coupled Receptors: Potential Mechanisms of Receptor Activation", Journal of Receptor & Signal Transduction Research, 1997, 17(1-3), 57-73.
Schiffer et al., "Optimizing Experimental Protocols for Quantitative Behavioral Imaging with 18f-Fdg in Rodents", J Nucl Med, 2007, 48, 277-287.
Schlumberger et al., "Comparison of the Mglu5 Receptor Positive Allosteric Modulator Adx47273 and the Mglu2/3 Receptor Agonist Ly354740 in Tests for Antipsychotic-Like Activity", European Journal of Pharmacology, 2009, 623, 73-83.
Schlumberger et al., "Effects of a Metabotropic Glutamate Receptor Group II Agonist Ly354740 in Animal Models of Positive Schizophrenia Symptoms and Cognition", Behav Pharmacol., 2009, 20, 56-66.
Schoepp et al., "Ly354740 is a Potent and Highly Selective Group II Metabotropic Glutamate Receptor Agonist in Cells Expressing Human Glutamate Receptors", Neuropharmacology, 1997, 36, 1-11.
Schoepp et al., "Ly354740, An Mglu2/3 Receptor Agonist as a Novel Approach to Treat Anxiety/Stress", Stress, 2003, 6(3), 189-197.
Schoepp et al., "Metabotropic Glutamate Receptors" Pharmacol Biochem Behav, 2002, 74, 255-256.
Schoepp et al., "Potent, Stereoselective, and Brain Region Selective Modulation of Second Messengers in the Rat Brain by (+)Ly354740, A Novel Group II Metabotropic Glutamate Receptor Agonist", Naunyn-Schmiedebergs Archives of Pharmacology, 1998, 358(2), 175-180.
Schoppa et al., "Modulation of Mepscs in Olfactory Bulb Mitral Cells by Metabotropic Glutamate Receptors", J Neurophysiol., 1997, 78(3), 1468-1475.
Schreiber et al., "Ly354740 Affects Startle Responding But Not Sensorimotor Gating or Discriminative Effects of Phencyclidine", Eur. J Pharmacol., 2000, 388(2), R3-R4.
Schulze-Osthoff et al., "Apoptosis Signaling by Death Receptors", European Journal of Biochemistry, 1998, 254(3), 439-459.
Schwartz et al., "Ago-Allosteric Modulation and Other Types of Allostery in Dimeric 7tm Receptors", J Recept. Signal. Transduct. Res., 2006, 26(1-2), 107-128.

(56) References Cited

OTHER PUBLICATIONS

Schwartz et al., "Allosteric Enhancers, Allosteric Agonists and Ago-Allosteric Modulators: Where Do They Bind and How Do They Act?", Trends Pharmacol. Sci., 2007, 28(8), 366-373.
Schweitzer et al., "Characterization of [(3)H]-Ly354740 Binding to Rat Mglu2 and Mglu3 Receptors Expressed in Cho Cells Using Semliki Forest Virus Vectors", Neuropharmacology, 2000, 39(10), 1700-1706.
Seebahn et al., "Ranbpm is Expressed in Synaptic Layers of the Mammalian Retina and Binds to Metabotropic Glutamate Receptors",. Febs Lett., 2008, 582(16), 2453-2457.
Seedat et al., "Measuring Anxiety in Patients with Schizophrenia", J Nerv Ment Dis. Apr. 2007, 195(4), 320-324.
Seeman et al., "Dopamine Partial Agonist Actions of the Glutamate Receptor Agonists Ly354740 and Ly379268", Synapse, 2008, 62, 154-158.
Seeman et al., "Glutamate Receptor Mglu2 and Mglu3 Knockout Striata are Dopamine Supersensitive, with Elevated D2(High) Receptors and Marked Supersensitivity to the Dopamine Agonist (+)Phno", Synapse, 2009, 63(3), 247-251.
Seeman, "An Agonist at Glutamate and Dopamine D2 Receptors, Ly404039" Neuropharmacology, 2012, 7 pages.
Seeman, "Glutamate Agonists for Schizophrenia Stimulate D2high Receptors", Schizophrenia Research, 2008, 99, 373-374.
Seeman, "Glutamate and Dopamine Components in Schizophrenia", J Psychiatry Neurosci., 2009, 34(2), 143-149.
Semba et al., "Regional Differences in the Effects of Glutamate Uptake Inhibitor L-Trans-Pyrrolidine-2,4-Dicarboxylic Acid on Extracellular Amino Acids and Dopamine in Rat Brain: An in Vivo Microdialysis Study", General Pharmacology, 1998, 31(3), 399-404.
Seneca, "Recent Advances in Positron Emission Tomography Imaging of Brain", Drugs of the Future, 2011, 36, 601-613.
Seo et al., "Distinctive Clinical Characteristics and Suicidal Tendencies of Patients with Anxious Depression", J Nerv Ment Dis, 2011, 199, 42-48.
Sharpe et al., "Systemic Pre-Treatment with a Group II Mglu Agonist, Ly379268, Reduces Hyperalgesia in Vivo", British Journal of Pharmacology, 2002, 135, 1255-1262.
Shear et al., "Multicenter Collaborative Panic Disorder Severity Scale", Am J Psychiatry, Nov. 1997, 154(11), 1571-1575.
Shear et al., "Reliability and Validity of a Structured Interview Guide for the Hamilton Axiety Rating Scale (Sigh-A)", Depress Anxiety, 2001, 13(4), 166-178.
Sheffler et al., "Recent Progress in the Synthesis and Characterization of Group II Metabotropic Glutamate Receptor Allosteric Modulators", Acs Chem Neurosci, 2011, 2, 382-393.
Shekhar et al., "Ly354740, a Potent Group II Metabotropic Glutamate Receptor Agonist Prevents Lactate-Induced Panic-Like Response in Panic-Prone Rats", Neuropharmacology, 2000, 39, 1139-1146.
Shekhar, "Gabe Receptors in the Region of the Dorsomedial Hypothalamus of Rats Regulate Anxiety in the Elevated Plus-Maze Test. I. Behavioral Measures", Brain Research, 1993, 627(1), 9-16.
Shekhar et al., "Dorsomedial Hypothalamic Gaba Dysfunction Produces Physiological Arousal Following Sodium Lactate Infusions", Pharmacol Biochem Behav., Oct. 1996, 55(2), 249-256.
Shekhar et al., "Dorsomedial Hypothalamic Gaba Regulates Anxiety in the Social Interaction Test", Pharmacology, Biochemistry and Behavior, 1995, 50(2), 253-258.
Shekhar et al., "The Circumventricular Organs Form a Potential Neural Pathway for Lactate Sensitivity: Implications for Panic Disorder", Journal of Neuroscience, 1997, 17(24), 9726-9735.
Shepherd et al., "Behavioural and Pharmacological Characterisation of the Elevated 'Zero-Maze' as an Animal Model of Anxiety", Psychopharmacology, 1994, 116, 56-64.
Sherbourne et al., "Course of Depression in Patients with Comorbid Anxiety Disorders" Journal of Affective Disorders 1997, 43, 245-250.

Shi et al., "L-Homocysteine Sulfinic Acid and Other Acidic Homocysteine Derivatives are Potent and Selective Metabotropic Glutamate Receptor Agonists", J Pharmacol Exp Ther, 2003, 305(1), 131-142.
Shigemoto et al., "Differential Presynaptic Localization of Metabotropic Glutamate Receptor Subtypes in the Rat Hippocampus", Journal of Neuroscience, 1997, 17(19), 7503-7522.
Shigemoto et al., "Metabotropic Glutamate Receptors—Immunocytochemical and in Situ Hybridization Analysis", Ottersen Op, Storm-Mathisen J (Eds) Handbook of Chemical Neuroanatomy, Elxevier Science, 2000, 63-98.
Shigemoto et al., "Target-Cell-Specific Concentration of a Metabotropic Glutamate Receptor in the Presynaptic Active Zone", Nature, 1996, 381(6582), 523-525.
Shih et al., "Protein Kinase C Deficiency Blocks Recovery From Agonist-Induced Desensitization", J. Biol. Chem., 1996, 271(35), 21478-21483.
Shimazaki et al., "Blockade of the Metabotropic Glutamate 2/3 Receptors Enhances Social Memory Via the Ampa Receptor in Rats", Eur.J.Pharmacol., 2007, 575, 94-97.
Shin et al., "Metabotropic Glutamate Receptors (Mglus) and Cellular Transformation", Neuropharmacology, 2008, 55(4), 396-402.
Shin et al., "The Neurocircuitry of Fear, Stress, and Anxiety Disorders", Neuropsychopharmacology, 2010, 35(1), 169-191.
Shipe et al., "Recent Advances in Positive Allosteric Modulators of Metabotropic Glutamate Receptors", Current Opinion in Drug Discovery & Development, 2005, 8(4), 449-457.
Sidique et al., "Orally Active Metabotropic Glutamate Subtype 2 Receptor Positive Allosteric Modulators: Structure-Activity Relationships and Assessment in a Rat Model of Nicotine Dependence", J Med Chem, 2012, 55, 9434-9445.
Silver et al., "Multifunctional Pharmacotherapy: What Can We Learn From Study of Selective Serotonin Reuptake Inhibitor Augmentation of Antipsychotics in Negative-Symptom Schizophrenia?", Neurotherapeutics, 2009, 6, 86-93.
Silverstone et al., "Defining Anxious Depression: Going Beyond Comorbidity", Can J Psychiatry, 2003, 48, 675-680.
Simon et al., "Advances in the Treatment of Anxiety: Targeting Glutamate", Journal of the American Society for Exp Neur, Jan. 2006, 3, 57-68.
Simon et al., "Comparing Anxiety Disorders and Anxiety-Related Traits in Bipolar Disorder and Unipolar Depression", Journal of Psychiatric Research, 2003, 37, 187-192.
Simonyi et al., "Chronic Ethanol-Induced Subtype- and Subregion-Specific Decrease in the Mrna Expression of Metabotropic Glutamate Receptors in Rat Hippocampus", Alcoholism: Clinical & Experimental Research, 2004, 28(9), 1419-1423.
Simonyi et al., "Expression of Groups I and II Metabotropic Glutamate Receptors in the Rat Brain During Aging", Brain Res, 2005, 1043, 95-106.
Simonyi et al., "Metabotropic Glutamate Receptor Subtype 5 Antagonism in Learning and Memory", European Journal of Pharmacology, 2010, 639, 17-25.
Simpson et al., "A Possible Role for the Striatum in the Pathogenesis of the Cognitive Symptoms of Schizophrenia", Neuron., 2010, 65(5), 585-596.
Siok et al., "Comparative Analysis of the Neurophysiological Profile of Group I Metabotropic Glutamate Receptor Activators and Diazepam: Effects on Hippocampal and Cortical Eeg Patterns in Rats", Neuropharmacology, 2012, 62, 226-236.
Skerry et al., "Glutamate Signalling in Non-Neuronal Tissues", Trends Pharmacol. Sci., 2001, 22(4), 174-181.
Sladeczek et al., "The Metabotropic Glutamate Receptor (Mgr): Pharmacology and Subcellular Location", Journal of Physiology, 1992, 86(1-3), 47-55.
Slattery et al., "Potentiation of Mouse Vagal Afferent Mechanosensitivity by Ionotropic and Metabotropic Glutamate Receptors", J Physiol, 2006, 577(Pt 1), 295-306.
Sleight et al., "Radiolabelling of the Human 5-Ht2a Receptor with an Agonist, a Partial Agonist and an Antagonist: Effects on Apparent Agonist Affinities", Biochemical Pharmacology, 1996, 51, 71-76.

(56) References Cited

OTHER PUBLICATIONS

Smialowska et al., "The Effect of Intrahippocampal Injection of Group II and III Metobotropic Glutamate Receptor Agonists on Anxiety; the Role of Neuropeptide Y", Neuropsychopharmacology, 2007, 32(6), 1242-1250.
Smith et al., "Ionotropic and Metabotropic Gaba and Glutamate Receptors in Primate Basal Ganglia", Journal of Chemical Neuroanatomy, 2001, 22(1-2), 13-42.
Smith et al., "Is Extended Clonazepam Cotherapy of Fluoxetine Effective for Outpatients with Major Depression?", Journal of Affective Disorders, 2002, 70, 251-259.
Smith et al., "Schizophrenia (Maintenance Treatment)", Clin Evid (Online), 2009, 1007.
Smith et al., "Short-Term Augmentation of Fluoxetine Clonazepam in the Treatment of Depression: A Double-Blind Study", Am J Psychiatry, 1998, 155, 1339-1345.
Smith, "Regulation of Glutamate Uptake in Astrocytes Continuously Exposed to Ethanol", Life Sciences, 1997, 61(25), 2499-2505.
Smits et al., "Outcomes of Acute Phase Cognitive Therapy in Outpatients with Anxious Versus Nonaxious Depression", Psychother Psychosom, 2012, 81, 153-160.
Smolders et al., "In Vivo Modulation of Extracellular Hippocampal Glutamate and Gaba Levels and Limbic Seizures by Group I and II Metabotropic Glutamate Receptor Ligands", Journal of Neurochemistry, 2004, 88(5), 1068-1077.
Sodhi et al., "Role of Glutamate in Schizophrenia: Integrating Excitatory Avenues of Research", Expert Rev Neurother, 2008, 8(9), 1389-1406.
Sokoloff et al., "The [14c]Deoxyglucose Method for the Measurement of Local Cerebral Glucose Utilization: Theory, Procedure, and Normal Values in the Conscious and Anesthetized Albino Rat", J Neurochem, 1977, 28, 897-916.
Sokolowski et al., "The Behavioral Effects of Sertraline, Fluoxetine, and Paroxetine Differ on the Differential-Reinforcement-Of-Low-Rate 72-Second Operant Schedule in the Rat", Psychopharmacology, 1999, 147, 153-161.
Sortino et al., "Immortalized Hypothalamic Neurons Express Metabotropic Glutamate Receptors Positively Coupled to Cyclic Amp Formation", Eur. J Neurosci., 1996, 8(11), 2407-2415.
Souery et al., "Group for the Study of Resistant Depression. Clinical Factors Associated with Treatment Resistance in Major Depressive Disorder: Results From a European Multicenter Study", J. Clin. Psychiatry, Jul. 2007, 68(7), 1062-1070.
Spencer et al., "Novel Strategies for Alzheimer's Disease Treatment", Expert Opin. Biol. Ther., 2007, 7(12), 1853-1867.
Spiegel et al., "Defects in G Protein-Coupled Signal Transduction in Human Disease", Annual Review of Physiology, 1996, 58, 143-170.
Spiegel et al., "Psychosis Induced by the Interaction of Memantine and Amantadine: Lending Evidence to the Glutamatergic Theory of Schizophrenia", Clinical Schizophrenia & Related Psychoses, 2007, 1(3), 273-276.
Spijker, "The Course of Anxiety and Depression in Nemesis and Nesda", Abstract AS36-04 of the 20th European Congress of Psychiatry, Mar. 2012, 1 page.
Spooren et al., "Anxiolytic-Like Effects of the Prototypical Metabotropic Glutamate Receptor 5 Antagonist 2-Methyl-6-(Phenylethynyl)Pyridine in Rodents", Journal of Pharmacology & Experimental Therapeutics, 2000, 295(3), 1267-1275.
Spooren et al., "Insight Into the Function of Group I and Group II Metabotropic Glutamate (Mglu) Receptors: Behavioural Characterization and Implications for the Treatment of CNS Disorders", Behavioural Pharmacology, 2003, 14(4), 257-277.
Spooren et al., "Lack of Effect of Ly314582 (A Group 2 Metabotropic Glutamate Receptor Agonist) on Phencyclidine-Induced Locomotor Activity in Metabotropic Glutamate Receptor 2 Knockout Mice", Eur J Pharmacol., 2000, 397, R1-R2.
Spooren et al., "Metabotropic Glutamate Receptors: Their Therapeutic Potential in Anxiety", Current Topics in Behavioral Neurosciences, 2010, 2, 391-413.

Spooren et al., "Pharmacological and Endocrinological Characterization of Stress-Induced Hypethermia in Singly Housed Mice Using Classical and Candidate Anxiolytics (Ly314582, Mpep and Nkp608)", Eur J Pharmacol, 2002, 435, 161-170.
Srivastava et al., "Novel Anchorage of Glur2/3 to the Postsynaptic Density by the Ampa Receptor-Binding Protein Abp", Neuron, 1998, 21(3), 581-591.
Stachowicz et al., "Anxiolytic-Like Activity of Mgs0039, A Selective Group II Mglu Receptor Antagonist, Is Serotonin- and Gaba-Dependent", Pharmacological Reports, 2011, 63, 880-887.
Stahl et al., "Negative Symptoms of Schizophrenia: A Problem That Will Not Go Away", Acta Psychiatr. Scand., 2007, 115(1), 4-11.
Star*D Research Methods Section (2001), Available from Http://Www.Edc.Gsph.Pitt.Edu/Stard/Public/Protocol/Star-D%20lll%20research%20design%20methods.Pdf, 2001, 50 pages.
Steckler, "Glutamatergic Anxiolytics Are They Any Better?", (Presentation Slides), European College of Neuropsychopharmacology, 2009, 18 pages.
Steckler et al., "Chapter 7—Neuroimaging as a Translational Tool in Animal and Human Models of Schizophrenia", Translational Neuroimaging, 2013, 195-220.
Steckler et al., "Effects of Mglu1 Receptor Blockade on Anxiety-Related Behavior in the Rat Lick Suppression Test", Psychopharmacology, 2005, 179, 198-206.
Steckler et al., "Pharmacological Treatment of PTSD—Established and New Approaches", Neuropharmacology, 2012, 62, 617-627.
Stefani et al., "Activation of Type 5 Metabotropic Glutamate Receptors Attenuates Deficits in Cognitive Flexibility Induced by NMDA Receptor Blockade", European Journal of Pharmacology, 2010, 639, 26-32.
Stefani et al., "The Modulation of Calcium Currents by the Activation of Mglurs. Functional Implications", Molecular Neurobiology, 1996, 13(1), 81-95.
Stepulak et al., "Expression of Glutamate Receptor Subunits in Human Cancers", Histochem. Cell Biol., 2009, 12 pages.
Steru et al., "The Automated Tail Suspension Test: A Computerized Device Which Differentiates Psychotropic Drugs", Prog. Neuropsychopharmacol. Exp. Psychiatry, 1987, 11, 659-671.
Steru et al., "The Tail Suspension Test: A New Method for Screening Antidepressants in Mice", Psychopharmacology, 1985, 85, 367-370.
Stone et al., "Glutamate and Dopamine Dysregulation in Schizophrenia—A Synthesis and Selective Review", J Psychopharmacol., 2007, 21(4), 440-452.
Stone, "Imaging the Glutamate System in Humans: Relevance to Drug Discovery for Schizophrenia", Curr. Pharm. Des, 2009, 15(22), 2594-2602.
Stout et al., "High-Affinity Calcium Indicators Underestimate Increases in Intracellular Calcium Concentrations Associated with Excitotoxic Glutamate Stimulations", Neuroscience, 1999, 89(1), 91-100.
Stowell et al., "Axon/Dendrite Targeting of Metabotropic Glutamate Receptors by Their Cytoplasmic Carboxy-Terminal Domains", Neuron, 1999, 22(3), 525-536.
Straiker et al., "Metabotropic Suppression of Excitation in Murine Autaptic Hippocampal Neurons", J Physiol, 2007, 578(Pt 3), 773-785.
Strange, "Use of the Gtpgs ([35s]Gtpgs and Eu-Gtpgs) Binding Assay for Analysis of Ligand Potency and Efficacy at G Protein-Coupled Receptors", British Journal of Pharmacology, 2010, 161, 1238-1249.
Stroup et al., "Results of Phase 3 of the Catie Schizophrenia Trial", Schizophr Res., 2009, 107(1),1-12.
Stulz et al., "Distinguishing Anxiety and Depression in Self-Report: Purification of the Beck Anxiety Inventory and Beck Depression Inventory-II", J Clin Psycho!, 2010, 66, 927-940.
Sun et al., "Mechanism of Glutamate Receptor Desensitization", Nature, 2002, 417, 245-253.
Sutton et al., "Regulation of Akt and Wnt Signaling by the Group II Metabotropic Glutamate Receptor Antagonist Ly341495 and Agonist Ly379268", Journal of Neurochemistry, 2011, 117, 973-983.
Svensson et al., "Ly2607540 (THLLC), A Novel Mglu2 Receptor Potentiator with Potential Anxiolytic/Antidepressant Properties: in Vivo Profiling Suggests a Link Between Behavioral and CNS

(56) References Cited

OTHER PUBLICATIONS

Neurochemical Changes" Poster 642.4, 40th Annual Meeting of Society for Neuroscience, Nov. 2010, 1 page.

Swanson et al., "A Role for Noradrenergic Transmission in the Actions of Phencyclidine and the Antipsychotic and Antistress Effects of Mglu2/3 Receptor Agonists", Annals of the New York Academy of Sciences, 2003, 1003, 309-17.

Swanson et al., "Metabotropic Glutamate Receptors as Novel Targets for Anxiety and Stress Disorders", Nature Reviews Drug Discovery, 2005, 4, 131-144.

Swanson et al., "The Group II Metabotropic Glutamate Receptor Agonist (−)-2-Oxa-4-Aminobicyclo[3.1.01]Hexane-4,6-Dicarboxylate (Ly379268) and Clozapine Reverse Phencyclidine-Induced Behaviors in Monoamine-Depleted Rats", Journal of Pharmacology & Experimental Therapeutics, 2002, 303(3), 919-927.

Swerdlow et al., "Assessing the Validity of an Animal Model of Deficient Sensorimotor Gating in Schizophrenic Patients", Arch. Gen. Psychiatry, 1994, 51, 139-154.

Swerdlow et al., "Strain Differences in the Disruption of Prepulse Inhibition of Startle After Systemic and Intra-Accumbens Amphetamine Administration",. Pharmacol. Biochem. Behav., 2007, 87 (1), 1-10.

Szapiro et al., "Facilitation and Inhibition of Retrieval in Two Aversive Tasks in Rats by Intrahippocampal Infusion of Agonists of Specific Glutamate Metabotropic Receptor Subtypes", Psychopharmacology, 2001, 156(4), 397-401.

Takahashi et al., "In Vitro Systems for the Study of Apoptosis", Advances in Pharmacology, 1997, 41, 89-106.

Takahashi et al., "Role of the Large Extracellular Domain of Metabotropic Glutamate Receptors in Agonist Selectivity Determination", J. Biol. Chem., 1993, 268(26), 19341-19345.

Takamori et al., "Antipsychotic Action of Selective Group II Metabotropic Glutamate Receptor Agonist Mgs0008 and Mgs0028 on Conditioned Avoidance Responses in the Rat", Life Sci., 2003, 73, 1721-1728.

Takamori, "Vgluts: 'Exciting' Times for Glutamatergic Research?", Neuroscience Research, 2006, 55(4), 343-351.

Takumi et al., "The Arrangement of Glutamate Receptors in Excitatory Synapses", Annals of the New York Academy of Sciences, 1999, 868, 474-482.

Tamminga et al., "Glutamate Pharmacology and the Treatment of Schizophrenia: Current Status and Future Directions", Intl Clinical Psychopharmacology, 1995, 10(Suppl-37), 29-37.

Tamminga, "Schizophrenia and Glutamatergic Transmission", Critical Reviews in Neurobiology, 1998, 12(1-2), 21-36.

Tanabe et al., "A Family of Metabotropic Glutamate Receptors", Neuron, 1992, 8(1), 169-179.

Tandon et al., "Schizophrenia, Just the Facts, 5.Treatment and Prevention Past, Present, and Future", Schizophr Res., Jul. 2010, 122, 1-23.

Tang et al., "Metabotropic Glutamate Receptors in the Control of Neuronal Activity and as Targets for Development of Anti-Epileptogenic Drugs", Curr. Med. Chem, 2009, 16(17), 2189-2204.

Tang et al., "Prolonged Anticonvulsant Action of Glutamate Metabotropic Receptor Agonists in Inferior Colliculus of Genetically Epilepsy-Prone Rats", European Journal of Pharmacology, 1997, 327(2-3), 109-115.

Targum et al., "Redefining Affective Disorders: Relevance for Drug Development", CNS Neuroscience and Therapeutics, 2008, 14, 2-9.

Targum et al., "The Relevance of Anxious Depression as a Distinct Entity for Psychopharmacology and Drug Development", US Psychiatry, 2009, 2(1), 29-31.

Tarrier et al., "A Trial of Two Cognitive Behavioural Methods of Treating Drug-Resistant Residual Psychotic Symptoms in Schizophrenic Patients: I. Outcome", Br J Psychiatry, 1993, 162, 524-532.

Tatarczyska et al., "The Antianxiety-Like Effects of Antagonists of Group I and Agonists of Group II and III Metabotropic Glutamate Receptors After Intrahippocampal Administration", Psychopharmacology, 2001, 158, 94-99.

Taylor et al., "Stimulation of Microglial Metabotropic Glutamate Receptor Mglu2 Triggers Tumor Necrosis Factor?-Induced Neurotoxicity in Concert with Microglial-Derived Fas Ligand", Journal of Neuroscience, 2005, 25(11), 2952-2964.

Taylor et al., "The Efficacy of Nefazodone Augmentation for Treatment-Resistant Depression with Anxiety Symptoms or Anxiety Disorder", Depression and Anxiety, 2003, 18, 83-88.

Teitler et al., "4-[125i]Iodo-(2,5-Dimethoxy)Phenylisopropylamine and [3h]Ketanserin Labeling of 5-Hydroxytryptamine2 (5ht2) Receptors in Mammalian Cells Transfected with a Rat 5ht2 Cdna: Evidence for Multiple States and Not Multiple 5ht2 Receptor Subtypes", Molecular Pharmacology, 1990, 38, 594-598.

Testa et al., "Immunohistochemical Localization of Metabotropic Glutamate Receptors Mglur1a and Mglur2/3 in the Rat Basal Ganglia", Journal of Comparative Neurology, 1998, 390(1), 5-19.

Testa et al., "Metabotropic Glutamate Receptor Mrna Expression in the Basal Ganglia of the Rat", Journal of Neuroscience, 1994, 14(5), 3005-3018.

Thase et al., "Extended Release Quetiapine Fumarate in Major Depressive Disorder: Analysis in Patients with Anxious Depression", Depression and Anxiety, 2012, 29, 574-586.

Thase et al., "Remission Rates Following Antidepressant Therapy with Bupropion or Selective Serotonin Reuptake Inhibitors: A Meta-Analysis of Original Data From 7 Randomized Controlled Trials", J Clin Psychiatry, 2005, 66(8), 974-981.

Thase, "Augmentation Strategies for Depression: History and Concepts", CNS Spectr, 2007, 12(12), (Suppl 22), 3-5.

Thase, "Depression and Sleep: Pathophysiology and Treatment", Dialogues Clin Neurosci, 2006, 8, 217-226.

Thathiah et al., "The Role of G Protein-Coupled Receptors in the Pathology of Alzheimer's Disease", Nature Reviews Neuroscience, 2011, 12, 73-87.

Thompson et al., "Activation of Group II and Group III Metabotropic Glutamate Receptors by Endogenous Ligand(S) and the Modulation of Synaptic Transmission in the Superficial Superior Colliculus", Neuropharmacology, 2004, 47(6), 822-832.

Thomsen et al., "Actions of Phenylglycine Analogs at Subtypes of the Metabotropic Glutamate Receptor Family", European Journal of Pharmacology, 1994, 267(1), 77-84.

Thomsen et al., "Roles of Metabotropic Glutamate Receptor Subtypes in Modulation of Pentylenetetrazole-Induced Seizure Activity in Mice", Neuropharmacology, 1998, 37(12), 1465-1473.

Tiihonen et al., "The Efficacy of Lamotrigine in Clozapine-Resistant Schizophrenia: A Systematic Review and Meta-Analysis", Schizophr Res. 2009, 109(1-3), 10-14.

Tilakaratne et al., "Chronic Fluoxetine or Desmethylimipramine Treatment Alters 5-Ht2 Receptor Mediated C-Fos Gene Expression", European Journal of Pharmacology, 1995, 290(3), 263-266.

Tizzano et al., "Induction or Protection of Limbic Seizures in Mice by Mglur Subtype Selective Agonists", Neuropharmacology, 1995, 34(8), 1063-1067.

Tizzano et al., "The Anxiolytic Action of Mglu2/3 Receptor Agonist, Ly354740, in the Fear-Potentiated Startle Model in Rats is Mechanistically Distinct From Diazepam", Pharmacology, Biochemistry and Behavior, 2002, 73, 367-374.

Tokita et al., "Roles of Glutamate Signaling in Preclinical and/or Mechanistic Models of Depression", Pharmacology, Biochemistry and Behavior, 2012, 100, 688-704.

Tokunaga et al., "Neuroimaging and Physiological Evidence for Involvement of Glutamatergic Transmission in Regulation of the Striatal Dopaminergic System", Journal of Neuroscience, 2009, 29(6), 1887-1896.

Tolchard et al., "Modulation of Synaptic Transmission in the Rat Ventral Septal Area by the Pharmacological Activation of Metabotropic Glutamate Receptors", European Journal of Neuroscience, 2000, 12(5), 1843-1847.

Tollefson et al., "Fluoxetine, Placebo, and Tricyclic Antidepressants in Major Depression with and without Anxious Features", J Clin Psychiatry, 1994, 55(2), 50-59.

Toms et al., "Latest Eruptions in Metabotropic Glutamate Receptors", Trends in Pharmacological Sciences, 1996, 17(12), 429-435.

Tong et al., "Signal Transduction in Neuronal Death", Journal of Neurochemistry, 1998, 71(2), 447-459.

(56) References Cited

OTHER PUBLICATIONS

Trabanco et al., "Discovery of 5- and 6-Substituted Isoquinolones: A New Class of Positive Allosteric Modulators of the Metabotropic Glutamate 2 Receptor", XXI'ST International Symposium on Medicinal Chemistry, Sep. 2010, 1 page.
Trabanco et al., "Imidazo[1,2-A]Pyridines: Orally Active Positive Allosteric Modulators of the Metabotropic Glutamate 2 Receptor", J Med Chem, 2012, 55, 2688-2701.
Trabanco et al., "Mglur2 Positive Allosteric Modulators (Pams): A Patent Review (2009-Present)", Expert Opin, 2013, 19 pages.
Trabanco et al., "New Positive Allosteric Modulators of the Metabotropic Glutamate Receptor 2 (Mglur2). Identification and Synthesis of N-Propyl-5-Substituted Isoquinolones", Med Chem Commun, 2011, 2, 132-139.
Trabanco et al., "New Positive Allosteric Modulators of the Metabotropic Glutamate Receptor 2 (Mglur2): Identification and Synthesis of N-Propyl-8-Chloro-6-Substituted Isoquinolones", Bioorganic & Medicinal Chemistry Letters, 2011, 21, 971-976.
Trabanco et al., "Progress in the Developement of Positive Allosteric Modulators of the Metabotropic Glutamate Receptor 2", Current Medicinal Chemistry, 2011, 18, 47-68.
Trabanco et al., "Synthesis, Evaluation, and Radiolabeling of New Potent Positive Allosteric Modulators of the Metabotropic Glutamate Receptor 2 as Potential Tracers for Positron Emission Tomography Imaging", J Med Chem, 2012, 55, 8685-8689.
Tresadern et al., "Scaffold Hopping From Pyridones to Imidazo[1,2-A]Pyridines. New Positive Allosteric Modulators of Metabotropic Glutamate 2 Receptor", Bioorganic & Medicinal Chemistry Letters, 2010, 20, 175-179.
Trettel et al., "Endocannabinoid Signalling Selectively Targets Perisomatic Inhibitory Inputs to Pyramidal Neurones in Juvenile Mouse Neocortex", Journal of Physiology, 2004, 556(Pt 1), 95-107.
Treutlein et al., "Dissection of Phenotype Reveals Possible Association Between Schizophrenia and Glutamate Receptor Delta 1 (Grid1) Gene Promoter", Schizophr. Res., 2009, 111(1-3), 123-130.
Trivedi et al., "Adjunctive Aripiprazole in Major Depressive Disorder: Analysis of Efficacy and Safety in Patients with Anxious and Atypical Features", J Clin Psychiatry, 2008, 69, 1928-1936.
Trivedi et al., "Evaluation of Outcomes with Citalopram for Depression Using Measurement-Based Care in Star*D: Implications for Clinical Practice", Am J Psychiatry, 2006; 163, 28-40.
Trofimova et al., "The Lability of Behavior as a Marker of Comorbid Depression and Anxiety", Advances in Bioscience and Biotechnology, 2010, 1, 190-199.
Trullas et al., "Functional Antagonists at the NMDA Receptor Complex Exhibit Antidepressant Actions", Eur J Pharmacol, Aug. 1990, 185(1), 1-10.
Tsai et al., "Immunocytochemical Distribution of N-Acetylaspartylglutamate in the Rat Forebrain and Glutamatergic Pathways", Journal of Chemical Neuroanatomy, 1993, 6(5), 277-292.
Tsai, "Central N-Acetyl Aspartylglutamate Deficit: A Possible Pathogenesis of Schizophrenia", Med Sci. Monit., 2005, 11(9), Hy39-Hy45.
Tsunoka et al., "Association Analysis of Grm2 and Htr2a with Methamphetamine-Induced Psychosis and Schizophrenia in the Japanese Population", Progress in Neuro-Psychopharmacology & Biological Psychiatry, 2010, 34(4), 639-644.
Tsunoka et al., "Association Analysis of Group II Metabotropic Glutamate Receptor Genes (Grm2 and Grm3) with Mood Disorders and Fluvoxamine Response in a Japanese Population", Progress in Neuro-Psychopharmacology & Biological Psychiatry, 2009, 33(5), 875-879.
Tuominen et al., "Glutamatergic Drugs for Schizophrenia", The Cochrane Collaboration, Cochrane Database Syst Rev., Apr. 2006, 1, 8 pages.
Tyrer, "The Case for Cothymia: Mixed Anxiety and Depression as a Single Diagnosis", British Journal of Psychiatry, 2001, 179, 191-193.

Uher et al., "Differential Efficacy of Escitalopram and Nortriptyline on Dimensional Measures of Depression", British Journal of Psychiatry, 2009, 194, 252-259.
Uher et al., "Melancholic, Atypical and Anxious Depression Subtypes and Outcome of Treatment with Escitalopram and Nortriptyline", Journal of Affective Disorders, 2011, 132, 112-120.
Um et al., "Alzheimer Amyloid-B Oligomer Bound to Postsynaptic Prion Protein Activates Fyn to Impair Neurons", Nature Neuroscience, 2012, 15(9), 1227-1235.
Undine et al., "Molecular Mechanisms of Schizophrenia", Cell Physiol Biochem, 2007, 20, 687-702.
Ung et al., "Synthesis and Biological Activities of Conformationally Restricted Cyclopentenyl-Glutamate Analogues", Journal of Organic Chemistry, 2002, 67(1), 227-233.
Urwyler, "Allosteric Modulation of Family C G-Protein-Coupled Receptors From Molecular Insights to Therapeutic Perspectives", Pharmacol Rev, 2011, 63, 59-126.
Uslaner et al., "Combined Administration of an Mglu2/3 Receptor Agonist and A 5-Ht 2a Receptor Antagonist Markedly Attenuate the Psychomotor-Activating and Neurochemical Effects of Psychostimulants", Psychopharmacology (Berl), 2009, 206(4), 641-651.
Uys et al., "Glutamate: the New Frontier in Pharmacotherapy for Cocaine Addiction", CNS & Neurological Disorders—Drug Targets, 2008, 7, 482-491.
Vaccarino et al., "Symptoms of Anxiety in Depression: Assessment of Item Performance of the Hamilton Anxiety Rating Scale in Patients with Depression", Depression and Anxiety, 2008, 25, 1006-1013.
Valentine et al., "Targeting Glial Physiology and Glutamate Cycling in the Treatment of Depression", Biochem. Pharmacol., 2009, 78(5), 431-439.
Vales et al., "The Difference in Effect of Mglu2/3 and Mglu5 Receptor Agonists on Cognitive Impairment Induced by Mk-801", European Journal of Pharmacology, 2010, 639, 91-98.
Van Beljouw et al., "The Course of Untreated Anxiety and Depression, and Determinants of Poor On-Year Outcome: A One-Year Cohort Study", BMC Psychiatry, 2010, 10, 86.
Van Berckel et al., "Modulation of Amphetamine-Induced Dopamine Release by Group Ii Metabotropic Glutamate Receptor Agonist Ly354740 in Non-Human Primates Studied with Positron Emission Tomography", Neuropsychopharmacology, 2006, 31, 967-977.
Van Den Pol, "Presynaptic Metabotropic Glutamate Receptors in Adult and Developing Neurons: Autoexcitation in the Olfactory Bulb", Journal of Comparative Neurology, 1995, 359(2), 253-271.
Van Der Linden et al., "In Vitro Chracterization of the Binding of the Mglu2 Receptor Positive Allosteric Modulator [3h]Jnj-40068782 to Native and Recombinant Mglu2 Receptors", $7^{th}$ Int. Meeting on Metabotropic Glutamate Receptors 2011, 1 page.
Van Tol et al., "Regional Brain Volume in Depression and Anxiety Disorders", Arch Gen Psychiatry, 2010, 67(10), 1002-1011.
Van Valkenberg et al., "Anxious Depressions. Clinical, Family History, and Naturalistic Outcome—Comparisons with Panic and Major Depressive Disorders", Journal of Affective Disorders, 1984, 6(1), 67-82.
Van Vliet et al., "Adaptive Changes in the Number of Gs- and Gi-Proteins Underlie Adenylyl Cyclase Sensitization in Morphine-Treated Rat Striatal Neurons", European Journal of Pharmacology, 1993, 245(1), 23-29.
Vandergriff et al., "The Selective Mglu2/3 Receptor Agonist Ly354740 Attenuates Morphine-Withdrawal-Induced Activation of Locus Coeruleus Neurons and Behavioral Signs of Morphine Withdrawal", Neuropharmacology, 1999, 38, 217-222.
Vandesompele et al., "Accurate Normalization of Real-Time Quantitative Rt-Pcr Data by Geometric Averaging of Multiple Internal Control Genes", Genome Biology, 2002, 3(7), 1-12.
Varney et al., "Metabotropic Glutamate Receptor Involvement in Models of Acute and Persistent Pain: Prospects for the Development of Novel Analgesics", Current Drug Targets—CNS & Neurological Disorders, 2002, 1, 283-296.
Vasilieva, "Clinical-Dynamic Characteristics of Depressive Disorders Comorbid with Anxiety Disorders", Abstract P01-109 of 18th European Congress of Psychiatry, 2010, 1 page.

(56) References Cited

OTHER PUBLICATIONS

Ver Donck et al., "Low Dose Subchronic Phencyclidine (PCP) Pretreatment Potentiates Acute PCP-Induced Hyperlocomotion in Adult Rats: A Model of Schizophrenia?", Presentation Abstract, Society for Neuroscience, 2011, 2 pages.
Verhagen et al., "Effect of the 5-Httlpr Polymorphism in the Serotonin Transporter Gene on Major Depressive Disorder and Related Comorbid Disorders", Psychiatric Genetics, 2009, 19, 39-44.
Verma et al., "Regulation of Striatal Dopamine Release by Metabotropic Glutamate Receptors", Synapse 1998, 28(3), 220-226.
Vernon et al., "Additive Neuroprotection by Metabotropic Glutamate Receptor Subtype-Selective Ligands in aRat Parkinson's Model", Neuroreport, 2008, 19(4), 475-478.
Versiani et al., "Fluoxetine Versus Amitriptyline in the Treatment of Major Depression with Associated Anxiety (Anxious Depression): A Double-Blind Comparison", International Clinical Psychopharmacology, 1999, 14, 321-327.
Vezina et al., "Metabotropic Glutamate Receptors and the Generation of Locomotor Activity: Interactions with Midbrain Dopamine", Neuroscience & Biobehavioral Reviews, 1999, 23(4), 577-589.
Vinson et al., "Metabotropic Glutamate Receptors as Therapeutic Targets for Schizophrenia", Neuropharmacology, 2012, 62, 1461-1472.
Vogel et al., "A Simple and Reliable Conflict Procedure for Testing Anti-Anxiety Agents", Psychopharmacologia, 1971, 21, 1-7.
Vogel et al., "Drug Effects on Rem Sleep and on Endogenous Depression", Neuroscience & Biobehavioral Reviews, 1990, 14, 49-63.
Vogel et al., "Evidence for REM Sleep Deprivation as the Mechanism of Action of Antidepressant Drugs", Prog Neuropsychopharmacol Biol Psychiatry, 1983, 7(2-3), 343-349.
Vollenweider et al., "A Systems Model of Altered Consciousness: Integrating Natural and Drug-Induced Psychoses", Brain Res. Bull., 2001, 56, 495-507.
Vollenweider et al., "Differential Psychopathology and Patterns of Cerebral Glucose Utilization Produced by (S)- and (R)-Ketamine in Healthy Volunteers Using Positron Emission Tomography (Pet)", Eur Neuropsychopharmacol, 1997, 7, 25-38.
Vollenweider et al., "Effect of Clozapine and Ketanserin on S-Ketamine-Induced Brain Activation and Psychotic Symptoms in Healthy Humans", Abstract, Symposia, 28th Cinp World Congress of Neuropsychopharmacology, 2012, 2 pages.
Vollenweider et al., "Metabolic Hyperfrontality and Psychopathology in the Ketamine Model of Psychosis Using Positron Emission Tomography (Pet) and [18f]fluorodeoxyglucose (Fdg)", Eur Neuropsychopharmacol, 1997, 7, 9-24.
Vollenweider et al., "Psilocybin Induces Schizophrenia-Like Psychosis in Humans Via a Serotonin-2 Agonist Action", Neuroreport, 1998, 9, 3897-3902.
Vollenweider, "Positron Emission Tomography and Fluorodeoxyglucose Studies of Metabolic Hyperfrontality and Psychopathology in the Psilocybin Model of Psychosis", Neuropsychopharmacology, 1997, 16, 357-372.
Wachtel et al., "Glutamate: A New Target in Schizophrenia?", Trends in Pharmacological Sciences, 1990, 11(6), 219-220.
Wadenberg, "Conditioned Avoidance Response in the Development of New Antipsychotics", Curr Pharm Des, 2010, 16, 358-370.
Wadenberg et al., "The Conditioned Avoidance Response Test Re-Evaluated: Is it a Sensitive Test for the Detection of Potentially Atypical Antipsychotics?", Neurosci. Biobehav. Rev., 1999, 23, 851-862.
Wainer, "Finding Time for Allosteric Interactions", Nature Biotechnology, 2004, 22(11), 1376-1377.
Walker et al., "Group II Metabotropic Glutamate Receptors Within the Amygadale Regulate Fear as Assessed with Potentiated Startle in Rats", Behav Neurosci, 2002, 116, 1075-1083.
Walker et al., "The Role of Amygdala Glutamate Receptors in Fear Learning, Fear-Potentiated Startle, and Extinction", Pharmacol. Biochem. Behav., 2002, 71(3), 379-392.

Wang et al., "Allosteric Modulators of G Protein-Coupled Receptors: Future Therapeutics for Complex Physiological Disorders", J Pharmacol. Exp. Ther., 2009, 331(2), 340-348.
Wang et al., "Development of Metabotropic Glutamate Receptor Ligands for Neuroimaging", Curr Med Imaging Rev, 2007, 3, 186-205.
Wang et al., "Radiosynthesis of Pet Radiotracer as a Prodrug for Imaging Group II Metabotropic Glutamate Receptors in Vivo", Bioorganic & Medicinal Chemistry Letters, 2012, 22, 1958-1962.
Warden et al., "The Star*D Project Results: A Comprehensive Review of Findings", Current Psychiatry Reports, 2007, 9, 449-459.
Warnock et al., "In Vivo Evidence for Ligand-Specific Receptor Activation in the Central CRF System, As Measured by Local Cerebral Glucose Utilization", Peptides, 2009, 30, 947-954.
Watanabe et al., "Mglur2 Postsynaptically Senses Granule Cell Inputs At Golgi Cell Synapses" Neuron, 2003, 39, 821-829.
Watkins, "L-Glutamate as a Central Neurotransmitter: Looking Back", Biochem Soc Trans, 2000, 28, 297-310.
Watkins et al., "Structure-Activity Relationships in the Development of Excitatory Amino Acid Receptor Agonists and Competitive Antagonists", Trends in Pharmacological Sciences, 1990, 11(1), 25-33.
Webb et al., "Apoptosis: An Overview of the Process and its Relevance in Disease", Advances in Pharmacology, 1997, 41, 1-34.
Weinberger et al., "Schizophrenia Drug Says Goodbye to Dopamine", Nature Medicine, 2007, 13, 1018-1019.
Weinberger, "The Biological Basis of Schizophrenia: New Directions", Journal of Clinical Psychiatry, 1997, 58(Suppl 10), 22-27.
Weiner et al., "5-Hydroxytryptamine2a Receptor Inverse Agonists as Antipsychotics", Journal of Pharmacology & Experimental Therapeutics, 2001, 299(1), 268-276.
Weisstaub, "Cortical 5-Ht2a Receptor Signaling Modulates Anxiety-Like Behaviors in Mice", Science, 2006, 313, 536-540.
Wheeler et al., "(2s,1's,2'r,3'r)-2(2'-Carboxy-3'-Hydroxymethyl-Cyclopropyl)Glycine-[3h], a Potent and Selective Radioligand for Labeling Group 2 and 3 Metabotropic Glutamate Receptors", Bioorganic & Medicinal Chemistry Letters, 2005, 15, 349-351.
Whitehouse et al., "Clinical Trial Designs for Demonstrating Disease-Course-Altering Effects in Dementia", Alzheimer Disease and Associated Disorders, 1998, 12, 281-294.
Wicke et al., "Effects of Metabotropic Glutamate Receptor (Mglur) 2/3 Agonists and Antagonist on Rat Sleep Eeg", Program No. 839.2/M9, Neuroscience Meeting Planner, Society for Neuroscience, 2009, 2 pages.
Wieronska et al., "Anxiolytic Action of Group II and III Metabotropic Glutamate Receptors Agonists Involves Neuropeptide Y in the Amygdala", Pharmacol. Rep., 2005, 57(6), 734-743.
Wieronska et al., "Glutamate-Based Anxiolytic Ligands in Clinical Trials", Expert Opin Investig Drugs, 2013, 22(8), 1007-1022.
Wieronska et al., "Metabotropic Glutamate Receptor 4 Novel Agonist Lsp1-2111 with Anxiolytic, but not Antidepressant-Like Activity, Mediated by Serotonergic and Gabaergic Systems", Neuropharmacology, 2010, 59, 627-634.
Wieronska et al., "Metabotropic Glutamate Receptors in the Tripartite Synapse as a Target for New Psychotropic Drugs", Neurochem. Int, 2009, 55(1-3), 85-97.
Wieronska et al., "On the Mechanism of Anti-Hyperthermic Effects of Ly379268 and Ly487379, Group II Mglu Receptors Activators, in the Stress-Induced Hyperthermia in Singly Housed Mice", Neuropharmacology, 2012, 62, 322-331.
Wieronska et al., "Opposing Efficacy of Group III Mglu Receptor Activators, Lsp1-2111 and Amn082, in Animal Models of Positive Symptoms of Schizophrenia", Psychopharmacology, Sep. 2011, 14 pages.
Wiethoff et al., "Prevalence and Treatment Outcome in Anxious Versus Nonanxious Depression: Results From the German Algorithm Project", J Clin Psychiatry, 2010, 71(8), 1047-1054.
Williams et al., "Characterization of Polyamines Having Agonist, Antagonist, and Inverse Agonist Effects at the Polyamine Recognition Site of the NMDA Receptor", Neuron, 1990, 5(2), 199-208.
Williams et al., "International Study to Predict Optimized Treatment for Depression (Ispot-D), A Randomized Clinical Trial: Rationale and Protocol", Trials, 2011, 12(4), 17 pages.

(56) References Cited

OTHER PUBLICATIONS

Wilsch et al., "Metabotropic Glutamate Receptor Agonist DCG-IV as NMDA Receptor Agonist in Immature Rat Hippocampal Neurons", European Journal of Pharmacology, 1994, 262(3), 287-291.
Wilson et al., "Antidepressants and Sleep: A Qualitative Review of the Literature", Drugs, 2005, 65, 927-947.
Winter et al., "Serotonergic/Glutamatergic Interactions: The Effects of Mglur2/3 Receptor Ligands in Rats Trained with LSD and PCP as Discriminative Stimuli.", Psychopharmacol. (Berl), 2004, 172, 233-240.
Wischhof et al., "Pre-Treatment with the Mglu2/3 Receptor Agonist Ly379268 Attenuates DOI-Induced Impulsive Responding and Regional C-Fos Protein Expression", Psychopharmacology, Aug. 2011, 14 pages.
Witkin et al., "Metabotropic Glutamate Receptors in the Control of Mood Disorders", CNS & Neurological Disorders—Drug Targets, 2007, 6, 87-100.
Wittchen et al., "Disabilities and Quality of Live in Pure and Comorbid Generalized Anxiety Disorder and Major Depression in a National Survey", Intl Clinical Psychopharmacology, 2000, 15, 319-328.
Wittchen et al., "DSM-III-R Generalized Anxiety Disorder in the National Comorbidity Survey", Arch Gen Psychiatry, 1994, 51, 355-364.
Wittchen et al., "The Size and Burden of Mental Disorders and Other Disorders of the Brain in Europe 2010", European Neuropsychopharmacology, 2011, 21, 655-679.
Wittmann et al., "Dopamine Modulates the Function of Group II and Group III Metabotropic Glutamate Receptors in the Substantia Nigra Pars Reticulata", J Pharmacol. Exp. Ther., 2002, 302(2), 433-441.
Wong et al., "The Role of Imaging in Proof of Concept for CNS Drug Discovery and Development", Neuropsychopharmacology, 2009, 34, 187-203.
Woolley et al., "The Mglu2 but not the Mglu3 Receptor Mediates the Actions of the Mglur2/3 Agonist, Ly379268, in Mouse Models Predictive of Antipsychotic Activity", Psychopharmacology, 2008, 196, 431-440.
World Health Organization, "Mental Health: New Understanding, New Hope", 2001, 169 pages.
Wright e al., "[3h]Ly341495 Binding to Group II Metabotropic Glutamate Receptors in Rat Brain", Journal of Pharmacology & Experimental Therapeutics, 2001, 298(2), 453-460.
Wroblewska et al., "N-Acetylaspartylglutamate Activates Cyclic Amp-Coupled Metabotropic Glutamate Receptors in Cerebellar Astrocytes", Glia, 1998, 24(2), 172-179.
Xi et al., "Group II Metabotropic Glutamate Receptors Modulate Extracellular Glutamate in the Nucleus Accumbens", Journal of Pharmacology & Experimental Therapeutics, 2002, 300(1), 162-171.
Xiao et al., "Desensitization of G-Protein-Coupled Receptors. Agonist-Induced Phosphorylation of the Chemoattractant Receptor Car1 Lowers its Intrinsic Affinity for Camp", J. Biol. Chem., 1999, 274(3), 1440-1448.
Xiao et al., "Metabotropic Glutamate Receptor Activation Causes a Rapid Redistribution of Ampa Receptors", Neuropharmacology, 2001, 41(6), 664-671.
Xu et al., "Neurotransmitter Receptors and Cognitive Dysfunction in Alzheimer's Disease and Parkinson's Disease", Progress in Neurobiology, 2012, 97, 1-13.
Yanamala et al., "Preferential Binding of Allosteric Modulators to Active and Inactive Conformational States of Metabotropic Glutamate Receptors", BMC Bioinformatics, 2008, 9(Suppl 1), S16.
Yao et al., "Enhancement of Glutamate Uptake Mediates the Neuroprotection Exerted by Activating Group II or III Metabotropic Glutamate Receptors on Astrocytes", Journal of Neurochemistry, 2005, 92(4), 948-961.
Yasuhara et al., "Metabotropic Glutamate Receptors: Potential Drug Targets for Psychiatric Disorders",Open Medicinal Chemistry Journal, 2010, 4, 20-36.

Ye et al., "Metabotropic Glutamate Receptor Agonists Reduce Glutamate Release From Cultured Astrocytes", Glia, 1999, 25(3), 270-281.
Yokoi et al., "Impairment of Hippocampal Mossy Fiber Ltd in Mice Lacking Mgiur2", Science, 1996, 273, 645-647.
Young et al., "Biomarkers of Oxidative Stress in Schizophrenic and Control Subjects", Prostaglandins Leukot. Essent. Fatty Acids, 2007, 76(2), 73-85.
Young et al., "Evidence for a Role of Metabotropic Glutamate Receptors in Sustained Nociceptive Inputs to Rat Dorsal Horn Neurons," Neuropharmacology, 1994, 33(1), 141-144.
Young et al., "The Involvement of Metabotropic Glutamate Receptors and Their Intracellular Signalling Pathways in Sustained Nociceptive Transmission in Rat Dorsal Horn Neurons", Neuropharmacology, 1995, 34(8), 1033-1041.
Yuan et al., "Glutamate-Induced Swelling of Cultured Astrocytes is Mediated by Metabotropic Glutamate Receptor", Science in China, Series C, Life Sciences, 1996, 39(5), 517-522.
Yucel et al., "Anterior Cingulate Volumes in Never-Treated Patients with Major Depressive Disorder", Neuropsychopharmacology, 2008, 33, 3157-3163.
Yuzaki et al., "Pharmacological and Immunocytochemical Characterization of Metabotropic Glutamate Receptors in Cultured Purkinje Cells", J. Neurosci., 1992, 12(11), 4253-4263.
Zarate et al., "An Open-Label Trial of Riluzole in Patients with Treatment-Resistant Major Depression", Am J Psychiatry, 2004, 161, 171-174.
Zeilhofer et al., "Differential Effects of Ketamine Enantiomers on NMDA Receptor Currents in Cultured Neurons", Eur J Pharmacol, 1992, 213, 155-158.
Zhang et al., "1-[(1-Methyl-1h-Imidazol-2-Yl)Methyl]-4-Phenylpiperidines as Mglur2 Positive Allosteric Modulators for the Treatment of Psychosis", J Med Chem, 2011, 54, 1724-1739.
Zhang et al., "3-(Imidazolyl Methyl)-3-Aza-Bicyclo[3.1.0]Hexan-6-Yl)Methyl Ethers: a Novel Series of Mglur2 Positive Allosteric Modulators", Bioorg Med Chem Lett, 2008, 18, 5493-5496.
Zhao et al., "Activation of Group II Metabotropic Glutamate Receptors Attenuates Both Stress and Cue-Induced Ethanol-Seeking and Modulates C-Fos Expression in the Hippocampus and Amygdala", Journal of Neuroscience, 2006, 26(39), 9967-9974.
Zhu et al., "Rapid Enhancement of High Affinity Glutamate Uptake by Glucocorticoids in Rat Cerebral Cortex Synaptosomes and Human Neuroblastoma Clone Sk-N-Sh: Possible Involvement of G-Protein", Biochemical & Biophysical Research Communications, 1998, 247(2), 261-265.
Zhu, "The Competitive and Noncompetitive Antagonism of Receptor-Mediated Drug Actions in the Presence of Spare Receptors", Journal of Pharmacological & Toxicological Methods, 1993, 29(2), 85-91.
Zimmerman et al., "Frequency of Anxiety Disorders in Psychiatric Outpatients with Major Depressive Disorder", Am J Psychiatry, 2000, 157, 1337-1340.
Zuena et al., "Prenatal Restraint Stress Generates Two Distinct Behavioral and Neurochemical Profiles in Male and Female Rats", Plos. One, 2008, 3(5), E2170.
Zusso et al., "Cerebellar Granular Cell Cultures as an In Vitro Model for Antidepressant Drug-Induced Meurogenesis", Critical Reviews in Neurobiology, 2004, 16(1&2), 59-65.
Zwart et al., "Sazetidine-A is a Potent and Selective Agonist at Native and Recombinant A4β32 Nicotinic Acetylcholine Receptors", Mol Pharmacol, 2008, 73, 1838-1843.
Abi-Saab et al. "The NMDA Antagonist Model for Schizophrenia: Promise and Pitfalls." Pharmacopschiatry. vol. 31. 1998. 104-9.
Agami et al. "An Efficient Synthesis of Polysubstituted 3-Halo-2(1H)-Pyridinones." Synthesis. (1). 2002. 79-82.
Armstrong et al. "Characterization of Competitive Inhibitors for the Transferase Activity of *Pseudomonas aeruginosa* Exotoxin A." Journal of Enzyme Inhibition and Medicinal Chemistry. vol. 17 (4). 2002. 235-46.
Arnt. "Differential effects of classical and newer antipsychotics on the hypermotility induced by two dose levels of D-amphetamine." European Journal of Pharmacology. vol. 283. 1995. 55-62.

(56) References Cited

OTHER PUBLICATIONS

Bick et al. "Photo-oxidative cleavage: an alternative method for degrading bisbenzylisoquinoline alkaloids." Journal of Natural Products. vol. 49 (3). May-Jun. 1986. 373-85.
Bohm et al. "Thieno Compounds Part 5: Basically Substituted Thieno[2,3-d]pyrimidines." Pharmazie. vol. 41. 1986. 23-25.
Borowitz et al. "Organophosphorus Chemistry. III. The Reactions of Triphenylphosphine with Secondary a-Bromo Ketones and with 2-Bromodimedone." Dec. 1966. 4031-7.
Cartmell et al. "Characterization of [3H]-(2S,2'R,3'R0-2-(2'3'-dicarboxycyclopropyl)glycine ([3H]-DCG IV) binding to metabotropic mGlu2 receptor-transfected cell membranes." British Journal of Pharmacology. vol. 123. 1998. 497-504.
Chakrasali et al. "Reaction of Acylketene S,N-Acetals with Malonyl Chloride: Synthesis of Novel 1,5-Substituted 4-Hydroxy-6-methylthio-2 (1H)-pyridones and 6,8-Substituted 4-Hydroxy-7-methylthio-2,5-dioxo-5,6-dihydro-2H-pyrano[3,2-c] pyridines." Jan. 1988. 87-9.
Chiarugi et al. "Novel Isoquinolinone-Derived Inhibitors of Poly(ADP-ribose) Polymerase-1: Pharmacological Characterization and Neuroprotective Effects in an in Vitro Model of Cerebral Ischemia." Journal of Pharmacology and Experimental Therapeutics. vol. 305 (3). 2003. 943-9.
Comins et al. "N- vs. O-Alkylation in the Mitsunobu Reaction of 2-Pyridone." Tetrahedron Letters. vol. 35 (18). 1994. 2819-22.
Costantino et al. "Modeling of Poly (ADP-ribose) polymerase (PARP) Inhibitors. Docking of Ligands and Quantitative Structure-Activity Relationship Analysis." Journal of Medicinal Chemistry. vol. 44. 2001. 3786-94.
Czapski et al. "Effect of poly (ADP-ribose) polymerase inhibitors on oxidative stress evoked hydroxyl radical level and macromolecules oxidation in cell free system of rat brain cortex." Neuroscience Letters. vol. 356. 2004. 45-8.
Davis et al. "2,1-Benzisothiazoles. XII. [1]. The Use of N-Substituted-2,1-Benzisothiazolium Salts as Synthetic Equivalents of o-Aminobenz-aldehydes. A Simple Synthesis of Some 2-Quinolones." Journal of Heterocyclic Chemistry. vol. 20. Nov.-Dec. 1983. 1707-8.
Fisher et al. "Non-Peptide RGD Surrogates Which Mimic a Gly-Asp B-Turn: Potent Antagonists of Platelet Glycoprotein llb-llla." J. Med. Chem. 1997. vol. 40. 2085-101.
Flohr et al. "Poly(ADP-ribosyl)ation accelerates DNA repair in a pathway dependent on Cockayne syndrome B protein." Nucleic Acids Research. vol. 31 (18). 2003. 5332-7.
Fujii et al. "Lactams. IX. Generation of Latam Carbonyl Function in 1,3-Disubstituted Piperidines by Mercuric Acetate-EDTA Oxidation: Effects of Hydrocarbon Substituents at the 3-Postion." Chem. Pharm. Bull. vol. 25 (9). 1977. 2336-42.
Fujita et al. "Studies on 1-Alkyl-2(1H)-pyridone Derivatives XXXII. The Friedel-Crafts Reaction of 1-Alkyl-2(1H)-pyridone Derivatives with Acid Anhydride." Journal of the Pharmaceutical Society of Japan. vol. 110. 1990. 449-52.
Gavezzotti. "Are Crystal Structures Predictable?" Accounts of Chemical Research. vol. 27. 1994. 309-14.
Gewald. "Heterocyclen aus CH-aciden Nitrilen, VII. 2-Aminothiophene aus a-Oxo-mercaptanen und methylenaktiven Nitrilen." Jahrg. vol. 98. 1965. 3571-7.
Gewald et al. "Heterocyclen aus CH-aciden Nitrilen, VIII. 2-Aminothiophene aus methylenaktiven Nitrilen Carbonylverbindungen und Schwefel." Jahrg. vol. 99. 1966. 94-100.
Giovannelli et al. "Comet Assay as a Novel Approach for Studying DNA Damage in Focal Cerebral Ischemia: Differential Effects of NMDA Receptor Antagonists and Poly(ADP-Ribose) Polymerase Inhibitors." Journal of Cerebral Blood Flow and Metabolism. vol. 22. 2002. 697-704.
Gleason et al. "Blockade of phencyclidine-induced hyperlocomotion by olanzapine, clozapine, and serotonin receptor subtype selective antagonists in mice." Psychopharmacology. vol. 129. 1997. 79-84.

Gnecco et al. "Oxidation of chiral non-racemic pyridinium salts to enantiopure 2-pyridine and 3-alkyl-2-pyridones." Tetrahedron: Asymmetry. vol. 9. 1998. 2027-9.
Gray et al. "Functionalisation of 2-Methoxy-6-Methylpyridine." Synthetic Communications. vol. 24 (10). 1994. 1367-79.
Gueremy et al. 2-Amino-6-chloro-4-(N-methylpiperazino)pyrimidines, Inhibitors of Spiroperidol Binding. Journal of Medicinal Chemistry. vol. 25. 1982. 1459-65.
He et al. "Conformational Color Polymorsphism and Control of Crystallization of 5-Methyl-2-[(4-methyl-2-mitrophenyl0amino}-3-thiophenecarbonitrile." Journal of Pharmaceutical Sciences. vol. 90 (3). Mar. 2001. 371-88.
Herdeis et al. "[4+2] Cycloadducts of 5-Benzyloxy-2-Pyrindone with Electron Deficient Dienophiles. Regio- and Stereochemistry." Heterocycles. vol. 29 (2). 1989. 287-96.
Herdeis et al. "A Facile Entry to the 2-Azabicyclo[2.2.2]octane-6-one Skeleton via [4+2]-Cycloaddition." Jan. 1988. 76-8.
Herdeis et al. "Stereochemistry and Reactivity of Phenylsulfonyl-substituted 2-Azabicyclo[2.2.2]octan-6-ones." Arch. Pharm. vol. 323. 1990. 937-42.
Herdeis et al. "A Three-Step Synthesis of b-Aminolaevulinic Acid." Arch. Pharm. vol. 317. 1984. 304-6.
Hickinbottom. "Reactions of organic compounds." 1939. 360-2.
Hirao et al. "Preparation of Optically Active 8,8'-Disubstituted 1,1'-Biisoquinoline." Heterocycles. vol. 42 (1). 1996. 415-22.
Imogai et al. "cis-Disubstituted Cyclopropanes via Asymmetric Catalytic Cyclopropenation: Synthesis of Cyclopropyl-dehydroamino Acids and of Dictyopterene C." Helvetica Chimica Acta. vol. 81. 1998. 1754-64.
Itaya et al. "Purines. LXXV. Dimroth Rearrangement, Hydrolytic Deamination, and Pyrimidine-Ring Breakdown of 7-Alkylated 1-Alkoxyadenines: N(1)-C(2) versus N(1)-C(6) Bond Fission." Chem. Pharm. Bull. vol. 45 (5). 1997. 832-41.
Kappe et al. "Aktive Malonester als Synthons fur Heterocyclen: Eine Methode zur Herstellung von 4-Hydroxy-2(1H)-pyridonen." Journal of Heterocyclic Chemistry. vol. 25. Mar./Apr. 1988. 463-8.
Krohnke et al. "Methylketon-Addukte der Chinolinium-und Isochinolinium-Reihe." 211-28, 1956.
Laurie et al. "Cloning, Distribution and Functional Expression of the Human mGlu6 Metabotropic Glutamate Receptor." Neuropharmacology. vol. 36 (2). 1997. 145-52.
Marino et al. "Glutamate-based therapeutic approaches: allosteric modulators of metabotropic glutamate receptors." Current Opinion in Pharmacology. vol. 6. 2006. 98-102.
Marquet et al. "VIII. Nouvelle methode de synthese des furo[2,3-d]pyrimidines sustituees en position 4 et de certains thieno[2,3-d]pyrimidines." Bulletin de la Societe Chimique de France. (12). 1969. 4344-8.
Mondon et al. "Synthesis of Narciprimine and Related Compounds." Chem. Ber. vol. 105. 1972. 3726-47.
Monn et al. "Synthesis, Pharmacological Characaterization, and Molecular Modeling of Heterobicyclic Amino Acids Related to (+)-2-Aminobicyclo[3.1.0]hexane-2,6-dicarboxylic Acid (LY354740): Identification of Two New Potent, Selective, and Systemically Active Agonists for Group II Metabotropic Glutamate Receptors." J. Med. Chem. vol. 42. 1999. 1027-40.
Moroni et al. "Poly(ADP-ribose) polymerase inhibitors attenuate necrotic but not apoptotic neuronal death in experimental models of cerebral ischemia." Cell Death and Differentiation. vol. 8. 2001. 921-32.
Nadin et al. "Synthesis of Tricyclic Pyridones by Radical Cyclization." Tetrahedron Letters. vol. 40. 1999. 4073-76.
Nielson et al. "Phosphoramides XIV. Phosphorus pentozide and amine hydrochlorides as reagents in the synthesis of thieno{2,3-d]pyrimidin-4(3H)-ones." Chemica Scripta. vol. 18. 1981. 135-8.
Ninomiya et al. "Photocyclisation of Enamides. Part 14. Substituent Effects in the Photocyclisation of N-a,B-Unsaturated Acylanilides." 1980. 197-202.
Nishi et al. "Pharmacological characterization of metabotropic glutamate receptor-mediated high-affinity GTPase activity in rat cerebral cortical membranes." British Journal of Pharmacology. vol. 130. 2000. 1664-70.

(56) References Cited

OTHER PUBLICATIONS

Noguchi et al. "Quantum Chemical Study on Conformational Properties of Bipyridine Cardiotonics." Chem. Pharm. Bull. vol. 41 (8). 1993. 1331-6.

Norman et al. "Structure-Activity Relationships of a Series of Pyrrolo[3,2-d]pyrimidine Derivatives and Related Compounds as Neuropeptide Y5 receptor Antagonists." J. Med. Chem. vol. 43. 2000. 4288-312.

Parry et al. "Functionalized Pyridylboronic Acids and Their Suzuki Cross-Coupling Reactions to Yield Novel Heteroarylpyridines." J. Org. Chem. vol. 67. 2002. 7541-3.

Patani et. al. "Bioisosterism: A Rational Approach in Drug Design" Chemical Reviews 1996, 96, 314 7-3176.

Wakefield, "Fluorinated Pharmaceuticals: Fluorinated Compounds are of Increasing Interest as Pharmaceuticals, and an Extensive Range of Techniques for Making Them is Now Available", Innovations in Pharmaceutical Technology, 2003, 74-78.

* cited by examiner

1,4-DISUBSTITUTED 3-CYANO-PYRIDONE DERIVATIVES AND THEIR USE AS POSITIVE ALLOSTERIC MODULATORS OF MGLUR2-RECEPTORS

IN THE CROSS-REFERENCE TO RELATED APPLICATIONS

This application claims priority to (EP) Application No. 06111215.7, filed Mar. 15, 2006, and to (EP) Application No. 07103654.5, filed Mar. 7, 2007, which are hereby incorporated herein by reference in its entirety for all purposes.

FIELD OF THE INVENTION

The present invention relates to novel compounds, in particular novel 1,4-disubstituted 3-cyano-pyridone-derivatives that are positive allosteric modulators of metabotropic receptors-subtype 2 ("mGluR2") which are useful for the treatment or prevention of neurological and psychiatric disorders associated with glutamate dysfunction and diseases in which the mGluR2 subtype of metabotropic receptors is involved. The invention is also directed to the pharmaceutical compositions, the processes to prepare such compounds and compositions and the use of such compounds for the prevention and treatment of such diseases in which mGluR2 is involved.

BACKGROUND OF THE INVENTION

Glutamate is the major amino-acid transmitter in the mammalian central nervous system (CNS). Glutamate plays a major role in numerous physiological functions, such as learning and memory but also sensory perception, development of synaptic plasticity, motor control, respiration, and regulation of cardiovascular function. Furthermore, glutamate is at the centre of several different neurological and psychiatric diseases, where there is an imbalance in glutamatergic neurotransmission.

Glutamate mediates synaptic neurotransmission through the activation of ionotropic glutamate receptors channels (iGluRs), the NMDA, AMPA and kainate receptors which are responsible for fast excitatory transmission (Nakanishi et al., (1998) Brain Res Brain Res Rev., 26:230-235).

In addition, glutamate activates metabotropic glutamate receptors (mGluRs) which have a more modulatory role that contributes to the fine-tuning of synaptic efficacy.

The mGluRs are seven-transmembrane G protein-coupled receptors (GPCRs) belonging to family 3 of GPCRs along with the calcium-sensing, GABAb, and pheromone receptors.

Glutamate activates the mGluRs through binding to the large extracellular amino-terminal domain of the receptor, herein called the orthosteric binding site. This binding induces a conformational change in the receptor which results in the activation of the G-protein and intracellular signalling pathways.

The mGluR family is composed of eight members. They are classified into three groups (group I comprising mGluR1 and mGluR5; group II comprising mGluR2 and mGluR3; group III comprising mGluR4, mGluR6, mGluR7, and mGluR8) according to sequence homology, pharmacological profile, and nature of intracellular signalling cascades activated (Schoepp et al. (1999) Neuropharmacology, 38:1431-76).

Among mGluR members, the mGluR2 subtype is negatively coupled to adenylate cyclase via activation of Gαi-protein, and its activation leads to inhibition of glutamate release in the synapse (Cartmell & Schoepp (2000) J Neurochem 75:889-907). In the CNS, mGluR2 receptors are abundant mainly throughout cortex, thalamic regions, accessory olfactory bulb, hippocampus, amygdala, caudate-putamen and nucleus accumbens (Ohishi et al. (1998) Neurosci Res 30:65-82).

Activating mGluR2 was shown in clinical trials to be efficacious to treat anxiety disorders (Levine et al. (2002) Neuropharmacology 43: 294; Holden (2003) Science 300:1866-68; Grillon et al. (2003) Psychopharmacology 168:446-54; Kellner et al. (2005) Psychopharmacology 179: 310-15). In addition, activating mGluR2 in various animal models was shown to be efficacious, thus representing a potential novel therapeutic approach for the treatment of schizophrenia (reviewed in Schoepp & Marek (2002) Curr Drug Targets. 1:215-25), epilepsy (reviewed in Moldrich et al. (2003) Eur J Pharmacol. 476:3-16), migraine (Johnson et al. (2002) Neuropharmacology 43:291), addiction/drug dependence (Helton et al. (1997) J Pharmacol Exp Ther 284: 651-660), Parkinson's disease (Bradley et al (2000) J. Neurosci. 20(9): 3085-94), pain (Simmons et al. (2002) Pharmacol Biochem Behav 73:419-27), sleep disorders (Feinberg et al. (2002) Pharmacol Biochem Behav 73:467-74) and Huntington's disease (Schiefer et al. (2004) Brain Res 1019:246-54).

To date, most of the available pharmacological tools targeting mGluRs are orthosteric ligands which activate several members of the family as they are structural analogs of glutamate (Schoepp et al. (1999) Neuropharmacology, 38:1431-76).

A new avenue for developing selective compounds acting at mGluRs is to identify molecules that act through allosteric mechanisms, modulating the receptor by binding to a site different from the highly conserved orthosteric binding site.

Positive allosteric modulators of mGluRs have emerged recently as novel pharmacological entities offering this attractive alternative. This type of molecule has been discovered for several mGluRs (reviewed in Mutel (2002) Expert Opin. Ther. Patents 12:1-8). In particular molecules have been described as mGluR2 positive allosteric modulators (Johnson M P et al. (2003) J Med Chem. 46:3189-92; Pinkerton et al. (2004) J Med Chem. 47:4595-9).

WO2004/092135 (NPS & Astra Zeneca), WO2004/018386, WO2006/014918 and WO2006/015158 (Merck) and WO2001/56990 (Eli Lilly) describe respectively phenyl sulfonamide, acetophenone, indanone and pyridylmethyl sulfonamide derivatives as mGluR2 positive allosteric modulators. However, none of the specifically disclosed compounds are structurally related to the compounds of the invention.

It was demonstrated that such molecules do not activate the receptor by themselves (Johnson M P et al. (2003) J Med Chem. 46:3189-92; Schaffhauser et al. (2003) Mol Pharmacol. 64:798-810). Rather, they enable the receptor to produce a maximal response to a concentration of glutamate which by itself induces a minimal response. Mutational analysis have demonstrated unequivocally that the binding of mGluR2 positive allosteric modulators does not occur at the orthosteric site, but instead at an allosteric site situated within the seven transmembrane region of the receptor (Schaffhauser et al. (2003) Mol Pharmacol. 64:798-810).

Animal data are suggesting that positive allosteric modulators of mGluR2 have the same effects in anxiety and psychosis models as those obtained with orthosteric agonists. Allosteric modulators of mGluR2 were shown to be active in fear-potentiated startle (Johnson et al. (2003) J Med Chem. 46:3189-92; Johnson et al. (2005) Psychopharmacology 179: 271-83), and in stress-induced hyperthermia (Johnson et al. (2005) Psychopharmacology 179:271-83) models of anxiety.

Furthermore, such compounds were shown to be active in reversal of ketamine- (Govek et al. (2005) Bioorg Med Chem Lett 15(18):4068-72) or amphetamine- (Galici et al. (2005) J Pharm Exp Ther 315(3), 1181-1187) induced hyperlocomotion, and in reversal of amphetamine-induced disruption of prepulse inhibition of the acoustic startle effect (Galici et al. (2005) J Pharm Exp Ther 315(3), 1181-1187) models of schizophrenia.

Positive allosteric modulators enable potentiation of the glutamate response, but they have also been shown to potentiate the response to orthosteric mGluR2 agonists such as LY379268 (Johnson et al. (2004) Biochem Soc Trans 32:881-87) or DCG-IV (Poisik et al. (2005) Neuropharmacology 49:57-69). These data provide evidence for yet another novel therapeutic approach to treat above mentioned neurological diseases involving mGluR2, which would use a combination of a positive allosteric modulator of mGluR2 together with an orthosteric agonist of mGluR2.

DESCRIPTION OF THE INVENTION

The invention relates to compounds having metabotropic glutamate receptor 2 modulator activity. In its most general compound aspect, the present invention provides a compound according to general Formula (I),

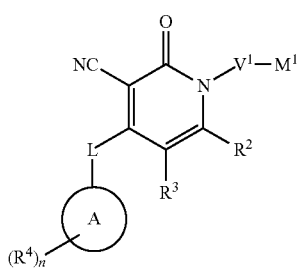

(I)

a pharmaceutically acceptable acid or base addition salt thereof, a stereochemically isomeric form thereof, an N-oxide form thereof or a quaternary ammonium salt thereof, wherein $V^1$ is selected from the group of a covalent bond and a bivalent saturated or unsaturated, straight or branched hydrocarbon radical having from 1 to 6 carbon atoms;

$M^1$ is selected from the group of hydrogen; cyclo$C_{3-7}$alkyl; aryl; alkylcarbonyl; alkyloxy; aryloxy; arylalkyloxy; arylcarbonyl; hexahydrothiopyranyl; and Het$^1$;

L is selected from the group of a covalent bond; —O—; —OCH$_2$—; —OCH$_2$CH$_2$—; —OCH$_2$CH$_2$O—; —OCH$_2$CH$_2$OCH$_2$—; —S—; —NR$^7$—; —NR$^7$CH$_2$—; —NR$^7$cycloC$_{3-7}$; —NR$^7$CH$_2$CH$_2$—; —OCH$_2$CH$_2$N(R$^7$)CH$_2$—; —CH$_2$—; —CH$_2$CH$_2$—; —CH$_2$CH$_2$CH$_2$; —C≡C—; —C=O—; and —C(R$^8$)=C(R$^9$)—; wherein each of R$^7$, independently of each other, is selected from the group of hydrogen and C$_{1-3}$alkyl; and wherein R$^8$ and R$^9$, independently of each other, are selected from the group of hydrogen, halo and C$_{1-3}$alkyl;

R$^2$ and R$^3$ are each independently of each other hydrogen, halo or alkyl;

A is Het$^2$ or phenyl, wherein each radical is optionally substituted with n radicals R$^4$, wherein n is an integer equal to zero, 1, 2 or 3;

R$^4$ is selected from the group of halo; cyano; hydroxy; oxo; formyl; ethanoyl; carboxyl; nitro; thio; alkyl; alkyloxy; alkyloxyalkyl; alkyloxycarbonyl; alkyloxycarbonylalkyl; alkylcarbonyl; alkylcarbonyloxy; alkylcarbonylalkyloxy; polyhaloC$_{1-3}$alkyl; polyhaloC$_{1-3}$alkyloxy; polyhaloC$_{1-3}$alkylthio; alkylthio; alkylsulfonyl; Het$^3$; Het$^3$-alkyl; Het$^3$-oxy; Het$^3$-oxyalkyl; Het$^3$-alkyloxy; Het$^3$-oxyalkyloxy; Het$^3$-carbonyl; Het$^3$-carbonylalkyl; Het$^3$-thio; Het$^3$-thioalkyl; Het$^3$-sulfonyl; aryl; arylalkyl; aryloxy; aryloxyalkyl; arylalkyloxy; arylalkenyl; arylcarbonylalkyl; arylthioalkyl; arylsulfonyl; —NR$^a$R$^b$; alkyl-NR$^a$R$^b$; O-alkyl-NR$^a$R$^b$; —C(=O)—NR$^a$R$^b$; —C(=O)-alkyl-NR$^a$R$^b$; and O-alkyl-C(=O)—NR$^a$R$^b$; wherein R$^a$ and R$^b$ are selected from the group of hydrogen, alkyl, alkylcarbonyl, arylalkyl, alkyloxyalkyl, Het$^3$, Het$^3$alkyl, alkylsulfonyl, alkyl-NR$^c$R$^d$ and C(=O)alkyl-NR$^c$R$^d$, wherein R$^c$ and R$^d$ are selected from the group of hydrogen, alkyl and alkylcarbonyl;

or two radicals R$^4$ may be combined to form a bivalent radical —X$^1$—C$_{1-6}$—X$^2$— wherein C$_{1-6}$ is a saturated or unsaturated, straight or branched hydrocarbon radical having 1 to 6 carbon atoms and X$^1$ and X$^2$ are each independently C, O or NH; wherein the bivalent radical is optionally substituted with one or more radicals selected from the group of halo, polyhaloC$_{1-3}$alkyl, cyano, hydroxy, amino, oxo, carboxyl, nitro, thio, formyl and ethanoyl;

Het$^1$ is selected from the group of tetrahydropyranyl and pyridinyl; wherein each radical is optionally substituted with 1, 2 or 3 substituents, each independently from each other, selected from the group of halo, C$_{1-3}$alkyl, polyhaloC$_{1-3}$alkyl, polyhaloC$_{1-3}$alkyloxy, cyano, hydroxy, amino, oxo, carboxyl, nitro, thio, formyl, ethanoyl, and C$_{1-3}$alkyloxy;

Het$^2$ is selected from the group of piperazinyl; piperidinyl; thienyl; furanyl; 1H-indazolyl; 1H-benzimidazolyl; 1,2,3,4-tetrahydro-isoquinolinyl; 2,5-diaza-bicyclo[2.2.1]heptyl; pyrrolidinyl; azetidinyl; 2,7-diaza-spiro[3.5]-nonyl; pyridinyl; pyrazolyl; indolinyl; 1H-indolyl; 1H-indazolyl; benzomorpholinyl; thiazolyl; 1,2,3,4-tetrahydroquinolinyl; 3,9-diazaspiro[5.5]undecyl; 1,2,3,4,4a,5,6,10b-octahydro-benzo[f]quinolinyl; 1,2,3,4,4a,10a-hexahydro-benzo[5,6][1,4]dioxino[2,3-c]pyridinyl; 2,3,4,9-tetrahydro-1H-indeno[2,1-c]-pyridinyl; 2,3,4,9-tetrahydro-1H-β-carbolinyl; 1,2,3,4-tetrahydro-benzo[4,5]-furo[2,3-c]pyridinyl; 1,2,3,4-tetrahydrobenzo[4,5]thieno[2,3-c]pyridinyl; [1,4]diazepyl; isoxazolyl; indanyl; and indolyl;

Het$^3$ is selected from the group of pyridinyl; pyrimidinyl; pyridazilyl; pyrazinyl; piperidinyl; pyrrolyl; pyrrolidinyl; piperazinyl; triazolyl; tetrazolyl; indolyl; thienyl; furanyl; tetrahydropyranyl; tetrahydro-thiopyran-1,1-dioxide; thiazolyl; thiadiazolyl; isothiazolyl; oxazolyl; morpholinyl; oxadiazolyl; isoxazolyl; imidazolyl; pyrazolyl; benzoimidazolyl; benzoxazolyl; benzothienyl; benzothiazolyl; benzofuranyl; benzomorpholinyl; 1,2,3,4-tetrahydro-isoquinolinyl; thionaphtyl; indolyl; indolinyl; quinolyl; isoquinolyl; quinoxalyl; phthalazyl; benzo[1,3]dioxyl; and quinazolyl; wherein each radical is optionally substituted with 1, 2 or 3 substituents, each independently from each other, selected from the group of halo, C$_{1-6}$alkyl, polyhaloC$_{1-3}$alkyl, cyano, hydroxy, amino, oxo, carboxyl, nitro, thio, formyl, ethanoyl, phenyl, pyrrolidinyl, piperidinyl, pyridinyl, morpholinyl, mono- and di(alkyl)amino, and C$_{1-3}$alkyloxy;

aryl is naphthyl, phenyl, or biphenyl; wherein each radical is optionally substituted with 1, 2 or 3 substituents, each independently from each other selected from the group of halo, C$_{1-3}$alkyl, polyhaloC$_{1-3}$alkyl, polyhaloC$_{1-3}$alkyloxy, cyano, hydroxy, amino, oxo, carboxyl, nitro, thio, formyl, ethanoyl, ethyloxycarbonyl, and $C_{1-3}$alkyloxy;

alkyl is a saturated, straight or branched hydrocarbon radical having from 1 to 6 carbon atoms; or is a saturated, cyclic hydrocarbon radical having from 3 to 7 carbon atoms; or is a saturated hydrocarbon radical from 4 to 12 carbon atoms, comprising at least one saturated, straight or branched hydrocarbon radical having from 1 to 6 carbon atoms and at least one saturated, cyclic hydrocarbon radical having from 3 to 7 carbon atoms; wherein each carbon atom may optionally be substituted with one or more radicals selected from the group of halo, polyhalo$C_{1-3}$alkyl, cyano, hydroxy, amino, oxo, carboxyl, nitro, thio, formyl, ethanoyl, carbamoyl, phenyl, and a bivalent radical —OCH$_2$CH$_2$O—; and alkenyl is alkyl, additionally containing one or more double bonds.

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable acid or base addition salt thereof, a stereochemically isomeric form thereof, an N-oxide form thereof or a quaternary ammonium salt thereof.

The invention also relates to the use of a compound according to the invention as a medicament and for the preparation of a medicament for the prevention and/or treatment of a condition in a mammal, including a human, the treatment or prevention of which is affected or facilitated by the neuromodulatory effect of mGluR2 positive allosteric modulators.

In particular, the invention relates to the use of a compound according to the invention for the preparation of a medicament for treating, or preventing, ameliorating, controlling or reducing the risk of various neurological and psychiatric disorders associated with glutamate dysfunction in a mammal, including a human, the treatment or prevention of which is affected or facilitated by the neuromodulatory effect of mGluR2 positive allosteric modulators.

DETAILED DESCRIPTION OF THE INVENTION

In one embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein $V^1$ is selected from the group of a covalent bond, —CH$_2$—; —CH$_2$—CH$_2$—; —CH$_2$—CH$_2$—CH$_2$—; —CH$_2$—CH=CH—; —CH$_2$—CH$_2$—CH$_2$—CH$_2$—; —CH$_2$—CH(CH$_3$)—CH$_2$—; —CH(CH$_3$)—CH$_2$—CH$_2$—CH$_2$—; —CH$_2$—CH(CH$_3$)CH$_2$—CH$_2$—; and —CH$_2$—CH$_2$—CH(CH$_3$)—CH$_2$—.

In one embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein $M^1$ is selected from the group of hydrogen; cyclo$C_{3-7}$alkyl; phenyl; biphenyl; phenyloxy; benzyloxy; furanyl; and pyridinyl; wherein $M^1$ is optionally substituted with one or more radicals selected from the group of halo; $C_{1-3}$alkyl; polyhalo$C_{1-3}$alkyl; polyhalo$C_{1-3}$alkyloxy; cyano; hydroxy; amino; oxo; carboxyl; nitro; thio; formyl; ethanoyl; and $C_{1-3}$alkyloxy.

In one embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein $M^1$ is selected from the group of hydrogen; cyclo$C_{3-7}$alkyl; phenyl; biphenyl; phenyloxy; benzyloxy; furanyl; and pyridinyl; wherein any one of said radicals is optionally substituted with one or more radicals selected from the group of halo; $C_{1-3}$alkyl; polyhalo$C_{1-3}$alkyl; polyhalo$C_{1-3}$alkyloxy; and $C_{1-3}$alkyloxy.

In one embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein $V^1$-$M^1$ is selected from the group of —CH$_2$—CH$_2$—CH$_2$—CH$_3$; —CH$_2$—CH(CH$_3$)—CH$_3$; —CH(CH$_3$)—CH$_2$—CH$_2$—CH$_3$; —CH$_2$—CH(CH$_3$)CH$_2$—CH$_3$; —CH$_2$—CH$_2$—CH(CH$_3$)—CH$_3$; or $V^1$ is selected from the group of covalent bond; —CH$_2$—; —CH$_2$—CH$_2$—; —CH$_2$—CH$_2$—CH$_2$—; and —CH$_2$—CH=CH—; and $M^1$ is selected from the group of cyclopropyl; cyclopentyl; cyclohexyl; phenyl; biphenyl; phenyloxy; benzyloxy; furanyl; and pyridinyl; wherein each radical $M^1$ is optionally substituted with one or more radicals selected from the group of halo; $C_{1-3}$alkyl; polyhalo$C_{1-3}$alkyl; polyhalo$C_{1-3}$alkyloxy; and $C_{1-3}$alkyloxy. In a particular embodiment, $V^1$-$M^1$ is —CH$_2$—CH$_2$—CH$_2$—CH$_3$.

In one embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein $R^2$ and $R^3$ are each independently hydrogen, chloro, fluoro or methyl. In one particular embodiment, $R^2$ and $R^3$ are each independently hydrogen or methyl. In another particular embodiment, $R^2$ and $R^3$ are each hydrogen. In another particular embodiment, $R^2$ is methyl and $R^3$ is hydrogen.

In one embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein L is selected from the group of a covalent bond; —O—; —OCH$_2$—; —OCH$_2$CH$_2$—; —OCH$_2$CH$_2$O—; —OCH$_2$CH$_2$OCH$_2$—; —NR$^7$—; —NR$^7$CH$_2$—; —NR$^7$cycloC$_{3-7}$; —OCH$_2$CH$_2$N(R$^7$)CH$_2$—; —CH$_2$CH$_2$—; —C≡C—; —C=O—; and —CH=CH—; wherein each of R$^7$, independently of each other, is selected from the group of hydrogen and $C_{1-3}$alkyl.

In another embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein A is selected from the group of phenyl, piperazinyl, and piperidinyl; wherein each of said radicals is optionally substituted with n radicals $R^4$, wherein n is an integer equal to zero, 1, 2 or 3. In one particular embodiment, n is equal to zero or 1. In another particular embodiment, n is equal to 1.

In one embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein $R^4$ is selected from the group of halo; cyano; hydroxy; ethanoyl; alkyl; alkyloxy; alkyloxyalkyl; alkyloxycarbonyl; alkyloxycarbonylalkyl; alkylcarbonyl; alkylcarbonyloxy; alkylcarbonylalkyloxy; polyhalo$C_{1-3}$alkyl; polyhalo$C_{1-3}$-alkyloxy; polyhalo$C_{1-3}$alkylthio; alkylthio; alkylsulfonyl; Het$^3$; Het$^3$-alkyl; Het$^3$-oxy; Het$^3$-oxyalkyl; Het$^3$-alkyloxy; Het$^3$-oxyalkyloxy; Het$^3$-carbonyl; Het$^3$-thioalkyl; aryl; arylalkyl; aryloxy; aryloxyalkyl; arylalkyloxy; arylalkenyl; arylcarbonylalkyl;

arylsulfonyl; —NR$^a$R$^b$; alkyl-NR$^a$R$^b$; O-alkyl-NR$^a$R$^b$; —C(=O)—NR$^a$R$^b$; —C(=O)-alkyl-NR$^a$R$^b$; and O-alkyl-C(=O)—NR$^a$R$^b$; wherein R$^a$ and R$^b$ are selected from the group of hydrogen, alkyl, alkylcarbonyl, arylalkyl, alkyloxyalkyl, Het$^3$, Het$^3$alkyl, alkylsulfonyl, alkyl-NR$^c$R$^d$ and C(=O)alkyl-NR$^c$R$^d$, wherein R$^c$ and R$^d$ are selected from the group of hydrogen, alkyl and alkylcarbonyl; or two radicals R$^4$ may be combined to form a bivalent radical —X$^1$—C$_{1-6}$—X$^2$— wherein C$_{1-6}$ is a saturated or unsaturated, straight or branched hydrocarbon radical having 1 to 6 carbon atoms and X$^1$ and X$^2$ are each independently C or O.

In another embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein two radicals R$^4$ may be combined to form a bivalent radical selected from the group of —CH$_2$CH$_2$—O—; —O—CH$_2$—O—; and —O—CH$_2$CH$_2$—O—.

In one embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein Het$^1$ is selected from the group of tetrahydropyranyl and pyridinyl; wherein each radical Het$^1$ is optionally substituted with 1, 2 or 3 polyhaloC$_{1-3}$alkyl substituents.

In one embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein Het$^3$ is selected from the group of pyridinyl; pyrimidinyl; pyridazilyl; pyrazinyl; piperidinyl; pyrrolidinyl; piperazinyl; triazolyl; tetrahydropyranyl; tetrahydro-thiopyran-1,1-dioxide; thiazolyl; oxazolyl; morpholinyl; oxadiazolyl; imidazolyl; benzoxazolyl; benzothienyl; benzofuranyl; 1,2,3,4-tetrahydro-isoquinolinyl; indolyl; indolinyl; phthalazyl; and benzo[1,3]dioxyl. In one embodiment, each radical is optionally substituted with 1, 2 or 3 substituents, each independently from each other, selected from the group of halo, C$_{1-6}$alkyl, polyhaloC$_{1-3}$alkyl, cyano, hydroxy, oxo, ethanoyl, phenyl, pyrrolidinyl, piperidinyl, pyridinyl, morpholinyl, mono- and di(alkyl)amino, and C$_{1-3}$alkyloxy.

In one further embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein V$^1$ is selected from the group of a covalent bond, —CH$_2$—; —CH$_2$—CH$_2$—; —CH$_2$—CH$_2$—CH$_2$—; —CH$_2$—CH=CH—; —CH$_2$—CH$_2$—CH$_2$—CH$_2$—; —CH$_2$—CH(CH$_3$)—CH$_2$—; —CH(CH$_3$)—CH$_2$—CH$_2$—CH$_2$—; —CH$_2$—CH(CH$_3$)CH$_2$—CH$_2$—; and —CH$_2$—CH$_2$—CH(CH$_3$)—CH$_2$—;

M$^1$ is selected from the group of hydrogen; cycloC$_{3-7}$alkyl; phenyl; biphenyl; phenyloxy; benzyloxy; furanyl; and pyridinyl; wherein M$^1$ is optionally substituted with one or more radicals selected from the group of halo; C$_{1-3}$alkyl; polyhaloC$_{1-3}$alkyl; polyhaloC$_{1-3}$alkyloxy; and C$_{1-3}$alkyloxy;

L is selected from the group of covalent bond; —O—; —OCH$_2$—; —OCH$_2$CH$_2$—; —OCH$_2$CH$_2$O—; —OCH$_2$CH$_2$OCH$_2$—; —NR$^7$—; —NR$^7$CH$_2$—; —NR$^7$cycloC$_{3-7}$; —OCH$_2$CH$_2$N(R$^7$)CH$_2$—; —CH$_2$CH$_2$—; —C≡C—; —C=O—; and —CH=CH—; wherein each of R$^7$, independently of each other, is selected from the group of hydrogen and C$_{1-3}$alkyl;

R$^2$ and R$^3$ are each independently of each other hydrogen, halo or alkyl;

A is selected from the group of phenyl, piperazinyl, and piperidinyl, wherein each radical is optionally substituted with n radicals R$^4$, wherein n is an integer equal to zero or 1;

R$^4$ is selected from the group of halo; cyano; hydroxy; ethanoyl; alkyl; alkyloxy; alkyloxyalkyl; alkyloxycarbonyl; alkyloxycarbonylalkyl; alkylcarbonyl; alkylcarbonyloxy; alkylcarbonylalkyloxy; polyhaloC$_{1-3}$alkyl; polyhaloC$_{1-3}$alkyloxy; polyhaloC$_{1-3}$alkylthio; alkylthio; alkylsulfonyl; Het$^3$; Het$^3$-alkyl; Het$^3$-oxy; Het$^3$-oxyalkyl; Het$^3$-alkyloxy; Het$^3$-oxyalkyloxy; Het$^3$-carbonyl; Het$^3$-thioalkyl; aryl; arylalkyl; aryloxy; aryloxyalkyl; arylalkyloxy; arylalkenyl; arylcarbonylalkyl; arylsulfonyl; —NR$^a$R$^b$; alkyl-NR$^a$R$^b$; O-alkyl-NR$^a$R$^b$ wherein R$^a$ and R$^b$ are selected from the group of hydrogen, alkyl, alkylcarbonyl, arylalkyl, alkyloxyalkyl, Het$^3$, Het$^3$alkyl, alkylsulfonyl, alkyl-NR$^c$R$^d$, and C(=O)alkyl-NR$^c$R$^d$, wherein R$^c$ and R$^d$ are selected from the group of hydrogen, alkyl and alkylcarbonyl; or two radicals R$^4$ may be combined to form a bivalent radical selected from the group of —CH$_2$CH$_2$—O—; —O—CH$_2$—O—; and —O—CH$_2$CH$_2$—O—;

Het$^1$ is selected from the group of tetrahydropyranyl and pyridinyl; wherein each radical Het$^1$ is optionally substituted with 1, 2 or 3 polyhaloC$_{1-3}$alkyl substituents;

Het$^2$ is selected from the group of piperazinyl; piperidinyl; thienyl; furanyl; 1H-indazolyl; 1H-benzimidazolyl; 1,2,3,4-tetrahydro-isoquinolinyl; 2,5-diaza-bicyclo[2.2.1]heptyl; pyrrolidinyl; azetidinyl; 2,7-diaza-spiro[3.5]-nonyl; pyridinyl; pyrazolyl; indolinyl; 1H-indolyl; 1H-indazolyl; benzomorpholinyl; thiazolyl; 1,2,3,4-tetrahydroquinolinyl; 3,9-diazaspiro[5.5]undecyl; 1,2,3,4,4a,5,6,10b-octahydro-benzo[f]quinolinyl; 1,2,3,4,4a,10a-hexahydro-benzo[5,6][1,4]dioxino[2,3-c]pyridinyl; 2,3,4,9-tetrahydro-1H-indeno[2,1-c]-pyridinyl; 2,3,4,9-tetrahydro-1H-β-carbolinyl; 1,2,3,4-tetrahydro-benzo[4,5]-furo[2,3-c]pyridinyl; 1,2,3,4-tetrahydrobenzo[4,5]thieno[2,3-c]pyridinyl; [1,4]diazepyl; isoxazolyl; indanyl; and indolyl;

Het$^3$ is selected from the group of pyridinyl; pyrimidinyl; pyridazilyl; pyrazinyl; piperidinyl; pyrrolidinyl; piperazinyl; triazolyl; tetrahydropyranyl; tetrahydro-thiopyran-1,1-dioxide; thiazolyl; oxazolyl; morpholinyl; oxadiazolyl; imidazolyl; benzoxazolyl; benzothienyl; benzofuranyl; 1,2,3,4-tetrahydro-isoquinolinyl; indolyl; indolinyl; phthalazyl; and benzo[1,3]dioxyl; wherein each radical is optionally substituted with 1, 2 or 3 substituents, each independently from each other, selected from the group of halo, C$_{1-6}$alkyl, polyhaloC$_{1-3}$alkyl, cyano, hydroxy, oxo, ethanoyl, phenyl, pyrrolidinyl, piperidinyl, pyridinyl, morpholinyl, mono- and di(alkyl)amino, and C$_{1-3}$alkyloxy;

aryl is phenyl or biphenyl; wherein each radical is optionally substituted with 1, 2 or 3 substituents, each independently from each other selected from the group of halo, C$_{1-3}$alkyl, polyhaloC$_{1-3}$alkyl, polyhaloC$_{1-3}$alkyloxy, cyano, nitro, ethyloxycarbonyl, and C$_{1-3}$alkyloxy; and alkyl is a saturated, straight or branched hydrocarbon radical having from 1 to 6 carbon atoms; or is a saturated, cyclic hydrocarbon radical having from 3 to 7 carbon atoms; or is saturated hydrocarbon radical from 4 to 12 carbon atoms, comprising at least one saturated, straight or branched hydrocarbon radical having from 1 to 6 carbon atoms and at least one saturated, cyclic hydrocarbon radical having from 3 to 7 carbon atoms; wherein each carbon atom may optionally be substituted with one or more radicals selected from the group of cyano, hydroxy, carboxyl, carbamoyl, phenyl, and a bivalent radical —OCH$_2$CH$_2$O—.

In further embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein the compound is selected from the group of:

4-(4-(N-acetylmethyl)phenyl)-3-cyano-1-(3-methylbutyl) pyridine-2(1H)-one (compound 1-179);

4-(3,4-dimethoxyphenyl)-3-cyano-1-(3-methylbutyl)pyridine-2(1H)-one (compound 1-110);

3-cyano-4-(3-fluoro-4-methoxyphenyl)-1-(3-methylbutyl) pyridine-2(1H)-one (compound 1-114);

3-cyano-4-(4-hydroxypropylphenyl)-1-(3-methylbutyl)pyridine-2(1H)-one (compound 1-095);

3-cyano-4-(4-methoxymethylphenyl)-1-(3-methylbutyl)pyridine-2(1H)-one (compound 1-103);

3-cyano-4-(2-fluoro-4-methoxyphenyl)-1-(3-methylbutyl) pyridine-2(1H)-one (compound 1-113);

3-cyano-4-(4-(N-morpholyl)phenyl)-1-(3-methylbutyl)pyridine-2(1H)-one (compound 1-223);

3-cyano-1-(3-methylbutyl)-4-(phenylethynyl)pyridine-2 (1H)-one (compound 1-267);

3-cyano-1-butyl-4-[4-(2-methyl-pyridin-4-yloxy)-phenyl]-pyridine-2(1H)-one (compound 1-064); and 3-cyano-1-cyclopropylmethyl-4-(4-phenyl-piperidin-1-yl)-pyridine-2(1H)-one (compound 4-047).

In the framework of this application, alkyl is a saturated, straight or branched hydrocarbon radical having from 1 to 6 carbon atoms; or is a saturated, cyclic hydrocarbon radical having from 3 to 7 carbon atoms; or is a saturated hydrocarbon radical from 4 to 12 carbon atoms, comprising at least one saturated, straight or branched hydrocarbon radical having from 1 to 6 carbon atoms and at least one saturated, cyclic hydrocarbon radical having from 3 to 7 carbon atoms; wherein each carbon atom may optionally be substituted with one or more radicals selected from the group of halo, polyhaloC$_{1-3}$alkyl, cyano, hydroxy, amino, oxo, carboxyl, nitro, thio, formyl, ethanoyl, carbamoyl, phenyl, and a bivalent radical —OCH$_2$CH$_2$O—. In one embodiment, alkyl is methyl, ethyl, n-propyl, isopropyl, butyl, pentyl, hexyl, cyclopropyl, cyclobutyl, cyclopentyl and cyclohexyl. In one embodiment, each carbon atom is optionally substituted with one or more radicals selected from the group of cyano, hydroxy, carboxyl, carbamoyl, phenyl, and the bivalent radical —OCH$_2$CH$_2$O—.

The notation C$_{1-6}$alkyl defines a saturated, straight or branched hydrocarbon radical having from 1 to 6 carbon atoms, such as C$_6$alkyl; C$_5$alkyl; C$_4$alkyl; C$_3$alkyl; C$_2$alkyl; and C$_1$alkyl. Examples of C$_{1-6}$alkyl are methyl, ethyl, n-propyl, iso-propyl, butyl, isobutyl, pentyl, and heptyl.

The notation cycloC$_{3-7}$alkyl defines a saturated, cyclic hydrocarbon radical having from 3 to 7 carbon atoms, such as cycloC$_7$alkyl; cycloC$_6$alkyl; cycloC$_6$alkyl; cycloC$_5$alkyl; cycloC$_4$alkyl; cycloC$_3$alkyl; and cycloC$_3$alkyl. Examples of cycloC$_{3-7}$alkyl are cyclopropyl, cyclobutyl, cyclopentyl, cycloheptyl, and cyclohexyl.

The notation C$_{1-3}$alkyl defines a saturated, straight or branched hydrocarbon radical having from 1 to 3 carbon atoms, such as methyl, ethyl, n-propyl and iso-propyl.

In one preferred embodiment, alkyl is C$_{1-6}$alkyl; in another preferred embodiment alkyl is C$_{3-7}$cycloalkyl.

In the framework of this application, alkenyl is alkyl, additionally containing one or more double bonds.

In the framework of this application, aryl is naphthyl, phenyl or biphenyl; wherein each radical is optionally substituted with 1, 2 or 3 substituents, each independently from each other selected from the group of halo, C$_{1-3}$alkyl, polyhalo C$_{1-3}$alkyl, polyhaloC$_{1-3}$alkyloxy, cyano, hydroxy, amino, oxo, carboxyl, nitro, thio, formyl, ethanoyl, ethyloxycarbonyl, and C$_{1-3}$alkyloxy. More preferred, aryl is phenyl or biphenyl. More preferred, aryl is optionally substituted with 1, 2 or 3 substituents, each independently from each other, selected from the group of halo, C$_{1-3}$alkyl, polyhaloC$_{1-3}$alkyl, polyhaloC$_{1-3}$alkyloxy, cyano, nitro, ethyloxycarbonyl, and C$_{1-3}$alkyloxy. More preferred, aryl is phenyl or biphenyl, optionally substituted with 1, 2 or 3 substituents, each independently from each other, selected from the group of halo, C$_{1-3}$alkyl, polyhaloC$_{1-3}$alkyl, polyhaloC$_{1-3}$alkyloxy, cyano, nitro, ethyloxycarbonyl, and C$_{1-3}$alkyloxy.

In the framework of this application, halo is a substituent selected from the group of fluoro, chloro, bromo and iodo. Preferably, halo is bromo, fluoro or chloro.

In the framework of this application, polyhaloC$_{1-3}$alkyl is a straight or branched saturated hydrocarbon radical having from 1 to 3 carbon atoms, wherein one or more carbon atoms is substituted with one or more halo-atoms. Preferably, polyhaloalkyl is trifluoromethyl.

In the framework of this application, with "compounds according to the invention" is meant a compound according to the general Formula (I), a pharmaceutically acceptable acid or base addition salt thereof, a stereochemically isomeric form thereof, an N-oxide form thereof or a quaternary ammonium salt thereof.

The pharmaceutically acceptable acid addition salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

Conversely said acid addition salt forms can be converted into the free base form by treatment with an appropriate base.

The compounds according to Formula (I) containing acidic protons may also be converted into their therapeutically active non-toxic metal or amine addition salts forms (base addition salts) by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate acid.

Quaternary ammonium salts of compounds according to Formula (I) defines said compounds which are able to form by a reaction between a basic nitrogen of a compound according to Formula (I) and an appropriate quaternizing agent, such as, for example, an optionally substituted alkylhalide, arylhalide or arylalkylhalide, in particular methyliodide and benzyliodide. Other reactants with good leaving groups may also be used, such as, for example, alkyl trifluoromethanesulfonates, alkyl methanesulfonates and alkyl p-toluenesulfonates. A quaternary ammonium salt has a positively charged nitrogen. Pharmaceutically acceptable counterions include chloro, bromo, iodo, trifluoroacetate and acetate ions.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g. of the piperazinyl or piperidinyl radical) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

The compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tent-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "a" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

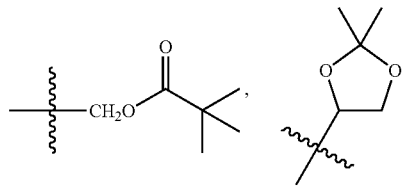

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl. Compounds according to the invention having an amino group may be derivatised with a ketone or an aldehyde such as, for example, formaldehyde to form a Mannich base. This base will hydrolyze with first order kinetics in aqueous solution.

In the framework of this application, with "compounds according to the invention" is meant a compound according to the general Formula (I), the pharmaceutically acceptable acid or base addition salts thereof, the stereochemically isomeric forms thereof, the N-oxide form thereof and a prodrug thereof.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. In particular, when hydrogen is mentioned, it is understood to refer to $^1$H, $^2$H, $^3$H and mixtures thereof;

when carbon is mentioned, it is understood to refer to $^{11}C$, $^{12}C$, $^{13}C$, $^{14}C$ and mixtures thereof; when nitrogen is mentioned, it is understood to refer to $^{13}N$, $^{14}N$, $^{15}N$ and mixtures thereof; when oxygen is mentioned, it is understood to refer to $^{14}O$, $^{15}O$, $^{16}O$, $^{17}O$, $^{18}O$ and mixtures thereof; and when fluor is mentioned, it is understood to refer to $^{18}F$, $^{19}F$ and mixtures thereof.

The compounds according to the invention therefore also comprise compounds with one or more isotopes of one or more element, and mixtures thereof, including radioactive compounds, also called radiolabelled compounds, wherein one or more non-radioactive atoms has been replaced by one of its radioactive isotopes. By the term "radiolabelled compound" is meant any compound according to Formula (I), an N-oxide form, a pharmaceutically acceptable addition salt or a stereochemically isomeric form thereof, which contains at least one radioactive atom. For example, compounds can be labelled with positron or with gamma emitting radioactive isotopes. For radioligand-binding techniques (membrane receptor assay), the $^{3}H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive isotope is selected from the group of $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{3}H$, $^{11}C$ and $^{18}F$.

A. Preparation of the Final Compounds

Experimental Procedure 1 (L is a Covalent Bond)

The final compounds according to Formula (I-a), wherein L is a covalent bond, can be prepared by reacting an intermediate compound of Formula (II) with a compound of Formula (III) according to reaction scheme (1), a reaction that is performed in a suitable reaction-inert solvent, such as, for example, 1,4-dioxane or mixtures of inert solvents such as, for example, 1,4-dioxane/DMF, in the presence of a suitable base, such as, for example, aqueous $NaHCO_3$ or $Na_2CO_3$, a Pd-complex catalyst such as, for example, $Pd(PPh_3)_4$ under thermal conditions such as, for example, heating the reaction mixture at 150° C. under microwave irradiation, for example for 10 min. In a reaction suitable for Pd mediated coupling with boronic acids or boronic esters, such as, for example, a halo, triflate or pyridinium moiety. Such intermediate compounds may be prepared according to reaction schemes (8), (9) and (10) (see below). $R^5$ and $R^6$ may be hydrogen or alkyl, or may be taken together to form for example the bivalent radical of formula $-CH_2CH_2-$, $-CH_2CH_2CH_2-$, or $-C(CH_3)_2C(CH_3)_2-$.

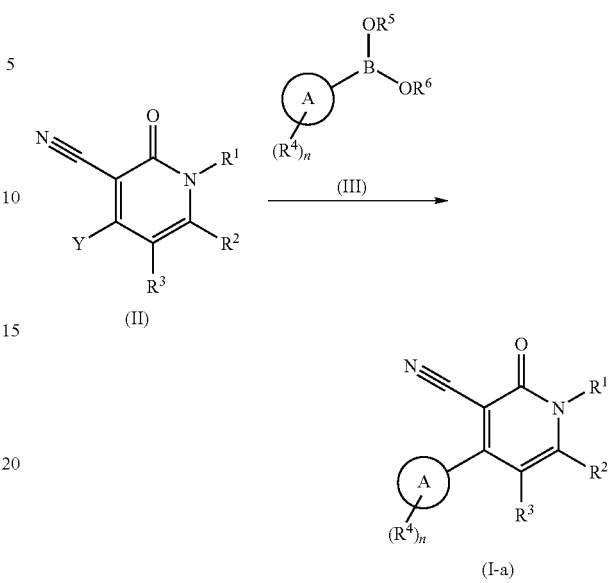

Experimental Procedure 2 (L is Oxygen or Sulfur)

The final compounds according to Formula (I-b), wherein L is oxygen or sulfur, can be prepared by reacting an intermediate compound of Formula (II) with a compound of Formula (IV) according to reaction scheme (2), a reaction that is performed in a suitable reaction-inert solvent, such as, for example, THF, in the presence of a suitable base, such as, for example, NaH, under thermal conditions such as, for example, heating the reaction mixture for example at 80° C. under microwave irradiation for 10 minutes. In reaction scheme (2), all variables are defined as in Formula (I), $R^1$ is $V^1$-$M^1$ and Y is a suitable leaving group, such as, for example, pyridinium.

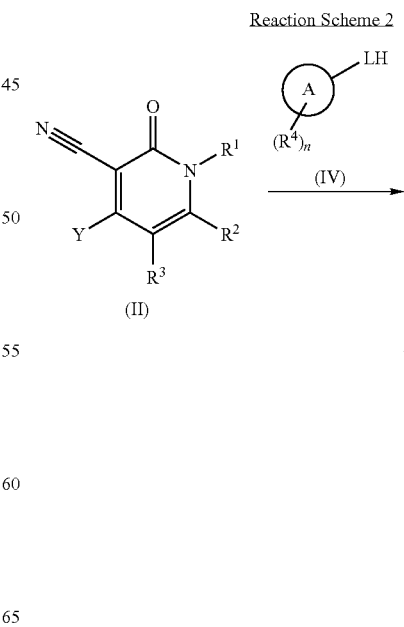

Experimental Procedure 3 (L is Aminoalkyl)

The final compounds according to Formula (I-c), wherein L is —NR$^7$—; —NR$^7$CH$_2$—; or —NR$^7$CH$_2$CH$_2$— wherein each of R$^7$, independently of each other, is selected from the group of hydrogen and alkyl, can be prepared by reacting an intermediate compound of Formula (II) with a compound of Formula (V) according to reaction scheme (3), a reaction that is performed in a suitable reaction-inert solvent, such as, for example, 1,4-dioxane, in the presence of a suitable base, such as, for example, K$_3$PO$_4$, a Pd-complex catalyst such as, for example

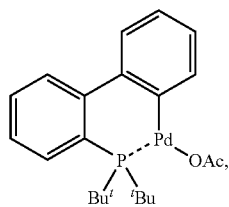

under thermal conditions such as, for example, heating the reaction mixture for example at 80° C. for 12 hours. In reaction scheme (3), all variables are defined as in Formula (I), R$^1$ is V$^1$-M$^1$ and Y is a suitable group for Pd-mediated coupling with amines, such as, for example, halo.

Alternatively, compounds according to Formula (I-c) can be prepared by reacting an intermediate compound of Formula (II) with a compound of Formula (V) according to reaction scheme (3), a reaction that is performed in a suitable reaction-inert solvent, such as, for example, dimethoxyethane or acetonitrile, in the presence of a suitable base, such as, for example, Cs$_2$CO$_3$ or N,N-diisopropylethylamine, under thermal conditions such as, for example, heating the reaction mixture for example at 160° C. under microwave irradiation for 30 minutes.

Reaction Scheme 3

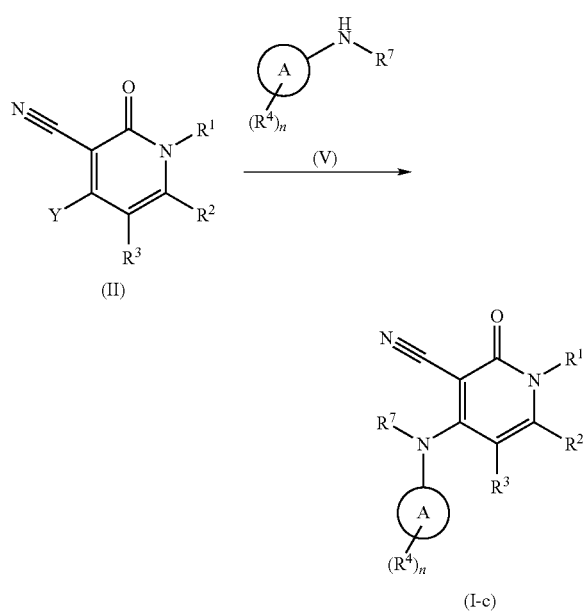

Experimental Procedure 4 (L is Alkynyl)

The final compounds according to Formula (I-d), wherein L is —C≡C—, can be prepared by reacting an intermediate compound of Formula (II) with a compound of Formula (VI) according to reaction scheme (4), a reaction that is performed in a suitable reaction-inert solvent, such as, for example, THF, in the presence of a suitable base, such as, for example, NEt$_3$, a Pd-complex catalyst such as, for example, PdCl$_2$(PPh$_3$)$_2$ a phosphine such as, for example, PPh$_3$, a copper salt such as, for example, CuI and under thermal conditions such as, for example, heating the reaction mixture for example at 80° C. for 12 hours. In reaction scheme (4), all variables are defined as in Formula (I), R$^1$ is V$^1$-M$^1$ and Y is a group suitable for Pd-mediated coupling with alkynes, such as, for example, halo.

Reaction Scheme 4

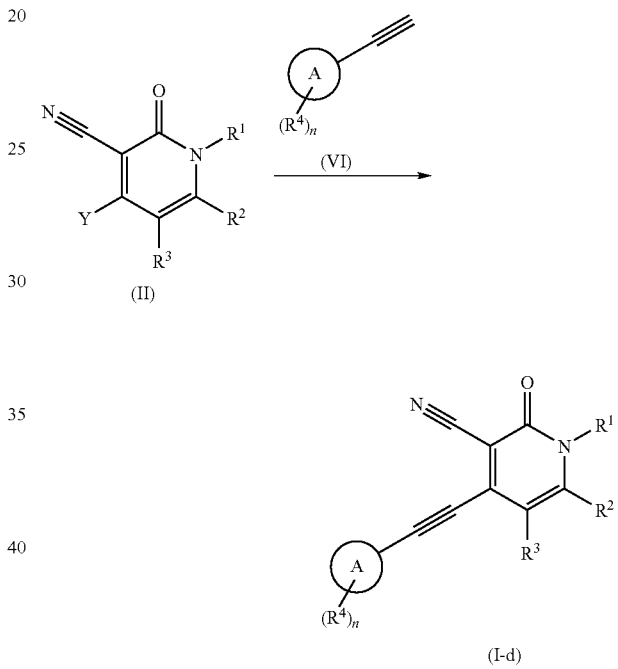

Experimental Procedure 5 (L is Alkenyl)

The final compounds according to Formula (I-e), wherein L is —C(R$^8$)=C(R$^9$)— can be prepared by reaction of an intermediate of Formula (II) with an intermediate of Formula (VII) in an inert solvent such as, for example, 1,4-dioxane, in the presence of a suitable base, such as, for example, NaHCO$_3$ or Na$_2$CO$_3$, a Pd-complex catalyst such as, for example, Pd(PPh$_3$)$_4$ under thermal conditions such as, for example, heating the reaction mixture at 85° C., for example for 8 hours. In reaction scheme (5), all variables are defined as in Formula (I) and Y is a group suitable for Pd-mediated coupling with boronic acids or boronic esters, such as, for example, a halo, trifluoromethanesulphonyl or pyridinium moiety. Such intermediate compounds may be prepared according to reaction schemes (8), (9) and (10) (see below). R$^5$ and R$^6$ may be hydrogen or alkyl, or may be taken together to form for example the bivalent radical of formula —CH$_2$CH$_2$—, —CH$_2$CH$_2$CH$_2$—, or —C(CH$_3$)$_2$C(CH$_3$)$_2$—. In reaction scheme (5), all variables are defined as in Formula (I) and R$^1$ is V$^1$-M$^1$.

Reaction Scheme 5

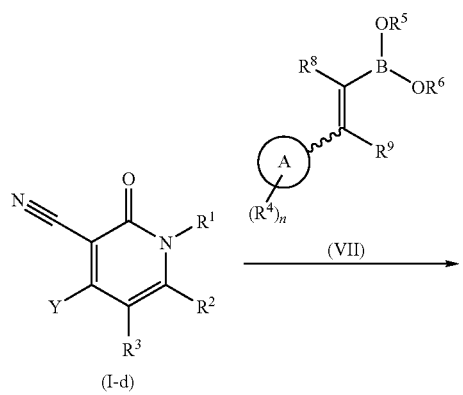

Experimental Procedure 6

The final compounds according to Formula (I-e2), wherein L is —CH=CH— and Formula (I-f2), wherein L is —CH$_2$CH$_2$—, can be prepared by art-known procedures such as, for example, hydrogenation of a final compound of Formula (I-d), prepared according to reaction scheme (6). Additionally, final compounds of Formula (I-f1) and Formula (I-f2) can be prepared from final compounds of Formula (I-e1) and Formula (I-e2) by art-known hydrogenation methods according to reaction scheme (6). Additionally, final compounds of Formula (I-e2) can be prepared by partial reduction of the triple bond of final compounds of Formula (I-d) by art known procedures. In reaction scheme (6), all variables are defined as in Formula (I) and R$^1$ is V$^1$-M$^1$.

Reaction Scheme 6

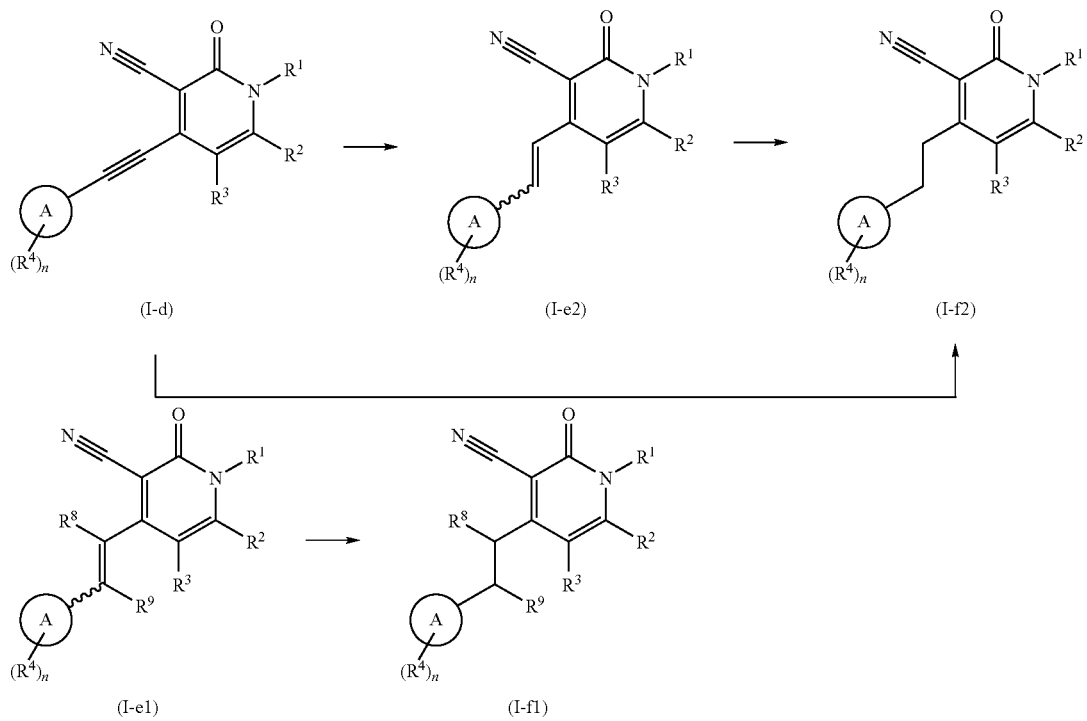

Experimental Procedure 7

The compounds according to Formula (I) can be prepared by art known procedures by reacting a compound of Formula (VIII) with an alkylating agent of Formula (IX), such as, for example, isopentylbromide, using a suitable base such as, for example, K$_2$CO$_3$, and an iodine salt such as, for example, KI, in an inert solvent such as, for example, acetonitrile at a moderately high temperature such as, for example, 120° C. In reaction scheme (7), all variables are defined as in Formula (I), R$^1$ is V$^1$-M$^1$ and Z is a suitable leaving group such as, for example, halo.

-continued

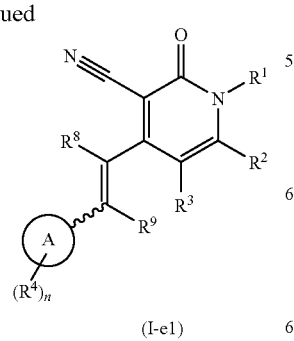

Reaction Scheme 7

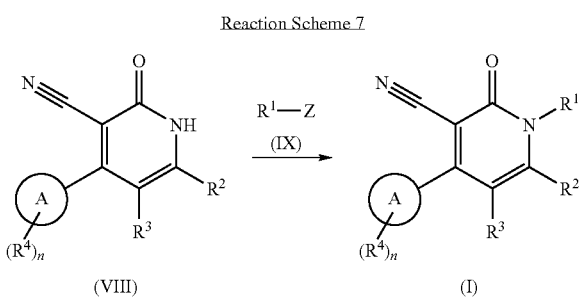

Additionally, final compounds according to Formula (I) can be prepared by a skilled person using art known procedures by further modifications of final compounds of Formula (I-a), (I-b), (I-c), (I-d), (I-e) and (I-f) such as, for example:

- Alkylation of final compounds of Formula (I-a), (I-b), (I-c), (I-d), (I-e) and (I-f) that contain in their structure one or more hydroxy- or amino-substituents with a suitable alkylating agent under thermal conditions using a suitable base.
- Saponification of final compounds of Formula (I-a), (I-b), (I-c), (I-d), (I-e) and (I-f) that contain in their structure one or more alkyloxycarbonyl function by using a suitable saponificating agent such as, for example, NaOH or LiOH.
- Reaction of final compounds of Formula (I-a), (I-b), (I-c), (I-d), (I-e) and (I-f) that contain in their structure one or more carboxylic acid function with ammonia or a primary or secondary amine by using a suitable coupling agent such as, for example O-(7-azabenzotriazol-1-yl)-N,N,N',N'-tetramethyluronium hexafluorophosphate, to yield the corresponding final compounds of Formula (I), bearing a primary, secondary or tertiary carboxamide function in their structures.
- Reaction of final compounds of Formula (I-a), (I-b), (I-c), (I-d), (I-e) and (I-f) that contain in their structure a primary or secondary amine function with a carboxylic acid by using a suitable coupling agent such as, for example, O-(7-azabenzotriazol-1-yl)-N,N,N',N'-tetramethyluronium hexafluorophosphate to yield the corresponding final compounds of Formula (I), bearing a primary, secondary or tertiary carboxamide function in their structures.
- Reductive amination of final compounds of Formula (I-a), (I-b), (I-c), (I-d), (I-e) and (I-f) that contain in their structure one or more amino-substituents with a suitable aldehyde under thermal conditions using a suitable reducing agent such as, for example, sodium cyanoborohydride.
- Reaction of final compounds of Formula (I-a), (I-b), (I-c), (I-d), (I-e) and (I-f) that contain in their structure one or more hydroxy-substituents with an alcohol derivative by using a suitable coupling system such as, for example, di-tert-butylazodicarboxylate/triphenylphosphine under thermal conditions.
- 1,3-Dipolar cyclo addition of final compounds of Formula (I-a), (I-b), (I-c), (I-d), (I-e) and (I-f) that contain in their structure a reactive double or triple bond with a suitable dipole to yield the corresponding [3+2] adduct final compounds.

B. Preparation of the Intermediate Compounds

Experimental Procedure 8

Intermediate compounds of Formula (II-a) can be prepared by reacting an intermediate of Formula (X) with a suitable halogenating agent such as, for example, $P(=O)Br_3$, a reaction that is performed in a suitable reaction-inert solvent such as, for example, DMF, at a moderately elevated temperature such as, for example, 110° C. In reaction scheme (8), all variables are defined as in Formula (I) and $R^1$ is $V^1$-$M^1$.

Reaction Scheme 8

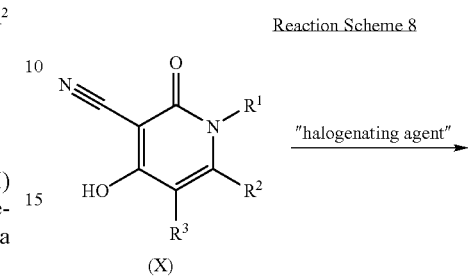

Experimental Procedure 9

Intermediate compounds of Formula (II-b) can be prepared by reacting an intermediate of Formula (X) with triflic anhydride (also called trifloromethanesulfonic anhydride), a reaction that is performed in a suitable reaction-inert solvent such as, for example, dichloromethane, in the presence of a base such as, for example, pyridine at a low temperature such as, for example, −78° C. In reaction scheme (9), all variables are defined as in Formula (I) and $R^1$ is $V^1$-$M^1$.

Reaction Scheme 9

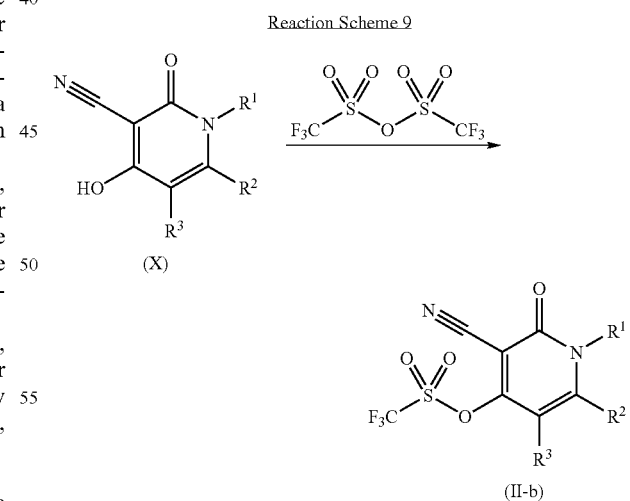

Experimental Procedure 10

Intermediate compounds of Formula (II-c) can be prepared by reacting an intermediate compound of Formula (II-b) with pyridine, at a moderately low temperature such as, for example, 40° C. In reaction scheme (10), all variables are defined as in Formula (I) and $R^1$ is $V^1$-$M^1$.

Reaction Scheme 10

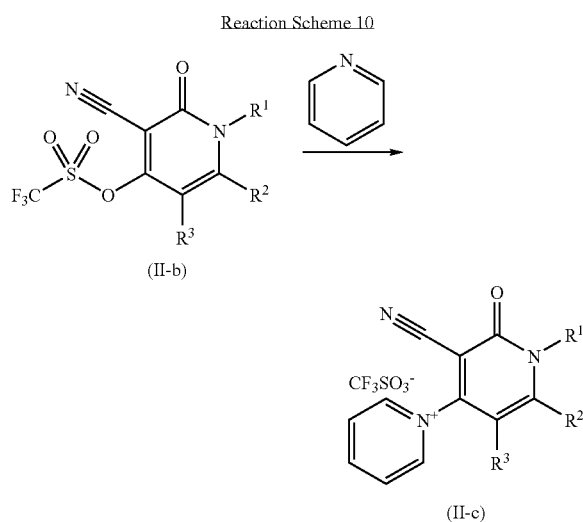

Experimental Procedure 11

Intermediate compounds of Formula (X) can be prepared by art known procedures by reacting an intermediate compound of Formula (XI) with a suitable reagent for methyl-ether-cleavage, such as, for example, NaOH, in a solvent such as, for example, water at a moderately high temperature such as, for example, 100° C. In reaction scheme (11), all variables are defined as in Formula (I) and $R^1$ is $V^1$-$M^1$.

Reaction Scheme 11

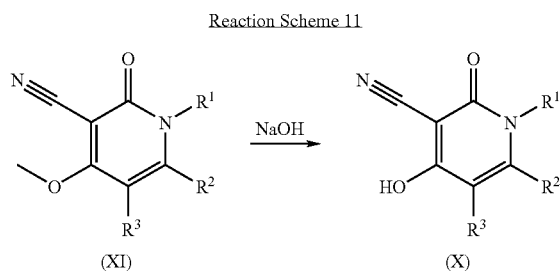

Experimental Procedure 12

Intermediate compounds of Formula (XI) can be prepared by art known procedures by reacting an intermediate of Formula (XII) with an alkylating agent of Formula (IX), such as, for example, isopentylbromide, using a base such as, for example, $K_2CO_3$, and, optionally an iodine salt such as, for example, KI, in an inert solvent such as, for example, acetonitrile at a moderately high temperature such as, for example, 120° C. In reaction scheme (12), all variables are defined as in Formula (I), $R^1$ is $V^1$-$M^1$ and Z is a suitable leaving group such as, for example, halo.

Reaction Scheme 12

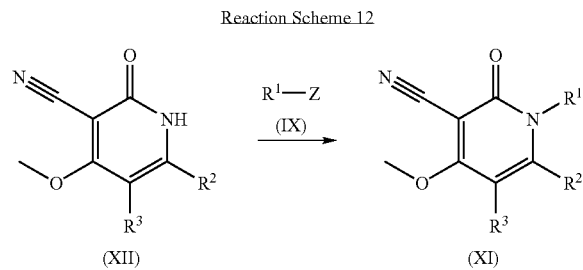

Experimental Procedure 13

Intermediate compounds of Formula (III) can be prepared by art known procedures by reacting an intermediate of Formula (XIII) with a suitable boron source such as, for example, bis(pinacolato)diboron in the presence of a Palladium catalyst such as, for example, 1,1'-bis(diphenylphosphino)ferrocenepalladium(II)dichloride in a inert solvent such as, for example, dichloromethane, in the presence of a suitable salt such as, for example, potassium acetate at moderately high temperature such as, for example, 110° C. for as for example 16 hours. Additionally, compounds of Formula (III) can be prepared by art known procedures of metal-halogen exchange and subsequent reaction with an appropriate boron source from compounds of Formula (XIII). Thus for example reaction of an intermediate compound of Formula (XIII) with an organolithium compound such as, for example, n-butyllithium at a moderately low temperature such as, for example, −40° C. in an inert solvent such as, for example, THF followed by subsequent reaction with an appropriate boron source such as, for example, trimethoxyborane. In reaction scheme (13), all variables are defined as in Formula (I) and $R^5$ and $R^6$ may be hydrogen or alkyl, or may be taken together to form for example the bivalent radical of formula —$CH_2CH_2$—, —$CH_2CH_2CH_2$—, or —$C(CH_3)_2C(CH_3)_2$—.

Reaction Scheme 13

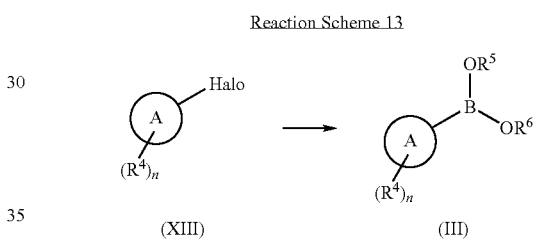

The starting materials of Formula (X) and the intermediate compounds according to Formula (III), (IV), (V), (VI), (VII), (IX), (XII) and (XIII) are compounds that are either commercially available or may be prepared according to conventional reaction procedures generally known in the art.

It is evident that in the foregoing and in the following reactions, the reaction products may be isolated from the reaction medium and, if necessary, further purified according to methodologies generally known in the art, such as, for example, extraction, crystallization and chromatography. It is further evident that reaction products that exist in more than one enantiomeric form, may be isolated from their mixture by known techniques, in particular preparative chromatography, such as, for example, preparative HPLC.

Pharmacology

The compounds provided in this invention are positive allosteric modulators of metabotropic receptors, in particular they are positive allosteric modulators of mGluR2. The compounds of the present invention do not appear to bind to the glutamate recognition site, the orthosteric ligand site, but instead to an allosteric site within the seven transmembrane region of the receptor. In the presence of glutamate or an agonist of mGluR2, the compounds of this invention increase the mGluR2 response. The compounds provided in this invention are expected to have their effect at mGluR2 by virtue of their ability to increase the response of such receptors to glutamate or mGluR2 agonists, enhancing the response of the receptor. Hence, the present invention relates to a compound for use as a medicine, as well as to the use of a compound according to the invention or a pharmaceutical composition according to the invention for the manufacture of a medicament for treating or preventing a condition in a mammal, including a human, the treatment or prevention of which is affected or facilitated by the neuromodulatory effect of mGluR2 allosteric modulators, in particular positive mGluR2 allosteric modulators.

Also, the present invention relates to the use of a compound according to the invention or a pharmaceutical composition according to the invention for the manufacture of a medicament for treating, or preventing, ameliorating, controlling or reducing the risk of various neurological and psychiatric disorders associated with glutamate dysfunction in a mammal, including a human, the treatment or prevention of which is affected or facilitated by the neuromodulatory effect of mGluR2 positive allosteric modulators.

Where the invention is said to relate to the use of a compound or composition according to the invention for the manufacture of a medicament for e.g. the treatment of a mammal, it is understood that such use is to be interpreted in certain jurisdictions as a method of e.g. treatment of a mammal, comprising administering to a mammal in need of such e.g. a treatment, an effective amount of a compound or composition according to the invention.

In particular, the neurological and psychiatric disorders associated with glutamate dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as, for example, opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In particular, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the central nervous system disorder is an anxiety disorder, selected from the group of agoraphobia, generalized anxiety disorder (GAD), obsessive-compulsive disorder (OCD), panic disorder, posttraumatic stress disorder (PTSD), social phobia and other phobias.

Preferably, the central nervous system disorder is a psychotic disorder selected from the group of schizophrenia, delusional disorder, schizoaffective disorder, schizophreniform disorder and substance-induced psychotic disorder Preferably, the central nervous system disorder is a personality disorder selected from the group of obsessive-compulsive personality disorder and schizoid, schizotypal disorder.

Preferably, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the central nervous system disorder is an eating disorder selected from the group of anorexia nervosa and bulimia nervosa.

Preferably, the central nervous system disorder is a mood disorder selected from the group of bipolar disorders (I & II), cyclothymic disorder, depression, dysthymic disorder, major depressive disorder and substance-induced mood disorder.

Preferably, the central nervous system disorder is migraine.

Preferably, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Of the disorders mentioned above, the treatment of anxiety, schizophrenia, migraine, depression, and epilepsy are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Because such positive allosteric modulators of mGluR2, including compounds of Formula (I), enhance the response of mGluR2 to glutamate, it is an advantage that the present methods utilize endogenous glutamate.

Because positive allosteric modulators of mGluR2, including compounds of Formula (I), enhance the response of mGluR2 to agonists, it is understood that the present invention extends to the treatment of neurological and psychiatric disorders associated with glutamate dysfunction by administering an effective amount of a positive allosteric modulator of mGluR2, including compounds of Formula (I), in combination with an mGluR2 agonist.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

Pharmaceutical Compositions

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable acid or base addition salt thereof, a stereochemically isomeric form thereof, an N-oxide form thereof or a quaternary ammonium salt thereof.

The compounds according to the invention, in particular the compounds according to Formula (I), the pharmaceutically acceptable acid or base addition salt thereof, a stereochemically isomeric form thereof, an N-oxide form thereof or a quaternary ammonium salt thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a trans-dermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. Since the compounds according to the invention are potent orally administrable dopamine antagonists, pharmaceutical compositions comprising said compounds for administration orally are especially advantageous.

As already mentioned, the invention also relates to a pharmaceutical composition comprising the compounds according to the invention and one or more other drugs in the treatment, prevention, control, amelioration, or reduction of risk of diseases or conditions for which compounds of Formula (I) or the other drugs may have utility as well as to the use of such a composition for the manufacture of a medicament.

The following examples are intended to illustrate but not to limit the scope of the present invention.

Experimental Part

Several methods for preparing the compounds of this invention are illustrated in the following Examples. Unless otherwise noted, all starting materials were obtained from commercial suppliers and used without further purification. Specifically, the following abbreviations may be used in the examples and throughout the specification:

| | |
|---|---|
| AcOEt (ethyl acetate) | M (molar) |
| AcOH (acetic acid) | MeOH (methanol) |
| BBr$_3$ (boron tribromide) | mg (milligrams) |
| BINAP (±)-1,1'-Bi(2-naphthol) | MgSO$_4$ (magnesium sulphate) |
| Br$_2$ (bromine) | MHz (megahertz) |
| CDCl$_3$ (deuterated chloroform) | min (minutes) |
| CCl$_4$ (carbon tetrachloride) | µl (microliters) |
| DCM (dichloromethane) | ml (milliliters) |
| MCPBA (3-chloroperbenzoic acid) | mmol (millimol) |
| DEAD (diethyl azodicarboxylate) | m.p. (melting point) |
| DIBAL (diisobutyl aluminium hydride) | NaBH(OAc)$_3$ (Sodium triacetoxyborohydride) |
| DME (dimethoxyethane) | Na$_2$CO$_3$ (sodium carbonate) |
| DMF (dimethylformamide) | NaH (sodium hydride) |
| DMSO (dimethyl sulfoxide) | NaHCO$_3$ (sodium bicarbonate) |
| Dppf (1,1'-bis(diphenylphosphanyl)ferrocene) | NaHMDS (sodium hexamethyldisilazane) |
| EDCl•HCl (1-3(dimethylaminopropyl)-3-ethylcarbodiimide, hydrochloride) | NaI (sodium iodide) |
| Et$_3$N (triethylamine) | NaO$^t$Bu (sodium tert-butoxide) |
| Et$_2$O (diethyl ether) | Na$_2$SO$_4$ (sodium sulphate) |
| EtOH (ethanol) | NBS (N-bromosuccinimide) |
| g (grams) | NH$_4$Cl (ammonium chloride) |
| $^1$H (proton) | NH$_4$OH (ammonium hydroxide) |
| H$_2$ (hydrogen) | NMR (Nuclear Magnetic Resonance) |
| HCl (hydrochloric acid) | Pd$_2$(dba)$_3$ (palladium (II)dibenzylideneacetone) |

| | |
|---|---|
| HPLC (High Pressure Liquid Chromatography) | PdCl$_2$(dppf)$_2$ (Bis(1,1'-bis(diphenyl-phosphanyl)ferrocene palladium (II) dichloride) |
| Hz (Hertz) | PdCl$_2$(PPh$_3$)$_2$ (Bis(triphenylphosphine) palladium (II) dichloride |
| KBr (potassium bromide) | Pd(OAc)$_2$ (Palladium acetate) |
| K$_2$CO$_3$ (potassium carbonate) | Pd(PPh$_3$)$_4$ (tetrakis(triphenylphosphine)palladium(0)) |
| KOAc (potassium acetate) | P(=O)Br$_3$ (phosphorousoxybromide) |
| KI (potassium iodide) | PPh$_3$ (triphenylphosphine) |
| KOtBu (potassium tert-butoxide) | TFA (trifluoroacetic acid) |
| KOH (potassium hydroxide) | THF (tetrahydrofuran) |
| K$_3$PO$_4$ (potassium phosphate) | TLC (thin layer chromatography) |
| LCMS (Liquid Chromatography Mass Spectrum) | Tf$_2$O (trifloromethanesulfonic anhydride) |
| LiAlH$_4$ (lithium aluminium hydride) | Xantphos (4,5-bis(diphenylphosphino)-9,9-dimethylxanthene |

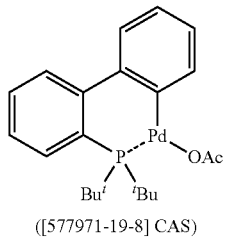

([577971-19-8] CAS)

All references to brine refer to a saturated aqueous solution of NaCl. Unless otherwise indicated, all temperatures are expressed in ° C. (degrees Celsius). All reactions are conducted not under an inert atmosphere at room temperature, unless otherwise noted.

Microwave assisted reactions were performed in a single-mode reactor: Emrys™ Optimizer microwave reactor (Personal Chemistry A.B., currently Biotage). Description of the instrument can be found in www.personalchemistry.com. And in a multimode reactor: MicroSYNTH Labstation (Milestone, Inc.). Description of the instrument can be found in www.milestonesci.com.

A. Preparation of the Intermediate Compounds

A1. Intermediate Compound 1

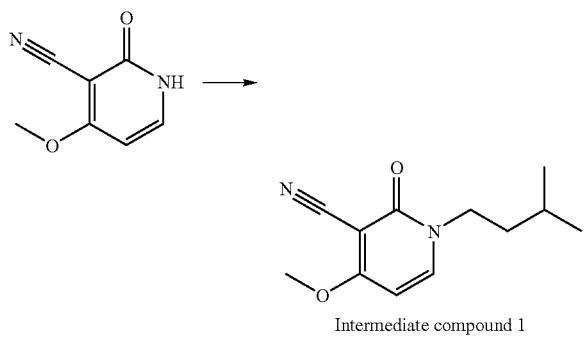

Intermediate compound 1

The reaction was carried out under N$_2$ atmosphere. To a solution of commercially available 4-methoxy-2-oxo-1,2-dihydro-pyridine-3-carbonitrile (1.00 g, 6.60 mmol, 1 eq) in acetonitrile (45 ml) was added K$_2$CO$_3$ (2.73 g, 19.8 mmol, 3 eq) and isopentylbromide (441 mg, 8.65 mmol, 1.3 eq). The resulting solution was heated at 100° C. for 12 hours. The reaction was then cooled to room temperature and filtered through a pad of celite. The filtrate was then concentrated in vacuo. Subsequently, the crude residue thus obtained was purified by flash chromatography (SiO$_2$, eluting with a gradient elution of between 0-2% MeOH in DCM) to yield intermediate compound 1 as a creamy solid (82%, 5.40 mmol).

A2. Intermediate Compounds 2 and 2'

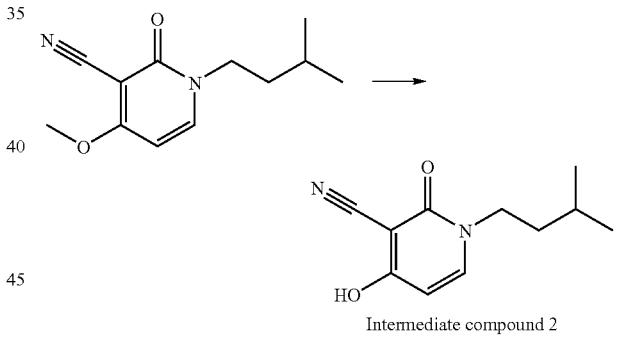

Intermediate compound 2

A solution of intermediate compound 1 (1.5 g, 6.81 mmol) in aqueous NaOH (0.1 N, 75 ml) and THF (20 ml) was heated to 100° C. for 1 hour. The reaction was cooled to 0° C. and acidified by the addition of 1M HCl, adjusting the pH to about 3, at which point a white solid precipitated. The solid was filtered off and dried in vacuo to yield the N-isopentyl substituted intermediate compound 2 as a white solid (1.3 g, 6.30 mmol). In an equal manner was prepared the N-n-butyl substituted intermediate compound 2'.

A3. Intermediate Compounds 3, 3' and 3"

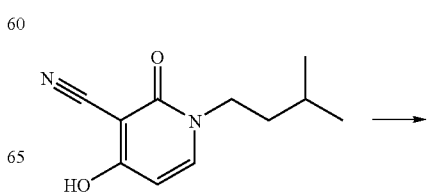

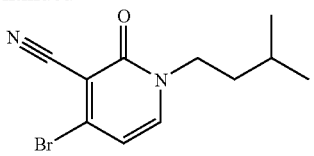

Intermediate compound 3

The reaction was carried out under N$_2$ atmosphere. To a solution of intermediate compound 2 (2.00 g, 9.66 mmol, 1 eq) in DMF (10 ml) was added cautiously P(=O)Br$_3$ (5.54 g, 19.0 mmol, 2 eq), the resulting solution was then heated at 100° C. into a sealed tube for 2 hours. The reaction was then cooled to room temperature and diluted by H$_2$O (30 ml), the resulting solution was subsequently extracted with AcOEt (3×30 ml). The organic layer was dried over Na$_2$SO$_4$ and concentrated in vacuo to yield an oil. The crude product was purified by flash chromatography (SiO$_2$, eluting with DCM) to yield N-isopentyl substituted intermediate compound 3 as a creamy solid (2.13 g, 82%, 7.92 mmol). In an equal manner was prepared the N-n-butyl substituted intermediate compound 3' and the N-methylcyclopropyl substituted intermediate compound 3".

A4. Intermediate Compound 4

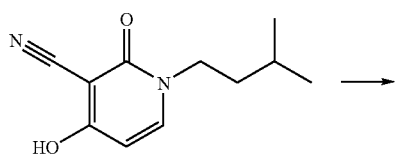

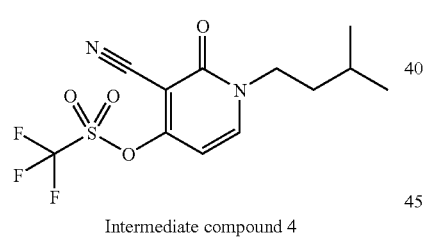

Intermediate compound 4

In a round flask containing intermediate compound 2 (100 mg, 0.48 mmol) in DCM (5 ml), were added 3 eq of pyridine (0.118 ml, 1.44 mmol). The mixture was cooled to −78° C. and Tf$_2$O (0.217 ml, 0.528 mmol) was added slowly. The solution was warmed to room temperature and stirred for ½ hour. The mixture was hydrolized with cold water, extracted with DCM (3×10 ml), washed twice with brine, dried over Na$_2$SO$_4$, filtered and evaporated under reduced pressure to yield intermediate compound 4 (133 mg).

A6. Intermediate Compound 6

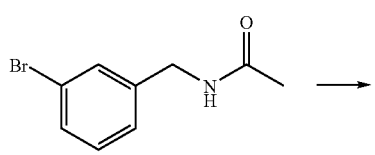

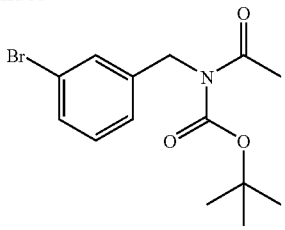

Intermediate compound 6

The reaction was carried out under nitrogen atmosphere. To a solution of N-(2-bromo-benzyl)-acetamide (468 mg, 2.02 mmol) in acetonitrile (45 ml) was added di-tent-butyl dicarbonate (1.34 g, 6.15 mmol) and N,N-dimethaminopyridine (501 mg, 4.1 mmol). The reaction mixture was then stirred at room temperature for 20 min, after which time it was diluted with AcOEt (40 ml) and washed with a saturated solution of NaHCO$_3$ (2×40 ml) and a saturated solution of NH$_4$Cl (3×40 ml). The organic layer was then dried over Na$_2$SO$_4$ and concentrated in vacuo to yield a crude solid. This was purified by short open column chromatography (SiO$_2$, eluting with 2% MeOH in DCM) to yield intermediate compound 6 as a yellow oil (590.00 mg, 89%, 1.79 mmol).

A7. Intermediate Compound 7

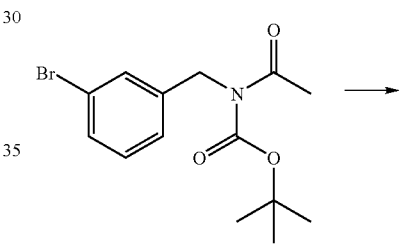

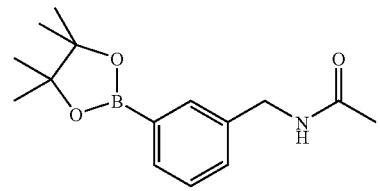

Intermediate compound 7

To a solution of intermediate compound 6 (200 mg, 0.61 mmol) in DMSO (4 ml) was added bis(pinacolato)diboron (232 mg, 0.913 mmol) and potassium KOAc (180 mg, 1.83 mmol) the solution was then degassed using a stream of nitrogen and then to the reaction mixture was added 1,1'-bis (diphenylphosphino)ferrocenepalladium (II) dichloride, DCM (20.0 mg, 0.0183 mmol). The reaction mixture was then heated at 110° C. under a nitrogen atmosphere for 16 hours. The reaction was then cooled to room temperature and diluted with AcOEt (30 ml) and the resulting solution was washed with water (3×15 ml), the organic fraction was then dried over Na$_2$SO$_4$ and concentrated in vacuo to yield the desired compound. The product was purified by short open column chromatography (SiO$_2$, eluting with DCM) to yield intermediate compound 7 as yellow oil (149.0 mg, 89%, 0.054 mmol).

A8. Intermediate Compound 8

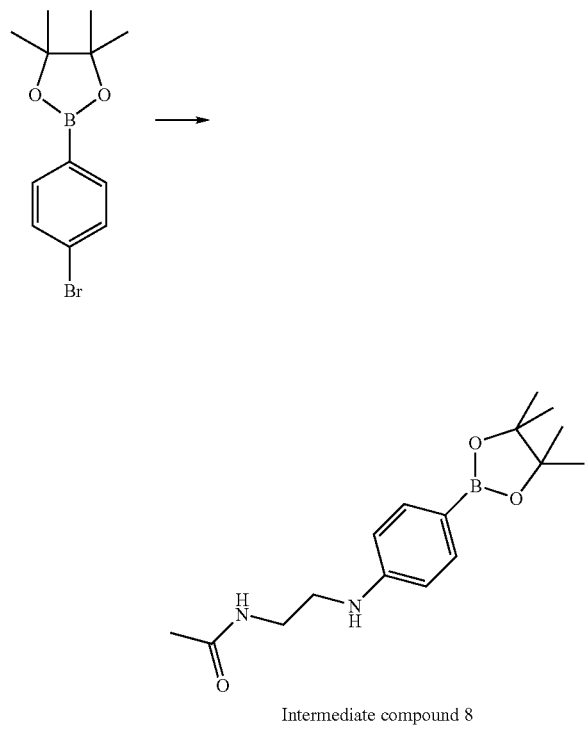

Intermediate compound 8

The reaction was carried out under N₂ atmosphere. 4-Bromobenzeneboronic acid pinacol cyclic ester (300 mg, 1.06 mmol), N-acetylethylenediamine (0.155 ml, 1.59 mmol), Xantphos (123 mg, 0.21 mmol), and $Cs_2CO_3$ (518 mg, 1.59 mmol) were added to a mixture of 1,4-dioxane (5.88 ml) and DMF (0.12 ml) at room temperature, and N₂ was fluxed through the mixture for 5 min. $Pd(OAc)_2$ (24 mg, 0.1 mmol) was added and the mixture was irradiated under microwave conditions at 170° C. for 10 min into a sealed tube. The reaction was then cooled to room temperature and filtered through a pad of celited. The volatiles were evaporated in vacuum and the residues thus obtained was purified by short open column chromatography ($SiO_2$, eluting with DCM/MeOH($NH_3$)) to yield intermediate compound 8 (80 mg).

A9. Intermediate Compound 9

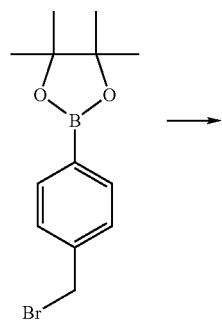

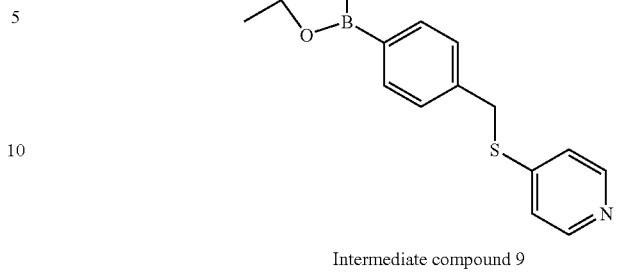

Intermediate compound 9

To a solution of 4-pyridinethiol (149 mg, 1.35 mmol) in dimethylformamide (5 ml) was added $K_2CO_3$ (186 mg, 1.35 mmol); the resulting solution was stirred for 12 min and to this subsequently was added a solution of 2-(4-bromomethyl-phenyl)-4,4,5,5-tetramethyl-[1,3,2]dioxaborolane (400 mg, 1.35 mmol) and the resulting solution was stirred for 2 hours. The mixture was then diluted by the addition of water (30 ml) and extracted with AcOEt (3×15 ml); the organic layer was subsequently dried over $Na_2SO_4$ and concentrated in vacuo to yield the crude product. The crude reaction mixture was subsequently purified by Biotage purification (eluting with DCM) to yield intermediate compound 9. (406.0 mg, 1.24 mmol, 92%).

A10. Intermediate Compound 10

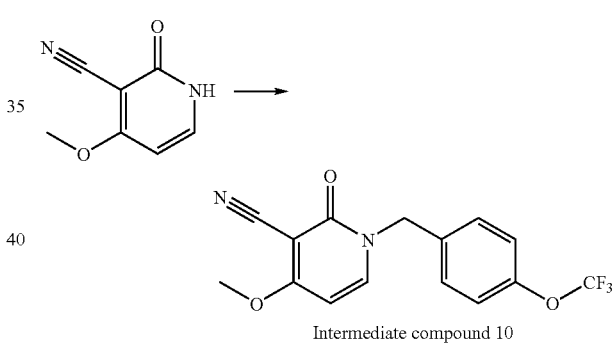

Intermediate compound 10

Commercially available 4-methoxy-2-oxo-1,2-dihydro-pyridine-3-carbonitrile (4.70 g, 31.29 mmol, 1 eq), 4-(trifluoromethoxy)benzylbromide (5.44 ml, 32.86 mmol, 1.05 eq) and $K_2CO_3$ (12.9 g, 93.8 mmol, 3 eq) were mixed in acetonitrile (200 ml). The mixture was heated at 140° C. for 16 hours into a sealed tube. The reaction was then cooled to room temperature and the solvents were evaporated in vacuum. The resulting residue was dissolved in DCM and filtered through a pad of celite. The filtrate was then concentrated in vacuo. Subsequently, the white solid thus obtained was triturated with diethylether to yield intermediate compound 10 as a white solid (9.20 g, 91%).

A11. Intermediate Compound 11

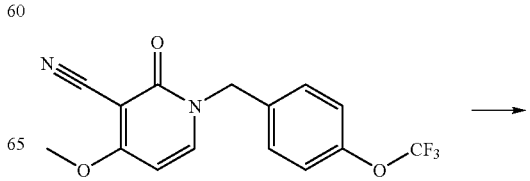

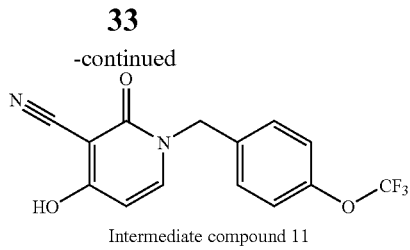
Intermediate compound 11

To a solution of intermediate compound 10 (9.20 g, 28.37 mmol) in THF (100 ml) was added aqueous NaOH (0.1 N, 300 ml). The reaction mixture was heated at 100° C. for 4 hours. The reaction was then cooled to room temperature and the THF was evaporated in vacuum. The resulting basic aqueous phase was acidified by the addition of 2 N HCl, adjusting the pH to about 3, at which point a white solid precipitated. The solid was filtered off, washed with diethylether and dried in vacuo to yield the intermediate compound 11 as a white solid (8.05 g, 91%).

A12. Intermediate Compound 12

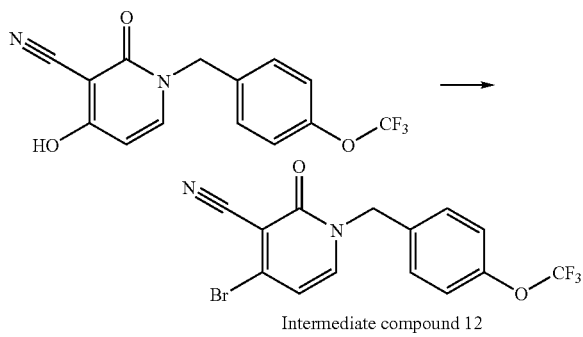
Intermediate compound 12

Intermediate compound 11 (6.57 g, 21.19 mmol, 1 eq) and P(=O)Br₃ (12.15 g, 42.39 mmol, 2 eq) were mixed in DMF (125 ml) and the resulting mixture was then heated at 110° C. for 1 hour. The reaction was then cooled to room temperature and diluted with H₂O (200 ml), the resulting solution was subsequently extracted with AcOEt (3×75 ml). The organic layer was dried over MgSO₄ and concentrated in vacuo. The crude product was purified by flash chromatography (SiO₂, eluting with DCM) to yield intermediate compound 12 as a white solid (6.75 g). In a similar manner was made intermediate compound 12' wherein the phenyl moiety in the para-position is substituted with a fluor instead of a trifluoromethoxy moiety.

A13. Intermediate Compound 13

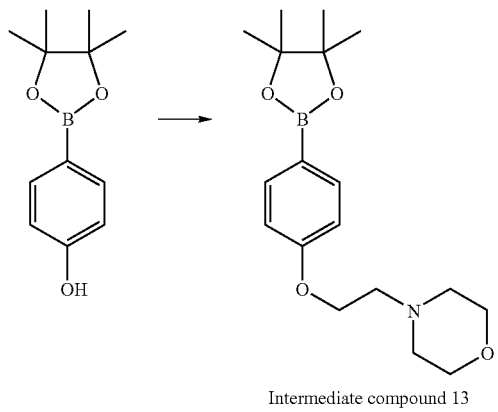
Intermediate compound 13

To a mixture of 4-(4,4,5,5-tetramethyl-1,3,2-dioxaborolan-2-yl)phenol (500 mg, 2.27 mmol), N-(2-hydroxyethyl)morpholine (330.8 mg, 2.72 mmol) and PPh₃ polymer bound (loading 2.15 mmol/g) (2.11 g, 4.54 mmol) in dry DCM (30 ml) at 0° C. was added di-tert-butylazodicarboxylate (784.0 mg, 3.40 mmol). The reaction mixture was stirred at room temperature for 2 hours. Then, the resin was filtered off, washed with DCM and the filtrate concentrated in vacuo. The residue (756.45 mg) was used in the next reaction step without further purification A14. Intermediate Compound 14

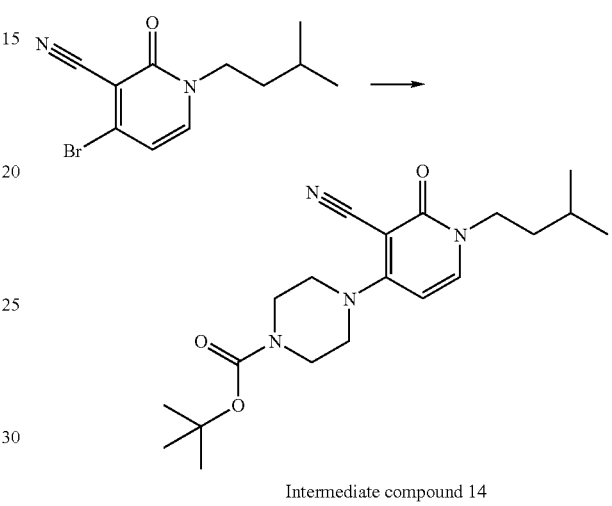
Intermediate compound 14

Intermediate compound 3 (200 mg, 0.74 mmol), 1-tert-butoxycarbonylpiperazine (151 mg, 0.81 mmol), K₃PO₄ (236 mg, 1.1 mmol) and catalyst [577971-19-8] CAS (10 mg) were mixed in 1,4-dioxane (3 ml) at room temperature. The corresponding mixture was heated at 85° C. in a sealed tube for 16 hours. The mixture was cooled to room temperature, filtered through a pad of celite and washed with DCM. The filtrate was concentrated in vacuo and the residue thus obtained was purified by flash chromatography to yield intermediate compound 14 (200 mg, 72%).

A16. Intermediate Compound 16

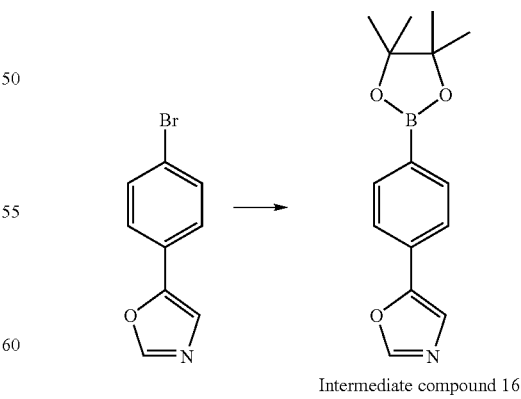
Intermediate compound 16

A mixture of 5-(4-bromophenyl)-1,3-oxazole (220 mg, 0.98 mmol), bis(pinacolato)-diboron (372 mg, 1.47 mmol), 1,1'-bis(diphenylphosphino)ferrocenepalladium(II) dichloride, DCM (24 mg, 0.0294 mmol), KOAc (288 mg, 2.93 mmol) in DMSO (7 ml) was heated at 110° C. for 16 hours. The mixture was cooled to room temperature, diluted with AcOEt (30 ml) and washed with water (3×15 ml). The combined organic layers were dried over Na$_2$SO$_4$, evaporated in vacuum and the residue thus obtained (200 mg) was used in the next reaction step without further purification.

A17. Intermediate Compound 17

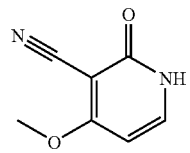

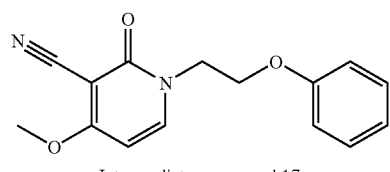

Intermediate compound 17

A solution of commercially available 4-methoxy-2-oxo-1,2-dihydro-pyridine-3-carbonitrile (4.0 g, 0.0266 mol), beta-bromophenetole (5.62 g, 0.0279 mol) and K$_2$CO$_3$ (11.0 g, 0.0799 mol) in CH$_3$CN (150 ml) was heated at reflux for 16 hours. The reaction mixture was then filtered off and the filtrate concentrated in vacuo. The residue was recrystallised from ethylether to yield intermediate compound 17 (7 g, 97%).

A18. Intermediate Compound 18

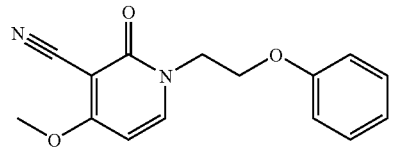

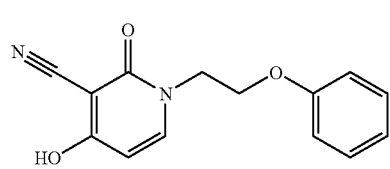

Intermediate compound 18

To a solution of intermediate compound 17 (7.0 g, 0.0259 mol) in MeOH (100 ml) was added aqueous NaOH (0.1 N, 200 ml). The reaction mixture was heated to 100° C. for 3 hours. The reaction was then cooled to room temperature and the MeOH was evaporated in vacuum. The resulting basic aqueous phase was acidified by the addition of 2 N HCl, adjusting the pH to about 3, at which point a white solid precipitated. The solid was collected using a sintered funnel, washed with ethylether and dried in vacuo to yield intermediate compound 18 as white solid (5.78 g, 87%).

A19. Intermediate Compound 19

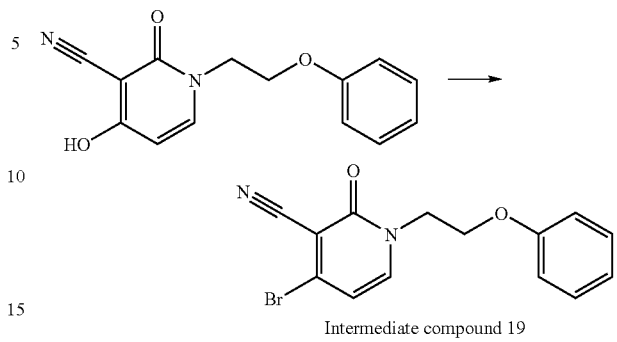

Intermediate compound 19

Intermediate compound 18 (7.10 g, 0.027 mol) and P(=O)Br$_3$ (15.886 g, 0.055 mol) were mixed in DMF (150 ml) and the resulting mixture was then heated at 110° C. for 3 hours. The reaction was then cooled to room temperature and diluted by H$_2$O (100 ml), the resulting solution was subsequently extracted with AcOEt (3×150 ml). The organic layer was dried over Na$_2$SO$_4$ and concentrated in vacuo. The crude product was purified by flash chromatography (SiO$_2$, eluting with DCM) to yield intermediate compound 19 (7.67 g, 89%).

A20. Intermediate Compound 20

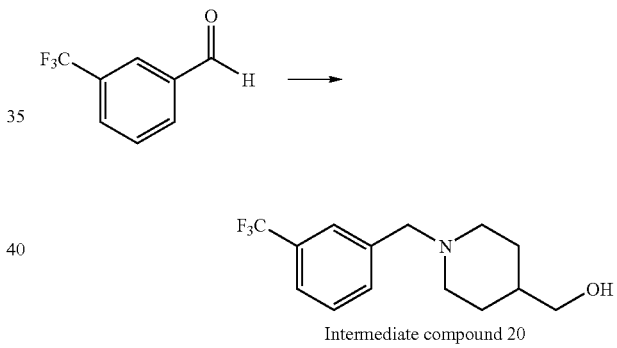

Intermediate compound 20

In a round flask containing 3-(trifluoromethyl)benzaldehyde ([454-89-7] CAS) (0.872 ml, 0.0065 mol) and 4-piperidinemethanol (0.5 g, 0.0043 mol) in DCE (20-30 ml) and a few drops of AcOH, NaBH(OAc)$_3$ (2.2 g, 0.0107 mol) was added. The mixture was stirred overnight at room temperature, after which time it was washed with a saturated solution of NaHCO$_3$ and extracted with DCM. The combined organic layers were dried over Na$_2$SO$_4$ and concentrated in vacuo. The crude product was purified by flash chromatography to yield intermediate compound 20 (0.610 g, 56%).

A23. Intermediate Compound 23

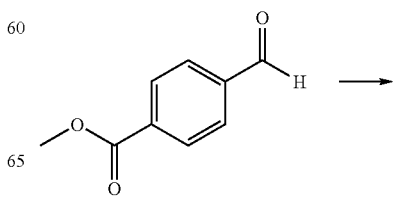

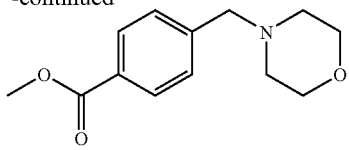

Intermediate compound 23

In a round flask containing methyl-4-formylbenzoate (5.6 g, 0.034 mol) and morpholine (2 g, 0.023 mol) in DCE (20 ml), few drops of AcOH and molecular sieves (4 A) were added. The reaction mixture was stirred at room temperature for 40 min and NaBH(OAc)$_3$ (5 g, 0.023 mol) was added. The mixture was stirred overnight at room temperature, after which time another equivalent of NaBH(OAc)$_3$ (5 g, 0.023 mol) was added. The mixture was stirred at room temperature for 5 hours and was subsequently washed with HCl (1 N) and extracted with DCM. The organic layer was finally washed with a saturated solution of NaHCO$_3$. The combined organic layers were dried over Na$_2$SO$_4$ and concentrated in vacuo. The crude product was purified by flash chromatography (DCM/MeOH(NH$_3$) mixtures) to yield intermediate compound 23 (3 g, 60%)

A24. Intermediate Compound 24

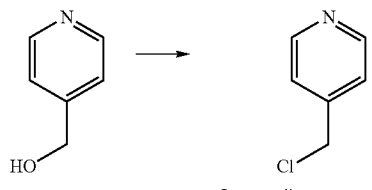

Intermediate compound 24

The reaction was carried out under N$_2$ atmosphere. To a solution of intermediate compound 23 (2 g, 0.0085 mol) in THF (12 ml), lithium aluminum hydride (1 M in THF) (17 ml, 0.017 mol) was slowly added. The reaction mixture was stirred at room temperature for 2 hours. Then, a saturated solution of NaHCO$_3$ was carefully added and the mixture was extracted with DCM. The combined organic layers were dried over Na$_2$SO$_4$ and concentrated in vacuo to yield intermediate compound 24 (1.75 g, 100%) which was used in the next reaction step without further purification.

A28. Intermediate Compound 28

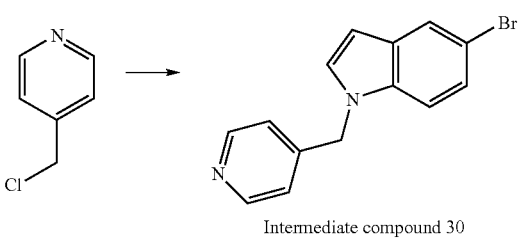 [SMILES: ClCc1ccncc1 ; Brc1ccc2c(ccn2Cc2ccncc2)c1]

Intermediate compound 28

A mixture of intermediate compound 3 (250 mg, 0.93 mmol), tributyl(vinyl)tin (0.325 ml, 1.11 mmol) and Pd(PPh$_3$)$_4$ (22 mg, 0.0186 mmol) in degassed toluene (10 ml) was microwaved at 130° C. for 25 min. The mixture was then cooled to room temperature and solvents were evaporated in vacuum. The residue was purified by flash chromatography (SiO$_2$, DCM/MeOH(NH$_3$) mixtures) to yield intermediate compound 28 (100 mg, 50%) as pale yellow solid.

A29. Intermediate Compound 29

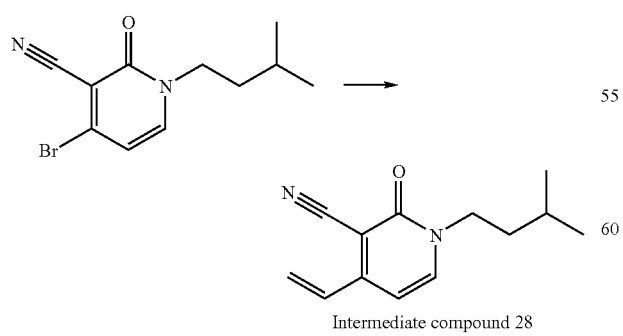

Intermediate compound 29

To a solution of 4-pyridylcarbinol (15 g, 137.4 mmol) in DCM (200 ml) was added thionyl chloride (43.6 ml) and the resulting reaction mixture was stirred at room temperature for 4 h. The mixture was cooled to room temperature and the solvent was evaporated in vacuo. The residue was diluted with DCM and washed with a saturated solution of NaHCO$_3$. The combined organic layers were dried over Na$_2$SO$_4$ and concentrated in vacuo to yield intermediate compound 29 (17.18 g, 99%).

A30. Intermediate Compound 30

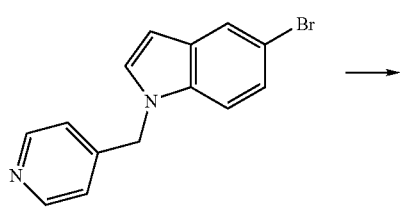

Intermediate compound 30

To a mixture of NaH (60% in mineral oil) (0.718 g, 17.96 mmol) in THF (20 ml), a solution of 5-bromoindole (2.34 g, 11.8 mmol) in THF (17 ml) was added dropwise. The resulting mixture was stirred at room temperature for 1 h. Then, intermediate compound 29 (1.81 g, 14.2 mmol) was added and the mixture was heated at 80° C. overnight. The cooled reaction mixture was washed with H$_2$O and extracted with AcOEt. The combined organic layers were dried over Na$_2$SO$_4$ and evaporated in vacuo. The residue was purified by flash chromatography (SiO$_2$, DCM/MeOH mixtures) to yield intermediate compound 30 (2.73 g, 80%).

A31. Intermediate Compound 31

-continued

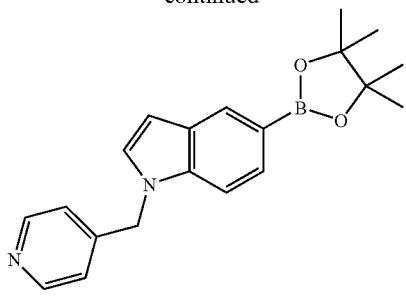

Intermediate compound 31

To a solution of intermediate compound 30 (2.73 g, 9.5 mmol) in DMSO (27 ml) was added bis(pinacolato)diboron (2.414 g, 9.5 mmol) and KOAc (2.8 g, 28.5 mmol). The solution was then degassed using a stream of nitrogen and then to the reaction mixture was added 1,1'-bis(diphenylphosphino)ferrocenepalladium (II) dichloride, DCM (0.23 g, 0.28 mmol). The reaction mixture was then heated at 110° C. overnight under a nitrogen atmosphere. The reaction was then cooled to room temperature and additional amounts of bis(pinacolato)diboron (1.63 g, 6.4 mmol), KOAc (1.89 g, 19.2 mmol) and 1,1'-bis(diphenylphosphino)ferrocenepalladium (II) dichloride, DCM (0.155 g, 0.19 mmol) were added and the mixture was heated at 130° C. overnight. The cooled reaction mixture was diluted with AcOEt, filtered through a pad of celite and the filtrate was washed with water. The combined organic layers were dried over $Na_2SO_4$ and concentrated in vacuo to yield intermediate compound 31 (4.5 g, quant.) used in the next reaction step without further purification.

A32. Intermediate Compound 32

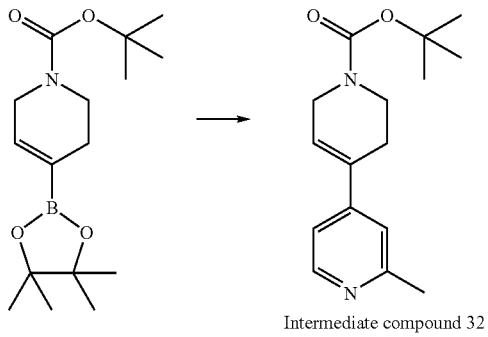 [SMILES: CC(C)(C)OC(=O)N1CC=C(B2OC(C)(C)C(C)(C)O2)CC1 ; Cc1cc(C2=CCN(C(=O)OC(C)(C)C)CC2)ccn1]

Intermediate compound 32

To a mixture of (N-tert-butoxycarbonyl)-1,2,3,6-tetrahydropyridine-4-boronic acid pinacol ester ([286961-14-6] CAS) (1.5 g, 4.8 mmol) in a mixture of 1,4-dioxane (8 ml) and DMF (2 ml) were added 4-chloro-2-picoline (0.308 g, 2.4 mmol), 1,1'-bis(diphenylphosphino)ferrocenepalladium(II) dichloride, DCM (0.293 g, 0.36 mmol) and potassium carbonate (0.993 g, 7.2 mmol). The mixture was then degassed using a stream of nitrogen and then microwaved at 160° C. for 90 min. The cooled reaction mixture was filtered through a pad of celite and the filtrate was concentrated in vacuo. The residue was purified by flash chromatography ($SiO_2$, DCM/MeOH($NH_3$) mixtures) to yield intermediate compound 32 (0.5 g, 38%).

A33. Intermediate Compound 33

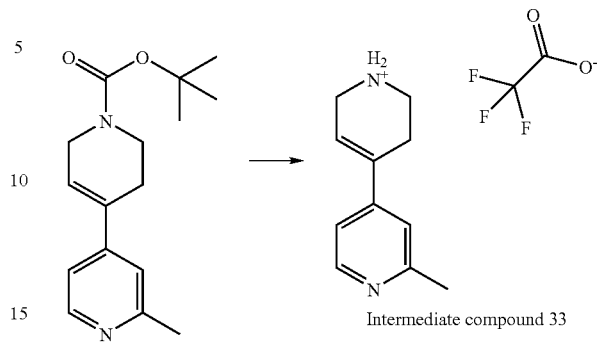

Intermediate compound 33

A solution of intermediate compound 32 (0.5 g, 1.82 mmol) in a 20% solution of TFA in DCM (10 ml) was stirred at room temperature for 4 hours, after which time the solvent was evaporated. The residue (0.5 g) was used in the next reaction step without further purification.

A35. Intermediate Compound 35

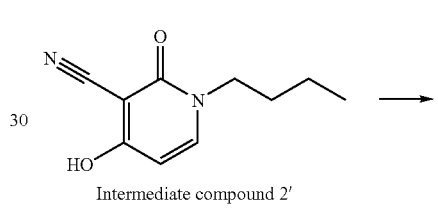

Intermediate compound 2'

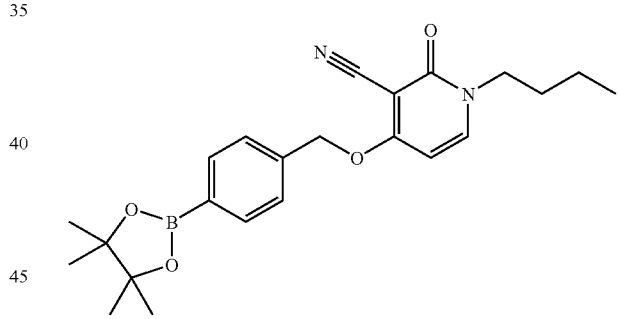

Intermediate compound 35

To a solution of intermediate compound 2' (1.5 g, 7.8 mmol) in acetonitrile (13 ml), (4-bromomethylphenyl)boronic acid, pinacol ester (3.0 g, 9.76 mmol) ([138500-85-3] CAS) and cesium carbonate (5.92 g, 15.6 mmol) were added. The reaction mixture was microwaved at 160° C. for 30 min. Then, solvents were evaporated in vacuo and the residue was purified by flash chromatography ($SiO_2$, DCM/MeOH mixtures) to yield intermediate compound 35 (2.93 g, 92%).

A36. Intermediate Compound 36

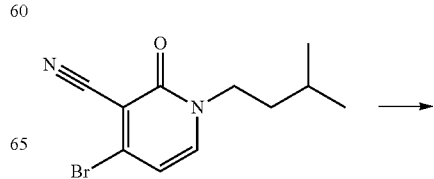

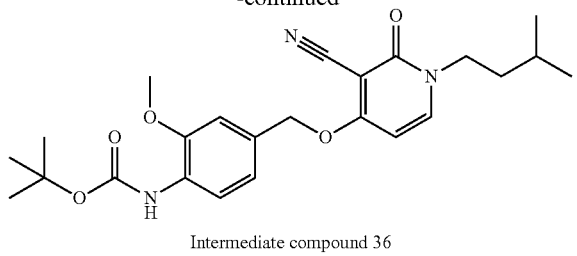

Intermediate compound 36

A mixture of intermediate compound 3 (0.366 g, 1.361 mmol),

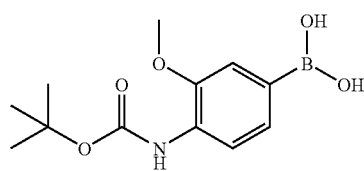 [SMILES: COc1cc(B(O)O)ccc1NC(=O)OC(C)(C)C]

(compound described in US 2005187277 A1) (0.436 g, 1.63 mmol, Pd(PPh$_3$)$_4$ (0.157 g, 0.136 mmol) in 1,4-dioxane (2 ml) and a saturated solution of Na$_2$CO$_3$ (2 ml) was microwaved at 150° C. for 10 min. The resulting reaction mixture was then filtered through a pad of celite and the filtrate evaporated in vacuum. The residue was subsequently purified by flash chromatography (SiO$_2$, DCM/MeOH(NH$_3$) mixtures) to yield intermediate compound 36 (0.55 g, 98%).

A39. Intermediate Compound 39

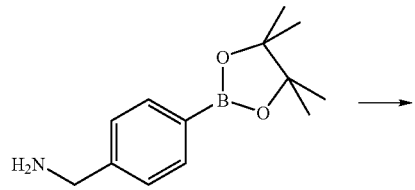

Intermediate compound 39

To a solution of 4-aminomethylphenylboronic acid, pinacol ester (CAS 138500-88-6) (1.2 g, 5.14 mmol) and Et$_3$N (1.42 ml, 10.28 mmol) in DCM (50 ml) stirred at room temperature, di-tert-butyldicarbonate (1.68 g, 7.72 mmol) was added. The mixture was stirred at room temperature for 2 hours. The solvent was evaporated in vacuum to yield a residue which was treated with diethylether to yield intermediate compound 39 (1.7 g) as a solid, 99%) used in the next reaction step without further purification.

A40. Intermediate Compound 40

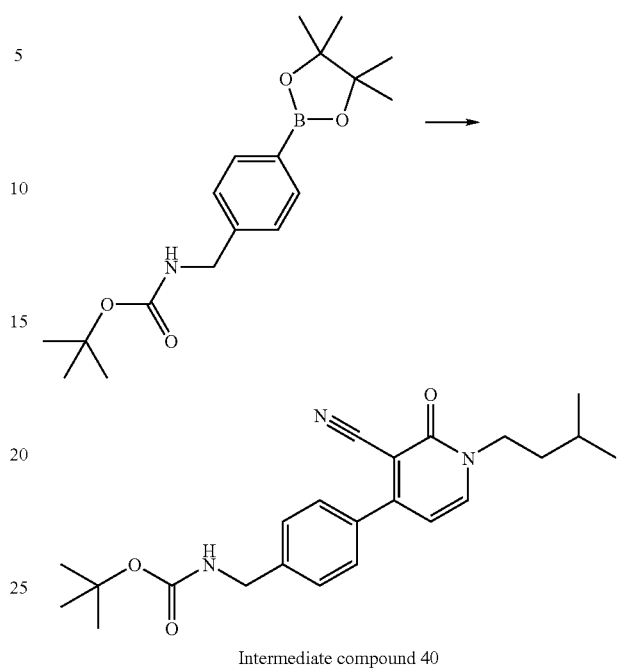

Intermediate compound 40

To a solution of intermediate compound 39 (1.7 g, 5.14 mmol) in 1,4-dioxane (3 ml) and a saturated solution of NaCO$_3$ (3 ml) was added intermediate compound 3 (1.15 g, 4.28 mmol). The resulting solution was degassed using a stream of nitrogen and to this was added Pd(PPh$_3$)$_4$ (485.0 mg, 0.42 mmol). The reaction was then microwaved into a sealed tube at 150° C. for 10 min. The resulting reaction mixture was then filtered through a pad of celite and the filtrate concentrated in vacuo. The crude reaction mixture was then purified by flash chromatography (SiO$_2$, DCM/MeOH (NH$_3$) 9:1) to yield intermediate compound 40 (1.3 g, 77%).

A41. Intermediate Compound 41

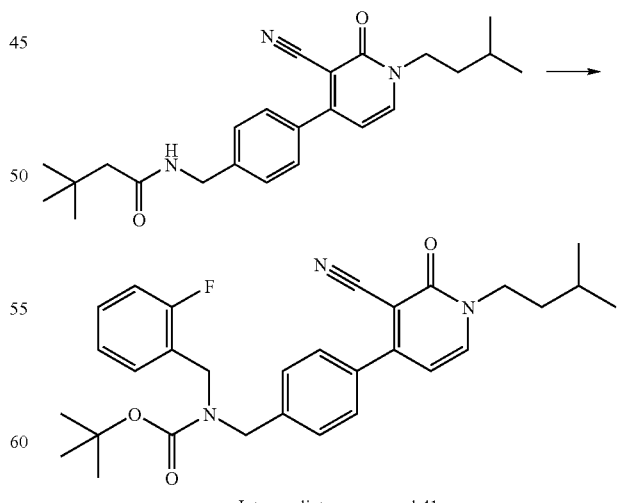

Intermediate compound 41

To a solution of intermediate compound 40 (0.125 g, 0.316 mmol) in DMF (dried, 5 ml) at 0° C., NaH (60% mineral oil; 0.019 mg, 0.474 mmol) was added. The resulting suspension was stirred at 0° C. (under nitrogen atmosphere) for 30 min. Then, 3-fluorobenzylbromide (0.059 ml, 0.474 mmol) was added. The reaction mixture was stirred at room temperature for 3 hours. Then, water was added and the resulting aqueous mixture was extracted with AcOEt. The organic layer was washed with a saturated solution of NaCl. The combined organic layers were dried over Na$_2$SO$_4$. The crude reaction mixture was then purified by flash chromatography (SiO$_2$, DCM/MeOH(NH$_3$) 9:1) to yield intermediate compound 41 (0.082 g, 51%) as a yellow oil.

A42. Intermediate Compound 42

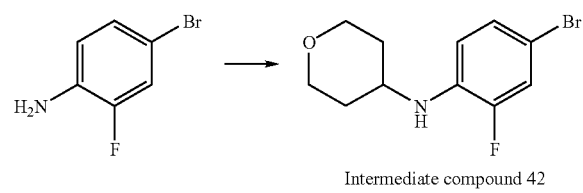 [SMILES: Nc1ccc(Br)cc1F ; Fc1cc(Br)ccc1NC1CCOCC1]

Intermediate compound 42

To a mixture of 4-bromo-2-fluoroaniline (0.6 g, 3.15 mmol), tetrahydro-4H-pyran-4-one (0.68 g, 6.31 mmol) and NaBH(OAc)$_3$ (0.96 g, 4.72 mmol) in DCE (20 ml), molecular sieves (4 A) (1 g) were added. The mixture was stirred at room temperature for 16 h. Then, additional amounts of tetrahydro-4H-pyran-4-one (0.34 g, 3.15 mmol) and NaBH(OAc)$_3$ (0.66 g, 3.15 mmol) were added and the mixture was stirred at room temperature for 48 h. Then, the reaction mixture was filtered through a pad of celite and washed with DCM. The filtrate was concentrated in vacuo to yield intermediate compound 42 (0.86 g, quant.) used in the next reaction step without further purification.

A43. Intermediate Compound 43

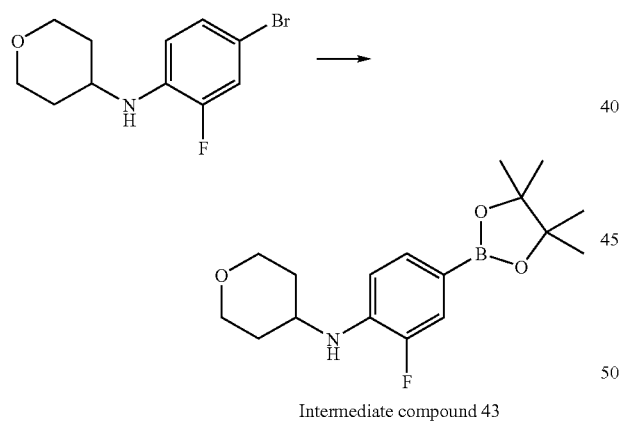

Intermediate compound 43

To a solution of intermediate compound 42 (0.86 g, 3.15 mmol) in DMSO (3 ml) was added bis(pinacolato)diboron (0.80 g, 3.15 mmol) and KOAc (0.93 g, 9.45 mmol) the solution was then degassed using a stream of nitrogen and then to the reaction mixture was added 1,1'-bis(diphenylphosphino)ferrocenepalladium (II) dichloride, DCM (0.07 g, 0.09 mmol). The reaction mixture was then heated at 120° C. under a nitrogen atmosphere for 16 hours. The reaction was then cooled to room temperature and diluted with water (50 ml) and the resulting solution was extracted with AcOEt, the organic fraction was then dried over Na$_2$SO$_4$ and concentrated in vacuo to yield intermediate compound 43 (1.01 g, 100%) used in the next reaction step without further purification.

A44. Intermediate Compound 44

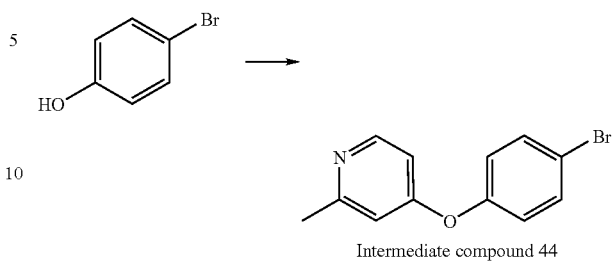

Intermediate compound 44

To a solution of NaH (60% in mineral oil) (0.13 g, 3.25 mmol) in DMF (5 ml) was added commercially available 4-bromophenol (0.50 g, 2.89 mmol) and the reaction was stirred at room temperature for 10 min. Then, 4-chloro-2-picoline (0.30 g, 2.40 mmol) was added and the resulting reaction mixture was then microwaved at 150° C. for 10 min. After cooling, the mixture was diluted with water and extracted with Et$_2$O. The combined organic layers were dried over Na$_2$SO$_4$ and concentrated in vacuo. The residue thus obtained was purified by flash chromatography (DCM) to yield intermediate compound 44 (0.52 g, 81%).

A45. Intermediate Compound 45

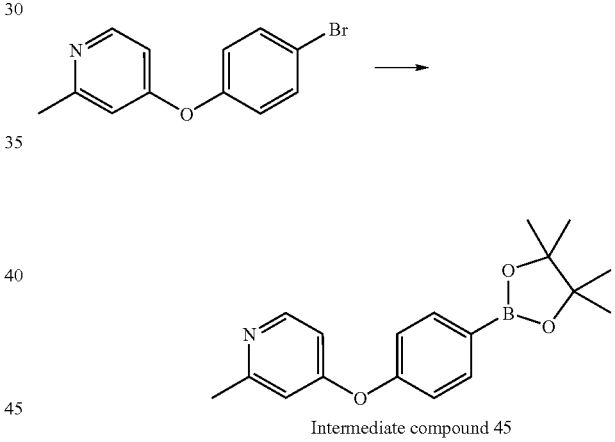

Intermediate compound 45

To a solution of intermediate compound 44 (0.50 g, 1.89 mmol) in DMSO (5 ml) was added bis(pinacolato)diboron (0.72 g, 2.84 mmol) and KOAc (0.56 g, 5.68 mmol) the solution was then degassed using a stream of nitrogen and then to the reaction mixture was added 1,1'-bis(diphenylphosphino)ferrocenepalladium (II) dichloride, DCM (0.05 g, 0.06 mmol). The reaction mixture was then heated at 110° C. under a nitrogen atmosphere for 16 hours. The reaction was then cooled to room temperature and diluted with water and the resulting solution was extracted with AcOEt, the organic fraction was then dried over Na$_2$SO$_4$ and concentrated in vacuo to yield intermediate compound 45 (0.58 g, 100%) used in the next reaction step without further purification.

B. Preparation of the Final Compounds

B1. Final Compound 1-110

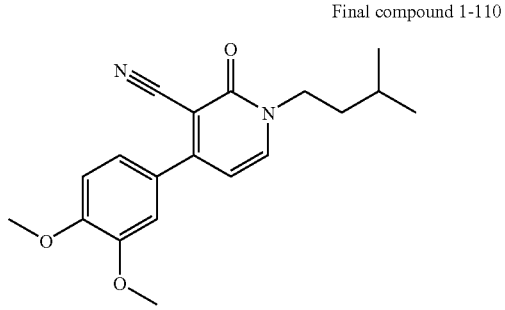 [SMILES: COc1ccc(-c2ccn(CCC(C)C)c(=O)c2C#N)cc1OC]

Final compound 1-110

To a solution of 3,4-dimethoxyphenylboronic acid (740.0 mg, 4.08 mmol) in 1,4-dioxane (14 ml) and a saturated solution of NaHCO$_3$ (14 ml) was added intermediate compound 3 (1.00 g, 3.70 mmol). The resulting solution was degassed using a stream of nitrogen and to this was added Pd(PPh$_3$)$_4$ (641.0 mg, 0.55 mmol). The reaction was then microwaved into a sealed tube at 150° C. for 10 min. The resulting reaction mixture was then filtered through a pad of celite and the filtrate concentrated in vacuo. The crude reaction mixture was then purified by flash chromatography (eluting with a solvent gradient 0-2% MeOH in DCM) to yield the desired compound. The compound was then recrystallised from diethylether to yield the final compound 1-110 (940.0 mg, 2.88 mmol, 78%).

B2. Final Compound 1-179

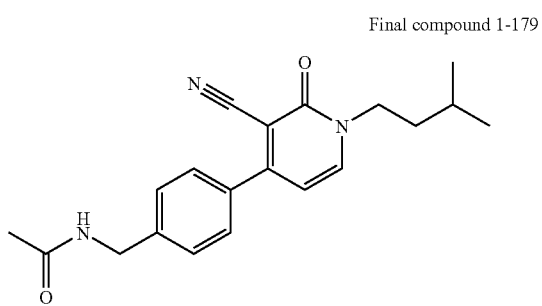 [SMILES: CC(=O)NCc1ccc(-c2ccn(CCC(C)C)c(=O)c2C#N)cc1]

Final compound 1-179

Intermediate compound 4 (150 mg, 0.44 mmol), and 4-(acetamidomethyl)phenylboronic acid (129 mg, 0.67 mmol) were mixed in 1,4-dioxane (5 ml) and Et$_3$N (0.12 ml, 0.89 mmol) at room temperature and N$_2$ was flushed through the mixture for 5 min. Pd(PPh$_3$)$_4$ (77 mg, 0.067 mmol) was added and the resulting mixture was heated at 90° C. for 2 hours. The mixture was cooled to room temperature, diluted with AcOEt and brine. The aqueous phase was extracted with AcOEt (3×20 ml). The combined organics layers were dried over Na$_2$SO$_4$, evaporated in vacuum and the residue thus obtained was purified by column chromatography (SiO$_2$, DCM/AcOEt) to yield 16 mg of final compound 1-179 as a white solid.

B3. Final Compound 1-114

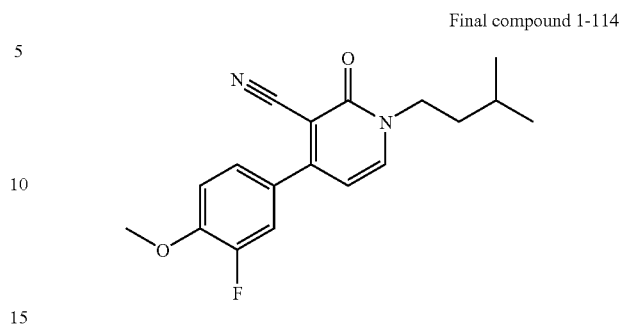

Final compound 1-114

Intermediate compound 4 (150 mg, 0.44 mmol), 3-fluoro-4-methoxyphenylboronic acid (110 mg, 0.67 mmol) were mixed in 1,4-dioxane (5 ml) and Et$_3$N (0.12 ml, 0.89 mmol) at room temperature and N$_2$ was flushed through the mixture for 5 min. Pd(PPh$_3$)$_4$ (77 mg, 0.067 mmol) was added and the resulting mixture was heated at 90° C. for 2 hours. The mixture was cooled to room temperature, diluted with AcOEt and brine. The aqueous phase was extracted with AcOEt (3×20 ml). The combined organics layers were dried over Na$_2$SO$_4$, evaporated in vacuum and the residue thus obtained was purified by column chromatography (SiO$_2$, DCM/AcOEt) to yield 43 mg of final compound 1-114 as a yellow solid.

B4. Final Compound 1-095

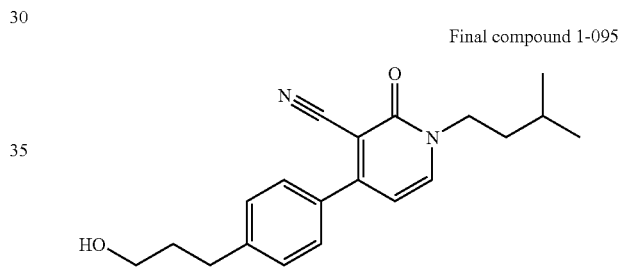

Final compound 1-095

Intermediate compound 4 (150 mg, 0.44 mmol) and 4-(3-hydroxypropyl)-phenylboronic acid (120 mg, 0.67 mmol) were mixed in 1,4-dioxane (5 ml) and Et$_3$N (0.12 ml, 0.89 mmol) at room temperature and N$_2$ was flushed through the mixture for 5 min. Pd(PPh$_3$)$_4$ (77 mg, 0.067 mmol) was added and the resulting mixture was heated at 90° C. for 2 hours. The mixture was cooled to room temperature, diluted with AcOEt and brine. The aqueous phase was extracted with AcOEt (3×20 ml). The combined organics layers were dried over Na$_2$SO$_4$, evaporated in vacuum and the residue thus obtained was purified by column chromatography (SiO$_2$, DCM/AcOEt) to yield 40 mg of final compound 1-095 as a white solid.

B5. Final Compound 1-103

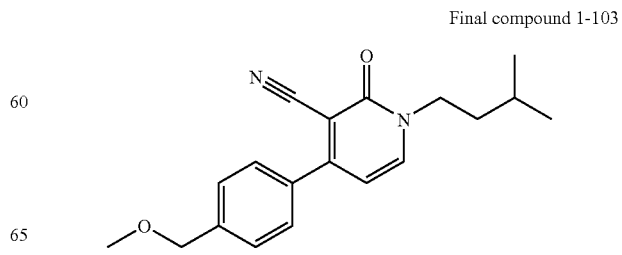

Final compound 1-103

Intermediate compound 4 (150 mg, 0.44 mmol), 4-(methoxymethyl)phenylboronic acid (110 mg, 0.67 mmol) were mixed in 1,4-dioxane (5 ml) and Et$_3$N (0.12 ml, 0.89 mmol) at room temperature and N$_2$ was flushed through the mixture for 5 min. Pd(PPh$_3$)$_4$ (77 mg, 0.067 mmol) was added and the resulting mixture was heated at 90° C. for 2 hours. The mixture was cooled to room temperature, diluted with AcOEt and brine. The aqueous phase was extracted with AcOEt (3×20 ml). The combined organics layers were dried over Na$_2$SO$_4$, evaporated in vacuum and the residue thus obtained was purified by column chromatography (SiO$_2$, DCM/AcOEt) to yield 52 mg of final compound 1-103 as a white solid.

B6. Final Compound 1-178

Final compound 1-178

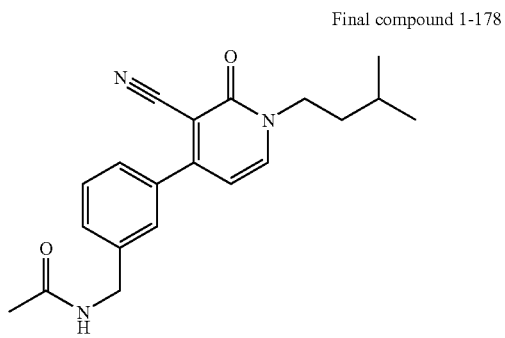 [SMILES: CC(=O)NCc1cccc(-c2ccn(CCC(C)C)c(=O)c2C#N)c1]

To a solution of intermediate compound 7 (220.0 mg, 0.58 mmol), in 1,4-dioxane (6 ml) and a saturated solution of Na$_2$CO$_3$ (6 ml) was added intermediate compound 3 (173 mg, 0.65 mmol). The resulting solution was degassed using a stream of nitrogen and to this was added Pd(PPh$_3$)$_4$ (101.0 mg, 0.088 mmol). The reaction was then microwaved at 150° C. for 10 min. The resulting reaction mixture was then filtered through a pad of celite and the filtrate concentrated in vacuo. The crude reaction mixture was then purified by preparative HPLC to yield the pure final compound 1-178 (51 mg, 0.15 mmol, 26%).

B7. Final Compound 1-097

Final compound 1-097

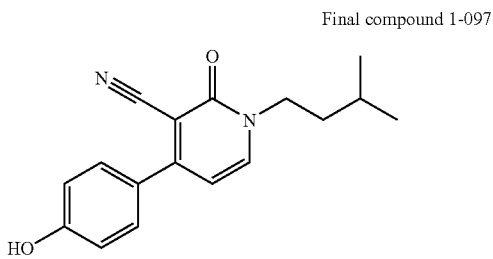 [SMILES: CC(C)CCn1ccc(-c2ccc(O)cc2)c(C#N)c1=O]

To a solution of 4-hydroxyphenylboronic acid (336 mg, 2.44 mmol), in 1,4-dioxane (20 ml) and a saturated solution of NEt$_3$ (0.615 ml, 4.43 mmol) was added final compound 5-052 (750 mg, 1.79 mmol). The resulting solution was degassed using a stream of nitrogen and to this was added Pd(PPh$_3$)$_4$ (384 mg, 0.33 mmol). The reaction was heated at 90° C. for 2 hours into a sealed tube. The resulting reaction mixture cooled to room temperature, was diluted with water and brine and extracted with AcOEt. The organic layer was dried over Na$_2$SO$_4$ and vacuum concentrated. The crude reaction mixture was then purified by flash chromatography (SiO$_2$, eluting with mixtures of heptane/AcOEt) to yield the final compound 1-097 (230 mg, 45%).

B8. Final Compound 1-274

Final compound 1-274

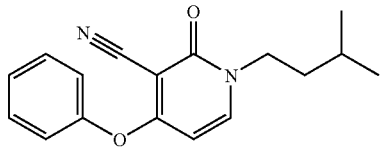

To a solution of phenol (0.042 ml, 0.48 mmol) in dry THF (3 ml) at room temperature, NaH (60% in mineral oil, 13.83 mg, 0.96 mmol) was added. The resulting mixture was stirred at room temperature for 5 min. Final compound 5-052 (100 mg, 0.24 mmol) was added. The mixture was microwaved into a sealed tube for 10 min at 80° C. The mixture was cooled to room temperature, solvents were evaporated in vacuo and the residue thus obtained was purified by column chromatography (SiO$_2$, DCM/MeOH(NH$_3$) mixtures) to yield 55 mg of final compound 1-274 as a white solid.

B9. Final Compound 1-298

Final compound 1-298

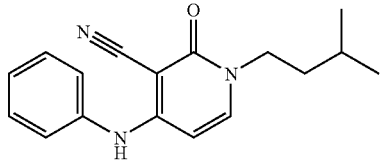

Intermediate compound 3 (100 mg, 0.371 mmol), aniline (0.067 ml, 0.743 mmol) K$_3$PO$_4$ (158 mg, 0.745 mmol) and catalyst [577971-19-8] CAS (10 mg) were mixed in 1,4-dioxane (15 ml) at room temperature. The corresponding mixture was stirred at 80° C. (oil bath temperature) into a sealed tube for 12 hours. The mixture was cooled to room temperature and AcOEt (30 ml) and NaHCO$_3$ (10 ml, aqueous saturated solution) were added to the reaction mixture. Layers were separated and the organic one was dried over Na$_2$SO$_4$. Solvents were evaporated in vacuum and the residue thus obtained was purified by flash chromatography to yield final compound 1-298 (50 mg).

B10. Final Compound 1-267

Final compound 1-267

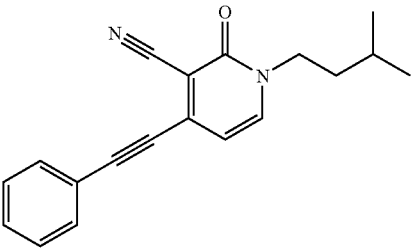

Reaction under nitrogen atmosphere. Intermediate compound 3 (150 mg, 0.557 mmol), phenylacetylene (0.064 ml, 0.580 mmol), PdCl$_2$(PPh$_3$)$_2$ (19.6 mg, 0.028 mmol) PPh$_3$ (3.7 mg, 0.014 mmol) and NEt$_3$ (0.078 ml, 2.23 mmol) were mixed in THF (6 ml) at room temperature and N$_2$ was flushed through the mixture for 5 min. CuI (1.3 mg, 0.007 mmol) was added and the resulting mixture was heated at 90° C. (oil bath temperature) into a sealed tube for 10 hours. The reaction mixture was cooled to room temperature and aqueous $Na_2S_2O_4$ (saturated solution) was added. DCM (30 ml) was added and the layers were separated. The organic layer was washed with aqueous $NaHCO_3$ (saturated solution), dried over $Na_2SO_4$ and vacuum concentrated. The residue thus obtained was purified by flash chromatography ($SiO_2$, DCM/MeOH($NH_3$) mixtures) to yield final compound 1-267 (57 mg).

B11. Final Compound 1-260

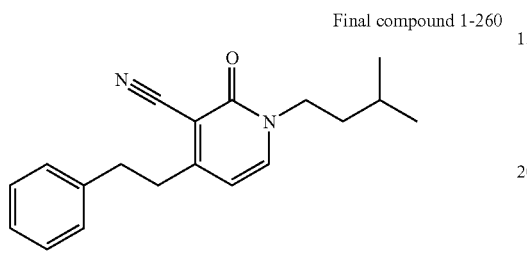

Final compound 1-260

10% Pd/C (10 mg) was added to a solution of final compound 1-267 (45 mg, 0.155 mmol) and 1,4-cyclohexadiene (0.22 ml, 2.32 mmol) in MeOH (5 ml) at room temperature. The resulting mixture was stirred into a sealed tube for 12 hours. The catalyst was filtered off and solvents were evaporated in vacuo. The residue thus obtained was taken up in MeOH (15 ml) and 10% Pd/C (10 mg) was added. The resulting mixture was hydrogenated with hydrogen (20 psi) for 3 hours. The catalyst was filtered off and the solvent was evaporated. The residue thus obtained was purified by flash chromatography ($SiO_2$, DCM/MeOH($NH_3$) mixtures) and then by reverse phase HPLC chromatography to yield final compound 1-260 as a white solid (1.63 mg).

B12. Final Compound 1-182

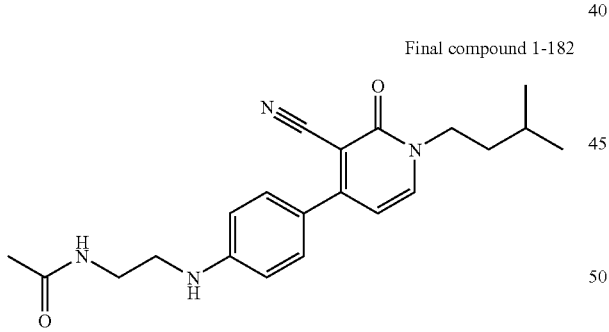

Final compound 1-182

To a solution of intermediate compound 8 (80 mg, 0.62 mmol), in 1,4-dioxane (1 ml) and a saturated solution of $Na_2CO_3$ (1 ml) was added intermediate compound 3 (64.34 mg, 0.239 mmol). The resulting solution was degassed using a stream of nitrogen and to this solution was added $Pd(PPh_3)_4$ (41.4 mg, 0.035 mmol). The reaction was then microwaved at 140° C. for 5 min. The resulting reaction mixture was subsequently filtered through a pad of celite and AcOEt (10 ml) was added. $H_2O$ (10 ml) was added and layers were separated. The organic layers were dried ($Mg_2SO_4$) and vacuum concentrated. The resulting residue was then purified by column chromatography ($SiO_2$, DCM/MeOH($NH_3$) mixtures) to yield the pure final compound 1-182 (28 mg) as bright yellow solid.

B13. Final Compound 1-258

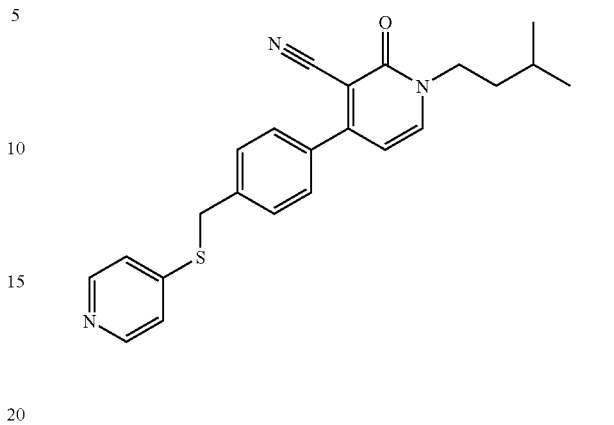

Final compound 1-258

To a solution of intermediate compound 9 (121 mg, 0.371 mmol), in 1,4-dioxane (3 ml) and a saturated solution of $NaHCO_3$ (3 ml) was added intermediate compound 3 (100 g, 3.71 mmol). The resulting solution was degassed using a stream of nitrogen and to this was added $Pd(PPh_3)_4$ (64.0 mg, 0.056 mmol). The reaction was then microwaved at 150° C. for 10 min. The resulting reaction mixture was then filtered through a pad of celite and the filtrate concentrated in vacuo. The crude reaction mixture was then purified by HPLC purification to yield final compound 1-258 (13.0 mg, 0.034 mmol, 10%).

B14. Final Compound 1-239

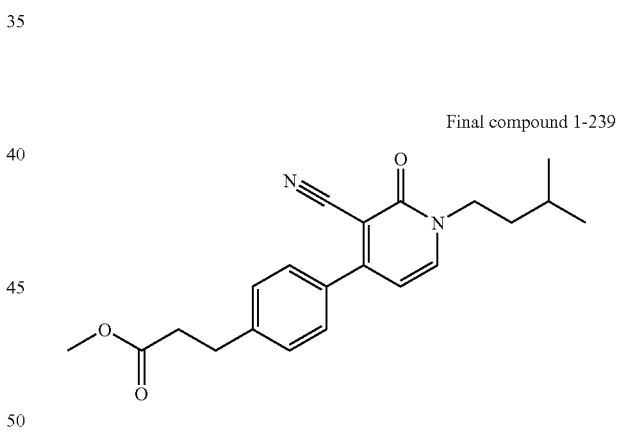

Final compound 1-239

Intermediate compound 4 (150 mg, 0.44 mmol) and 4-(methyl-3-propanoate)phenylboronic acid (140 mg, 0.67 mmol) were mixed in 1,4-dioxane (5 ml) and $Et_3N$ (0.12 ml, 0.89 mmol) at room temperature, and $N_2$ was flushed through the mixture for 5 min. $Pd(PPh_3)_4$ (77 mg, 0.06 mmol) was added to the mixture and the resulting mixture was heated at 90° C. for 2 hours. The mixture was cooled to room temperature, diluted with AcOEt and brine. The aqueous phase was extracted with AcOEt (3×20 ml). The combined organics layers were dried over $Na_2SO_4$, evaporated in vacuum and the residue thus obtained was purified by column chromatography ($SiO_2$, DCM/AcOEt) to yield 63 mg of final compound 1-239 as a yellow solid.

B15. Final Compound 1-240

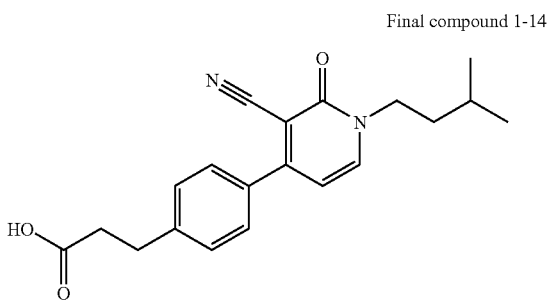 [SMILES: CC(C)CCn1ccc(-c2ccc(CCC(=O)O)cc2)c(C#N)c1=O]

Final compound 1-14

To a solution of final compound 1-239 (20 mg, 0.057 mmol) in THF/H$_2$O 1:1 (4 ml) at 0° C. was added lithium hydroxide (24 mg, 0.57 mmol). The reaction mixture was stirred for 30 min and the solution was concentrated. The pH was adjusted to pH=2 with a 1 N solution of HCl and the precipite thus formed was filtered off and dried, to yield 10 mg of the final compound 1-240 as a white solid.

B16. Final Compound 2-043

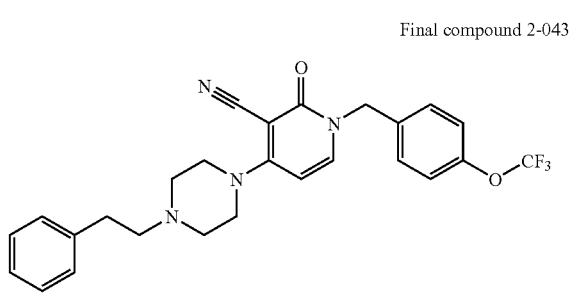 [SMILES: N#Cc1c(N2CCN(CCc3ccccc3)CC2)ccn(Cc2ccc(OC(F)(F)F)cc2)c1=O]

Final compound 2-043

Intermediate compound 12 (300 mg, 0.804 mmol), 1-(2-phenylethyl)piperazine (0.176 ml, 0.964 mmol) K$_3$PO$_4$ (341 mg, 1.60 mmol) and catalyst [577971-19-8] CAS (10 mg) were mixed in 1,4-dioxane (6 ml) at room temperature. The corresponding mixture was heated at 110° C. into a sealed tube for 16 hours. The mixture was cooled to room temperature, filtered through a pad of celite and washed with AcOEt. The filtrate was concentrated in vacuo and the residue thus obtained was purified by flash chromatography to yield final compound 2-043 as a pale yellow solid (349 mg, 90%).

B17. Final Compound 1-037

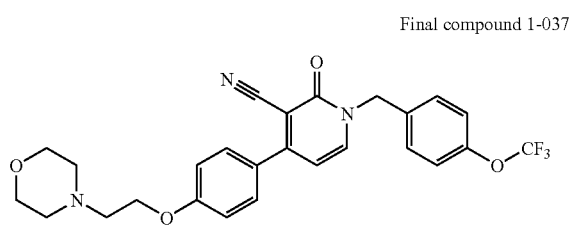 [SMILES: N#Cc1c(-c2ccc(OCCN3CCOCC3)cc2)ccn(Cc2ccc(OC(F)(F)F)cc2)c1=O]

Final compound 1-037

Intermediate compound 12 (350 mg, 0.938 mmol) and intermediate compound 13 (375 mg, 1.12 mmol) were mixed in 1,4-dioxane (3 ml) and a saturated solution of Na$_2$CO$_3$ (3 ml). The resulting solution was degassed using a stream of nitrogen and to this was added Pd(PPh$_3$)$_4$ (108.3 mg, 0.093 mmol). The reaction was then microwaved into a sealed tube at 150° C. for 10 min. The resulting reaction mixture was then filtered through a pad of celite and washed with AcOEt. The filtrate was concentrated in vacuo and the residue thus obtained was purified by flash chromatography to yield the final compound 1-037 (305.6 mg, 65%).

B18. Final Compound 2-022

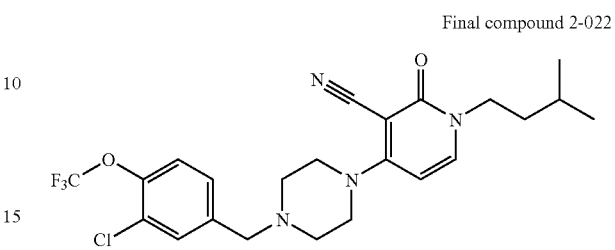

Final compound 2-022

A mixture of final compound 2-056 (150 mg, 0.55 mmol), 3-chloro-4-(trifluoromethoxy)benzyl bromide (0.16 ml, 0.55 mmol) and K$_2$CO$_3$ (150 mg, 1.1 mmol) in DMF (2 ml) was stirred overnight at room temperature. The resulting reaction mixture was then filtered through a pad of celite and washed with AcOEt. The filtrate was concentrated in vacuo and the residue thus obtained was purified by flash chromatography to yield the desired compound. The compound was then recrystallised from diethylether to yield the final compound 2-022 (170 mg, 64%).

B19. Final Compound 1-250

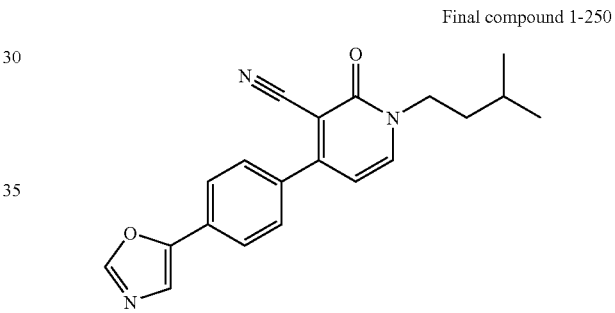

Final compound 1-250

Intermediate compound 3 (198 mg, 0.74 mmol) and intermediate compound 16 (200 mg, 0.74 mmol) were mixed in 1,4-dioxane (5 ml) and a saturated solution of Na$_2$CO$_3$ (5 ml). The resulting solution was degassed using a stream of nitrogen and to this was added Pd(PPh$_3$)$_4$ (128 mg, 0.115 mmol). The reaction was then microwaved into a sealed tube at 150° C. for 10 min. The resulting reaction mixture was then filtered through a pad of celite and washed with AcOEt. The filtrate was concentrated in vacuo and the residue thus obtained was purified by flash chromatography to yield the final compound 1-250 (63.9 mg, 26%, yield based on two subsequent reaction steps).

B20. Final Compound 1-223

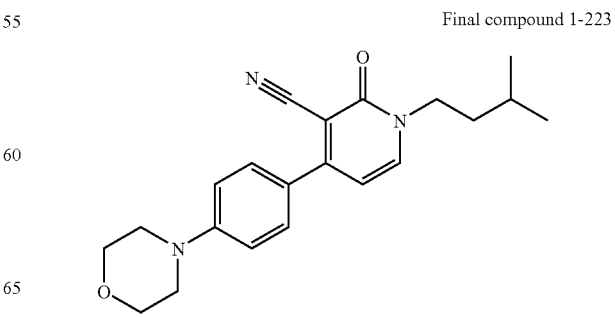

Final compound 1-223

Intermediate compound 3 (727 mg, 2.70 mmol) and commercially available 4-(morpholino)phenylboronic acid (560 mg, 2.70 mmol) were mixed in 1,4-dioxane (10 ml) and a saturated solution of $Na_2CO_3$ (10 ml). The resulting solution was degassed using a stream of nitrogen and to this was added $Pd(PPh_3)_4$ (468 mg, 0.405 mmol). The reaction was then microwaved into a sealed tube at 150° C. for 10 min. The resulting reaction mixture was then filtered through a pad of celite and the filtrate was washed with water (10 ml). The combined organic layers were dried over $Na_2SO_4$ and evaporated in vacuum. The crude reaction mixture was subsequently purified by flash chromatography to yield the desired compound. The compound was then recrystallised from ethylether to yield the final compound 1-223 (620 mg, 65%).

B21. Final Compound 1-049

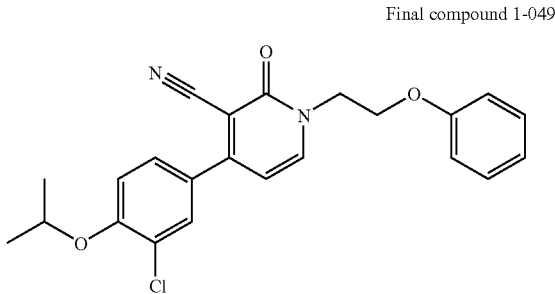 [SMILES: CC(C)Oc1ccc(-c2ccn(CCOc3ccccc3)c(=O)c2C#N)cc1Cl]

Final compound 1-049

Intermediate compound 19 (250 mg, 0.783 mmol) and 3-chloro-4-isopropoxy-phenylboronic acid (159 mg, 0.86 mmol) were mixed in 1,4-dioxane (2.5 ml) and a saturated solution of $NaHCO_3$ (2.5 ml). The resulting solution was degassed using a stream of nitrogen and to this was added $Pd(PPh_3)_4$ (130 mg, 0.11 mmol). The reaction was then microwaved into a sealed tube at 150° C. for 10 min. The resulting reaction mixture was then filtered through a pad of celite and the filtrate evaporated in vacuum. The crude reaction mixture was subsequently purified by flash chromatography to yield the desired compound. The compound was then recrystallised from diethylether to yield the final compound 1-049 as a white solid (65 mg, 21%).

B22. Final Compound 4-020

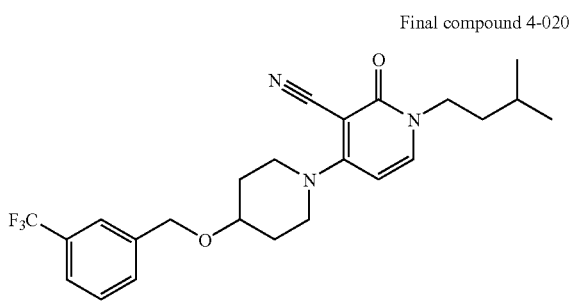 [SMILES: CC(C)CCn1ccc(N2CCC(OCc3cccc(C(F)(F)F)c3)CC2)c(C#N)c1=O]

Final compound 4-020

Intermediate compound 3 (100 mg, 0.37 mmol), 4-(3-trifluoromethylbenzyloxy)-piperidine (115.11 mg, 0.444 mmol), $K_3PO_4$ (150 mg, 0.70 mmol) and catalyst [577971-19-8] CAS (10 mg) were mixed in 1,4-dioxane (5 ml) at room temperature. The corresponding mixture was heated at 85° C. into a sealed tube for 16 hours. The mixture was cooled to room temperature and filtered through a pad of celite. The filtrate was concentrated in vacuo and the residue thus obtained was purified by flash chromatography to yield final compound 4-020 as a white gummy solid (90 mg, 55%).

B23. Final Compound 4-044

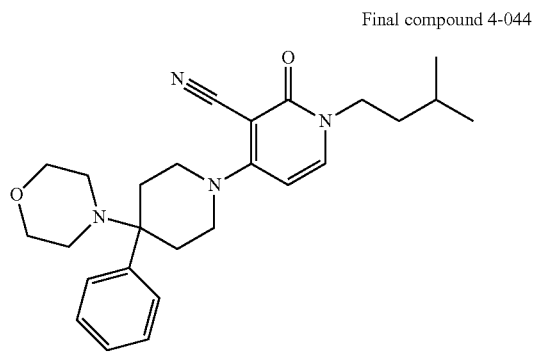 [SMILES: CC(C)CCn1ccc(N2CCC(c3ccccc3)(N3CCOCC3)CC2)c(C#N)c1=O]

Final compound 4-044

Intermediate compound 3 (150 mg, 0.406 mmol), 4,4-(phenylpiperidin-4-yl)-morpholine (113.3 mg, 0.46 mmol), $K_3PO_4$ (200 mg, 0.94 mmol) and catalyst [577971-19-8] CAS (10 mg) were mixed in 1,4-dioxane (4 ml) at room temperature. The corresponding mixture was heated at 85° C. into a sealed tube for 36 hours. The mixture was cooled to room temperature and filtered through a pad of celite. The filtrate was concentrated in vacuo and the residue thus obtained was purified by prep. HPLC to yield final compound 4-044 as pale yellow solid (123 mg, 51%).

B24. Final Compound 2-028

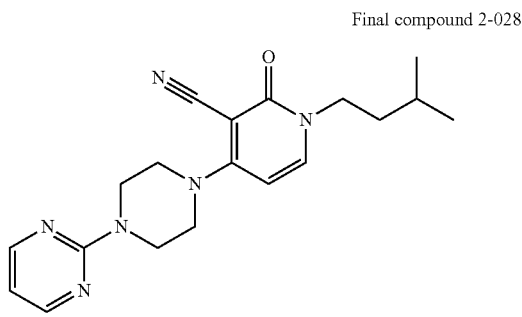 [SMILES: CC(C)CCn1ccc(N2CCN(c3ncccn3)CC2)c(C#N)c1=O]

Final compound 2-028

Intermediate compound 3 (226 mg, 0.84 mmol), 1-(2-pyrimidyl)piperazine dihydro-chloride (228 mg, 0.96 mmol), $K_3PO_4$ (612 mg, 2.88 mmol) and catalyst [577971-19-8] CAS (10 mg) were mixed in 1,4-dioxane (5 ml) at room temperature. The corresponding mixture was heated at 85° C. into a sealed tube for 36 hours. The mixture was cooled to room temperature and filtered through a pad of celite. The filtrate was concentrated in vacuo and the residue thus obtained was purified by flash chromatography to yield final compound 2-028 as a pale creamy solid (258 mg, 87%).

B25. Final Compound 3-009

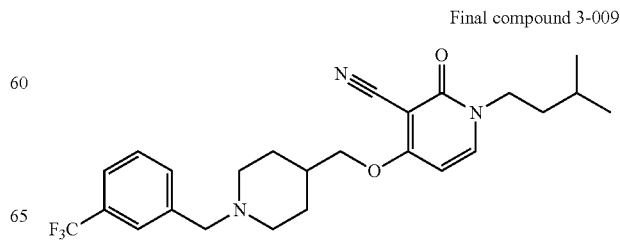

Final compound 3-009

A mixture of intermediate compound 20 (0.223 g, 0.00081 mol, 1.1 eq.) and NaH (60% dispersion in mineral oil, 0.035 g, 0.00088 mol, 1.2 eq.) in DME (1.5 ml) was stirred at room temperature over 10 min. Then, intermediate compound 3 (0.20 g, 0.00074 mol, 1 eq.) was added slowly. The resulting reaction mixture was microwaved at 130° C. for 20 min. The mixture was cooled to room temperature and solvents were evaporated in vacuum. The residue was suspended in DCM, filtered off and the filtrate concentrated in vacuo. The crude reaction mixture was then purified by flash chromatography to yield final compound 3-009 (146 mg, 47%).

B26. Final Compound 3-008

Final compound 3-008

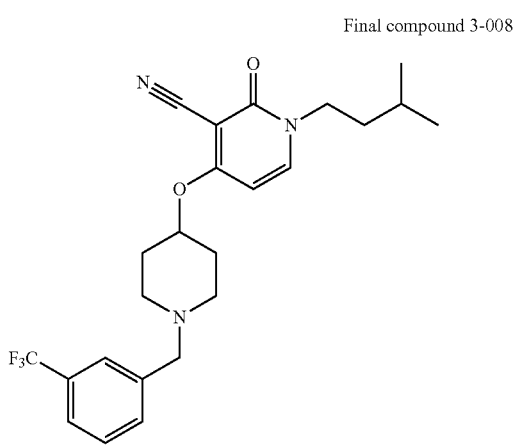 [SMILES: CC(C)CCn1ccc(OC2CCN(Cc3cccc(C(F)(F)F)c3)CC2)c(C#N)c1=O]

To a solution of final compound 3-016 (346 mg, 1.19 mmol) and 3-(trifluoromethyl)benzaldehyde ([454-89-7] CAS) (262 mg, 1.5 mmol) in DCE (40 ml), NaBH(OAc)$_3$ (760 mg, 3.6 mmol) was added portionwise. The reaction mixture was stirred at room temperature for 3 hours. Then, the mixture was quenched with an aqueous solution of NH$_4$Cl. The combined organic layers were concentrated in vacuo. The crude product was purified by flash chromatography to yield final compound 3-008 (370 mg) as a pale brown solid.

B27. Final Compound 1-271

Final compound 1-271

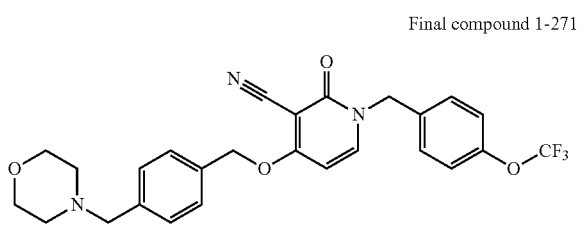 [SMILES: N#Cc1c(OCc2ccc(CN3CCOCC3)cc2)ccn(Cc2ccc(OC(F)(F)F)cc2)c1=O]

To a mixture of intermediate compound 11 (200 mg, 0.64 mmol), intermediate compound 24 (267 mg, 1.28 mmol) and PPh$_3$ (309 mg, 1.15 mmol) in THF (5 ml) was added di-tert-butylazodicarboxylate (279 mg, 1.21 mmol). The reaction mixture was microwaved at 120° C. over 20 min. The reaction mixture was then cooled to room temperature and concentrated in vacuo. The residue was purified by flash chromatography (eluting with a solvent gradient 10-20% DCM/MeOH (NH$_3$) to give the final compound 1-271 (219.7 mg, 70%).

B28. Final Compound 3-014

Final compound 3-014

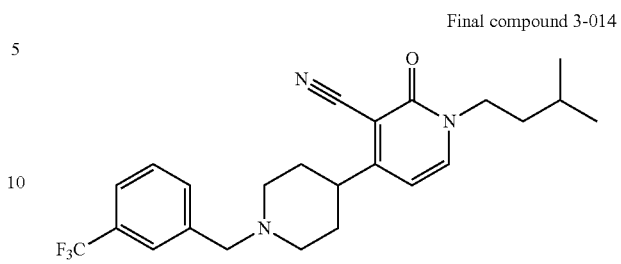

To a solution of final compound 3-018 (191 mg, 0.70 mmol) and 3-(trifluoromethyl)benzaldehyde ([454-89-7] CAS) (174 mg, 1 mmol) in DCE (16 ml), NaBH(OAc)$_3$ (443 mg, 2.1 mmol) was added portionwise. The mixture was stirred at room temperature for 3 hours, after which time it was quenched with a saturated solution of NH$_4$Cl. The combined organic layers were dried over Na$_2$SO$_4$ and concentrated in vacuo. The crude product was purified by flash chromatography to yield final compound 3-014 as white solid (270 mg, 89%).

B29. Final Compound 2-036

Final compound 2-036

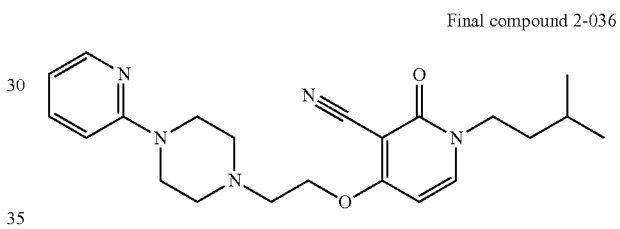

To a mixture of intermediate compound 2 (0.2 g, 0.971 mmol), K$_2$CO$_3$ (0.268 g, 1.942 mmol) and NaI (cat.) in acetonitrile (12 ml), 1-(2-chloroethyl)-4-pyridin-2-yl-piperazine (0.393 g, 1.748 mmol) was added. The reaction mixture was microwaved twice at 150° C. for 10 min. Then, DCM was added and the mixture was filtered off. The filtrate was washed with a saturated solution of NaHCO$_3$. The combined organic layers were dried over Na$_2$SO$_4$ and concentrated in vacuo. The residue was purified by flash chromatography (DCM/MeOH(NH$_3$) mixtures) to give final compound 2-036 (152.5 mg, 40%) as off white solid.

B30. Final Compound 5-007

Final compound 1-131

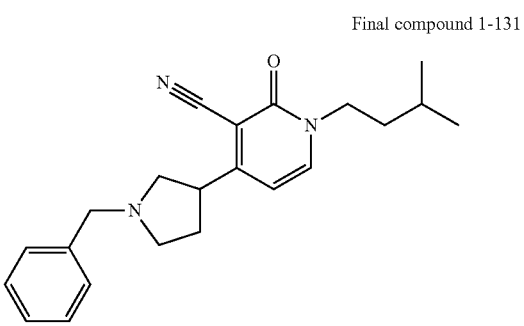 [SMILES: CC(C)CCn1ccc(C2CCN(Cc3ccccc3)C2)c(C#N)c1=O]

To a solution of intermediate compound 28 (35 mg, 0.161 mmol) in DCM (6 ml) a drop of TFA was added. Then, N-(methoxymethyl)-N-(trimethylsilylmethyl)-benzylamine (46 mg, 0.193 mmol) was slowly added and the resulting reaction mixture was stirred at room temperature for 2 hours. Then, solvents were evaporated in vacuum and the residue was purified by flash chromatography (SiO$_2$, DCM/MeOH (NH$_3$) mixtures) to yield final compound 1-131 (6 mg, 10%).

B31. Final Compound 2-055

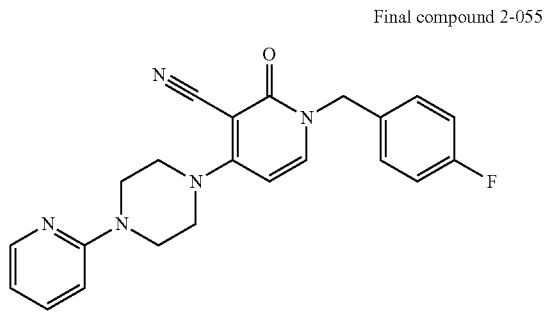 [SMILES: N#Cc1c(N2CCN(c3ccccn3)CC2)ccn(Cc2ccc(F)cc2)c1=O]

Final compound 2-055

A mixture of intermediate compound 12' (250 mg, 0.81 mmol), 1-(2-pyridyl)-piperazine (0.129 ml, 0.85 mmol) and diisopropylethylamine (0.416 ml, 2.4 mmol) in acetonitrile (5 ml) was microwaved at 160° C. for 30 min. The mixture was cooled to room temperature and the solvents were evaporated in vacuum. The residue thus obtained was purified by flash chromatography (SiO$_2$, DCM/MeOH mixtures) to yield final compound 2-055 (192 mg, 61%) as a white solid.

B32. Final Compound 5-020

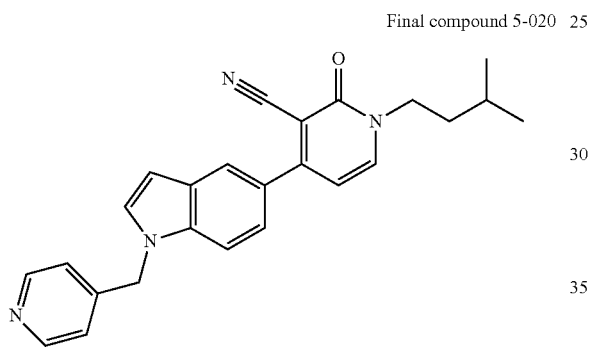

Final compound 5-020

Intermediate compound 3 (0.6 g, 2.20 mmol) and intermediate compound 31 (3.69 g, 3.79 mmol) were mixed in 1,4-dioxane (7 ml) and a saturated solution of Na$_2$CO$_3$ (6 ml). The resulting solution was degassed using a stream of nitrogen and to this was added Pd(PPh$_3$)$_4$ (0.39 g, 0.33 mmol). The reaction was then microwaved into a sealed tube at 140° C. for 5 min. The resulting reaction mixture was then diluted with AcOEt, filtered through a pad of celite and the filtrate was washed with water (10 ml). The combined organic layers were dried over Na$_2$SO$_4$ and evaporated in vacuum. The crude reaction mixture was subsequently purified by flash chromatography to yield the desired compound. The compound was then recrystallised from diethylether to yield the final compound 5-020 (0.39 g, 44%).

B33. Final Compound 4-047

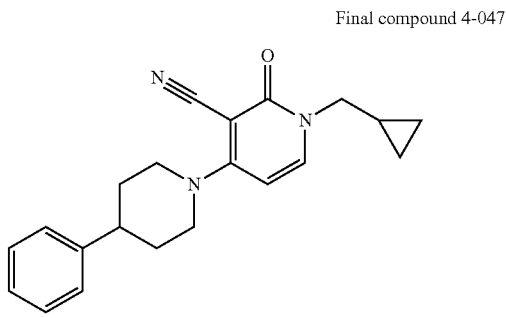 [SMILES: N#Cc1c(N2CCC(c3ccccc3)CC2)ccn(CC2CC2)c1=O]

Final compound 4-047

A mixture of intermediate compound 3" (0.3 g, 1.18 mmol), 4-phenylpiperidine (0.286 g, 1.77 mmol) and diisopropylethylamine (0.615 ml, 3.54 mmol) in acetonitrile (5 ml) was microwaved at 150° C. for 20 min. The mixture was cooled to room temperature and the solvents were evaporated in vacuum. The residue thus obtained was purified by flash chromatography (SiO$_2$, DCM/MeOH(NH$_3$) mixtures) to yield the desired compound. The compound was then recrystallised from ethylether to yield the final compound 4-047 (0.29 g, 73%)

B34. Final Compound 4-003

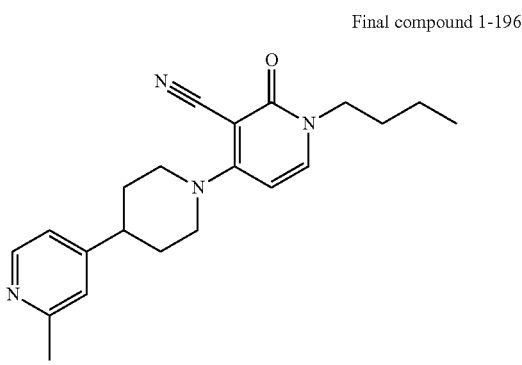 [SMILES: CCCCn1ccc(N2CCC(c3ccnc(C)c3)CC2)c(C#N)c1=O]

Final compound 1-196

A mixture of final compound 5-054 (0.37 g, 1.05 mmol) and palladium (10% on activated carbon) (catalytic amount) in EtOH (10 ml) was stirred under a hydrogen atmosphere at 50 psi for 3 hours. The catalyst was then filtered off and the filtrate was concentrated in vacuo. The residue thus obtained was purified by flash chromatography (SiO$_2$, DCM/MeOH (NH$_3$) mixtures) to yield final compound 4-003 (0.21 g, 57%).

B35. Final Compound 1-306

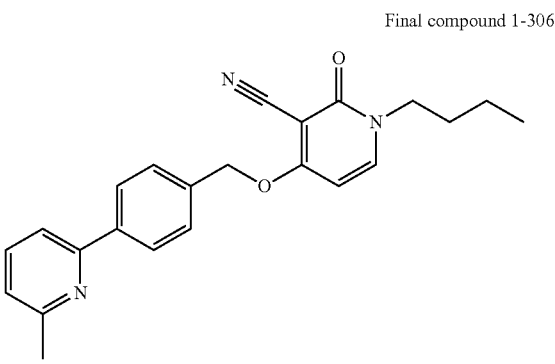 [SMILES: CCCCn1ccc(OCc2ccc(-c3cccc(C)n3)cc2)c(C#N)c1=O]

Final compound 1-306

Intermediate compound 35 (0.25 g, 0.61 mmol) and commercially available 2-bromo-6-methylpyridine (0.158 g, 0.92 mmol) were mixed in 1,4-dioxane (2 ml) and a saturated solution of NaHCO$_3$ (2 ml). The resulting solution was degassed using a stream of nitrogen and to this was added Pd(PPh$_3$)$_4$ (0.10 g, 0.09 mmol). The reaction was then microwaved into a sealed tube at 150° C. for 10 min. The resulting reaction mixture was then filtered through a pad of celite and the filtrate was washed with water (10 ml). The combined organic layers were dried over Na$_2$SO$_4$ and evaporated in vacuum. The crude reaction mixture was subsequently purified by flash chromatography to yield final compound 1-306 (0.078 g, 34%).

B36. Final Compound 5-015

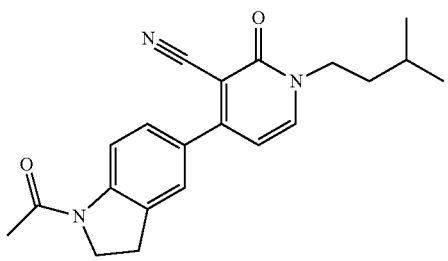
Final compound 5-015

To a solution of final compound 5-014 (0.04 g, 0.130 mmol), prepared by the reaction pathway B1, and diisopropylethylamine (0.068 ml, 0.392 mmol) in DCM (2 ml), acetyl chloride (0.014 ml, 0.196 mmol) was added. The reaction mixture was stirred at room temperature for 12 hours. Then, the solvents were evaporated in vacuum and the residue thus obtained was purified by flash chromatography (SiO$_2$, DCM/MeOH(NH$_3$) mixtures) to yield final compound 5-015 (0.045 g, 99%).

B37. Final Compound 1-198

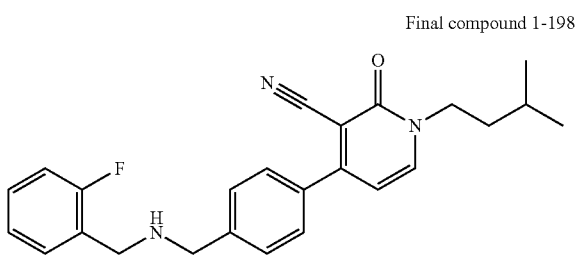 [SMILES: CC(C)CCn1ccc(-c2ccc(CNCc3ccccc3F)cc2)c(C#N)c1=O]
Final compound 1-198

To a solution of intermediate compound 41 (0.082 mg, 0.163 mmol) in DCM (10 ml), TFA (5 ml) was added. The resulting solution was stirred at room temperature for 3 hours. Then, solvent was evaporated in vacuo and the residue was dissolved in DCM, washed with a saturated solution of NaHCO$_3$ and NaCl. The combined organic layers were dried over Na$_2$SO$_4$ and concentrated in vacuo The residue was purified by flash chromatography (DCM/MeOH(NH$_3$) mixtures) to give final compound 1-198 (17 mg, 26%) as a white solid.

B38. Final Compound 1-185

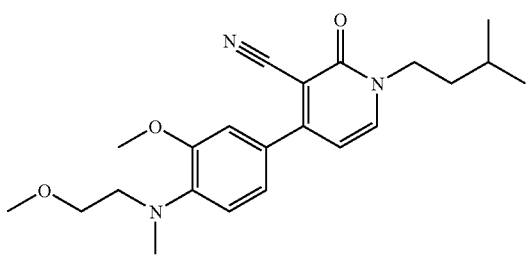
Final compound 1-185

To a mixture of final compound 1-308 (0.2 g, 0.533 mmol) in 1,4-dioxane (10 ml), N-methyl-2-methoxyethylamine (0.0711 mg, 0.8 mmol), Paladium diacetate (0.0118 mg, 0.053 mmol) and Xantphos (0.0616 mg, 0.8 mmol) were added. The reaction mixture was stirred in a sealed tube at 120° C. for 16 hours. The resulting reaction mixture was then filtered through a pad of celite, washed with AcOEt. The filtrate was washed with a saturated solution of NaCl. The combined organic layers were dried over Na$_2$SO$_4$ and concentrated in vacuo. The residue was purified by flash chromatography (DCM/MeOH 9:1) to give final compound 1-185 (24 mg, 12%) as a yellow solid.

B39. Final Compound 1-226

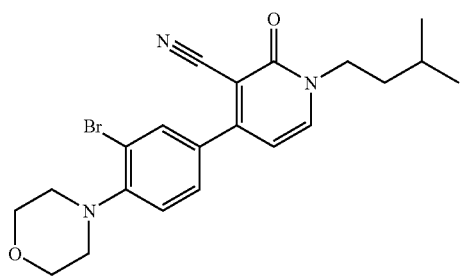
Final compound 1-226

To a solution of final compound 1-224 (0.147 mg, 0.385 mmol) in DCM (20 ml) at 0° C., BBr$_3$ (0.182 ml, 1.92 mmol) was added. The resulting solution was warmed up to room temperature and stirred for 16 hours. Then, an aqueous solution of NH$_4$OH was added. The resulting aqueous solution was extracted with methylenchlorine, washed with a saturated solution of NaCl. The combined organic layers were dried over MgSO$_4$ and concentrated in vacuo The residue was purified by flash chromatography (DCM/MeOH(NH$_3$) 9:1) to give final compound 1-226 (28 mg, 20%) as yellow solid.

B40. Final Compound 5-052

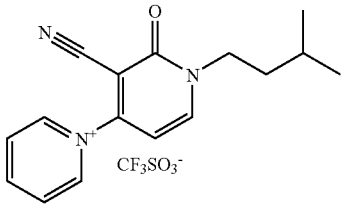
Final compound 5-052

The reaction was carried out under N$_2$ atmosphere. Intermediate compound 4 (26 mg, 0.077 mmol) was dissolved in pyridine (1 ml, 12.26 mmol). The resulting solution was heated for 1 hour at 40° C. The mixture was cooled to room temperature and solvents were evaporated in vacuum. The residue thus obtained was treated with 1,4-dioxane to yield a white solid that was filtered off, dried in vacuum and identified as final compound 5-052 (25 mg; white solid).

B41. Final Compound 2-056

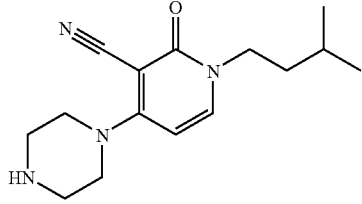
Final compound 2-056

A solution of intermediate compound 14 (200 mg, 0.53 mmol) in a mixture of TFA/DCM (20%) (5 ml) was stirred overnight at room temperature. The mixture was basified by the addition of $K_2CO_3$ (saturated solution). The organic layer was then dried over $MgSO_4$ and concentrated in vacuo. The residue was identified as final compound 2-056 (150 mg) and was used in the next reaction step without further purification.

B42. Final Compound 3-015

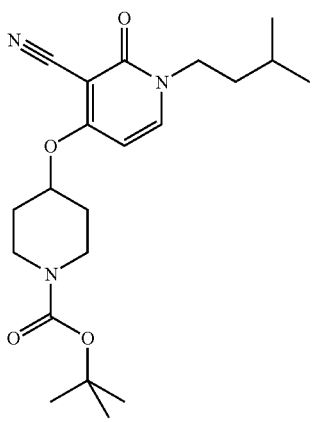

Final compound 3-015

To a mixture of 1-tert-butoxycarbonyl-4-hydroxypiperidine (447 mg, 2.22 mmol) in DME (8 ml), NaH (60% in mineral oil) was added and the reaction mixture was stirred at room temperature for 5 min. Then, intermediate compound 3 (500 mg, 1.85 mmol) was added and the resulting reaction mixture was microwaved at 130° C. for 30 min. The reaction was then cooled to room temperature and filtered off. The filtrate was concentrated in vacuo to yield final compound 3-015 as brown oil (460 mg).

B43. Final Compound 3-016

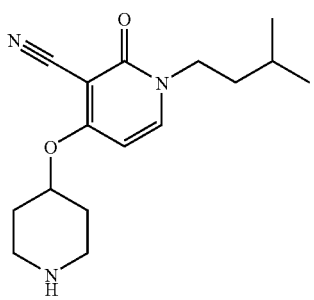

Final compound 3-016

To a solution of final compound 3-015 (460 mg, 1.18 mmol) in MeOH (50 ml), amberlyst-15 polymer bound (loading 4.6 mmol/g) (0.77 g, 3.54 mmol) was added. The resulting mixture was shaken at room temperature for 12 hours. Then, the resin was filtered off and the solvent was discarded. The resin was suspended in MeOH/$NH_3$ (50 ml) and shaken at room temperature for 3 hours. The resin was filtered off and the filtrate was concentrated in vacuo to give the final compound 3-016 (350 mg) as a pale brown solid.

B44. Final Compound 5-053

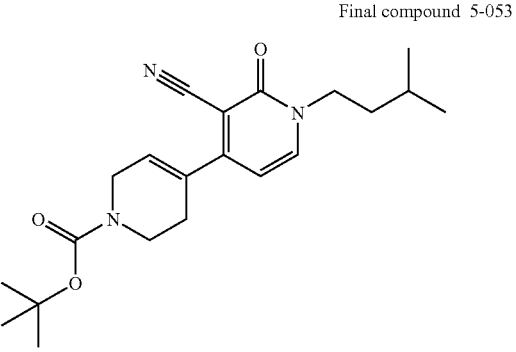

Final compound 5-053

A mixture of intermediate compound 3 (1 g, 3.71 mmol), (N-tert-butoxycarbonyl)-1,2,3,6-tetrahydropyridine-4-boronic acid pinacol ester (1.26 g, 4.08 mmol) and $Pd(PPh_3)_4$ (0.642 g, 0.556 mmol) in 1,4-dioxane (6 ml) and a saturated solution of Na—$HCO_3$ (6 ml) was microwaved at 150° C. for 10 min. The resulting reaction mixture was then filtered through a pad of celite and the filtrate evaporated in vacuum. The crude reaction mixture was subsequently purified by flash chromatography ($SiO_2$, DCM/MeOH($NH_3$) mixtures) to yield final compound 5-053 (0.57 g, 41%) as a white solid.

B45. Final Compound 3-017

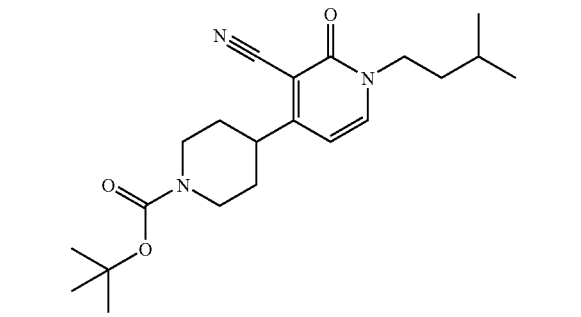

Final compound 3-017

A mixture of final compound 5-053 (530 mg, 1.42 mmol) and palladium (10% on activated carbon) (catalytic amount) in AcOEt (50 ml) was stirred under a hydrogen atmosphere at 50 psi for 4 hours. The catalyst was then filtered off and the filtrate was concentrated in vacuo to give final compound 3-017 as colorless oil (540 mg, quant.). The compound thus obtained was used in the next reaction steps without further purification.

B46. Final Compound 3-018

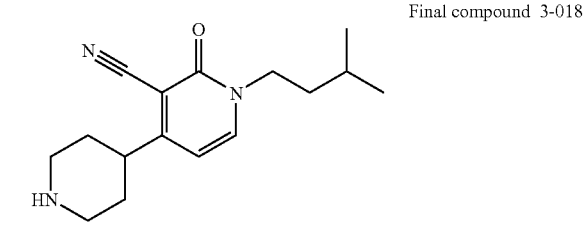 [SMILES: CC(C)CCn1ccc(N2CCNCC2)c(C#N)c1=O]

Final compound 3-018

To a solution of final compound 3-017 (540 mg, 1.44 mmol) in MeOH (50 ml), amberlyst-15 (loading 4.6 mmol/g)

63

(1 g, 4.6 mmol) was added. The resulting mixture was shaken at room temperature for 12 hours. Then, the resin was filtered off and the solvent was discarded. The resin was suspended in MeOH/NH$_3$ (50 ml) and shaken at room temperature for 3 hours. The resin was filtered off and the filtrate was concentrated in vacuo to yield final compound 3-018 (198 mg) as yellow oil.

B47. Final Compound 5-054

Final compound 5-054

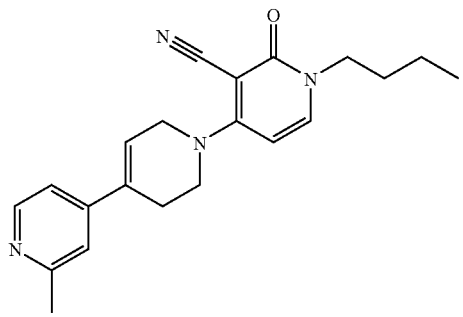

A mixture of intermediate compound 3' (0.34 g, 1.33 mmol), intermediate compound 33 (0.5 g, 1.73 mmol) and diisopropylethylamine (0.925 ml, 5.32 mmol) in acetonitrile (3 ml) was microwaved at 150° C. for 20 min. The mixture was cooled to room temperature and the solvents were evaporated in vacuum. The residue thus obtained was purified by flash chromatography (SiO$_2$, DCM/MeOH(NH$_3$) mixtures) to yield final compound 5-054 (0.37 g, 79%).

B48. Final Compound 1-307

Final compound 1-307

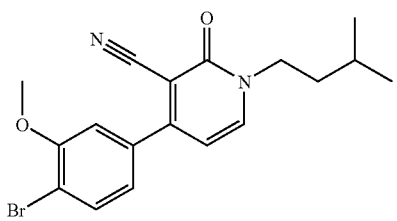

To a solution of intermediate compound 36 (0.55 mg. 1.76 mmol) in DCM (20 ml), TFA (10 ml) was added. The resulting solution was stirred at room temperature for 2 hours. Then, solvent was evaporated in vacuo and the residue was dissolved in DCM, washed with a saturated solution of NaHCO$_3$ and NaCl. The combined organic layers were dried over Na$_2$SO$_4$ and concentrated in vacuo to yield final compound 1-307 (0.310 g, 74%) used in the next reaction step without further purification.

B49. Final Compound 1-308

Final compound 1-308

64

To a suspension of copper (II) bromide (0.2 g, 0.89 mmol) and tert-butylnitrite (0.178 ml, 1.48 mmol) in acetonitrile (29 ml) at 0° C. was added dropwise final compound 1-307 (0.31 g, 0.99 mmol) within 5 min at 0° C. The mixture was stirred at 0° C. for 1 hour, then warmed to room temperature and gradually heated at 65° C. for 1 hour. The resulting reaction mixture was then filtered through a pad of celite, washed with acetonitrile and the filtrate evaporated in vacuum to yield final compound 1-308 (0.464 g) used in the next reaction step without further purification.

B50. Final Compound 1-190

Final compound 1-190

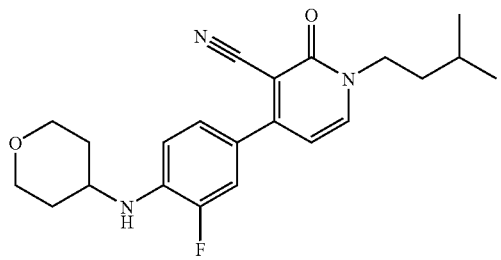

Intermediate compound 43 (0.30 g, 1.11 mmol) and intermediate compound 3 (0.43 g, 1.33 mmol) were mixed in 1,4-dioxane (3 ml) and a saturated solution of Na$_2$CO$_3$ (3 ml). The resulting solution was degassed using a stream of nitrogen and to this was added Pd(PPh$_3$)$_4$ (0.12 g, 0.1 mmol). The reaction was then microwaved into a sealed tube at 150° C. for 10 min. The resulting reaction mixture was then filtered through a pad of celite and washed with AcOEt. The filtrate was washed with brine. The combined organic layers were dried over MgSO$_4$ and concentrated in vacuo. The residue thus obtained was purified by prep. HPLC to yield final compound 1-190 (0.04 g, 9%).

B51. Final Compound 1-064

Final compound 1-064

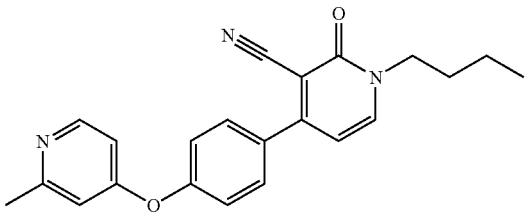

Intermediate compound 3 (0.48 g, 1.89 mmol) and intermediate compound 45 (0.59 g, 1.89 mmol) were mixed in 1,4-dioxane (4 ml) and a saturated solution of NaHCO$_3$ (4 ml). The resulting solution was degassed using a stream of nitrogen and to this was added Pd(PPh$_3$)$_4$ (0.22 g, 0.19 mmol). The reaction was then microwaved into a sealed tube at 150° C. for 10 min. The resulting reaction mixture was then filtered through a pad of celite and washed with AcOEt. The filtrate was washed with brine. The combined organic layers were dried over MgSO$_4$ and concentrated in vacuo. The residue thus obtained was purified by flash chromatography (DCM/MeOH mixtures) to yield final compound 1-064 (0.16 g, 25%).

The final compounds in the following Tables have been synthesised according to the previous examples, as denoted in the column denoted as "Exp. Nr". The compound denoted with the asterisk has been exemplified in the Examples.

TABLE 1A
Compounds wherein L is a covalent bond.
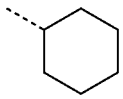
| Co. nr. | Exp nr. | V¹ | M¹ | ----L—A |
|---|---|---|---|---|
| 1-001 | B2 | cb | 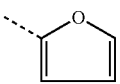 | 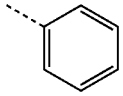 |
| 1-002 | B2 | cb | 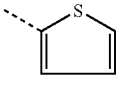 |  |
| 1-003 | B1 | ----CH₂--- | 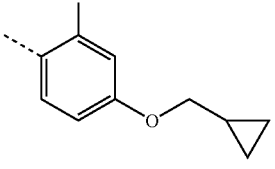 |  |
| 1-004 | B3 | ----CH₂--- | 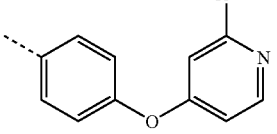 |  |
| 1-005 | B3 | ----CH₂--- | 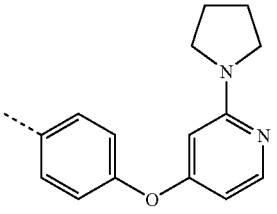 |  |
| 1-006 | B3 | ----CH₂--- | 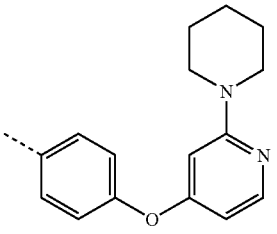 | 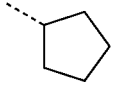 |
| 1-007 | B1 | ----CH₂--- | 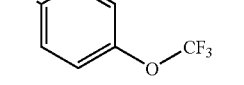 | 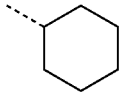 |
| 1-008 | B2 | ----CH₂--- | 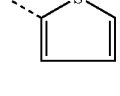 | 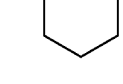 |
| 1-009 | B2 | ----CH₂--- | 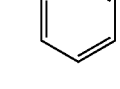 | |

TABLE 1A-continued

Compounds wherein L is a covalent bond.

| Co. nr. | Exp nr. | V¹ | M¹ | ----L—A |
|---|---|---|---|---|
| 1-010 | B1 | ----CH₂--- | cyclohexyl | 4-(N,N-dimethylamino)phenyl |
| 1-011 | B1 | ----CH₂--- | cyclohexyl | 2-methoxyphenyl |
| 1-012 | B1 | ----CH₂--- | cyclohexyl | 4-methoxyphenyl |
| 1-013 | B1 | ----CH₂--- | 4-methylcyclohexyl | 4-methoxyphenyl |
| 1-014 | B1 | ----CH₂--- | 4-methylcyclohexyl | 4-(trifluoromethoxy)phenyl |
| 1-015 | B2 | ----CH₂--- | 2-methylphenyl | 2-thienyl |
| 1-016 | B1 | ----CH₂--- | 2,3-dimethylphenyl | 4-methoxyphenyl |
| 1-017 | B1 | ----CH₂--- | 3-methylphenyl | 4-methoxyphenyl |
| 1-018 | B2 | ----CH₂--- | 4-methylphenyl | 2-furyl |
| 1-019 | B2 | ----CH₂--- | 4-methylphenyl | 2-thienyl |

TABLE 1A-continued

Compounds wherein L is a covalent bond.

| Co. nr. | Exp nr. | V¹ | M¹ | ----L—A |
|---|---|---|---|---|
| 1-020 | B2 | ---CH₂--- | 4-CH₃-C₆H₄- | C₆H₅- |
| 1-021 | B1 | ---CH₂--- | 4-CH₃-C₆H₄- | 4-OCH₃-C₆H₄- |
| 1-022 | B1 | ---CH₂--- | 4-F-C₆H₄- | 4-OCH₃-C₆H₄- |
| 1-023 | B2 | ---CH₂--- | 4-F-C₆H₄- | furan-2-yl |
| 1-024 | B1 | ---CH₂--- | 4-CF₃-C₆H₄- | 4-OCH₃-C₆H₄- |
| 1-025 | B1 | ---CH₂--- | 4-F-C₆H₄- | 3-Cl-4-OCH(CH₃)₂-C₆H₃- |
| 1-026 | B1 | ---CH₂--- | 3-Cl-C₆H₄- | 4-OCH₃-C₆H₄- |
| 1-027 | B1 | ---CH₂--- | 4-Cl-C₆H₄- | 4-OCH₃-C₆H₄- |
| 1-028 | B2 | ---CH₂--- | 4-Cl-C₆H₄- | thien-2-yl |
| 1-029 | B2 | ---CH₂--- | 4-OCH₃-C₆H₄- | C₆H₅- |
| 1-030 | B1 | ---CH₂--- | 3-OCF₃-C₆H₄- | C₆H₅- |

TABLE 1A-continued
Compounds wherein L is a covalent bond.
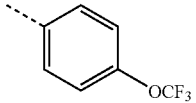
| Co. nr. | Exp nr. | V¹ | M¹ | ----L—A |
|---|---|---|---|---|
| 1-031 | B1 | ----CH$_2$---- | 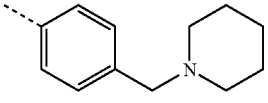 | 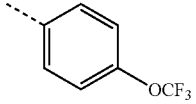 |
| 1-032 | B1 | ----CH$_2$---- | 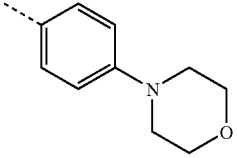 | 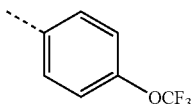 |
| 1-033 | B1 | ----CH$_2$---- | 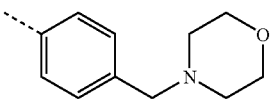 | 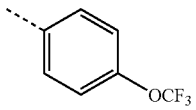 |
| 1-034 | B1 | ----CH$_2$---- | 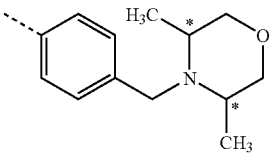 | 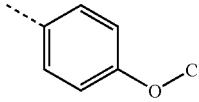 racemic mixture-CIS |
| 1-035 | B1 | ----CH$_2$---- | 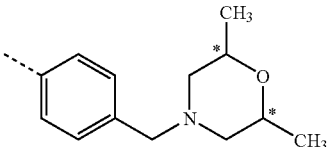 | 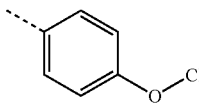 racemic mixture-CIS |
| 1-036 | B1 | ----CH$_2$---- | 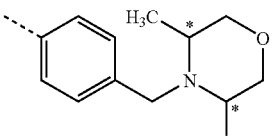 | 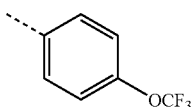 racemic mixture-TRANS |
| 1-037 | B17* | ----CH$_2$---- | 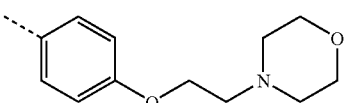 | 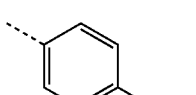 |
| 1-038 | B1 | ----CH$_2$---- | 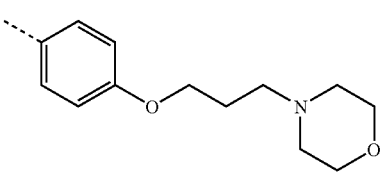 | |

TABLE 1A-continued

Compounds wherein L is a covalent bond.

| Co. nr. | Exp nr. | V¹ | M¹ | ----L—A |
|---|---|---|---|---|
| 1-039 | B1 | ----CH₂--- | 4-(OCF₃)phenyl | 4-(OCH₃)phenyl |
| 1-040 | B1 | ----CH₂--- | 4-(OCF₃)phenyl | 4-(3-hydroxypropyl)phenyl |
| 1-041 | B1 | ----CH₂--- | 4-(OCF₃)phenyl | 4-phenoxyphenyl |
| 1-042 | B1 | ----CH₂--- | 4-biphenyl | phenyl |
| 1-043 | B2 | ----CH₂--- | pyridin-4-yl | phenyl |
| 1-044 | B1 | ----CH₂--- | pyridin-2-yl | phenyl |
| 1-045 | B1 | ----CH₂--- | pyridin-3-yl | phenyl |
| 1-046 | B2 | ----CH₂--- | 6-(CF₃)pyridin-3-yl | thiophen-2-yl |
| 1-047 | B2 | ----CH₂--CH₂--- | phenoxy | phenyl |
| 1-048 | B1 | ----CH₂--CH₂--- | phenoxy | 4-(OCH₃)phenyl |

TABLE 1A-continued
Compounds wherein L is a covalent bond.
| Co. nr. | Exp nr. | V[1] | M[1] | ----L—A |
|---|---|---|---|---|
| 1-049 | B21* | ----CH$_2$- -CH$_2$--- | 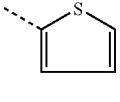 | 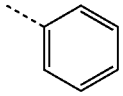 |
| 1-050 | B2 | ----CH$_2$—CH$_2$—CH$_2$--- | ----H | 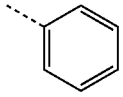 |
| 1-051 | B2 | ----CH$_2$—CH$_2$—CH$_2$--- | 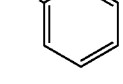 | 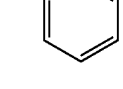 |
| 1-052 | B2 | ----CH$_2$—CH$_2$—CH$_2$--- | 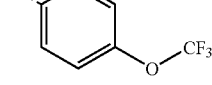 | 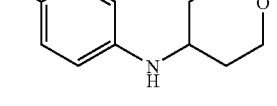 |
| 1-053 | B1 | ----CH$_2$—CH$_2$—CH$_2$--- | 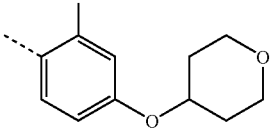 | 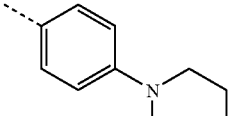 |
| 1-054 | B2 | ----CH$_2$—CH=CH---- | | |
| 1-055 | B1 | ----CH$_2$—CH$_2$—CH$_2$—CH$_2$--- | ----H | |
| 1-056 | B3 | ----CH$_2$—CH$_2$—CH$_2$—CH$_2$--- | ----H | |
| 1-057 | B3 | ----CH$_2$—CH$_2$—CH$_2$—CH$_2$--- | ----H | |
| 1-058 | B1 | ----CH$_2$—CH$_2$—CH$_2$—CH$_2$--- | ----H | |
| 1-059 | B2 | ----CH$_2$—CH$_2$—CH$_2$—CH$_2$--- | ----H | 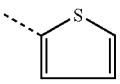 |

TABLE 1A-continued
Compounds wherein L is a covalent bond.
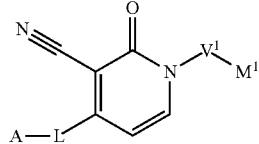
| Co. nr. | Exp nr. | V¹ | M¹ | ----L—A |
|---|---|---|---|---|
| 1-060 | B1 | ----CH₂—CH₂—CH₂—CH₂--- | ----H | 4-((2-methylimidazol-1-yl)methyl)phenyl |
| 1-061 | B3 | ----CH₂—CH₂—CH₂—CH₂--- | ----H | 3-(pyridin-2-yloxy)phenyl |
| 1-062 | B3 | ----CH₂—CH₂—CH₂—CH₂--- | ----H | 3-(pyridin-4-yloxy)phenyl |
| 1-063 | B1 | ----CH₂—CH₂—CH₂—CH₂--- | ----H | 4-((6-methylpyridin-2-yl)methoxy)phenyl |
| 1-064 | B51* | ----CH₂—CH₂—CH₂—CH₂--- | ----H | 4-((2-methylpyridin-4-yl)oxy)phenyl |
| 1-065 | B3 | ----CH₂—CH₂—CH₂—CH₂--- | ----H | 4-((4-methylpyridin-2-yl)oxy)phenyl |

TABLE 1A-continued
Compounds wherein L is a covalent bond.
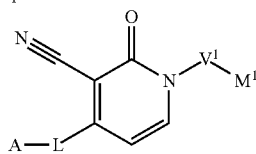
| Co. nr. | Exp nr. | V¹ | M¹ | ----L—A |
|---|---|---|---|---|
| 1-066 | B3 | ----CH₂—CH₂—CH₂—CH₂--- | ----H | 3-F, 4-(4-pyridyloxy)phenyl |
| 1-067 | B3 | ----CH₂—CH₂—CH₂—CH₂--- | ----H | 4-(3-CF₃-2-pyridyloxy)phenyl |
| 1-068 | B3 | ----CH₂—CH₂—CH₂—CH₂--- | ----H | 4-(6-CF₃-2-pyridyloxy)phenyl |
| 1-069 | B29 | ----CH₂—CH₂—CH₂—CH₂--- | ----H | 3-(3-CF₃-4-pyridyloxy)phenyl |
| 1-070 | B3 | ----CH₂—CH₂—CH₂—CH₂--- | ----H | 4-(3-Cl-4-pyridyloxy)phenyl |
| 1-071 | B3 | ----CH₂—CH₂—CH₂—CH₂--- | ----H | 4-(3-CN-2-pyridyloxy)phenyl |
| 1-072 | B3 | ----CH₂—CH₂—CH₂—CH₂--- | ----H | 4-(5-CN-2-pyridyloxy)phenyl |

TABLE 1A-continued
Compounds wherein L is a covalent bond.
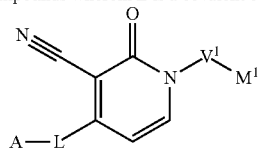
| Co. nr. | Exp nr. | V$^1$ | M$^1$ | ----L—A |
|---|---|---|---|---|
| 1-073 | B3 | ----CH$_2$—CH$_2$—CH$_2$—CH$_2$---- | ----H | 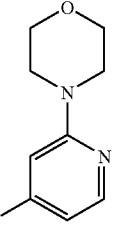 |
| 1-074 | B3 | ----CH$_2$—CH$_2$—CH$_2$—CH$_2$---- | ----H | 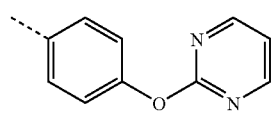 |
| 1-075 | B3 | ----CH$_2$—CH$_2$—CH$_2$—CH$_2$---- | ----H | 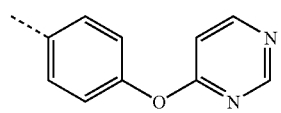 |
| 1-076 | B3 | ----CH$_2$—CH$_2$—CH$_2$—CH$_2$---- | ----H | 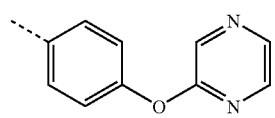 |
| 1-077 | B2 | ----CH$_2$—CH$_2$—CH$_2$—CH$_2$---- | ----H | 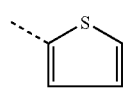 |
| 1-078 | B3 | ----CH$_2$—CH$_2$—CH$_2$—CH$_2$---- | ----H | 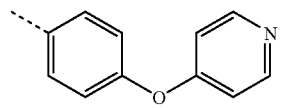 |
| 1-079 | B2 | ----CH(CH$_3$)—CH$_2$—CH$_2$—CH$_2$---- | ----H | 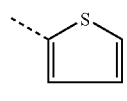 |
| 1-080 | B2 | ----CH$_2$—CH(CH$_3$)—CH$_2$—CH$_2$---- | ----H | 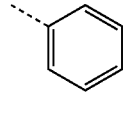 |
| 1-081 | B2 | ----CH$_2$—CH$_2$—CH(CH$_3$)—CH$_2$---- | ----H |  |
| 1-082 | B2 | ----CH$_2$—CH$_2$—CH(CH$_3$)—CH$_2$---- | ----H |  |
| 1-083 | B1 | ----CH$_2$—CH$_2$—CH(CH$_3$)—CH$_2$---- | ----H | 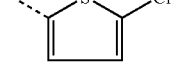 |

TABLE 1A-continued

Compounds wherein L is a covalent bond.

| Co. nr. | Exp nr. | V¹ | M¹ | ----L—A |
|---|---|---|---|---|
| 1-084 | B2 | ----CH₂—CH₂—CH(CH₃)—CH₂--- | ----H | phenyl |
| 1-085 | B1 | ----CH₂—CH₂—CH(CH₃)—CH₂--- | ----H | 4-methylphenyl |
| 1-086 | B1 | ----CH₂—CH₂—CH(CH₃)—CH₂--- | ----H | 4-tert-butylphenyl |
| 1-087 | B1 | ----CH₂—CH₂—CH(CH₃)—CH₂--- | ----H | 2-fluorophenyl |
| 1-088 | B1 | ----CH₂—CH₂—CH(CH₃)—CH₂--- | ----H | 3-fluorophenyl |
| 1-089 | B1 | ----CH₂—CH₂—CH(CH₃)—CH₂--- | ----H | 4-fluorophenyl |
| 1-090 | B1 | ----CH₂—CH₂—CH(CH₃)—CH₂--- | ----H | 3-chlorophenyl |
| 1-091 | B1 | ----CH₂—CH₂—CH(CH₃)—CH₂--- | ----H | 4-chlorophenyl |
| 1-092 | B1 | ----CH₂—CH₂—CH(CH₃)—CH₂--- | ----H | 3,4-dibromophenyl |
| 1-093 | B1 | ----CH₂—CH₂—CH(CH₃)—CH₂--- | ----H | 4-biphenyl |

TABLE 1A-continued

Compounds wherein L is a covalent bond.

| Co. nr. | Exp nr. | V¹ | M¹ | ----L—A |
|---|---|---|---|---|
| 1-094 | B1 | —CH₂—CH₂—CH(CH₃)—CH₂— | | biphenyl (3-position) |
| 1-095 | B4* | —CH₂—CH₂—CH(CH₃)—CH₂— | —H | 4-(3-hydroxypropyl)phenyl |
| 1-096 | B2 | —CH₂—CH₂—CH(CH₃)—CH₂— | —H | 3-hydroxyphenyl |
| 1-097 | B7* | —CH₂—CH₂—CH(CH₃)—CH₂— | —H | 4-hydroxyphenyl |
| 1-098 | B1 | —CH₂—CH₂—CH(CH₃)—CH₂— | —H | 4-(hydroxymethyl)phenyl |
| 1-099 | B37 | —CH₂—CH₂—CH(CH₃)—CH₂— | —H | 4-(2-hydroxyethoxy)phenyl |
| 1-100 | B1 | —CH₂—CH₂—CH(CH₃)—CH₂— | —H | 2-methoxyphenyl |
| 1-101 | B1 | —CH₂—CH₂—CH(CH₃)—CH₂— | —H | 3-methoxyphenyl |
| 1-102 | B2 | —CH₂—CH₂—CH(CH₃)—CH₂— | —H | 4-methoxyphenyl |
| 1-103 | B5* | —CH₂—CH₂—CH(CH₃)—CH₂— | —H | 4-(methoxymethyl)phenyl |

TABLE 1A-continued

Compounds wherein L is a covalent bond.

| Co. nr. | Exp nr. | V¹ | M¹ | ----L—A |
|---|---|---|---|---|
| 1-104 | B1 | ----CH₂—CH₂—CH(CH₃)—CH₂---- | ----H | 4-ethoxyphenyl |
| 1-105 | B1 | ----CH₂—CH₂—CH(CH₃)—CH₂---- | ----H | 4-propoxyphenyl |
| 1-106 | B1 | ----CH₂—CH₂—CH(CH₃)—CH₂---- | ----H | 4-(3-methoxypropyl)phenyl |
| 1-107 | B1 | ----CH₂—CH₂—CH(CH₃)—CH₂---- | ----H | 3-(methoxymethyl)phenyl |
| 1-108 | B1 | ----CH₂—CH₂—CH(CH₃)—CH₂---- | ----H | 3-methoxy-4-hydroxyphenyl |
| 1-109 | B1 | ----CH₂—CH₂—CH(CH₃)—CH₂---- | ----H | 3-methoxy-4-(2-hydroxyethoxy)phenyl |
| 1-110 | B1* | ----CH₂—CH₂—CH(CH₃)—CH₂---- | ----H | 3,4-dimethoxyphenyl |
| 1-111 | B1 | ----CH₂—CH₂—CH(CH₃)—CH₂---- | ----H | 4-isopropoxyphenyl |
| 1-112 | B1 | ----CH₂—CH₂—CH(CH₃)—CH₂---- | ----H | 3-chloro-4-methoxyphenyl |
| 1-113 | B2 | ----CH₂—CH₂—CH(CH₃)—CH₂---- | ----H | 3-fluoro-4-methoxyphenyl |
| 1-114 | B3* | ----CH₂—CH₂—CH(CH₃)—CH₂---- | ----H | 3-fluoro-4-methoxyphenyl |

TABLE 1A-continued
Compounds wherein L is a covalent bond.
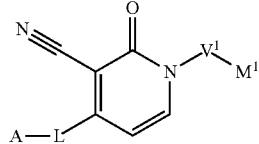
| Co. nr. | Exp nr. | V¹ | M¹ | ----L—A |
|---|---|---|---|---|
| 1-115 | B1 | ----CH$_2$—CH$_2$—CH(CH$_3$)—CH$_2$---- | ----H | 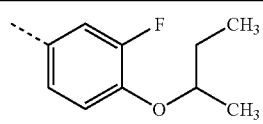 |
| 1-116 | B1 | ----CH$_2$—CH$_2$—CH(CH$_3$)—CH$_2$---- | ----H | 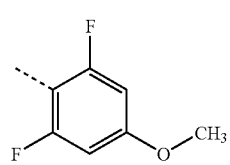 |
| 1-308 | B49* | ----CH$_2$—CH$_2$—CH(CH$_3$)—CH$_2$---- | ----H | 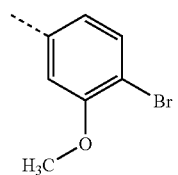 |
| 1-117 | B1 | ----CH$_2$—CH$_2$—CH(CH$_3$)—CH$_2$---- | ----H | 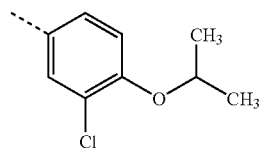 |
| 1-118 | B2 | ----CH$_2$—CH$_2$—CH(CH$_3$)—CH$_2$---- | ----H | 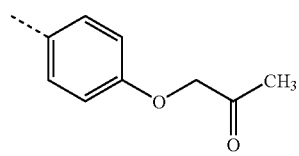 |
| 1-119 | B1 | ----CH$_2$—CH$_2$—CH(CH$_3$)—CH$_2$---- | ----H | 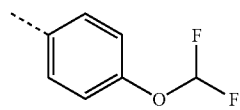 |
| 1-120 | B1 | ----CH$_2$—CH$_2$—CH(CH$_3$)—CH$_2$---- | ----H | 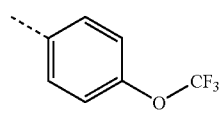 |
| 1-121 | B1 | ----CH$_2$—CH$_2$—CH(CH$_3$)—CH$_2$---- | ----H | 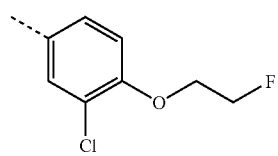 |
| 1-122 | B1 | ----CH$_2$—CH$_2$—CH(CH$_3$)—CH$_2$---- | ----H | 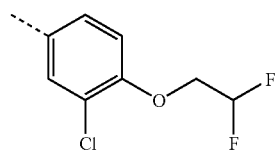 |

TABLE 1A-continued
Compounds wherein L is a covalent bond.
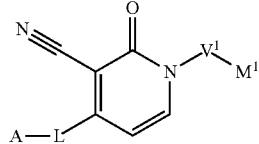
| Co. nr. | Exp nr. | V¹ | M¹ | ----L—A |
|---|---|---|---|---|
| 1-123 | B1 | ----CH₂—CH₂—CH(CH₃)—CH₂---- | ----H | 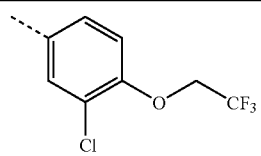 |
| 1-124 | B1 | ----CH₂—CH₂—CH(CH₃)—CH₂---- | ----H | 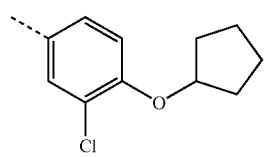 |
| 1-125 | B3 | ----CH₂—CH₂—CH(CH₃)—CH₂---- | ----H | 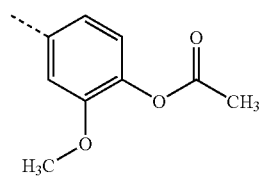 |
| 1-126 | B1 | ----CH₂—CH₂—CH(CH₃)—CH₂---- | ----H | 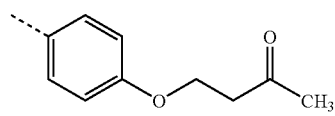 |
| 1-127 | B1 | ----CH₂—CH₂—CH(CH₃)—CH₂---- | ----H | 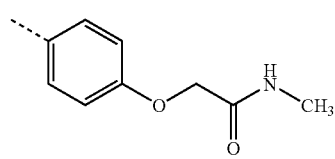 |
| 1-128 | B1 | ----CH₂—CH₂—CH(CH₃)—CH₂---- | ----H | 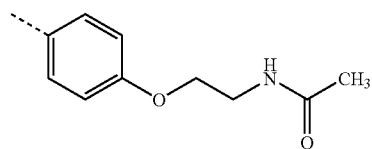 |
| 1-129 | B1 | ----CH₂—CH₂—CH(CH₃)—CH₂---- | ----H | 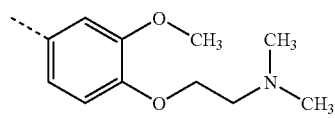 |
| 1-130 | B2 | ----CH₂—CH₂—CH(CH₃)—CH₂---- | ----H | 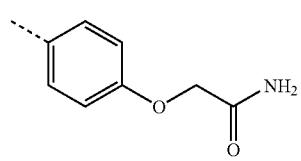 |
| 1-131 | B1 | ----CH₂—CH₂—CH(CH₃)—CH₂---- | ----H | 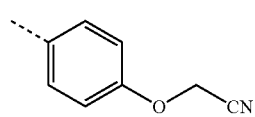 |

TABLE 1A-continued

Compounds wherein L is a covalent bond.

| Co. nr. | Exp nr. | V¹ | M¹ | ----L—A |
|---|---|---|---|---|
| 1-132 | B1 | ----CH₂—CH₂—CH(CH₃)—CH₂---- | ----H | 4-(cyanomethoxymethyl)phenyl |
| 1-133 | B1 | ----CH₂—CH₂—CH(CH₃)—CH₂---- | ----H | 4-(cyclopropylmethoxy)phenyl |
| 1-134 | B1 | ----CH₂—CH₂—CH(CH₃)—CH₂---- | ----H | 3-chloro-4-(cyclopropylmethoxy)phenyl |
| 1-135 | B1 | ----CH₂—CH₂—CH(CH₃)—CH₂---- | ----H | 4-(cyclopentyloxy)phenyl |
| 1-136 | B1 | ----CH₂—CH₂—CH(CH₃)—CH₂---- | ----H | 4-[2-(2-methyl-1,3-dioxolan-2-yl)ethoxy]phenyl |
| 1-137 | B3 | ----CH₂—CH₂—CH(CH₃)—CH₂---- | ----H | 4-[2-(tetrahydropyran-2-yloxy)ethoxy]phenyl |
| 1-138 | B3 | ----CH₂—CH₂—CH(CH₃)—CH₂---- | ----H | 3-methoxy-4-[2-(tetrahydropyran-2-yloxy)ethoxy]phenyl |

TABLE 1A-continued
Compounds wherein L is a covalent bond.
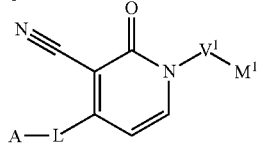
| Co. nr. | Exp nr. | V¹ | M¹ | ----L—A |
|---|---|---|---|---|
| 1-139 | B1 | ----CH₂—CH₂—CH(CH₃)—CH₂---- | ----H | 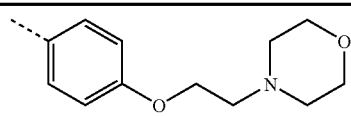 |
| 1-140 | B1 | ----CH₂—CH₂—CH(CH₃)—CH₂---- | ----H | 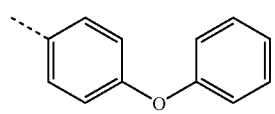 |
| 1-141 | B1 | ----CH₂—CH₂—CH(CH₃)—CH₂---- | ----H | 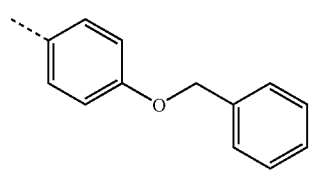 |
| 1-142 | B1 | ----CH₂—CH₂—CH(CH₃)—CH₂---- | ----H | 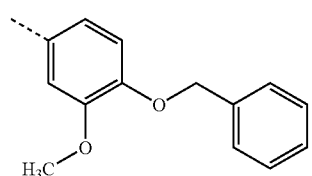 |
| 1-143 | B1 | ----CH₂—CH₂—CH(CH₃)—CH₂---- | ----H | 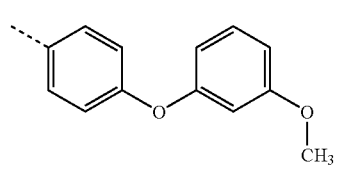 |
| 1-144 | B29 | ----CH₂—CH₂—CH(CH₃)—CH₂---- | ----H | 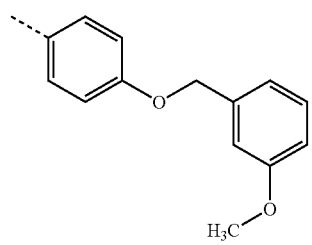 |
| 1-145 | B29 | ----CH₂—CH₂—CH(CH₃)—CH₂---- | ----H | 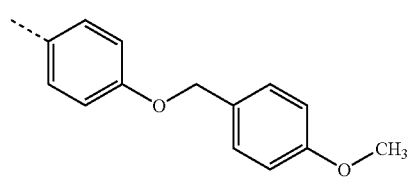 |
| 1-146 | B29 | ----CH₂—CH₂—CH(CH₃)—CH₂---- | ----H | 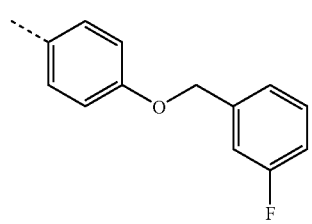 |

TABLE 1A-continued
Compounds wherein L is a covalent bond.
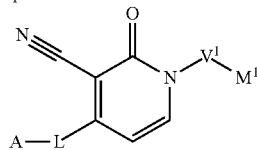
| Co. nr. | Exp nr. | V¹ | M¹ | ----L—A |
|---|---|---|---|---|
| 1-147 | B29 | ----CH₂—CH₂—CH(CH₃)—CH₂---- | ----H | 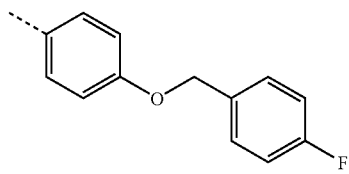 |
| 1-148 | B29 | ----CH₂—CH₂—CH(CH₃)—CH₂---- | ----H | 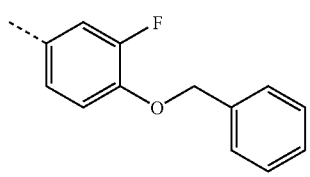 |
| 1-149 | B29 | ----CH₂—CH₂—CH(CH₃)—CH₂---- | ----H | 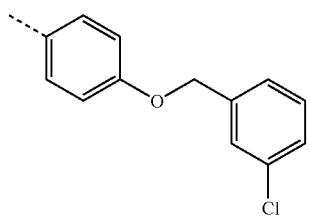 |
| 1-150 | B29 | ----CH₂—CH₂—CH(CH₃)—CH₂---- | ----H | 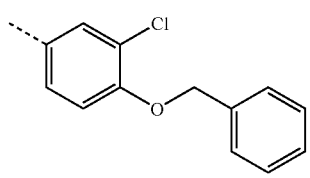 |
| 1-151 | B29 | ----CH₂—CH₂—CH(CH₃)—CH₂---- | ----H | 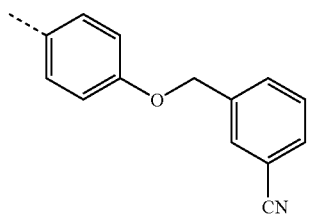 |
| 1-152 | B1 | ----CH₂—CH₂—CH(CH₃)—CH₂---- | ----H | 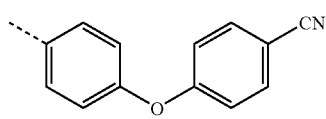 |
| 1-153 | B29 | ----CH₂—CH₂—CH(CH₃)—CH₂---- | ----H | 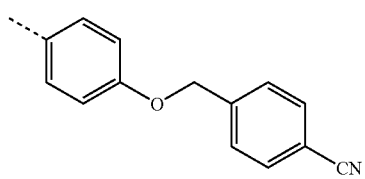 |

TABLE 1A-continued

Compounds wherein L is a covalent bond.

| Co. nr. | Exp nr. | V¹ | M¹ | ----L—A |
|---|---|---|---|---|
| 1-154 | B1 | ----CH₂—CH₂—CH(CH₃)—CH₂---- | ----H | 4-(pyridin-2-yloxy)phenyl |
| 1-155 | B3 | ----CH₂—CH₂—CH(CH₃)—CH₂---- | ----H | 4-(pyridin-3-yloxy)phenyl |
| 1-156 | B1 | ----CH₂—CH₂—CH(CH₃)—CH₂---- | ----H | 4-(pyridin-4-yloxy)phenyl |
| 1-157 | B1 | ----CH₂—CH₂—CH(CH₃)—CH₂---- | ----H | 4-(pyridin-2-ylmethoxy)phenyl |
| 1-158 | B1 | ----CH₂—CH₂—CH(CH₃)—CH₂---- | ----H | 4-(pyridin-3-ylmethoxy)phenyl |
| 1-159 | B1 | ----CH₂—CH₂—CH(CH₃)—CH₂---- | ----H | 4-(pyridin-4-ylmethoxy)phenyl |
| 1-160 | B1 | ----CH₂—CH₂—CH(CH₃)—CH₂---- | ----H | 4-(pyridin-4-ylmethoxy)phenyl |
| 1-161 | B3 | ----CH₂—CH₂—CH(CH₃)—CH₂---- | ----H | 3-fluoro-4-(pyridin-4-yloxy)phenyl |
| 1-162 | B29 | ----CH₂—CH₂—CH(CH₃)—CH₂---- | ----H | 3-fluoro-4-(pyridin-4-ylmethoxy)phenyl |

TABLE 1A-continued
Compounds wherein L is a covalent bond.
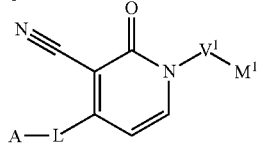
| Co. nr. | Exp nr. | V¹ | M¹ | ----L—A |
|---|---|---|---|---|
| 1-163 | B29 | ----CH₂—CH₂—CH(CH₃)—CH₂--- | ----H | 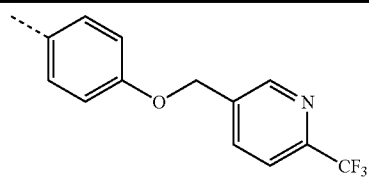 |
| 1-164 | B29 | ----CH₂—CH₂—CH(CH₃)—CH₂--- | ----H | 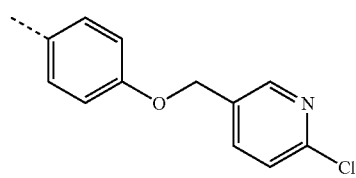 |
| 1-165 | B29 | ----CH₂—CH₂—CH(CH₃)—CH₂--- | ----H | 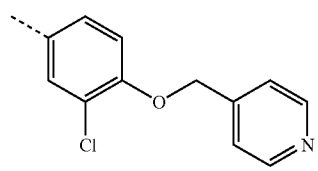 |
| 1-166 | B1 | ----CH₂—CH₂—CH(CH₃)—CH₂--- | ----H | 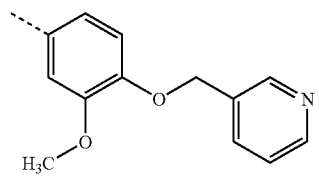 |
| 1-167 | B1 | ----CH₂—CH₂—CH(CH₃)—CH₂--- | ----H | 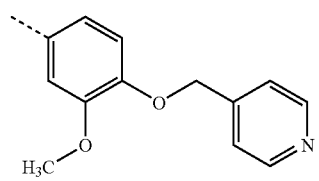 |
| 1-168 | B1 | ----CH₂—CH₂—CH(CH₃)—CH₂--- | ----H | 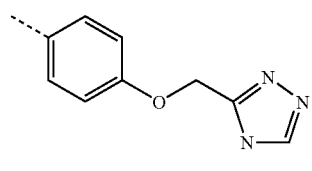 |
| 1-169 | B29 | ----CH₂—CH₂—CH(CH₃)—CH₂--- | ----H | 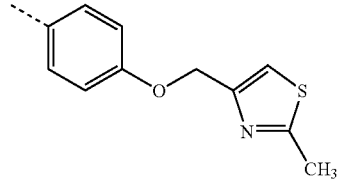 |
| 1-170 | B1 | ----CH₂—CH₂—CH(CH₃)—CH₂--- | ----H | 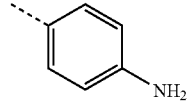 |

TABLE 1A-continued

Compounds wherein L is a covalent bond.

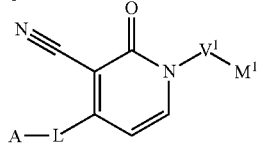

| Co. nr. | Exp nr. | V¹ | M¹ | ----L—A |
|---|---|---|---|---|
| 1-305 | B37 | ----CH₂—CH₂—CH(CH₃)—CH₂---- | ----H | 4-aminophenyl · CF₃COOH |
| 1-171 | B1 | ----CH₂—CH₂—CH(CH₃)—CH₂---- | ----H | 4-(methylamino)phenyl |
| 1-172 | B1 | ----CH₂—CH₂—CH(CH₃)—CH₂---- | ----H | 4-(dimethylamino)phenyl |
| 1-173 | B1 | ----CH₂—CH₂—CH(CH₃)—CH₂---- | ----H | 4-((dimethylamino)methyl)phenyl |
| 1-174 | B37 | ----CH₂—CH₂—CH(CH₃)—CH₂---- | ----H | 4-((2-methoxyethyl)amino)phenyl |
| 1-307 | B48* | ----CH₂—CH₂—CH(CH₃)—CH₂---- | ----H | 2-amino-3-methoxyphenyl |
| 1-175 | B1 | ----CH₂—CH₂—CH(CH₃)—CH₂---- | ----H | 3-acetamidophenyl |
| 1-176 | B1 | ----CH₂—CH₂—CH(CH₃)—CH₂---- | ----H | 4-acetamidophenyl |
| 1-177 | B1 | ----CH₂—CH₂—CH(CH₃)—CH₂---- | ----H | 4-((N-methylacetamido)methyl)phenyl |
| 1-178 | B6* | ----CH₂—CH₂—CH(CH₃)—CH₂---- | ----H | 3-(acetamidomethyl)phenyl |

TABLE 1A-continued
Compounds wherein L is a covalent bond.
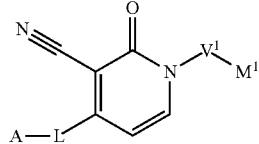
| Co. nr. | Exp nr. | V[1] | M[1] | ----L—A |
|---|---|---|---|---|
| 1-179 | B2* | ----CH$_2$—CH$_2$—CH(CH$_3$)—CH$_2$---- | ----H | 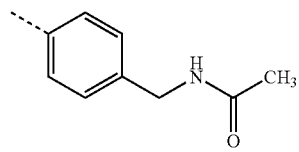 |
| 1-180 | B1 | ----CH$_2$—CH$_2$—CH(CH$_3$)—CH$_2$---- | ----H | 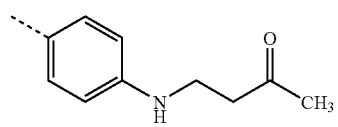 |
| 1-181 | B1 | ----CH$_2$—CH$_2$—CH(CH$_3$)—CH$_2$---- | ----H | 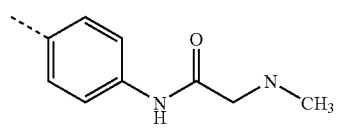 |
| 1-182 | B12* | ----CH$_2$—CH$_2$—CH(CH$_3$)—CH$_2$---- | ----H | 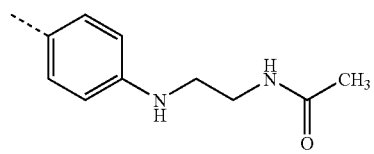 |
| 1-183 | B1 | ----CH$_2$—CH$_2$—CH(CH$_3$)—CH$_2$---- | ----H | 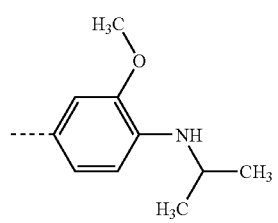 |
| 1-184 | B1 | ----CH$_2$—CH$_2$—CH(CH$_3$)—CH$_2$---- | ----H | 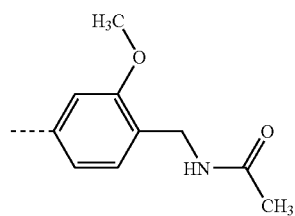 |
| 1-185 | B38* | ----CH$_2$—CH$_2$—CH(CH$_3$)—CH$_2$---- | ----H | 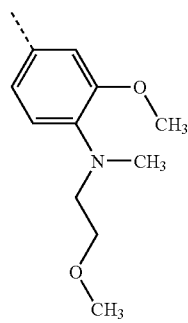 |

TABLE 1A-continued
Compounds wherein L is a covalent bond.
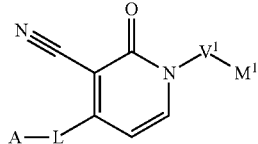
| Co. nr. | Exp nr. | V¹ | M¹ | ----L—A |
|---|---|---|---|---|
| 1-186 | B3 | ----CH₂—CH₂—CH(CH₃)—CH₂---- | ----H | 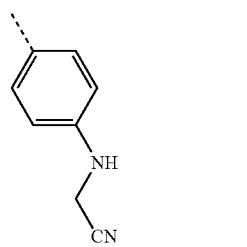 |
| 1-187 | B1 | ----CH₂—CH₂—CH(CH₃)—CH₂---- | ----H | 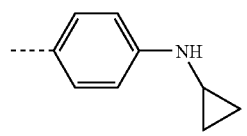 |
| 1-188 | B1 | ----CH₂—CH₂—CH(CH₃)—CH₂---- | ----H | 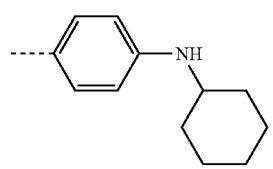 |
| 1-189 | B3 | ----CH₂—CH₂—CH(CH₃)—CH₂---- | ----H | 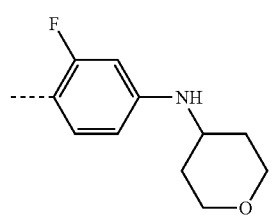 |
| 1-190 | B50* | ----CH₂—CH₂—CH(CH₃)—CH₂---- | ----H | 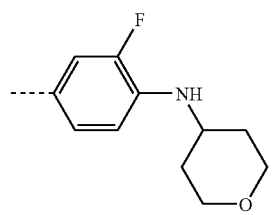 |
| 1-191 | B3 | ----CH₂—CH₂—CH(CH₃)—CH₂---- | ----H | 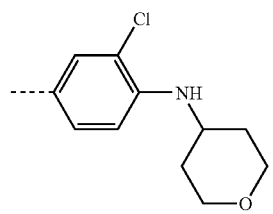 |
| 1-192 | B1 | ----CH₂—CH₂—CH(CH₃)—CH₂---- | ----H | 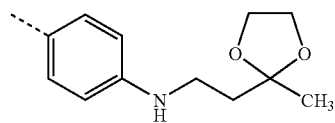 |

TABLE 1A-continued

Compounds wherein L is a covalent bond.

| Co. nr. | Exp nr. | V¹ | M¹ | ----L—A |
|---|---|---|---|---|
| 1-193 | B3 | ----CH₂—CH₂—CH(CH₃)—CH₂--- | ----H | 4-(phenylamino)phenyl |
| 1-194 | B3 | ----CH₂—CH₂—CH(CH₃)—CH₂--- | ----H | 4-(benzylamino)phenyl |
| 1-195 | B3 | ----CH₂—CH₂—CH(CH₃)—CH₂--- | ----H | 4-(N-methyl-N-phenylamino)phenyl |
| 1-196 | B3 | ----CH₂—CH₂—CH(CH₃)—CH₂--- | ----H | 4-(N-methyl-N-benzylamino)phenyl |
| 1-197 | B1 | ----CH₂—CH₂—CH(CH₃)—CH₂--- | ----H | 4-[N-methyl-N-(4-fluorobenzyl)aminomethyl]phenyl |
| 1-198 | B37* | ----CH₂—CH₂—CH(CH₃)—CH₂--- | ----H | 4-[(2-fluorobenzyl)aminomethyl]phenyl |
| 1-199 | B1 | ----CH₂—CH₂—CH(CH₃)—CH₂--- | ----H | 4-[(3-fluorobenzyl)amino]phenyl |
| 1-200 | B1 | ----CH₂—CH₂—CH(CH₃)—CH₂--- | ----H | 4-[(4-fluorobenzyl)amino]phenyl |
| 1-201 | B1 | ----CH₂—CH₂—CH(CH₃)—CH₂--- | ----H | 4-(acetylamino)-3-fluorophenyl |

TABLE 1A-continued
Compounds wherein L is a covalent bond.
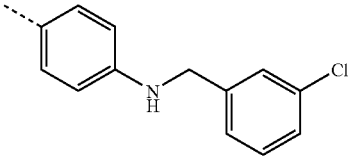
| Co. nr. | Exp nr. | V¹ | M¹ | ----L—A |
|---|---|---|---|---|
| 1-202 | B1 | ----CH₂—CH₂—CH(CH₃)—CH₂---- | ----H | 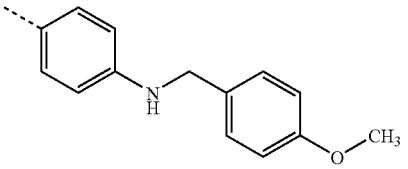 |
| 1-203 | B1 | ----CH₂—CH₂—CH(CH₃)—CH₂---- | ----H | 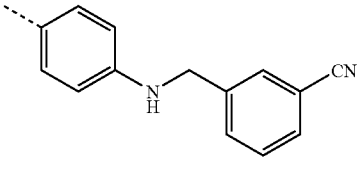 |
| 1-204 | B1 | ----CH₂—CH₂—CH(CH₃)—CH₂---- | ----H | 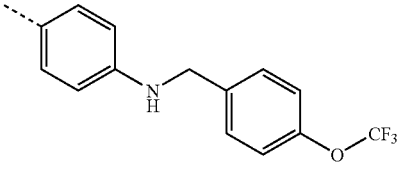 |
| 1-205 | B3 | ----CH₂—CH₂—CH(CH₃)—CH₂---- | ----H | 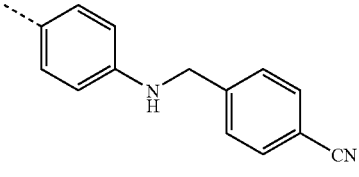 |
| 1-206 | B1 | ----CH₂—CH₂—CH(CH₃)—CH₂---- | ----H | 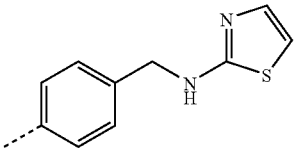 |
| 1-207 | B1 | ----CH₂—CH₂—CH(CH₃)—CH₂---- | ----H | 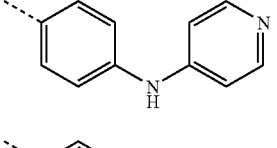 |
| 1-208 | B1 | ----CH₂—CH₂—CH(CH₃)—CH₂---- | ----H | 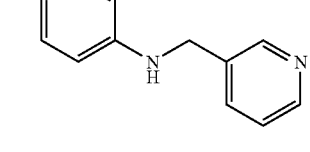 |
| 1-209 | B1 | ----CH₂—CH₂—CH(CH₃)—CH₂---- | ----H |  |

TABLE 1A-continued

Compounds wherein L is a covalent bond.

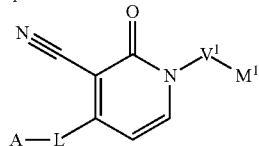

| Co. nr. | Exp nr. | V¹ | M¹ | ----L—A |
|---|---|---|---|---|
| 1-210 | B1 | ----CH₂—CH₂—CH(CH₃)—CH₂--- | ----H | 4-[(pyridin-4-ylmethyl)amino]phenyl |
| 1-211 | B28 | ----CH₂—CH₂—CH(CH₃)—CH₂--- | ----H | 4-{[methyl(pyridin-4-ylmethyl)amino]methyl}phenyl |
| 1-212 | B29 | ----CH₂—CH₂—CH(CH₃)—CH₂--- | ----H | 4-{[methyl(pyridin-2-ylmethyl)amino]methyl}phenyl |
| 1-213 | B1 | ----CH₂—CH₂—CH(CH₃)—CH₂--- | ----H | 4-[(pyridin-4-ylmethyl)carbamoyl]phenyl |
| 1-214 | B2 | ----CH₂—CH₂—CH(CH₃)—CH₂--- | ----H | 2-nitro-4-methylphenyl (with nitro and CH₃) |
| 1-215 | B1 | ----CH₂—CH₂—CH(CH₃)—CH₂--- | ----H | 3-(methanesulfonamido)phenyl |
| 1-216 | B1 | ----CH₂—CH₂—CH(CH₃)—CH₂--- | ----H | 4-(methanesulfonamido)phenyl |
| 1-217 | B3 | ----CH₂—CH₂—CH(CH₃)—CH₂--- | ----H | 4-[(1,1-dioxidotetrahydro-2H-thiopyran-4-yl)amino]phenyl |

TABLE 1A-continued
Compounds wherein L is a covalent bond.
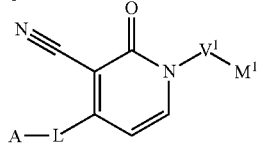
| Co. nr. | Exp nr. | V¹ | M¹ | ----L—A |
|---|---|---|---|---|
| 1-218 | B1 | ----CH₂—CH₂—CH(CH₃)—CH₂---- | ----H | 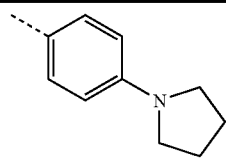 |
| 1-219 | B1 | ----CH₂—CH₂—CH(CH₃)—CH₂---- | ----H | 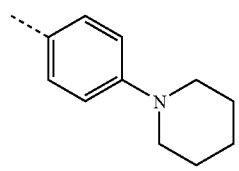 |
| 1-220 | B9 | ----CH₂—CH₂—CH(CH₃)—CH₂---- | ----H | 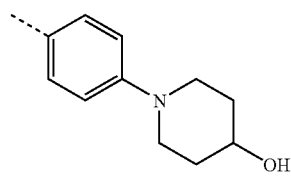 |
| 1-221 | B1 | ----CH₂—CH₂—CH(CH₃)—CH₂---- | ----H | 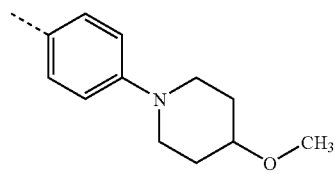 |
| 1-222 | B1 | ----CH₂—CH₂—CH(CH₃)—CH₂---- | ----H | 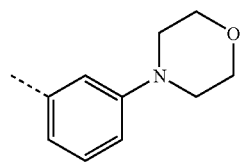 |
| 1-223 | B20* | ----CH₂—CH₂—CH(CH₃)—CH₂---- | ----H | 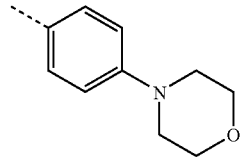 |
| 1-224 | B1 | ----CH₂—CH₂—CH(CH₃)—CH₂---- | ----H | 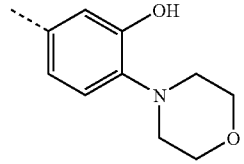 |
| 1-225 | B1 | ----CH₂—CH₂—CH(CH₃)—CH₂---- | ----H | 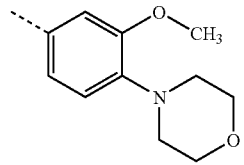 |

TABLE 1A-continued
Compounds wherein L is a covalent bond.
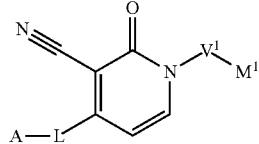
| Co. nr. | Exp nr. | V¹ | M¹ | ----L—A |
|---|---|---|---|---|
| 1-226 | B39* | ----CH₂—CH₂—CH(CH₃)—CH₂--- | ----H |  |
| 1-227 | B1 | ----CH₂—CH₂—CH(CH₃)—CH₂--- | ----H | 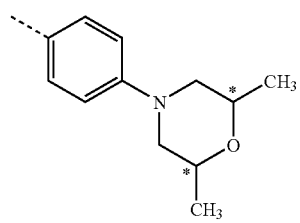<br>CIS-TRANS mixture<br>80:20 |
| 1-228 | B3 | ----CH₂—CH₂—CH(CH₃)—CH₂--- | ----H | 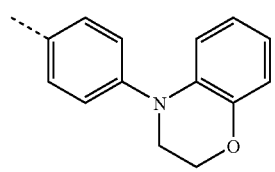 |
| 1-229 | B1 | ----CH₂—CH₂—CH(CH₃)—CH₂--- | ----H | 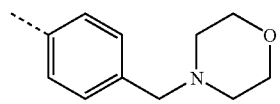 |
| 1-230 | B1 | ----CH₂—CH₂—CH(CH₃)—CH₂--- | ----H | 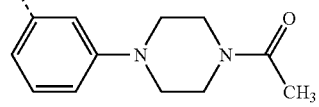 |
| 1-231 | B38 | ----CH₂—CH₂—CH(CH₃)—CH₂--- | ----H | 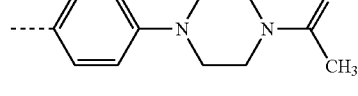 |
| 1-232 | B1 | ----CH₂—CH₂—CH(CH₃)—CH₂--- | ----H | 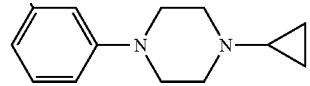 |
| 1-233 | B3 | ----CH₂—CH₂—CH(CH₃)—CH₂--- | ----H | 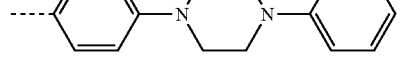 |
| 1-234 | B3 | ----CH₂—CH₂—CH(CH₃)—CH₂--- | ----H | 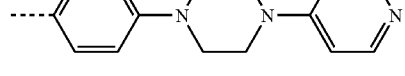 |

TABLE 1A-continued
Compounds wherein L is a covalent bond.
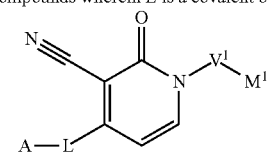
| Co. nr. | Exp nr. | V¹ | M¹ | ----L—A |
|---|---|---|---|---|
| 1-235 | B1 | ----CH₂—CH₂—CH(CH₃)—CH₂---- | ----H | 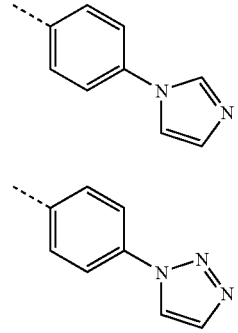 |
| 1-236 | B1 | ----CH₂—CH₂—CH(CH₃)—CH₂---- | ----H | 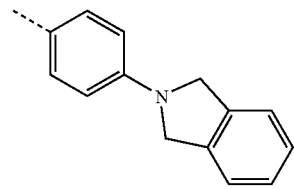 |
| 1-237 | B1 | ----CH₂—CH₂—CH(CH₃)—CH₂---- | ----H | 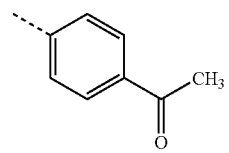 |
| 1-238 | B2 | ----CH₂—CH₂—CH(CH₃)—CH₂---- | ----H | 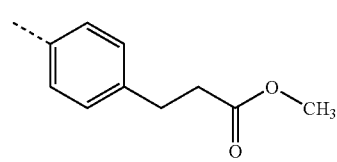 |
| 1-239 | B14* | ----CH₂—CH₂—CH(CH₃)—CH₂---- | ----H | 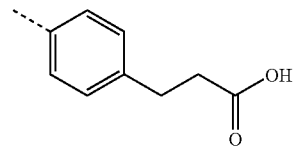 |
| 1-240 | B15* | ----CH₂—CH₂—CH(CH₃)—CH₂---- | ----H | 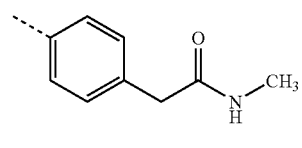 |
| 1-241 | B1 | ----CH₂—CH₂—CH(CH₃)—CH₂---- | ----H | 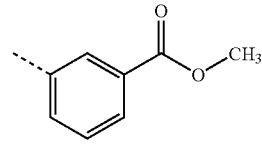 |
| 1-242 | B3 | ----CH₂—CH₂—CH(CH₃)—CH₂---- | ----H |  |

TABLE 1A-continued

Compounds wherein L is a covalent bond.

| Co. nr. | Exp nr. | V¹ | M¹ | ----L—A |
|---|---|---|---|---|
| 1-243 | B1 | ----CH$_2$—CH$_2$—CH(CH$_3$)—CH$_2$---- | ----H | 4-(N,N-dimethylcarbamoyl)phenyl |
| 1-244 | B3 | ----CH$_2$—CH$_2$—CH(CH$_3$)—CH$_2$---- | ----H | 4-(N,N-dimethylcarbamoylmethyl)phenyl |
| 1-245 | B1 | ----CH$_2$—CH$_2$—CH(CH$_3$)—CH$_2$---- | ----H | 4-(N-benzyl-N-methylcarbamoyl)phenyl |
| 1-246 | B1 | ----CH$_2$—CH$_2$—CH(CH$_3$)—CH$_2$---- | ----H | 4-(1-carbamoylcyclopropyl)phenyl |
| 1-247 | B3 | ----CH$_2$—CH$_2$—CH(CH$_3$)—CH$_2$---- | ----H | 4-{[4-(3-chloro-4-trifluoromethoxybenzyl)piperazin-1-yl]carbonyl}phenyl |
| 1-248 | B1 | ----CH$_2$—CH$_2$—CH(CH$_3$)—CH$_2$---- | ----H | 4-(imidazol-1-ylmethyl)phenyl |
| 1-249 | B1 | ----CH$_2$—CH$_2$—CH(CH$_3$)—CH$_2$---- | ----H | 4-(2-oxopyrrolidin-1-yl)phenyl |

TABLE 1A-continued
Compounds wherein L is a covalent bond.
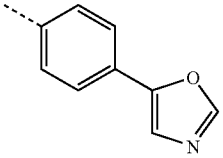
| Co. nr. | Exp nr. | V¹ | M¹ | ----L—A |
|---|---|---|---|---|
| 1-250 | B19* | ----CH₂—CH₂—CH(CH₃)—CH₂---- | ----H | 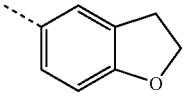 |
| 1-251 | B1 | ----CH₂—CH₂—CH(CH₃)—CH₂---- | ----H | 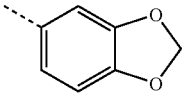 |
| 1-252 | B1 | ----CH₂—CH₂—CH(CH₃)—CH₂---- | ----H | 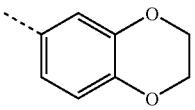 |
| 1-253 | B1 | ----CH₂—CH₂—CH(CH₃)—CH₂---- | ----H | 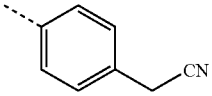 |
| 1-254 | B1 | ----CH₂—CH₂—CH(CH₃)—CH₂---- | ----H | 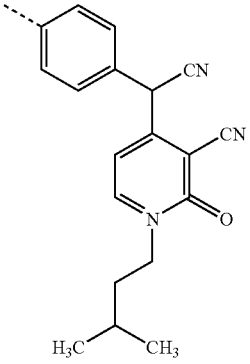 |
| 1-255 | B1 | ----CH₂—CH₂—CH(CH₃)—CH₂---- | ----H | 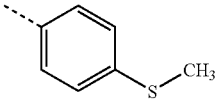 |
| 1-256 | B1 | ----CH₂—CH₂—CH(CH₃)—CH₂---- | ----H | 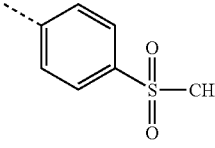 |
| 1-257 | B1 | ----CH₂—CH₂—CH(CH₃)—CH₂---- | ----H | |

TABLE 1A-continued
Compounds wherein L is a covalent bond.
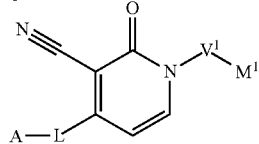
| Co. nr. | Exp nr. | V¹ | M¹ | ----L—A |
|---|---|---|---|---|
| 1-258 | B13* | ----CH₂—CH₂—CH(CH₃)—CH₂--- | ----H | 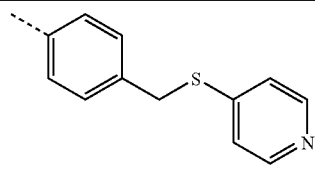 |
| 1-259 | B1 | ----CH₂—CH₂—CH(CH₃)—CH₂--- | ----H | 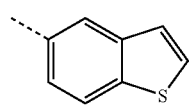 |
TABLE 1B
Compounds wherein L is a saturated or unsaturated alkyl chain.
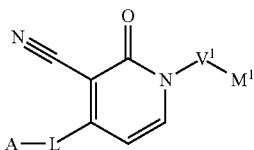
| Co. nr. | Exp nr. | V¹ | M¹ | ----L—A |
|---|---|---|---|---|
| 1-260 | B11* | ----CH₂—CH₂—CH(CH₃)—CH₂--- | ----H | 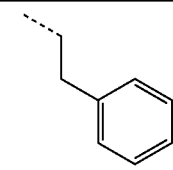 |
| 1-261 | B11 | ----CH₂—CH₂—CH(CH₃)—CH₂--- | ----H | 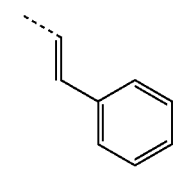 |
| 1-262 | B11 | ----CH₂—CH₂—CH(CH₃)—CH₂--- | ----H | 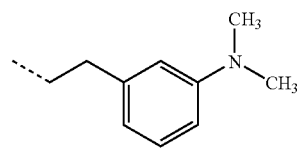 |
| 1-263 | B11 | ----CH₂—CH₂—CH(CH₃)—CH₂--- | ----H | 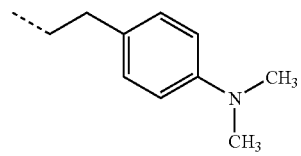 |
| 1-264 | B11 | ----CH₂—CH₂—CH(CH₃)—CH₂--- | ----H | 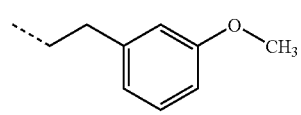 |

TABLE 1B-continued
Compounds wherein L is a saturated or unsaturated alkyl chain.
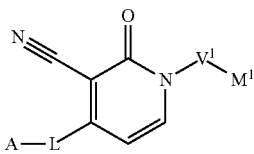
| Co. nr. | Exp nr. | V¹ | M¹ | ----L—A |
|---|---|---|---|---|
| 1-265 | B11 | ----CH₂—CH₂—CH(CH₃)—CH₂--- | ----H | 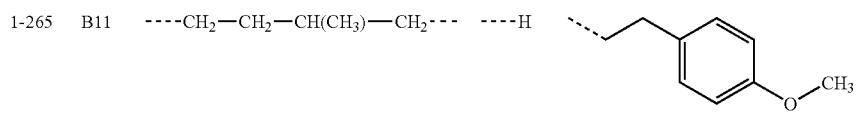 |
| 1-266 | B11 | ----CH₂—CH₂—CH(CH₃)—CH₂--- | ----H | 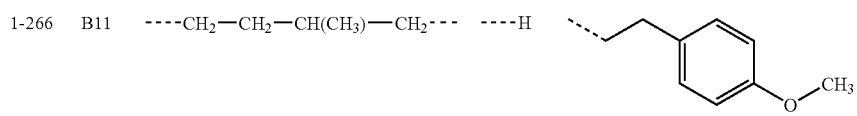 |
| 1-267 | B10* | ----CH₂—CH₂—CH(CH₃)—CH₂--- | ----H | 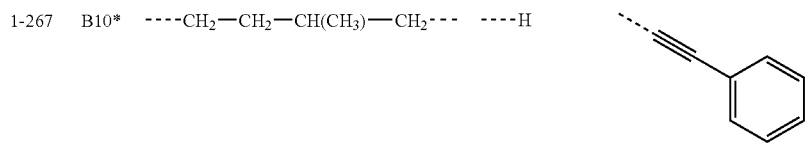 |
| 1-268 | B10 | ----CH₂—CH₂—CH(CH₃)—CH₂--- | ----H | 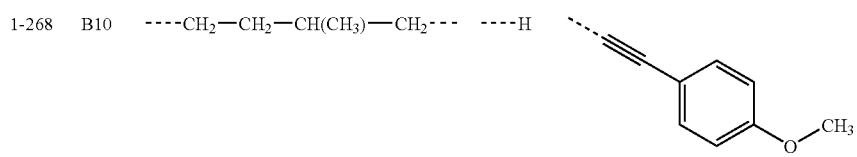 |
| 1-269 | B10 | ----CH₂—CH₂—CH(CH₃)—CH₂--- | ----H | 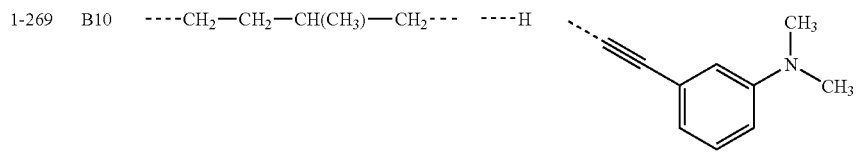 |
| 1-270 | B10 | ----CH₂—CH₂—CH(CH₃)—CH₂--- | ----H | 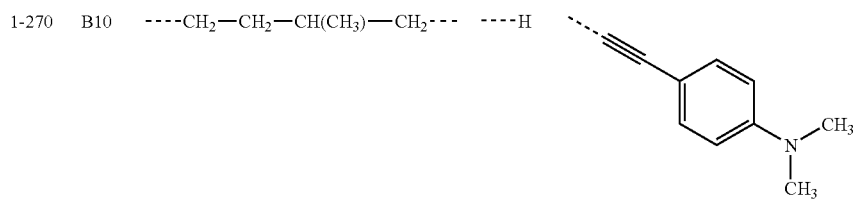 |

TABLE 1C
Compounds wherein L contains an O-atom.
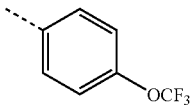
| Co. nr. | Exp nr. | V¹ | M¹ | ----L—A |
|---|---|---|---|---|
| 1-271 | B27* | ----CH₂--- | 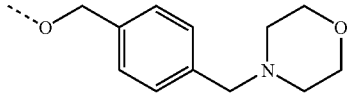 | 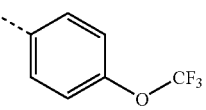 |
| 1-272 | B29 | ----CH₂--- | 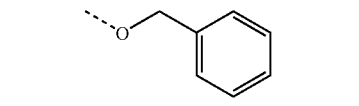 | 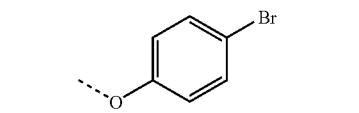 |
| 1-273 | B8 | ----CH₂—CH₂—CH₂—CH₂--- | ----H | 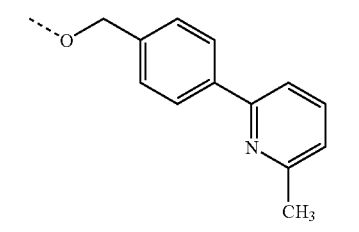 |
| 1-306 | B35* | ----CH₂—CH₂—CH₂—CH₂--- | ----H | 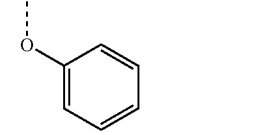 |
| 1-274 | B8* | ----CH₂—CH₂—CH(CH₃)—CH₂--- | ----H | 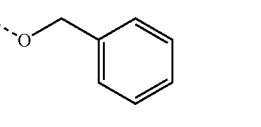 |
| 1-275 | B29 | ----CH₂—CH₂—CH(CH₃)—CH₂--- | ----H | 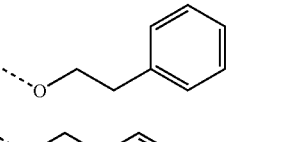 |
| 1-276 | B29 | ----CH₂—CH₂—CH(CH₃)—CH₂--- | ----H | 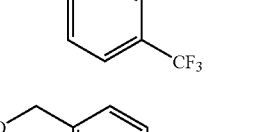 |
| 1-277 | B29 | ----CH₂—CH₂—CH(CH₃)—CH₂--- | ----H | 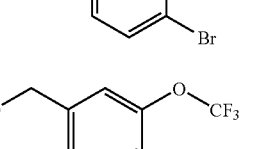 |
| 1-278 | B29 | ----CH₂—CH₂—CH(CH₃)—CH₂--- | ----H | 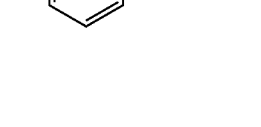 |
| 1-279 | B29 | ----CH₂—CH₂—CH(CH₃)—CH₂--- | ----H | |

TABLE 1C-continued

Compounds wherein L contains an O-atom.

| Co. nr. | Exp nr. | V¹ | M¹ | ----L—A |
|---|---|---|---|---|
| 1-280 | B29 | ----CH₂—CH₂—CH(CH₃)—CH₂--- | ----H | 2-phenoxyethoxy |
| 1-281 | B29 | ----CH₂—CH₂—CH(CH₃)—CH₂--- | ----H | 2-(benzyloxy)ethoxy |
| 1-282 | B8 | ----CH₂—CH₂—CH(CH₃)—CH₂--- | ----H | 4-methoxyphenoxy |
| 1-283 | B29 | ----CH₂—CH₂—CH(CH₃)—CH₂--- | ----H | (3-fluoro-4-methoxyphenyl)methoxy |
| 1-284 | B29 | ----CH₂—CH₂—CH(CH₃)—CH₂--- | ----H | (4-(difluoromethoxy)phenyl)methoxy |
| 1-285 | B29 | ----CH₂—CH₂—CH(CH₃)—CH₂--- | ----H | (4-(trifluoromethoxy)phenyl)methoxy |
| 1-286 | B29 | ----CH₂—CH₂—CH(CH₃)—CH₂--- | ----H | (4-cyanophenyl)methoxy |
| 1-287 | B29 | ----CH₂—CH₂—CH(CH₃)—CH₂--- | ----H | (4-((trifluoromethyl)thio)phenyl)methoxy |
| 1-288 | B27 | ----CH₂—CH₂—CH(CH₃)—CH₂--- | ----H | 2,3-dihydro-1H-inden-2-yloxy |
| 1-289 | B29 | ----CH₂—CH₂—CH(CH₃)—CH₂--- | ----H | (4-(benzyloxy)phenyl)methoxy |

TABLE 1C-continued

Compounds wherein L contains an O-atom.

| Co. nr. | Exp nr. | V¹ | M¹ | ----L—A |
|---|---|---|---|---|
| 1-290 | B29 | ----CH₂—CH₂—CH(CH₃)—CH₂--- | ----H | (3-biphenyl-CH₂-O-)-4'-C(O)OCH₂CH₃ |
| 1-291 | B8 | ----CH₂—CH₂—CH(CH₃)—CH₂--- | ----H | 4-(pyrrolidin-1-yl)phenyl-O- |
| 1-292 | B27 | ----CH₂—CH₂—CH(CH₃)—CH₂--- | ----H | 4-(morpholin-4-ylmethyl)benzyl-O- |
| 1-293 | B29 | ----CH₂—CH₂—CH(CH₃)—CH₂--- | ----H | (3-fluorobenzyl)(methyl)amino-CH₂CH₂-O- •HCl |

TABLE 1D

Compounds wherein L contains a N-atom.

| Co. nr. | Exp nr. | V¹ | M¹ | ----L—A |
|---|---|---|---|---|
| 1-294 | B31 | ----CH₂--- | cyclopropyl | trans-2-phenylcyclopropyl-NH- racemic mixture - TRANS |

TABLE 1D-continued
Compounds wherein L contains a N-atom.
| Co. nr. | Exp nr. | V¹ | M¹ | ----L—A |
|---|---|---|---|---|
| 1-295 | B29 | ----CH₂--- | 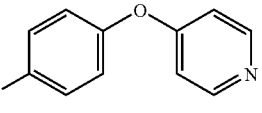 | 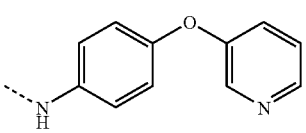 |
| 1-296 | B29 | ----CH₂—CH₂—CH₂—CH₂--- | ----H | 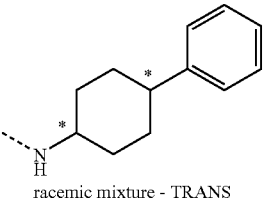 |
| 1-297 | B31 | ----CH₂—CH₂—CH₂—CH₂--- | ----H | 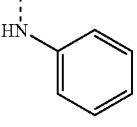<br>racemic mixture - TRANS |
| 1-298 | B9* | ----CH₂—CH₂—CH(CH₃)—CH₂--- | ----H | 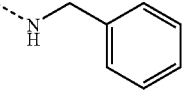 |
| 1-299 | B9 | ----CH₂—CH₂—CH(CH₃)—CH₂--- | ----H | 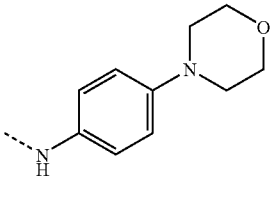 |
| 1-300 | B9 | ----CH₂—CH₂—CH(CH₃)—CH₂--- | ----H | 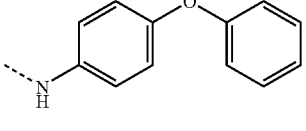 |
| 1-301 | B9 | ----CH₂—CH₂—CH(CH₃)—CH₂--- | ----H | 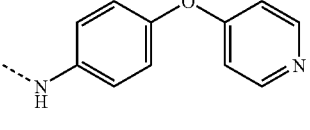 |
| 1-302 | B9 | ----CH₂—CH₂—CH(CH₃)—CH₂--- | ----H | 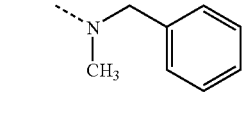 |
| 1-303 | B9 | ----CH₂—CH₂—CH(CH₃)—CH₂--- | ----H |  |

TABLE 1D-continued

Compounds wherein L contains a N-atom.

| Co. nr. | Exp nr. | V¹ | M¹ | ----L—A |
|---|---|---|---|---|
| 1-304 | B9 | ----CH₂—CH₂—CH(CH₃)—CH₂--- | ----H | HN-cyclopropyl-phenyl (racemic mixture - TRANS) |

TABLE 2

Compounds prepared according to the Examples wherein A is piperazinyl.

| Co. nr. | Exp nr. | ----V¹—M¹ | ----L---- | ----R⁴ |
|---|---|---|---|---|
| 2-001 | B28 | ----CH₂—CH₂—CH₂—CH₃ | cb | 3-CF₃-5-F-benzyl |
| 2-002 | B18 | ----CH₂—CH₂—CH₂—CH₃ | cb | 3-Cl-4-OCF₃-benzyl |
| 2-003 | B28 | ----CH₂—CH₂—CH₂—CH₃ | cb | 3-Cl-4-(cyclopropylmethoxy)-benzyl |
| 2-004 | B33 | ----CH₂—CH₂—CH₂—CH₃ | cb | 2-pyridyl |

TABLE 2-continued
Compounds prepared according to the Examples wherein A is piperazinyl.
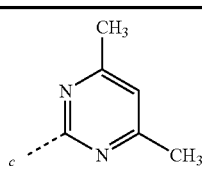
| Co. nr. | Exp nr. | ----V$^1$—M$^1$ | ----L---- | ----R$^4$ |
|---|---|---|---|---|
| 2-005 | B33 | ----CH$_2$—CH$_2$—CH$_2$—CH$_3$ | cb | 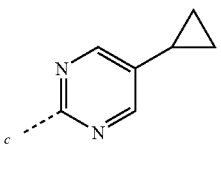 |
| 2-006 | B33 | ----CH$_2$—CH$_2$—CH$_2$—CH$_3$ | cb | 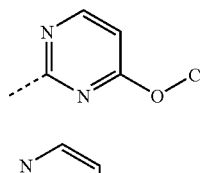 |
| 2-007 | B33 | ----CH$_2$—CH$_2$—CH$_2$—CH$_3$ | cb | 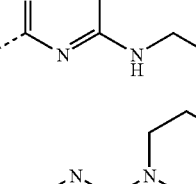 |
| 2-008 | B33 | ----CH$_2$—CH$_2$—CH$_2$—CH$_3$ | cb | 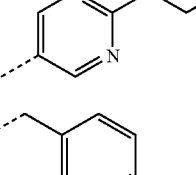 |
| 2-009 | B33 | ----CH$_2$—CH$_2$—CH$_2$—CH$_3$ | cb | 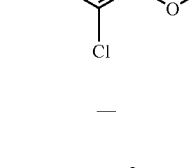 |
| 2-010 | B18 | ----CH$_2$CH(CH$_3$)$_2$ | cb | 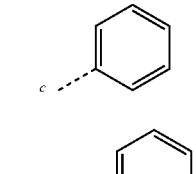 |
| 2-056 | B41* | ----CH$_2$—CH$_2$—CH(CH$_3$)$_2$ | cb | — |
| 2-011 | B23 | ----CH$_2$—CH$_2$—CH(CH$_3$)$_2$ | cb | 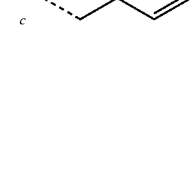 |
| 2-012 | B23 | ----CH$_2$—CH$_2$—CH(CH$_3$)$_2$ | cb | 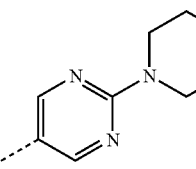 |

TABLE 2-continued
Compounds prepared according to the Examples wherein A is piperazinyl.
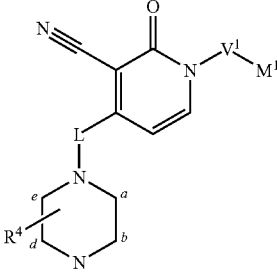
| Co. nr. | Exp nr. | ----V$^1$—M$^1$ | ----L---- | ----R$^4$ |
|---|---|---|---|---|
| 2-013 | B33 | ----CH$_2$—CH$_2$—CH(CH$_3$)$_2$ | cb | 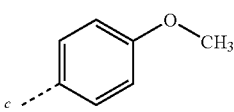 |
| 2-014 | B33 | ----CH$_2$—CH$_2$—CH(CH$_3$)$_2$ | cb | 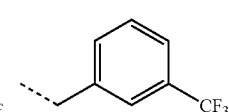 |
| 2-015 | B23 | ----CH$_2$—CH$_2$—CH(CH$_3$)$_2$ | cb | 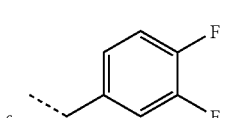 |
| 2-016 | B33 | ----CH$_2$—CH$_2$—CH(CH$_3$)$_2$ | cb | 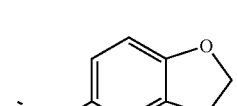 |
| 2-017 | B33 | ----CH$_2$—CH$_2$—CH(CH$_3$)$_2$ | cb | 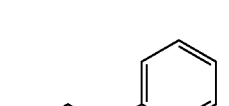 |
| 2-018 | B33 | ----CH$_2$—CH$_2$—CH(CH$_3$)$_2$ | cb |  |
| 2-019 | B33 | ----CH$_2$—CH$_2$—CH(CH$_3$)$_2$ | cb | 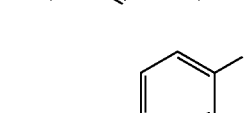 |
| 2-020 | B33 | ----CH$_2$—CH$_2$—CH(CH$_3$)$_2$ | cb | 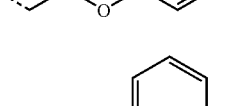 |
| 2-021 | B33 | ----CH$_2$—CH$_2$—CH(CH$_3$)$_2$ | cb | 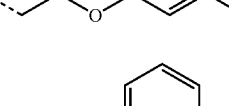<br>*a* ----CH$_3$ |

TABLE 2-continued

Compounds prepared according to the Examples wherein A is piperazinyl.

| Co. nr. | Exp nr. | ----V¹—M¹ | ----L---- | ----R⁴ |
|---|---|---|---|---|
| 2-022 | B33 | ----CH₂—CH₂—CH(CH₃)₂ | cb | 3-Cl, 4-OCF₃-benzyl |
| 2-023 | B23 | ----CH₂—CH₂—CH(CH₃)₂ | cb | 4-pyridylmethyl |
| 2-024 | B23 | ----CH₂—CH₂—CH(CH₃)₂ | cb | 2-pyridyl |
| 2-025 | B23 | ----CH₂—CH₂—CH(CH₃)₂ | cb | 5-methyl-2-pyridyl |
| 2-026 | B23 | ----CH₂—CH₂—CH(CH₃)₂ | cb | 3-trifluoromethyl-2-pyridyl |
| 2-027 | B23 | ----CH₂—CH₂—CH(CH₃)₂ | cb | 5-cyano-2-pyridyl |
| 2-028 | B24* | ----CH₂—CH₂—CH(CH₃)₂ | cb | 2-pyrimidinyl |
| 2-029 | B23 | ----CH₂—CH₂—CH(CH₃)₂ | cb | 4-trifluoromethyl-2-pyrimidinyl |
| 2-030 | B23 | ----CH₂—CH₂—CH(CH₃)₂ | cb | 3-pyridazinyl |

TABLE 2-continued
Compounds prepared according to the Examples wherein A is piperazinyl.
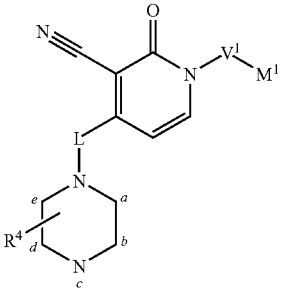
| Co. nr. | Exp nr. | ----V¹—M¹---- | ----L---- | ----R⁴ |
|---|---|---|---|---|
| 2-031 | B23 | ----CH₂—CH₂—CH(CH₃)₂ | cb | 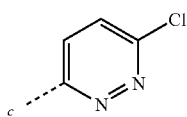 |
| 2-032 | B23 | ----CH₂—CH₂—CH(CH₃)₂ | cb | 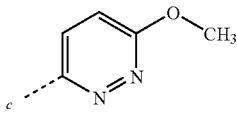 |
| 2-033 | B23 | ----CH₂—CH₂—CH(CH₃)₂ | cb | 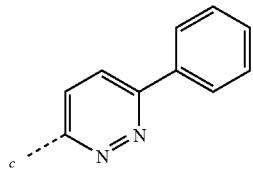 |
| 2-034 | B23 | ----CH₂—CH₂—CH(CH₃)₂ | cb | 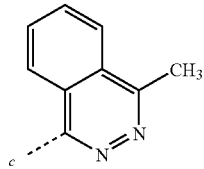 |
| 2-035 | B23 | ----CH₂—CH₂—CH(CH₃)₂ | cb | 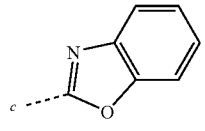 |
| 2-036 | B29* | ----CH₂—CH₂—CH(CH₃)₂ | ----O(CH₂)₂---- | 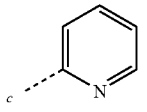 |
| 2-037 | B33 | ----CH₂—CH₂—CH(CH₃)₂ | ----(C=O)---- | 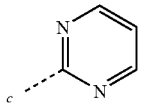 |
| 2-038 | B28 | 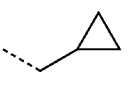 | cb | 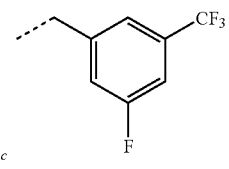 |

TABLE 2-continued

Compounds prepared according to the Examples wherein A is piperazinyl.

| Co. nr. | Exp nr. | ----V¹—M¹ | ----L---- | ----R⁴ |
|---|---|---|---|---|
| 2-039 | B28 | cyclopropylmethyl | cb | 3-chloro-4-(trifluoromethoxy)benzyl |
| 2-040 | B28 | cyclopropylmethyl | cb | 3-chloro-4-(cyclopropylmethoxy)benzyl |
| 2-041 | B33 | cyclopropylmethyl | cb | b: CH₃; d: H₃C; c: pyrimidin-2-yl; racemix mixture - CIS |
| 2-042 | B23 | 4-(OCF₃)benzyl | cb | benzyl (c) |
| 2-043 | B16* | 4-(OCF₃)benzyl | cb | phenethyl (c) |
| 2-044 | B23 | 4-(OCF₃)benzyl | cb | 4-fluorobenzyl (c) |
| 2-045 | B33 | 4-(OCF₃)benzyl | cb | a: ---CH₃; c: 3,5-difluorobenzyl; •HCl |

TABLE 2-continued
Compounds prepared according to the Examples wherein A is piperazinyl.
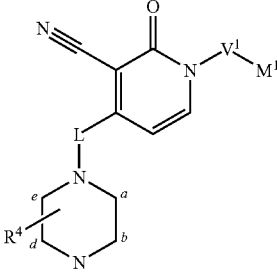
| Co. nr. | Exp nr. | ----V¹—M¹ | ----L---- | ----R⁴ |
|---|---|---|---|---|
| 2-046 | B18 | 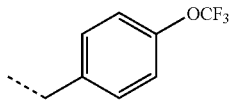 | cb | 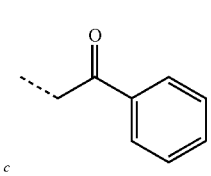 |
| 2047 | B23 | 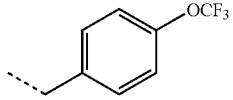 | cb | 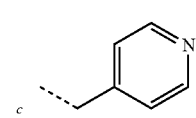 |
| 2-048 | B23 | 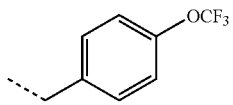 | cb | 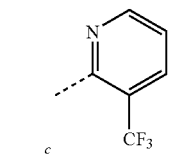 |
| 2-049 | B18* | 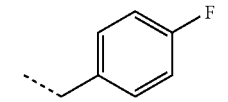 | cb | 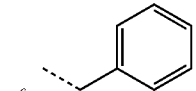 |
| 2-050 | B18 | 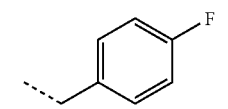 | cb | 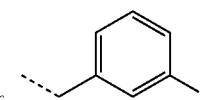 |
| 2-051 | B18 | 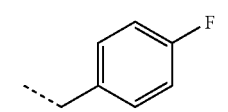 | cb | 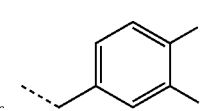 |
| 2-052 | B18 | 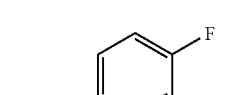 | cb | 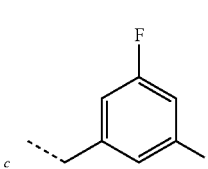 |
| 2-055 | B31* | 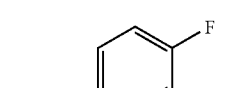 | cb | 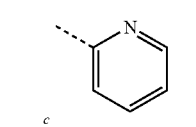 |

TABLE 2-continued

Compounds prepared according to the Examples wherein A is piperazinyl.

| Co. nr. | Exp nr. | ----V¹—M¹---- | ----L---- | ----R⁴ |
|---|---|---|---|---|
| 2-053 | B18 | phenoxypropyl | cb | benzyl |
| 2-054 | B18 | benzyloxyethyl | cb | benzyl |

TABLE 3

Compounds prepared according to the Examples wherein A is 4-piperidinyl.

| Co. nr. | Exp nr. | ----V¹—M¹---- | ----L---- | ----R⁴ |
|---|---|---|---|---|
| 3-001 | B10 | ----CH₂—CH₂—CH₂—CH₃ | cb | 2-pyrimidinyl |
| 3-002 | B18 | ----CH₂—CH₂—CH₂—CH₃ | ----O---- | 3-(trifluoromethyl)benzyl |
| 3-018 | B46* | ----CH₂—CH₂—CH(CH₃)₂ | cb | — |
| 3-017 | B45* | ----CH₂—CH₂—CH(CH₃)₂ | cb | tert-butoxycarbonyl |

TABLE 3-continued

Compounds prepared according to the Examples wherein A is 4-piperidinyl.

| Co. nr. | Exp nr. | ----V¹—M¹ | ----L---- | ---R⁴ |
|---|---|---|---|---|
| 3-014 | B28* | ----CH₂—CH₂—CH(CH₃)₂ | cb | 3-CF₃-benzyl |
| 3-003 | B23 | ----CH₂—CH₂—CH(CH₃)₂ | ----NH---- | benzyl |
| 3-004 | B18 | ----CH₂—CH₂—CH(CH₃)₂ | ----NH---- | 5-CF₃-pyridin-2-yl |
| 3-005 | B23 | ----CH₂—CH₂—CH(CH₃)₂ | ----N(CH₃)---- | benzyl |
| 3-006 | B23 | ----CH₂—CH₂—CH(CH₃)₂ | ----N(CH₃)---- | 3-CF₃-benzyl |
| 3-016 | B43* | ----CH₂—CH₂—CH(CH₃)₂ | ----O---- | — |
| 3-007 | B25 | ----CH₂—CH₂—CH(CH₃)₂ | ----O---- | benzyl |
| 3-015 | B42* | ----CH₂—CH₂—CH(CH₃)₂ | ----O---- | C(=O)OC(CH₃)₃ |
| 3-008 | B26* | ----CH₂—CH₂—CH(CH₃)₂ | ----O---- | 3-CF₃-benzyl |
| 3-009 | B25* | ----CH₂—CH₂—CH(CH₃)₂ | ----OCH₂--- | 3-CF₃-benzyl |

TABLE 3-continued
Compounds prepared according to the Examples wherein A is 4-piperidinyl.
| Co. nr. | Exp nr. | ----V¹—M¹ | ----L---- | ----R⁴ |
|---|---|---|---|---|
| 3-010 | B18 | 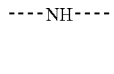 | ----NH---- | 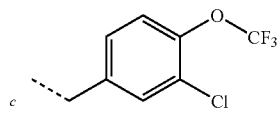 |
| 3-011 | B33 |  | ----NH---- | 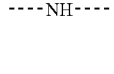 |
| 3-012 | B18 | 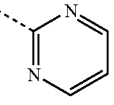 | ----O---- | 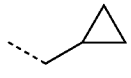 |
| 3-013 | B23 |  | ----N(CH₃)---- | 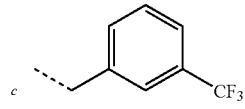 |
TABLE 4
Compounds prepared according to the Examples wherein A is 1-piperidinyl.
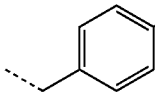
| Co. nr. | Exp nr. | ----V¹—M¹ | ----L---- | ----R⁴ |
|---|---|---|---|---|
| 4-001 | B10 | ----CH₂CH₂CH₂CH₃ | cb |  |
| 4-002 | B10 | ----CH₂CH₂CH₂CH₃ | cb | 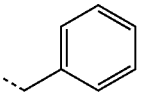 |

TABLE 4-continued
Compounds prepared according to the Examples wherein A is 1-piperidinyl.
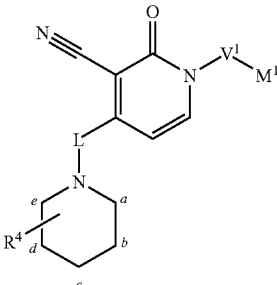
| Co. nr. | Exp nr. | ----V¹—M¹ | ----L---- | ----R⁴ |
|---|---|---|---|---|
| 4-003 | B34* | ----CH$_2$CH$_2$CH$_2$CH$_3$ | cb | 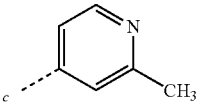 |
| 4-004 | B27 | ----CH$_2$CH$_2$CH$_2$CH$_3$ | cb | 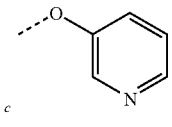 |
| 4-005 | B25 | ----CH$_2$CH$_2$CH$_2$CH$_3$ | cb | 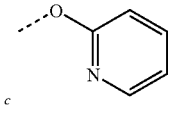 |
| 4-006 | B33 | ----CH$_2$CH$_2$CH$_2$CH$_3$ | cb | 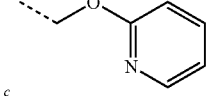 |
| 4-007 | B27 | ----CH$_2$CH$_2$CH$_2$CH$_3$ | cb | 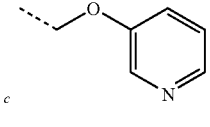 |
| 4-008 | B27 | ----CH$_2$CH$_2$CH$_2$CH$_3$ | cb | 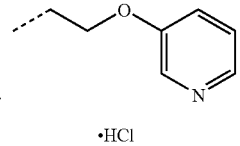<br>•HCl |
| 4-009 | B33 | ----CH$_2$CH$_2$CH$_2$CH$_3$ | cb | 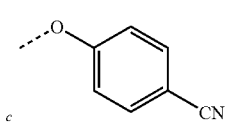 |
| 4-010 | B23 | ----CH$_2$—CH$_2$—CH(CH$_3$)$_2$ | cb | c ----CF$_3$ |
| 4-012 | B33 | ----CH$_2$—CH$_2$—CH(CH$_3$)$_2$ | cb | 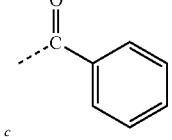 |

TABLE 4-continued

Compounds prepared according to the Examples wherein A is 1-piperidinyl.

| Co. nr. | Exp nr. | ----V¹—M¹---- | ----L---- | ----R⁴ |
|---|---|---|---|---|
| 4-013 | B33 | ----CH₂—CH₂—CH(CH₃)₂ | cb | phenyl (b, RS) |
| 4-014 | B33 | ----CH₂—CH₂—CH(CH₃)₂ | cb | phenyl (c) |
| 4-015 | B33 | ----CH₂—CH₂—CH(CH₃)₂ | cb | benzyl (c) |
| 4-016 | B33 | ----CH₂—CH₂—CH(CH₃)₂ | cb | 3-CF₃-phenyl (c) |
| 4-017 | B33 | ----CH₂—CH₂—CH(CH₃)₂ | cb | 4-methylphenoxy (c) |
| 4-018 | B33 | ----CH₂—CH₂—CH(CH₃)₂ | cb | 4-fluorophenoxy (c) |
| 4-019 | B33 | ----CH₂—CH₂—CH(CH₃)₂ | cb | 2-(4-fluorophenoxy)ethyl (c) |
| 4-020 | B22* | ----CH₂—CH₂—CH(CH₃)₂ | cb | 3-CF₃-benzyloxy (c) |
| 4-021 | B33 | ----CH₂—CH₂—CH(CH₃)₂ | cb | 2-ethoxyphenoxy (c) |

TABLE 4-continued

Compounds prepared according to the Examples wherein A is 1-piperidinyl.

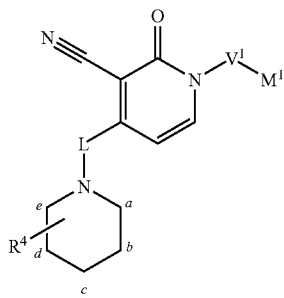

| Co. nr. | Exp nr. | ----V¹—M¹ | ----L---- | ----R⁴ |
|---|---|---|---|---|
| 4-022 | B33 | ----CH₂—CH₂—CH(CH₃)₂ | cb | 4-(trifluoromethoxy)benzyloxy |
| 4-023 | B23 | ----CH₂—CH₂—CH(CH₃)₂ | cb | phenylamino (b, RS) |
| 4-024 | B23 | ----CH₂—CH₂—CH(CH₃)₂ | cb | (3-trifluoromethylbenzyl)amino |
| 4-025 | B23 | ----CH₂—CH₂—CH(CH₃)₂ | cb | (3-trifluoromethylbenzyl)amino ·HCl |
| 4-026 | B23 | ----CH₂—CH₂—CH(CH₃)₂ | cb | N-methyl-N-benzylamino |
| 4-027 | B23 | ----CH₂—CH₂—CH(CH₃)₂ | cb | N-methyl-N-(4-fluorobenzyl)amino |
| 4-028 | B23 | ----CH₂—CH₂—CH(CH₃)₂ | cb | N-methyl-N-(3-trifluoromethylbenzyl)amino |
| 4-029 | B23 | ----CH₂—CH₂—CH(CH₃)₂ | cb | N-methyl-N-(4-trifluoromethylbenzyl)amino |
| 4-030 | B23 | ----CH₂—CH₂—CH(CH₃)₂ | cb | N-methyl-N-(4-fluorobenzyl)amino ·HCl |

TABLE 4-continued

Compounds prepared according to the Examples wherein A is 1-piperidinyl.

| Co. nr. | Exp nr. | ----V$^1$—M$^1$ | ----L---- | ----R$^4$ |
|---|---|---|---|---|
| 4-031 | B23 | ----CH$_2$—CH$_2$—CH(CH$_3$)$_2$ | cb | N(CH$_3$)-(3-CF$_3$-phenyl) |
| 4-032 | B23 | ----CH$_2$—CH$_2$—CH(CH$_3$)$_2$ | cb | N(CH$_3$)-CH$_2$CH$_2$-(3-CF$_3$-phenyl) |
| 4-033 | B23 | ----CH$_2$—CH$_2$—CH(CH$_3$)$_2$ | cb | N(CH$_3$)-CH$_2$CH$_2$-(3-CF$_3$-phenyl) ·HCl |
| 4-034 | B23 | ----CH$_2$—CH$_2$—CH(CH$_3$)$_2$ | cb | 1,2,3,4-tetrahydroisoquinolin-2-yl |
| 4-035 | B23 | ----CH$_2$—CH$_2$—CH(CH$_3$)$_2$ | cb | indol-1-yl |
| 4-036 | B23 | ----CH$_2$—CH$_2$—CH(CH$_3$)$_2$ | cb | indol-1-ylmethyl |

TABLE 4-continued

Compounds prepared according to the Examples wherein A is 1-piperidinyl.

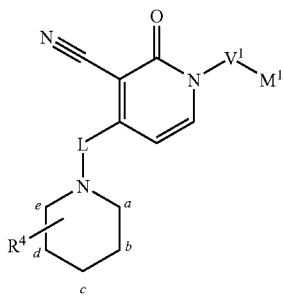

| Co. nr. | Exp nr. | ----V¹—M¹---- | ----L---- | ----R⁴ |
|---|---|---|---|---|
| 4-037 | B23 | ----CH$_2$—CH$_2$—CH(CH$_3$)$_2$ | cb | 5-fluoro-1H-indol-1-yl |
| 4-038 | B23 | ----CH$_2$—CH$_2$—CH(CH$_3$)$_2$ | cb | benzoxazol-2-yl |
| 4-039 | B23 | ----CH$_2$—CH$_2$—CH(CH$_3$)$_2$ | cb | 6-fluorobenzofuran-3-yl |
| 4-040 | B23 | ----CH$_2$—CH$_2$—CH(CH$_3$)$_2$ | cb | 5-neopentyl-1,2,4-oxadiazol-3-yl |
| 4-041 | B23 | ----CH$_2$—CH$_2$—CH(CH$_3$)$_2$ | cb | 5-phenyl-1,2,4-oxadiazol-3-yl |
| 4-042 | B25 | ----CH$_2$—CH$_2$—CH(CH$_3$)$_2$ | cb | 2-oxopyrrolidin-1-yl |

TABLE 4-continued
Compounds prepared according to the Examples wherein A is 1-piperidinyl.
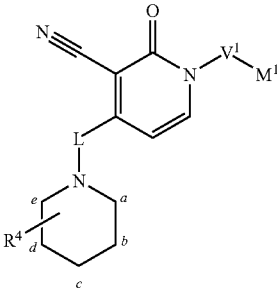
| Co. nr. | Exp nr. | ----V¹—M¹---- | ----L---- | ----R⁴ |
|---|---|---|---|---|
| 4-043 | B23 | ----CH₂—CH₂—CH(CH₃)₂ | cb | *b* ----CH₃<br>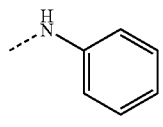<br>racemic mixture - CIS |
| 4-044 | B23* | ----CH₂—CH₂—CH(CH₃)₂ | cb | 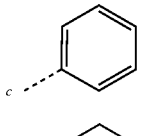 |
| 4-045 | B33 | ----CH₂—CH₂—CH(CH₃)₂ | cb | 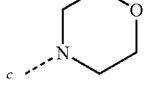<br>*c* ----OCH₃ |
| 4-046 | B33 | ----CH₂—CH₂—CH(CH₃)₂ | cb | 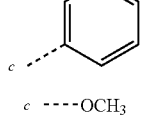 |
| 4-047 | B33* | 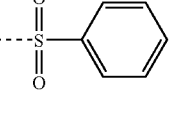 | cb | 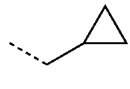 |
| 4-048 | B33 | 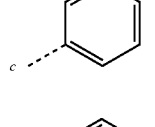 | cb | 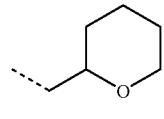 |
| 4-049 | B23 | 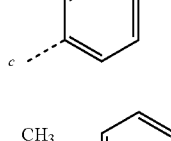 | cb | 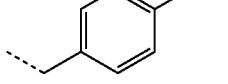 |

TABLE 4-continued
Compounds prepared according to the Examples wherein A is 1-piperidinyl.
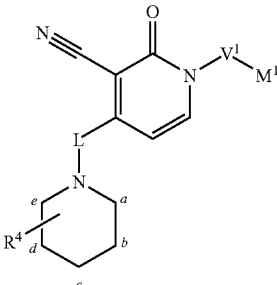
| Co. nr. | Exp nr. | ----V¹—M¹ | ----L---- | ----R⁴ |
|---|---|---|---|---|
| 4-050 | B23 | 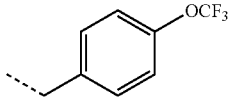 | cb | 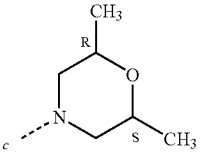 |
| 4-051 | B23 | 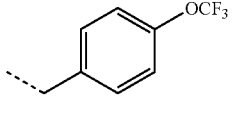 | cb | 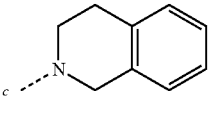 |
| 4-052 | B25 | 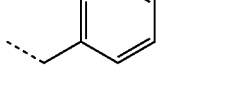 | cb | 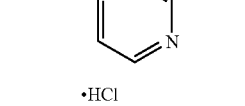<br>•HCl |
| 4-053 | B33 | 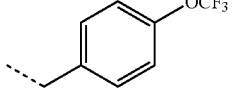 | cb | 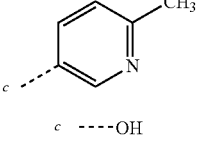<br>c ----OH |
| 4-054 | B33 | 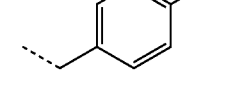 | cb | 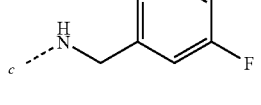 |
| 4-055 | B37 | 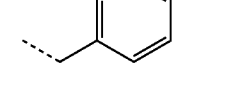 | cb | 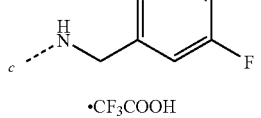<br>•CF₃COOH |
| 4-056 | B23 | 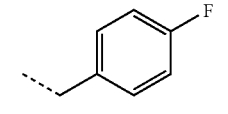 | cb | 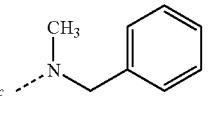 |
| 4-057 | B26 | 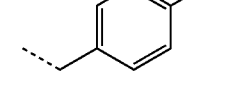 | cb | 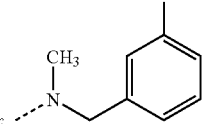 |

TABLE 4-continued
Compounds prepared according to the Examples wherein A is 1-piperidinyl.
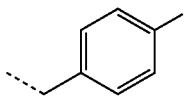
| Co. nr. | Exp nr. | ----V¹—M¹ | ----L---- | ----R⁴ |
|---|---|---|---|---|
| 4-058 | B23 | 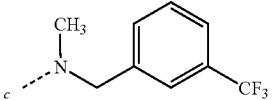 | cb | 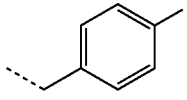 |
| 4-059 | B26 | 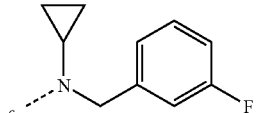 | cb | 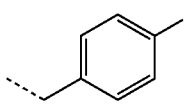 |
| 4-060 | B26 | 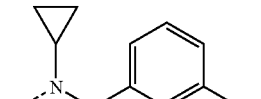 | cb | 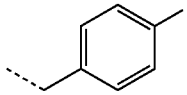 •HCl |
| 4-061 | B23 | 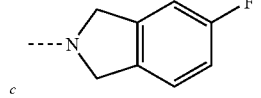 | cb | 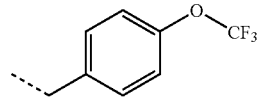 |
| 4-062 | B33 | 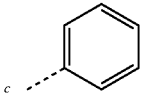 | cb | 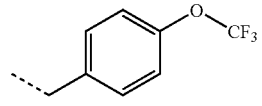 |
| 4-063 | B33 | 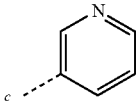 | cb | 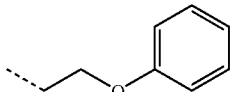 c ----OH |
| 4-064 | B23 | 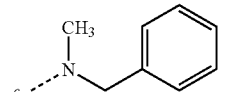 | cb |  |
| 4-065 | B23 |  | cb |  |
| 4-066 | B33 | 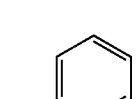 | cb | |

TABLE 5
Other compounds prepared according to the Examples wherein A is a N-containing heterocycle
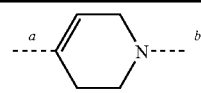
| Co. nr. | Exp nr. | ----V¹—M¹---- | ----L---- | a---A---b | ----R⁴ |
|---|---|---|---|---|---|
| 5-054 | B47* | ----CH$_2$CH$_2$CH$_2$CH$_3$ | cb | 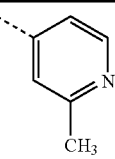 | 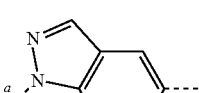 |
| 5-023 | B1 | ----CH$_2$CH$_2$CH$_2$CH$_3$ | cb | 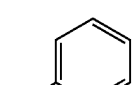 | 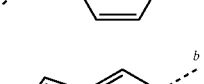 |
| 5-001 | B11 | ----CH$_2$CH$_2$CH$_2$CH$_3$ | cb | 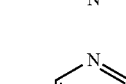 | 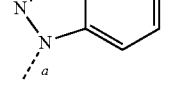 |
| 5-002 | B1 | ----CH$_2$CH$_2$CH$_2$CH$_3$ | cb | 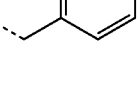 | $a_1$ ----CH$_3$<br>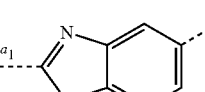 |
| 5-003 | B23 | ----CH$_2$—CH$_2$—CH(CH$_3$)$_2$ | cb | 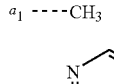 | — |
| 5-004 | B33 | ----CH$_2$—CH$_2$—CH(CH$_3$)$_2$ | cb | 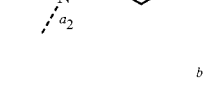 | 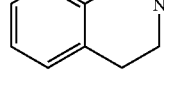 |
| 5-005 | B33 | ----CH$_2$—CH$_2$—CH(CH$_3$)$_2$ | cb |  | 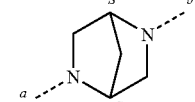 |
| 5-006 | B33 | ----CH$_2$—CH$_2$—CH(CH$_3$)$_2$ | cb | 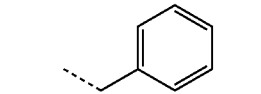 | 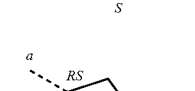 |
| 5-007* | B30 | ----CH$_2$—CH$_2$—CH(CH$_3$)$_2$ | cb | 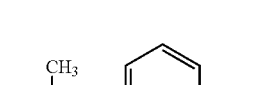 | 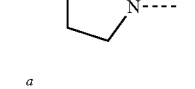 |

TABLE 5-continued

Other compounds prepared according to the Examples wherein A is a N-containing heterocycle

| Co. nr. | Exp nr. | ----V¹—M¹ | ----L---- | a---A---b | ----R⁴ |
|---|---|---|---|---|---|
| 5-008 | B23 | ----CH₂—CH₂—CH(CH₃)₂ | cb | azetidine (a-N-b) | 4-(trifluoromethoxy)benzyloxy |
| 5-009 | B33 | ----CH₂—CH₂—CH(CH₃)₂ | cb | 2,7-diazaspiro[3.5]nonane | 3-(trifluoromethyl)benzyl |
| 5-053 | B44* | ----CH₂—CH₂—CH(CH₃)₂ | cb | 1,2,3,6-tetrahydropyridine | tert-butyl carbonate |
| 5-052 | B40* | ----CH₂—CH₂—CH(CH₃)₂ | cb | pyridine (NH-b) | — trifluoromethylsulfonic acid (salt form) |
| 5-010 | B1 | ----CH₂—CH₂—CH(CH₃)₂ | cb | pyridine (2,5-) | ----O—CH₃ |
| 5-011 | B1 | ----CH₂—CH₂—CH(CH₃)₂ | cb | pyridine (2,5-) | ----(CH₂)₃OH |
| 5-012 | B1 | ----CH₂—CH₂—CH(CH₃)₂ | cb | 4,5-dihydro-1H-pyrazole | — |
| 5-013 | B1 | ----CH₂—CH₂—CH(CH₃)₂ | cb | 4,5-dihydro-pyrazole (N-a) | benzyl |
| 5-014 | B1 | ----CH₂—CH₂—CH(CH₃)₂ | cb | 2,3-dihydro-1H-indole (5-b) | — |
| 5-015 | B36* | ----CH₂—CH₂—CH(CH₃)₂ | cb | 2,3-dihydro-1H-indole (N-a, 5-b) | acetyl |

TABLE 5-continued
Other compounds prepared according to the Examples wherein A is a N-containing heterocycle
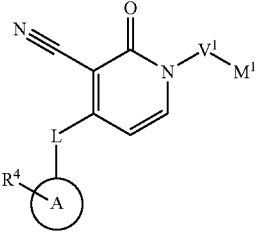
| Co. nr. | Exp nr. | ----V¹—M¹ | ----L---- | a---A---b | ----R⁴ |
|---|---|---|---|---|---|
| 5-016 | B1 | ----CH$_2$—CH$_2$—CH(CH$_3$)$_2$ | cb | 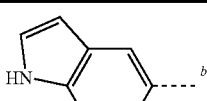 | — |
| 5-017 | B1 | ----CH$_2$—CH$_2$—CH(CH$_3$)$_2$ | cb | 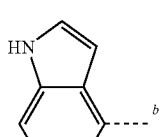 | — |
| 5-018 | B1 | ----CH$_2$—CH$_2$—CH(CH$_3$)$_2$ | cb | 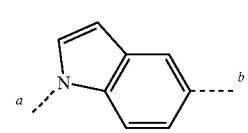 | ----CH$_3$ |
| 5-019 | B1 | ----CH$_2$—CH$_2$—CH(CH$_3$)$_2$ | cb | 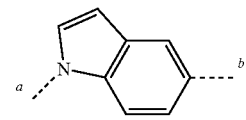 | 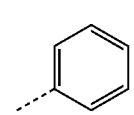 |
| 5-020 | B32 | ----CH$_2$—CH$_2$—CH(CH$_3$)$_2$ | cb | 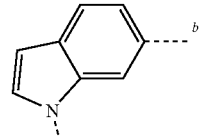 | 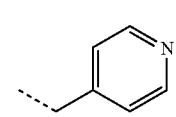 |
| 5-021 | B1 | ----CH$_2$—CH$_2$—CH(CH$_3$)$_2$ | cb | 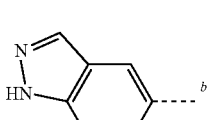 | — |
| 5-022 | B1 | ----CH$_2$—CH$_2$—CH(CH$_3$)$_2$ | cb | 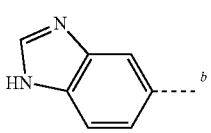 | — |
| 5-024 | B1 | ----CH$_2$—CH$_2$—CH(CH$_3$)$_2$ | cb | 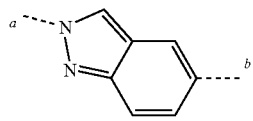 | 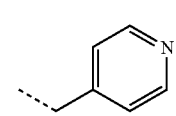 |
| 5-025 | B1 | ----CH$_2$—CH$_2$—CH(CH$_3$)$_2$ | cb | 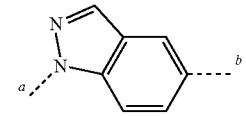 | 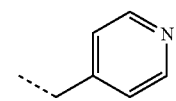 |

TABLE 5-continued

Other compounds prepared according to the Examples wherein A is a N-containing heterocycle

| Co. nr. | Exp nr. | ----V$^1$—M$^1$ | ----L---- | a---A---b | ----R$^4$ |
|---|---|---|---|---|---|
| 5-026 | B1 | ----CH$_2$—CH$_2$—CH(CH$_3$)$_2$ | cb | benzoxazine (N-a, b on ring) | ----CH$_3$ |
| 5-027 | B1 | ----CH$_2$—CH$_2$—CH(CH$_3$)$_2$ | cb | pyrazole (a$_1$ on N, a$_2$, b) | a$_1$ phenyl; a$_2$ ----CH$_3$ |
| 5-028 | B1 | ----CH$_2$—CH$_2$—CH(CH$_3$)$_2$ | cb | thiazole (a$_1$, a$_2$, b) | a$_1$ phenyl; a$_2$ ----CH$_3$ |
| 5-029 | B23 | ----CH$_2$—CH$_2$—CH(CH$_3$)$_2$ | cb | indazole (N-b) | — |
| 5-030 | B23 | ----CH$_2$—CH$_2$—CH(CH$_3$)$_2$ | cb | benzoxazine (N-b) | — |
| 5-031 | B23 | ----CH$_2$—CH$_2$—CH(CH$_3$)$_2$ | cb | tetrahydroquinoline (N-b) | — |
| 5-032 | B23 | ----CH$_2$—CH$_2$—CH(CH$_3$)$_2$ | cb | tetrahydroisoquinoline (a$_1$, a$_2$, N-b) | a$_1$ ----OCH$_3$; a$_2$ ----OCH$_3$ |

TABLE 5-continued
Other compounds prepared according to the Examples wherein A is a N-containing heterocycle
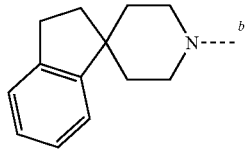
| Co. nr. | Exp nr. | ----V¹—M¹ | ----L---- | a---A---b | ----R⁴ |
|---|---|---|---|---|---|
| 5-033 | B23 | ----CH₂—CH₂—CH(CH₃)₂ | cb |  | — |
| 5-034 | B33 | ----CH₂—CH₂—CH(CH₃)₂ | cb | 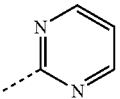 | 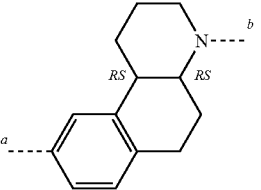 |
| 5-035 | B33 | ----CH₂—CH₂—CH(CH₃)₂ | cb | 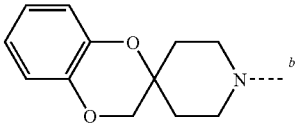 | ----OCH₃ |
| 5-036 | B33 | ----CH₂—CH₂—CH(CH₃)₂ | cb | 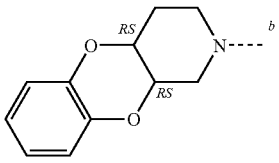 | — |
| 5-037 | B33 | ----CH₂—CH₂—CH(CH₃)₂ | cb | 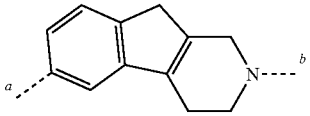 | — |
| 5-038 | B33 | ----CH₂—CH₂—CH(CH₃)₂ | cb | 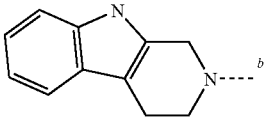 | ----F |
| 5-039 | B33 | ----CH₂—CH₂—CH(CH₃)₂ | cb | 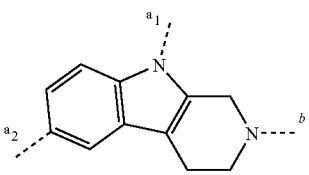 | — |
| 5-040 | B33 | ----CH₂—CH₂—CH(CH₃)₂ | cb |  | $a_1$ ----CH₃<br>$a_2$ ----F |

TABLE 5-continued

Other compounds prepared according to the Examples wherein A is a N-containing heterocycle

| Co. nr. | Exp nr. | ----V¹—M¹ | ----L---- | a---A---b | ----R⁴ |
|---|---|---|---|---|---|
| 5-041 | B33 | ----CH₂—CH₂—CH(CH₃)₂ | cb | benzofuro-tetrahydropyridine | — |
| 5-042 | B33 | ----CH₂—CH₂—CH(CH₃)₂ | cb | benzothieno-tetrahydropyridine | ----Cl |
| 5-043 | B33 | ----CH₂—CH₂—CH(CH₃)₂ | cb | diazepane | phenyl |
| 5-044 | B33 | ----CH₂—CH₂—CH(CH₃)₂ | cb | diazepane | 2-methoxyphenyl |
| 5-045 | B1 | ----CH₂—CH₂—CH(CH₃)₂ | ----OCH₂--- | isoxazole | $a_1$ ----CH₃ ; $a_2$ phenyl |
| 5-046 | B29 | ----CH₂—CH₂—CH(CH₃)₂ | ----O(CH₂)₂---- | isoindoline | ----F |
| 5-047 | B1 | ----CH₂—CH₂—CH(CH₃)₂ | ----NH---- | isoxazole | phenyl |
| 5-048 | B33 | ----CH₂—CH₂—CH(CH₃)₂ | ----N(CH₃)---- | azetidine | diphenylmethyl |
| 5-049 | B10 | cyclohexylmethyl | propynyl | pyridine | — |

TABLE 5-continued

Other compounds prepared according to the Examples wherein A is a N-containing heterocycle

| Co. nr. | Exp nr. | ----V¹—M¹ | ----L---- | a---A---b | ----R⁴ |
|---|---|---|---|---|---|
| 5-050 | B33 | 4-OCF₃-benzyl | cb | (RS)-pyrrolidin-3-yl (a at C3, b at N) | ----N(CH₃)₂ |
| 5-051 | B1 | 4-OCF₃-benzyl | cb | 1H-indol-5-yl (b at C5) | — | a---L---b $^a$ is the side with the R⁴ moiety;
$^b$ is the side with the L moiety

TABLE 6

Compounds prepared according to the Examples wherein R² is not hydrogen.

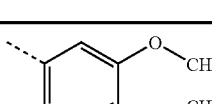

| Co. nr. | Exp. nr. | V¹ | M¹ | R² | ----L—A |
|---|---|---|---|---|---|
| 6-001 | B1 | ----CH₂—CH₂—CH(CH₃)—CH₂--- | ----H | ----CH₃ | 2,3-dimethoxyphenyl |

C. Physico-Chemical Data

LCMS—Methods:
LCMS—General Procedure A

The HPLC gradient was supplied by a Alliance 2795XE comprising a quaternary pump with degasser, an autosampler, a column oven, a photo diode-array detector (PDA 2996) and a column as specified in the respective methods below. Flow from the column was split to a MS detector. MS detectors were configured with electrospray ionization source. Nitrogen was used as the nebulizer gas. Mass spectra were acquired from 50 to 600 in 0.5 seconds. The capillary needle voltage was 3.5 kV and the source temperature was maintained at 140° C. Data acquisition was performed with a Waters-Micromass MassLynx-Openlynx data system.

LCMS—General Procedure B

The HPLC gradient was supplied by a HP 1100 from Agilent Technologies comprising a pump (quaternary or binary) with degasser, an autosampler, a column oven, a diode-array detector (DAD) and a column as specified in the respective methods below. Flow from the column was split to a MS detector. The MS detector was configured with an electrospray ionization source. Nitrogen was used as the nebulizer gas. The source temperature was maintained at 140° C. Data acquisition was performed with MassLynx-Openlynx software.

LCMS—General Procedure C

The LC gradient was supplied by an Acquity HPLC (Waters) system comprising a binary pump, a sample organizer, a column heater (set at 55° C.) and diode-array detector (DAD). Flow from the column was split to a MS detector. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

Method 1

In addition to general procedure A: Reversed phase HPLC was carried out on an Zorbax-C18 cartridge (3.5 µm, 4.6×50 mm) from Agilent Technologies, with a flow rate of 1 ml/min. The column oven was set at 25° C. Two mobile phases (mobile phase A: water+0.5% of formic acid; mobile phase B: acetonitrile+0.5% of formic acid) were used. First, 95% A and 5% B was hold for 0.1 minutes. Then a gradient was applied to 100% B at 5 minutes, kept till 6.0 minutes and equilibrated to initial conditions at 6.5 minutes until 7.0 minutes. Typical injection volumes of 5-20 µl, were used. ES MS detector was used, acquiring both in positive and negative ionization modes. Cone voltage was 30 V for positive and 63 V for negative ionization mode.

Method 2

In addition to general procedure A: Reversed phase HPLC was carried out on an Zorbax-C18 cartridge (1.8 µm, 4.6×30 mm) from Agilent Technologies, with a flow rate of 1.5 ml/min. The column oven was set at 30° C. Two mobile phases (mobile phase A: water+0.05% of formic acid; mobile phase B: acetonitrile+0.05% of formic acid) were used. The gradient conditions used are: 90% A and 10% B to 100% B at 3.5 minutes, kept till 3.7 minutes and equilibrated to initial conditions at 3.8 minutes until 4.5 minutes. Typical injection volumes of 5-20 µl, were used. ES MS detector was used, acquiring both in positive and negative ionization modes. Cone voltage was 30 V for positive and 63 V for negative ionization mode.

Method 3

In addition to general procedure B: Reversed phase HPLC was carried out on an ACE-C18 column (3.0 µm, 4.6×30 mm) from Advanced Chromatography Technologies, with a flow rate of 1.5 ml/min, at 40° C. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 54 High-resolution mass spectra (Time of Flight, TOF) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

Method 4

In addition to general procedure B: Same as Method 3, but using 10 µL of injection volume.

Method 5

In addition to general procedure B: Reversed phase HPLC was carried out on an ACE-C18 column (3.0 µm, 4.6×30 mm) from Advanced Chromatography Technologies, with a flow rate of 1.5 ml/min, at 40° C. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 µl. Low-resolution mass spectra (ZQ detector; quadrupole) were acquired by scanning from 100 to 1000 in 1.0 second using a dwell time of 0.3 seconds. The capillary needle voltage was 3 kV. The cone voltage was 20 V and 50 V for positive ionization mode and 20 V for negative ionization mode.

Method 6

In addition to general procedure C: Reversed phase HPLC was carried out on a bridged ethylsiloxane/silica (BEH) C18 column (1.7 µm, 2.1×50 mm) with a flow rate of 0.8 ml/min. Two mobile phases (mobile phase A: 0.1% formic acid in $H_2O$/methanol 95/5; mobile phase B: methanol) were used to run a gradient condition from 95% A to 5% A, 95% B in 1.3 minutes and hold for 0.2 minutes. An injection volume of 0.5 was used. Cone voltage was 10 V for positive ionization mode and 20 V for negative ionization mode.

Method 7

In addition to general procedure B: Reversed phase HPLC was carried out on an XDB-C18 cartridge (1.8 µm, 2.1×30 mm) from Agilent, at 60° C. with a flow rate of 1 ml/min, at 60° C. The gradient conditions used are: 90% A (0.5 g/l ammonium acetate solution), 5% B (acetonitrile), 5% C (methanol) to 50% B and 50% C in 6.5 minutes, to 100% B at 7 minutes and equilibrated to initial conditions at 7.5 minutes until 9.0 minutes. Injection volume 2 µl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV and the cone voltage was 20 V. Leucine-Enkephaline was the standard substance used for the lock mass calibration.

Method 8

In addition to general procedure B: Reversed phase HPLC was carried out on a XDB-C18 cartridge (1.8 µm, 4.6×30 mm) from Agilent, with a flow rate of 1.5 ml/min, at 60° C. The gradient conditions used are: 80% A (0.5 g/l ammonium acetate solution), 20% B (mixture of Acetonitrile/Methanol, 1/1) to 100% B in 6.5 minutes, kept till 7 minutes and equilibrated to initial conditions at 7.5 minutes until 9.0 minutes. Injection volume 5 µl. Low-resolution mass spectra (ZQ detector; quadrupole) were acquired by scanning from 100 to 1000 in 1.0 second using a dwell time of 0.3 second. The capillary needle voltage was 3 kV. The cone voltage was 20 V and 50 V for positive ionization mode and 20 V for negative ionization mode.

Method 9

In addition to general procedure B: Reversed phase HPLC was carried out on an ACE-C18 column (3.0 4.6×30 mm) from Advanced Chromatography Technologies, with a flow rate of 1.5 ml/min, at 40° C. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 µl. High-resolution mass spectra (Time of Flight, TOF) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Melting point determination was performed in open capillary tubes either on a Buchi B-540 or Mettler FP62.

TABLE 7

Physico-chemical data for the compounds. For salt forms, the [MH+] of the free base was reported.

| Co. Nr | Melting point (° C.) | [MH+] | RT (min) | LCMS Method | Physical form |
|---|---|---|---|---|---|
| 1-003 | | 339 | 4.38 | Method 3 | White solid |
| 1-004 | | 378 | 4.00 | Method 3 | White solid |
| 1-005 | | 413 | 4.54 | Method 3 | Pale yellow solid |
| 1-006 | | 427 | 4.43 | Method 8 | Pale yellow solid |
| 1-007 | 159 | 363 | 2.92 | Method 2 | Light yellow solid |
| 1-008 | 148 | 299 | 4.59 | Method 1 | White solid |
| 1-009 | 149 | 293 | 4.43 | Method 3 | Yellow solid |

TABLE 7-continued

Physico-chemical data for the compounds. For salt forms, the [MH+] of the free base was reported.

| Co. Nr | Melting point (° C.) | [MH+] | RT (min) | LCMS Method | Physical form |
|---|---|---|---|---|---|
| 1-010 | decomposes | 336 | 5.00 | Method 5 | Yellow solid |
| 1-011 | 60 | 323 | 4.43 | Method 3 | Yellow solid |
| 1-012 | decomposes | 323 | 4.55 | Method 3 | Yellow solid |
| 1-013 | 128 | 337 | 2.95 | Method 2 | White solid |
| 1-014 | 143 | 391 | 3.22 | Method 2 | Yellow solid |
| 1-015 | | 307 | | Method 1 | Solid |
| 1-016 | | 331 | 2.56 | Method 2 | Light yellow solid |
| 1-017 | | 331 | 2.60 | Method 2 | Light brown solid |
| 1-018 | 155 | 291 | 4.19 | Method 1 | Yellow solid |
| 1-019 | 118 | 307 | 4.45 | Method 1 | White solid |
| 1-021 | | 331 | 2.59 | Method 2 | Light yellow solid |
| 1-022 | | 335 | 3.92 | Method 3 | Light brown solid |
| 1-023 | | 295 | 1.15 | Method 6 | Beige solid |
| 1-024 | 181 | 385 | 2.70 | Method 2 | Light yellow solid |
| 1-025 | | 397 | 4.92 | Method 3 | Light brown solid |
| 1-026 | | 351 | 2.62 | Method 2 | White solid |
| 1-027 | | 351 | 2.63 | Method 2 | Light yellow solid |
| 1-028 | 180 | 327 | 4.54 | Method 1 | Pink solid |
| 1-030 | 153 | 371 | 2.76 | Method 2 | White solid |
| 1-031 | 167 | 468 | 4.62 | Method 3 | White solid |
| 1-032 | 190 | 456 | 2.70 | Method 2 | Yellow solid |
| 1-033 | 97 | 470 | 4.47 | Method 3 | White solid |
| 1-034 | | 498 | 4.53 | Method 8 | White solid |
| 1-035 | 136 | 498 | 4.52 | Method 8 | White solid |
| 1-036 | | 498 | 5.19 | Method 3 | White solid |
| 1-037 | 184 | 500 | 4.47 | Method 3 | White solid |
| 1-038 | 140 | 514 | 4.64 | Method 3 | White solid |
| 1-039 | 169 | 401 | 2.78 | Method 2 | White solid |
| 1-040 | 180 | 429 | 2.47 | Method 2 | White solid |
| 1-041 | 155 | 463 | 3.17 | Method 2 | Beige solid |
| 1-042 | 185 | 363 | 2.90 | Method 2 | White solid |
| 1-043 | 185 | 288 | 2.71 | Method 1 | Beige solid |
| 1-044 | 141 | 288 | 3.34 | Method 1 | White solid |
| 1-045 | 160 | 288 | 2.81 | Method 1 | Solid |
| 1-046 | 185 | 362 | 3.96 | Method 1 | White solid |
| 1-047 | | 317 | 4.09 | Method 3 | Pale yellow solid |
| 1-048 | 188 | 347 | 4.20 | Method 4 | White solid |
| 1-049 | decomposes | 409 | 5.13 | Method 3 | White solid |
| 1-050 | 135 | 245 | 3.85 | Method 1 | Yellow solid |
| 1-051 | | 305 | 4.29 | Method 1 | Yellow solid |
| 1-052 | 118 | 321 | 4.40 | Method 1 | Yellow solid |
| 1-053 | decomposes | 315 | 4.25 | Method 3 | White solid |
| 1-055 | 123 | 337 | 2.73 | Method 2 | White solid |
| 1-056 | 195 | 352 | 3.64 | Method 7 | Bright yellow solid |
| 1-057 | 136 | 371 | 4.04 | Method 3 | White solid |
| 1-058 | 122 | 336 | 4.72 | Method 7 | Yellow solid |
| 1-059 | 103 | 259 | 4.18 | Method 1 | Yellow solid |
| 1-060 | | 347 | 3.00 | Method 3 | Pale brown solid |
| 1-061 | | 346 | 3.93 | Method 3 | Pale yellow solid |
| 1-062 | | 346 | 3.61 | Method 7 | White solid |
| 1-063 | 102 | 374 | 4.16 | Method 3 | White solid |
| 1-064 | 121 | 360 | 3.97 | Method 7 | White solid |
| 1-065 | | 360 | 4.22 | Method 7 | White solid |
| 1-066 | | 364 | 3.79 | Method 3 | White solid |
| 1-067 | | 414 | 4.68 | Method 7 | White solid |
| 1-068 | decomposes | 414 | 4.67 | Method 7 | Off white solid |
| 1-069 | | 414 | 4.40 | Method 7 | Off white solid |
| 1-070 | | 380 | 4.10 | Method 7 | Off white solid |
| 1-071 | | 371 | 3.86 | Method 7 | White solid |
| 1-072 | | 371 | 3.90 | Method 7 | White solid |
| 1-073 | | 431 | 4.32 | Method 3 | Off white solid |
| 1-074 | | 347 | 3.32 | Method 7 | White solid |
| 1-075 | | 347 | 3.36 | Method 7 | White solid |
| 1-076 | | 347 | 3.55 | Method 7 | White solid |
| 1-077 | 108 | 259 | 3.92 | Method 1 | Beige solid |
| 1-078 | 170 | 346 | 3.06 | Method 8 | White solid |
| 1-079 | 103 | 273 | 4.22 | Method 1 | White solid |
| 1-080 | 149 | 267 | 4.45 | Method 1 | White solid |
| 1-081 | | 257 | 4.13 | Method 1 | Yellow solid |
| 1-082 | 123 | 273 | 4.29 | Method 1 | Yellow solid |
| 1-083 | | 307 | 4.66 | Method 4 | Yellow solid |
| 1-084 | 142 | 267 | 4.25 | Method 1 | White solid |
| 1-085 | 102 | 281 | 2.72 | Method 2 | White solid |
| 1-086 | 168 | 323 | 3.16 | Method 2 | Orange solid |
| 1-087 | 125 | 285 | 3.97 | Method 3 | Pale yellow solid |
| 1-088 | 161 | 285 | 4.09 | Method 4 | White solid |
| 1-089 | decomposes | 285 | 4.07 | Method 3 | White solid |
| 1-090 | 123 | 301 | 2.74 | Method 2 | White solid |
| 1-091 | 137 | 301 | 2.76 | Method 2 | Yellow solid |
| 1-092 | | 423 | 5.01 | Method 3 | White solid |
| 1-093 | 172 | 343 | 3.05 | Method 2 | Off white solid |
| 1-094 | 131 | 343 | 3.03 | Method 2 | Light yellow solid |
| 1-095 | 85 | 325 | 3.76 | Method 1 | White solid |
| 1-096 | 201 | 283 | 3.72 | Method 1 | Light brown solid |
| 1-097 | 210 | 283 | 3.66 | Method 1 | White solid |
| 1-098 | 145 | 297 | 2.04 | Method 2 | White solid |
| 1-099 | | 327 | 3.35 | Method 3 | Beige solid |
| 1-100 | | 297 | 4.11 | Method 5 | Yellow oil |
| 1-101 | 96 | 297 | 4.31 | Method 1 | White solid |
| 1-102 | 99 | 270 | 4.07 | Method 1 | Light yellow solid |
| 1-103 | 91 | 311 | 4.22 | Method 1 | White solid |
| 1-104 | | 311 | 4.52 | Method 3 | Cream solid |
| 1-105 | 107 | 325 | 2.96 | Method 2 | Light orange solid |
| 1-106 | | 339 | 4.54 | Method 3 | Pale yellow solid |
| 1-107 | 67 | 311 | 2.51 | Method 2 | Light yellow solid |
| 1-108 | | 313 | 3.51 | Method 3 | Cream solid |
| 1-109 | | 357 | 3.35 | Method 3 | White solid |
| 1-110 | 52 | 327 | 4.03 | Method 3 | Yellow solid |
| 1-111 | 129 | 325 | 2.89 | Method 2 | Light yellow solid |
| 1-112 | 149 | 331 | 4.33 | Method 7 | White solid |
| 1-113 | 65 | 315 | 4.35 | Method 1 | White solid |
| 1-114 | 133 | 315 | 4.30 | Method 1 | Yellow solid |
| 1-115 | 154 | 357 | 3.06 | Method 2 | White solid |
| 1-116 | | 333 | 2.69 | Method 2 | White oil |
| 1-117 | 166 | 359 | 5.21 | Method 5 | White solid |
| 1-118 | decomposes | 339 | 3.68 | Method 3 | White solid |
| 1-119 | decomposes | 333 | 4.39 | Method 5 | Cream solid |
| 1-120 | | 351 | 4.74 | Method 3 | Yellow solid |
| 1-121 | | 363 | 4.67 | Method 3 | White solid |
| 1-122 | 131 | 381 | 4.61 | Method 3 | White solid |
| 1-123 | 189 | 399 | 4.92 | Method 3 | White solid |
| 1-124 | | 385 | 5.88 | Method 3 | Pale yellow solid |
| 1-125 | | 355 | 4.00 | Method 3 | White solid |
| 1-126 | decomposes | 353 | 4.08 | Method 5 | Cream solid |
| 1-127 | 156 | 354 | 3.52 | Method 1 | White solid |
| 1-128 | 107 | 368 | 2.05 | Method 1 | White solid |
| 1-129 | | 384 | 3.23 | Method 3 | Cream solid |
| 1-130 | 159 | 340 | 3.06 | Method 3 | White Solid |
| 1-131 | 132 | 322 | 2.42 | Method 2 | Pink solid |
| 1-132 | | 336 | 3.98 | Method 3 | White solid |
| 1-133 | | 337 | 4.72 | Method 7 | White solid |
| 1-134 | 294 | 371 | 5.40 | Method 3 | Cream solid |
| 1-135 | | 351 | 5.33 | Method 4 | White solid |
| 1-136 | | 397 | 4.64 | Method 5 | Cream solid |
| 1-137 | | 411 | 4.78 | Method 3 | White solid |
| 1-138 | | 441 | 4.70 | Method 3 | Cream solid |
| 1-139 | | 396 | 3.95 | Method 3 | Pale brown solid |
| 1-140 | | 359 | 5.13 | Method 3 | White solid |
| 1-141 | | 373 | 5.38 | Method 3 | White solid |
| 1-142 | | 403 | 5.01 | Method 3 | White solid |
| 1-143 | 118 | 389 | 3.07 | Method 2 | White solid |
| 1-144 | 100 | 403 | 3.03 | Method 2 | White solid |
| 1-145 | 212 | 403 | 3.02 | Method 2 | White solid |
| 1-146 | 139 | 391 | 3.07 | Method 2 | Whitesolid |
| 1-147 | 146 | 391 | 3.07 | Method 2 | White solid |
| 1-148 | 173 | 391 | 3.06 | Method 2 | Yellow solid |
| 1-149 | 120 | 407 | 3.23 | Method 2 | White solid |
| 1-150 | 177 | 407 | 3.18 | Method 2 | White solid |
| 1-151 | 154 | 398 | 2.89 | Method 2 | White solid |
| 1-152 | 193 | 384 | 2.86 | Method 2 | White solid |
| 1-153 | 171 | 398 | 2.89 | Method 2 | Yellow solid |
| 1-154 | | 360 | 4.23 | Method 3 | White solid |
| 1-155 | 132 | 360 | 4.07 | Method 7 | Off white solid |
| 1-156 | 139 | 360 | 4.09 | Method 3 | Off white solid |
| 1-157 | 162 | 374 | 4.36 | Method 5 | White solid |
| 1-158 | 142 | 374 | 4.23 | Method 5 | Cream solid |

TABLE 7-continued

Physico-chemical data for the compounds. For salt forms, the [MH+] of the free base was reported.

| Co. Nr | Melting point (° C.) | [MH+] | RT (min) | LCMS Method | Physical form |
|---|---|---|---|---|---|
| 1-159 | 171 | 374 | 4.25 | Method 5 | White solid |
| 1-160 |  | 374 | 4.18 | Method 3 | Cream solid |
| 1-161 |  | 378 | 4.17 | Method 3 | White solid |
| 1-162 | 156 | 392 | 4.21 | Method 3 | Pale brown solid |
| 1-163 | 202 | 442 | 2.94 | Method 2 | White solid |
| 1-164 | 165 | 408 | 2.82 | Method 2 | White solid |
| 1-165 |  | 408 | 2.15 | Method 2 | White solid |
| 1-166 |  | 404 | 4.05 | Method 3 | Cream solid |
| 1-167 |  | 404 | 4.05 | Method 3 | White solid |
| 1-168 | decomposes | 364 | 3.27 | Method 5 | Freeze-dried |
| 1-169 | 144 | 3.94 | 2.62 | Method 2 | Beige solid |
| 1-170 |  | 282 | 3.10 | Method 3 | Yellow solid |
| 1-171 | 189 | 296 | 3.97 | Method 3 | Bright yellow solid |
| 1-172 | 137 | 310 | 4.51 | Method 1 | Green solid |
| 1-173 | 130 | 324 | 1.81 | Method 2 | Grey solid |
| 1-174 |  | 340 | 4.02 | Method 9 | Yellow solid |
| 1-175 | 75 | 324 | 3.54 | Method 1 | Brown solid |
| 1-176 | 198 | 324 | 3.55 | Method 1 | White solid |
| 1-177 | 112 | 352 | 2.13 | Method 2 | White solid |
| 1-178 | 157 | 338 | 3.39 | Method 1 | Beige solid |
| 1-179 | 144 | 338 | 3.39 | Method 1 | White solid |
| 1-180 |  |  |  |  | Yellow solid |
| 1-181 | decomposes | 353 | 2.79 | Method 3 | Pale yellow solid |
| 1-182 |  | 367 | 3.31 | Method 3 | Bright yellow solid |
| 1-183 |  | 354 | 5.04 | Method 3 | Pale yellow solid |
| 1-184 |  | 368 | 3.30 | Method 3 | White solid |
| 1-185 |  | 384 | 4.45 | Method 4 | Yellow solid |
| 1-186 | 269 | 321 | 3.47 | Method 3 | Pale brown solid |
| 1-187 |  | 322 | 4.52 | Method 3 | Yellow |
| 1-188 |  | 364 | 5.66 | Method 3 | Bright yellow solid |
| 1-189 |  | 384 | 4.22 | Method 3 | Yellow solid |
| 1-190 |  | 384 | 4.21 | Method 7 | Yellow solid |
| 1-191 | decomposes | 400 | 4.48 | Method 7 | Pale yellow solid |
| 1-192 | 119 |  |  |  | Bright yellow solid |
| 1-193 |  | 358 | 5.21 | Method 3 | Brown solid |
| 1-194 |  | 372 | 5.17 | Method 3 | Yellow solid |
| 1-195 |  | 372 | 5.35 | Method 3 | Bright yellow oil |
| 1-196 |  | 386 | 5.33 | Method 3 | Yellow solid |
| 1-197 |  | 418 | 5.47 | Method 3 | White solid |
| 1-198 |  | 404 | 4.71 | Method 3 | White solid |
| 1-199 | 136 | 390 | 2.93 | Method 2 | Yellow solid |
| 1-200 | 162 | 390 | 2.94 | Method 2 | Yellow solid |
| 1-201 |  | 342 | 3.35 | Method 3 | Cream solid |
| 1-202 | 146 | 406 | 3.07 | Method 2 | Yellow solid |
| 1-203 | 173 | 402 | 2.90 | Method 2 | Yellow solid |
| 1-204 | 157 | 397 | 2.75 | Method 2 | Yellow solid |
| 1-205 |  | 456 | 5.69 | Method 3 | Yellow solid |
| 1-206 | 209 | 397 | 2.74 | Method 2 | Yellow solid |
| 1-207 |  | 379 | 2.68 | Method 3 | Yellow solid |
| 1-208 |  | 359 | 3.35 | Method 7 | Pale yellow solid |
| 1-209 |  | 373 | 4.08 | Method 3 | Yellow solid |
| 1-210 | 73 | 373 | 4.01 | Method 3 | Yellow solid |
| 1-211 | 142 | 401 | 4.53 | Method 3 | Pale yellow solid |
| 1-212 | 294 | 401 | 4.44 | Method 3 | Pale yellow solid |
| 1-213 | 96 | 401 | 1.61 | Method 2 | White solid |
| 1-214 |  | 326 | 4.26 | Method 3 | Brown solid |
| 1-215 | 70 | 360 | 3.70 | Method 1 | White solid |
| 1-216 | 191 | 360 | 3.67 | Method 1 | White solid |
| 1-217 |  | 414 | 3.49 | Method 7 | Bright yellow solid |
| 1-218 |  | 336 | 5.10 | Method 3 | Yellow solid |
| 1-219 |  | 350 | 5.32 | Method 5 | Bright yellow solid |
| 1-220 | 213 | 366 | 3.79 | Method 3 | Yellow solid |
| 1-221 |  | 380 | 4.60 | Method 4 | Yellow solid |
| 1-222 |  | 352 | 4.17 | Method 5 | Yellow solid |
| 1-223 | 171 | 352 | 4.09 | Method 3 | Yellow solid |
| 1-224 | decomposes | 368 | 3.67 | Method 4 | Yellow solid |
| 1-225 | 151 | 382 | 4.08 | Method 3 | Yellow solid |
| 1-226 | 118 | 430 | 4.80 | Method 3 | Yellow solid |
| 1-227 | 162 | 380 | 4.79 | Method 3 | Yellow solid |
| 1-228 | 148 | 400 | 5.19 | Method 3 | Bright yellow solid |
| 1-229 | 148 | 366 | 3.94 | Method 3 | White solid |
| 1-230 | 143 | 393 | 3.98 | Method 3 | Yellow solid |
| 1-231 | decomposes | 393 | 3.68 | Method 3 | Yellow solid |
| 1-232 |  | 391 | 4.77 | Method 3 | Yellow solid |
| 1-233 |  | 427 | 5.45 | Method 4 | Orange solid |
| 1-234 |  | 428 | 3.94 | Method 3 | Orange solid |
| 1-235 | 151 | 333 | 3.57 | Method 5 | White solid |
| 1-236 | decomposes | 334 | 3.50 | Method 5 | Pale yellow solid |
| 1-237 |  |  |  |  | Yellow solid |
| 1-238 | 130 | 309 | 4.02 | Method 1 | Beige Solid |
| 1-239 | 120 | 353 | 4.34 | Method 1 | Yellow solid |
| 1-240 | 169 | 339 | 3.73 | Method 1 | White solid |
| 1-241 | 172 | 338 | 1.94 | Method 2 | White solid |
| 1-242 | (oil) | 325 | 2.54 | Method 2 | Black oil |
| 1-243 | 166 | 338 | 2.05 | Method 2 | Off white solid |
| 1-244 | 122 | 352 | 2.10 | Method 2 | White solid |
| 1-245 | 135-140 | 414 | 2.62 | Method 2 | White solid |
| 1-246 |  | 350 | 3.50 | Method 3 | Cream solid |
| 1-247 | 217 | 587 | 5.02 | Method 8 | White solid |
| 1-248 |  | 347 | 3.44 | Method 3 | White solid |
| 1-249 |  | 350 | 3.68 | Method 7 | Yellow solid |
| 1-250 |  | 334 | 3.89 | Method 3 | White solid |
| 1-251 | 117 | 309 | 4.09 | Method 3 | Off white solid |
| 1-252 | 120-121 | 311 | 4.24 | Method 1 | Beige solid |
| 1-253 |  | 325 | 4.14 | Method 3 | White solid |
| 1-254 | 122 | 306 | 2.37 | Method 2 | White solid |
| 1-255 | 233 | 494 | 2.78 | Method 2 | Yellow solid |
| 1-256 | 128 | 313 | 4.55 | Method 1 | Yellow solid |
| 1-257 | 181 | 345 | 3.69 | Method 1 | White solid |
| 1-258 |  | 390 | 4.35 | Method 4 | Colourless oil |
| 1-259 |  | 323 | 4.62 | Method 3 | Pale grey solid |
| 1-260 |  | 295 | 4.46 | Method 4 | White solid |
| 1-261 |  | 293 | 4.70 | Method 3 | Yellow solid |
| 1-262 |  | 338 | 4.75 | Method 3 | White solid |
| 1-263 | decomposes | 338 | 4.83 | Method 5 | Creamy green solid |
| 1-264 |  | 325 | 4.46 | Method 3 | White solid |
| 1-265 | 88 | 325 | 4.52 | Method 5 | White solid |
| 1-266 |  | 323 | 4.51 | Method 3 | Yellow solid |
| 1-267 |  | 291 | 4.78 | Method 3 | Brown solid |
| 1-268 |  | 321 | 4.85 | Method 3 | Cream solid |
| 1-269 |  | 334 | 5.24 | Method 3 | White solid |
| 1-270 | 166 | 334 | 5.24 | Method 5 | Orange solid |
| 1-271 |  | 500 | 4.41 | Method 3 | White solid |
| 1-272 |  | 401 | 4.78 | Method 3 | White solid |
| 1-273 |  | 347 | 4.15 | Method 7 | White solid |
| 1-274 | decomposes | 283 | 4.05 | Method 3 | White solid |
| 1-275 | 174 | 297 | 4.10 | Method 5 | White solid |
| 1-276 |  | 311 | 4.33 | Method 5 | White |
| 1-277 |  | 365 | 4.65 | Method 3 | White solid |
| 1-278 |  | 375 | 4.54 | Method 3 | White solid |
| 1-279 | 116 | 381 | 4.69 | Method 3 | White solid |
| 1-280 |  | 327 | 4.18 | Method 5 | White solid |
| 1-281 | 83 | 341 | 4.21 | Method 5 | White solid |
| 1-282 | 153 | 313 | 4.12 | Method 3 | White solid |
| 1-283 |  | 345 | 4.08 | Method 3 | Pale pink solid |
| 1-284 | 190 | 363 | 4.32 | Method 5 | White solid |
| 1-285 | 200 | 381 | 4.83 | Method 5 | White solid |
| 1-286 |  | 322 | 3.73 | Method 3 | Pale yellow solid |
| 1-287 |  | 397 | 4.99 | Method 3 | Pale yellow solid |
| 1-288 | 169 | 323 | 4.30 | Method 3 | White solid |
| 1-289 |  | 403 | 5.02 | Method 3 | Pale yellow |
| 1-290 | 148 | 445 | 5.24 | Method 3 | White solid |
| 1-291 |  | 352 | 5.16 | Method 3 | Pale yellow solid |
| 1-292 | 154 | 396 | 3.82 | Method 3 | White solid |
| 1-293 | 209 | 372 | 4.43 | Method 3 | White solid |
| 1-294 |  | 306 | 3.97 | Method 3 | White solid |
| 1-295 |  | 359 | 3.31 | Method 3 | Yellow solid |
| 1-296 | 151 | 361 | 3.57 | Method 7 | Off white solid |
| 1-297 |  | 350 | 4.78 | Method 7 | Pale yellow solid |
| 1-298 | decomposes | 282 | 3.97 | Method 3 | Cream solid |
| 1-299 |  | 296 | 4.00 | Method 3 | Pale brown oil |
| 1-300 | decomposes | 367 | 3.91 | Method 3 | White solid |
| 1-301 | decomposes | 374 | 5.13 | Method 3 | Yellow solid |
| 1-302 |  | 375 | 4.01 | Method 3 | Yellow solid |
| 1-303 |  | 310 | 4.14 | Method 3 | White solid |
| 1-304 |  | 322 | 4.51 | Method 7 | White solid |

TABLE 7-continued

Physico-chemical data for the compounds. For salt forms, the [MH+] of the free base was reported.

| Co. Nr | Melting point (° C.) | [MH+] | RT (min) | LCMS Method | Physical form |
|---|---|---|---|---|---|
| 1-306 |  | 374 | 4.22 | Method 7 |  |
| 2-001 | 183 | 437 | 4.95 | Method 3 | Pale yellow solid |
| 2-002 | 127 | 469 | 5.26 | Method 3 | White solid |
| 2-003 | 134 | 455 | 5.13 | Method 3 | Pale yellow solid |
| 2-004 |  | 338 | 3.36 | Method 3 | Pale yellow solid |
| 2-005 |  | 367 | 4.07 | Method 3 | White solid |
| 2-006 |  | 379 | 4.08 | Method 3 | Pale yellow solid |
| 2-007 |  | 369 | 3.76 | Method 3 | Off white solid |
| 2-008 |  | 382 | 3.45 | Method 3 | Pale yellow solid |
| 2-009 |  | 424 | 3.34 | Method 3 | Pale yellow solid |
| 2-010 | 112 | 469 | 5.21 | Method 3 | White solid |
| 2-011 |  | 351 | 4.40 | Method 3 | Yellow solid |
| 2-012 |  | 365 | 4.44 | Method 3 | White solid |
| 2-013 |  | 381 | 4.32 | Method 3 | Pale yellow solid |
| 2-014 |  | 433 | 5.04 | Method 3 | White solid |
| 2-015 | decomposes | 401 | 4.66 | Method 3 | Beige solid |
| 2-016 |  | 409 | 4.33 | Method 3 | White solid |
| 2-017 |  | 379 | 4.55 | Method 3 | Pale brown solid |
| 2-018 |  | 391 | 4.75 | Method 3 | Pale yellow oil |
| 2-019 |  | 413 | 4.49 | Method 3 | Yellow gum |
| 2-020 |  | 463 | 5.05 | Method 3 | Pale yellow solid |
| 2-021 |  | 379 | 4.99 | Method 3 | Pale yellow solid |
| 2-022 | 256 | 483 | 5.49 | Method 3 | White solid |
| 2-023 |  | 366 | 3.32 | Method 3 | Yellow gum |
| 2-024 |  | 352 | 3.83 | Method 3 | Yellow solid |
| 2-025 |  | 366 | 4.17 | Method 3 | Yellow solid |
| 2-026 | 135 | 420 | 4.69 | Method 3 | White solid |
| 2-027 |  | 377 | 3.72 | Method 3 | Off white solid |
| 2-028 |  | 353 | 3.56 | Method 3 | Pale creamy solid |
| 2-029 | 155 | 421 | 4.71 | Method 3 | Pale brown solid |
| 2-030 |  | 353 | 2.80 | Method 3 | Yellow solid |
| 2-031 | 245 | 387 | 3.38 | Method 3 | Yellow solid |
| 2-032 |  | 383 | 3.40 | Method 3 | Yellow solid |
| 2-033 |  | 429 | 4.23 | Method 3 | Yellow gum |
| 2-034 | decomposes | 417 | 3.89 | Method 3 | Pale yellow solid |
| 2-035 | 288 | 392 | 4.15 | Method 3 | White solid |
| 2-036 | 159 | 396 | 3.67 | Method 3 | Off white solid |
| 2-037 | 223 |  |  |  | White solid |
| 2-038 | 140 | 435 | 4.73 | Method 3 | White solid |
| 2-039 | 125 | 467 | 5.05 | Method 3 | White solid |
| 2-040 | 157 |  |  |  | Pale yellow solid |
| 2-041 | decomposes | 365 | 3.38 | Method 3 | Pale brown solid |
| 2-042 | decomposes | 469 | 4.91 | Method 3 | White solid |
| 2-043 | 110 | 483 | 4.97 | Method 3 | Pale yellow solid |
| 2-044 | 156 | 487 | 4.93 | Method 4 | White solid |
| 2-045 | decomposes | 519 | 5.47 | Method 3 | Pale yellow solid |
| 2-046 | 92 | 497 | 3.96 | Method 8 | Yellow solid |
| 2-047 |  | 470 | 3.94 | Method 3 | Yellow solid |
| 2-048 | 258 | 524 | 5.04 | Method 3 | White solid |
| 2-049 |  | 403 | 4.27 | Method 4 | Light brown solid |
| 2-050 |  | 421 | 4.39 | Method 3 | White solid |
| 2-051 | 239 | 439 | 4.49 | Method 3 | White solid |
| 2-052 |  | 439 | 4.59 | Method 3 | White solid |
| 2-053 |  | 415 | 4.48 | Method 3 | White solid |
| 2-054 |  | 429 | 4.42 | Method 3 | Yellow oil |
| 2-055 |  | 390 | 3.59 | Method 3 | White solid |
| 3-001 | 124 | 338 | 3.57 | Method 7 | Pale yellow solid |
| 3-002 |  |  |  |  | White solid |
| 3-003 | 125 | 379 | 4.41 | Method 3 | White solid |
| 3-004 | 188 | 434 | 4.90 | Method 3 | Off white solid |
| 3-005 |  | 393 | 4.47 | Method 3 | White solid |
| 3-006 | 131 | 461 | 5.22 | Method 3 | White solid |
| 3-007 | 208 | 380 | 4.35 | Method 3 | White solid |
| 3-008 |  | 448 | 5.10 | Method 3 | Pale brown solid |
| 3-009 | 117 | 462 | 5.20 | Method 3 | Off white solid |
| 3-010 | 187 |  |  |  | White solid |
| 3-011 | decomposes | 351 | 2.55 | Method 3 | White solid |
| 3-012 |  | 432 | 4.60 | Method 3 | Cream solid |
| 3-013 | 211 | 497 | 4.95 | Method 3 | White solid |
| 3-014 |  | 432 | 5.35 | Method 3 | White solid |
| 4-001 |  | 337 | 3.28 | Method 3 | White solid |
| 4-002 |  | 337 | 3.22 | Method 7 | White solid |
| 4-003 | 132 | 351 | 3.33 | Method 7 |  |
| 4-004 |  | 353 | 3.20 | Method 3 | Cream solid |
| 4-005 | 188 | 353 | 3.87 | Method 3 | Cream solid |
| 4-006 |  | 367 | 3.94 | Method 7 | White solid |
| 4-007 |  | 367 | 3.51 | Method 7 | Pale yellow solid |
| 4-008 |  | 381 | 3.79 | Method 7 | White solid |
| 4-009 |  | 377 | 3.91 | Method 7 | White solid |
| 4-010 |  | 342 | 4.19 | Method 3 | White solid |
| 4-012 | 296 | 378 | 4.48 | Method 3 | White solid |
| 4-013 |  | 350 | 5.06 | Method 3 | White solid |
| 4-014 | decomposes | 350 | 4.76 | Method 3 | White solid |
| 4-015 |  | 364 | 5.33 | Method 3 | Yellow oil |
| 4-016 | 112 | 418 | 5.09 | Method 7 | White solid |
| 4-017 |  | 380 | 5.18 | Method 3 | White solid |
| 4-018 |  | 384 | 4.94 | Method 3 | White solid |
| 4-019 | 100 | 412 | 5.18 | Method 3 | White solid |
| 4-020 |  | 448 | 5.43 | Method 3 | White gummy solid |
| 4-021 | decomposes | 410 | 4.82 | Method 3 | White solid |
| 4-022 |  | 464 | 5.30 | Method 3 | White solid |
| 4-023 |  | 365 | 4.43 | Method 3 | Beige solid |
| 4-025 | 283 | 447 | 4.63 | Method 3 | White solid |
| 4-026 |  | 393 | 4.41 | Method 3 | Brown solid |
| 4-027 | 113 | 411 | 4.57 | Method 3 | White solid |
| 4-028 |  | 461 | 5.25 | Method 3 | White solid |
| 4-029 | 91 | 461 | 5.28 | Method 3 | White solid |
| 4-030 |  | 425 | 5.09 | Method 3 | White foam |
| 4-031 | 141 | 447 | 5.31 | Method 3 | White solid |
| 4-032 |  | 475 | 5.02 | Method 3 |  |
| 4-033 |  | 475 | 5.03 | Method 3 | Yellow solid |
| 4-034 | 253 | 405 | 4.4 | Method 3 | Pale brown solid |
| 4-035 |  | 389 | 4.93 | Method 3 | Pale yellow solid |
| 4-036 |  | 405 | 5.29 | Method 3 | Browm gummy oil |
| 4-037 | 78 | 407 | 4.86 | Method 3 | Yellow solid |
| 4-038 | 214 | 391 | 4.35 | Method 3 | Beige solid |
| 4-039 | 123 | 408 | 5.09 | Method 3 | White solid |
| 4-040 | 113 | 412 | 4.91 | Method 3 | Pale cream solid |
| 4-041 |  | 418 | 4.82 | Method 3 | Pale brown solid |
| 4-042 | decomposes | 433 | 4.13 | Method 7 | Yellow solid |
| 4-043 | 138 | 379 | 4.64 | Method 3 | White solid |
| 4-044 |  | 435 | 4.53 | Method 3 | Pale yellow solid |
| 4-045 |  | 380 | 4.93 | Method 3 | White solid |
| 4-046 | 282 | 414 | 3.73 | Method 3 | White solid |
| 4-047 | 128 | 334 | 4.05 | Method 7 | White solid |
| 4-048 |  | 378 | 4.38 | Method 7 | Off white solid |
| 4-049 | 138 | 497 | 4.89 | Method 3 | White solid |
| 4-050 | decomposes | 491 | 4.20 | Method 3 | White solid |
| 4-051 | decomposes | 509 | 4.88 | Method 3 | Pale brown solid |
| 4-052 |  | 499 | 4.39 | Method 3 | Pale brown solid |
| 4-053 |  | 485 | 3.85 | Method 7 | Yellow solid |
| 4-054 |  |  |  |  | Cream solid |
| 4-055 | 155 | 435 | 3.85 | Method 3 | Cream solid |
| 4-056 |  | 431 | 4.16 | Method 3 | Cream solid |
| 4-057 | 242 | 449 | 4.54 | Method 3 | Cream solid |
| 4-058 |  | 499 | 5.05 | Method 3 | White solid |
| 4-059 | 157 | 475 | 5.27 | Method 3 | White solid |
| 4-060 | 96 |  |  |  | Off white solid |
| 4-061 | 175 | 447 | 4.20 | Method 3 | Cream solid |
| 4-062 | 139 | 454 | 5.06 | Method 3 | White solid |
| 4-063 |  | 471 | 3.56 | Method 7 | Off white solid |
| 4-064 | 159 | 443 | 4.43 | Method 3 | White solid |
| 4-065 |  | 511 | 5.24 | Method 3 | White solid |
| 4-066 |  | 400 | 4.83 | Method 3 | White solid |
| 5-001 | decomposes | 384 | 3.31 | Method 3 | Off white solid |
| 5-002 | 164.7 | 398 | 3.24 | Method 3 | White solid |
| 5-003 | decomposes | 322 | 4.33 | Method 3 | White solid |
| 5-004 |  | 377 | 4.2 | Method 3 | Pale cream gum |
| 5-005 | 96 | 447 | 5.16 | Method 3 | White solid |
| 5-006 | 100 | 397 | 4.71 | Method 3 | White solid |
| 5-007 |  | 350 | 4.75 | Method 3 | Colourless oil |
| 5-008 | 102 | 436 | 5.11 | Method 3 | White solid |
| 5-009 |  | 473 | 4.97 | Method 3 | White solid |
| 5-010 | 118 | 298 | 2.37 | Method 2 | White solid |
| 5-011 |  | 326 | 2.96 | Method 3 | Pale brown solid |
| 5-012 |  | 257 | 2.72 | Method 3 | White solid |

TABLE 7-continued

Physico-chemical data for the compounds. For salt forms, the [MH+] of the free base was reported.

| Co. Nr | Melting point (° C.) | [MH+] | RT (min) | LCMS Method | Physical form |
|---|---|---|---|---|---|
| 5-013 | | 347 | 4.26 | Method 3 | White solid |
| 5-014 | | 308 | 3.92 | Method 5 | Orange solid |
| 5-015 | | 350 | 3.75 | Method 5 | Pale yellow solid |
| 5-016 | decomposes | 306 | 3.93 | Method 3 | Pale brown solid |
| 5-017 | decomposes | 306 | 3.84 | Method 3 | Pale green solid |
| 5-018 | 281 | 320 | 4.37 | Method 3 | Pale yellow solid |
| 5-019 | | 382 | 5.31 | Method 3 | Pale yellow solid |
| 5-020 | 232 | 397 | 4.21 | Method 3 | Cream solid |
| 5-021 | decomposes | 307 | 3.31 | Method 3 | Syrup |
| 5-022 | | 307 | 2.93 | Method 3 | Beige solid |
| 5-023 | decomposes | 384 | 3.51 | Method 3 | Cream solid |
| 5-024 | 284 | 398 | 3.53 | Method 3 | Cream solid |
| 5-025 | | 398 | 3.72 | Method 3 | Cream solid |
| 5-026 | decomposes | 338 | 4.43 | Method 5 | Bright yellow solid |
| 5-027 | decomposes | 347 | 4.08 | Method 7 | White solid |
| 5-028 | | 364 | 4.87 | Method 3 | White solid |
| 5-029 | 234 | 307 | 3.89 | Method 3 | Pale yellow solid |
| 5-030 | | 324 | 4.4 | Method 3 | Cream solid |
| 5-031 | 134 | 322 | 4.72 | Method 3 | Yellow solid |
| 5-032 | | 382 | 4.04 | Method 3 | White solid |
| 5-033 | | 376 | 5.35 | Method 3 | White solid |
| 5-034 | | 421 | 4.44 | Method 3 | Pale cream solid |
| 5-035 | 169 | 406 | 5.04 | Method 3 | White solid |
| 5-036 | | 394 | 4.96 | Method 3 | White solid |
| 5-037 | 217 | 380 | 4.57 | Method 3 | Cream solid |
| 5-038 | 141 | | | | Cream solid |
| 5-039 | 276 | 361 | 4.52 | Method 3 | White solid |
| 5-040 | 111 | 393 | 4.87 | Method 3 | Cream solid |
| 5-041 | 130 | 362 | 4.85 | Method 3 | White solid |
| 5-042 | | 412 | 5.73 | Method 3 | Pale yellow |
| 5-043 | decomposes | 365 | 4.57 | Method 3 | Pale yellow solid |
| 5-044 | | 395 | 4.51 | Method 3 | Brown gummy solid |
| 5-045 | | 378 | 4.06 | Method 3 | White solid |
| 5-046 | | 370 | 4.08 | Method 4 | White solid |
| 5-047 | | 349 | 4.37 | Method 3 | White solid |
| 5-048 | | 441 | 5.22 | Method 3 | Colourless oil |
| 5-049 | | 318 | 4.39 | Method 3 | Pale grey solid |
| 5-050 | | 407 | 3.66 | Method 3 | White solid |
| 5-051 | 166 | 410 | 2.63 | Method 2 | Grey solid |
| 6-001 | 175 | 341 | 5.54 | Method 2 | Beige solid | decomposes = product decomposes in the course of the determination.

D. Pharmacological Examples

The compounds provided in the present invention are positive allosteric modulators of mGluR2. These compounds appear to potentiate glutamate responses by binding to an allosteric site other than the glutamate binding site. The response of mGluR2 to a concentration of glutamate is increased when compounds of Formula (I) are present. Compounds of Formula (I) are expected to have their effect substantially at mGluR2 by virtue of their ability to enhance the function of the receptor. The behaviour of positive allosteric modulators tested at mGluR2 using the [$^{35}$S]GTPγS binding assay method described below and which is suitable for the identification of such compounds, and more particularly the compounds according to Formula (I), are shown in Table 4.

[$^{35}$S]GTPγS Binding Assay

The [$^{35}$S]GTPγS binding is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein α subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the agonist can be determined. mGluR2 receptors are shown to be preferentially coupled to Gαi-protein, a preferential coupling for this method, and hence it is widely used to study receptor activation of mGluR2 receptors both in recombinant cell lines and in tissues (Schaffhauser et al 2003, Pinkerton et al, 2004, Mutel et al (1998) Journal of Neurochemistry. 71:2558-64; Schaffhauser et al (1998) Molecular Pharmacology 53:228-33). Here we describe the use of the [$^{35}$S]GTPγS binding assay using membranes from cells transfected with the human mGluR2 receptor and adapted from Schaffhauser et al ((2003) Molecular Pharmacology 4:798-810) for the detection of the positive allosteric modulation (PAM) properties of the compounds of this invention.

Membrane Preparation

CHO-cells were cultured to pre-confluence and stimulated with 5 mM butyrate for 24 hours, prior to washing in PBS, and then collection by scraping in homogenisation buffer (50 mM Tris-HCl buffer, pH 7.4, 4° C.). Cell lysates were homogenized briefly (15 s) using an ultra-turrax homogenizer. The homogenate was centrifuged at 23 500×g for 10 minutes and the supernatant discarded. The pellet was resuspended in 5 mM Tris-HCl, pH 7.4 and centrifuged again (30 000×g, 20 min, 4° C.). The final pellet was resuspended in 50 mM HEPES, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 positive allosteric modulators in membranes containing human mGluR2 was performed using frozen membranes that were thawed and briefly homogenised prior to pre-incubation in 96-well microplates (15 μg/assay well, 30 minutes, 30° C.) in assay buffer (50 mM HEPES pH 7.4, 100 mM NaCl, 3 mM MgCl$_2$, 50 μM GDP, 10 μg/ml saponin), with increasing concentrations of positive allosteric modulator (from 0.3 nM to 50 μM) and either a minimal pre-determined concentration of glutamate (PAM assay), or no added glutamate. For the PAM assay, membranes were pre-incubated with glutamate at EC$_{25}$ concentration, i.e. a concentration that gives 25% of the maximal response glutamate, and is in accordance to published data (Pin et al. (1999) Eur. J. Pharmacol. 375:277-294). After addition of [$^{35}$S]GTPγS (0.1 nM, f.c.) to achieve a total reaction volume of 200 μl, microplates were shaken briefly and further incubated to allow [$^{35}$S]GTPγS incorporation on activation (30 minutes, 30° C.). The reaction was stopped by rapid vacuum filtration over glass-fibre filter plates (Unifilter 96-well GF/B filter plates, Perkin-Elmer, Downers Grove, USA) microplate using a 96-well plate cell harvester (Filtermate, Perkin-Elmer, USA), and then by washing three times with 300 μl of ice-cold wash buffer (Na$_2$PO$_4$.2H$_2$O 10 mM, NaH$_2$PO$_4$.H$_2$O 10 mM, pH=7.4). Filters were then air-dried, and 40 μl of liquid scintillation cocktail (Microscint-O) was added to each well, and membrane-bound [$^{35}$S]GTPγS was measured in a 96-well scintillation plate reader (Top-Count, Perkin-Elmer, USA). Non-specific [$^{35}$S]GTPγS binding is determined in the presence of cold 10 μM GTP. Each curve was performed at least once using duplicate sample per data point and at 11 concentrations.

Data Analysis

The concentration-response curves of representative compounds of the present invention in the presence of added EC$_{25}$ of mGluR2 agonist glutamate to determine positive allosteric modulation (PAM), were generated using the Prism Graph-Pad software (Graph Pad Inc, San Diego, USA). The curves were fitted to a four-parameter logistic equation (Y=Bottom+(Top−Bottom)/(1+10^((LogEC$_{50}$−X)*Hill Slope) allowing determination of EC$_{50}$ values.

TABLE 8

Pharmacological data for compounds according to the invention. All compounds were tested in presence of mGluR2 agonist, glutamate at a predetermined EC$_{25}$ concentration, to determine positive allosteric modulation (GTPγS-PAM). Values shown are averages of duplicate values of 11-concentration response curves, from at least one experiment. All compounds showed a pEC$_{50}$ value of more than 5.0, from 5.1 (weak activity) to 7.6 (very high activity). The error of determination of a pEC$_{50}$ value for a single experiment is estimated to be about 0.3 log-units.

| Co. Nr. | GTPgS-hR2 PAM pEC$_{50}$ |
|---|---|
| 1-093 | 7.6 |
| 5-020 | 7.6 |
| 1-204 | 7.6 |
| 1-202 | 7.5 |
| 4-065 | 7.5 |
| 4-066 | 7.5 |
| 1-140 | 7.4 |
| 1-196 | 7.4 |
| 5-033 | 7.4 |
| 4-062 | 7.4 |
| 4-039 | 7.4 |
| 1-151 | 7.4 |
| 1-145 | 7.4 |
| 1-268 | 7.3 |
| 4-016 | 7.3 |
| 1-188 | 7.3 |
| 1-124 | 7.3 |
| 5-041 | 7.3 |
| 1-153 | 7.3 |
| 1-149 | 7.3 |
| 5-019 | 7.3 |
| 4-022 | 7.3 |
| 1-148 | 7.3 |
| 1-206 | 7.3 |
| 4-060 | 7.3 |
| 1-194 | 7.2 |
| 1-141 | 7.2 |
| 1-117 | 7.2 |
| 4-014 | 7.2 |
| 1-287 | 7.2 |
| 1-086 | 7.2 |
| 1-092 | 7.2 |
| 1-144 | 7.2 |
| 1-146 | 7.2 |
| 1-199 | 7.2 |
| 4-031 | 7.2 |
| 1-267 | 7.1 |
| 1-289 | 7.1 |
| 5-039 | 7.1 |
| 1-134 | 7.1 |
| 2-048 | 7.1 |
| 4-019 | 7.1 |
| 1-147 | 7.1 |
| 1-228 | 7.1 |
| 1-143 | 7.1 |
| 1-200 | 7.1 |
| 1-165 | 7.1 |
| 1-163 | 7.1 |
| 1-150 | 7.1 |
| 1-010 | 7.0 |
| 1-270 | 7.0 |
| 1-014 | 7.0 |
| 1-115 | 7.0 |
| 4-015 | 7.0 |
| 4-035 | 7.0 |
| 4-028 | 7.0 |
| 1-152 | 7.0 |
| 1-025 | 7.0 |
| 1-172 | 6.9 |
| 1-285 | 6.9 |
| 1-187 | 6.9 |
| 1-024 | 6.9 |
| 1-013 | 6.9 |
| 1-195 | 6.9 |
| 1-272 | 6.9 |
| 4-020 | 6.9 |
| 4-045 | 6.9 |
| 4-017 | 6.9 |
| 4-037 | 6.9 |
| 5-018 | 6.9 |
| 4-041 | 6.9 |
| 1-226 | 6.9 |
| 1-049 | 6.9 |
| 4-064 | 6.9 |
| 4-029 | 6.9 |
| 1-256 | 6.8 |
| 1-290 | 6.8 |
| 1-269 | 6.8 |
| 1-042 | 6.8 |
| 1-039 | 6.8 |
| 1-123 | 6.8 |
| 1-164 | 6.8 |
| 3-009 | 6.8 |
| 2-022 | 6.8 |
| 1-271 | 6.8 |
| 2-003 | 6.8 |
| 1-004 | 6.8 |
| 2-006 | 6.8 |
| 1-067 | 6.8 |
| 1-083 | 6.7 |
| 1-218 | 6.7 |
| 5-026 | 6.7 |
| 1-219 | 6.7 |
| 1-133 | 6.7 |
| 3-014 | 6.7 |
| 2-026 | 6.7 |
| 1-301 | 6.7 |
| 1-259 | 6.7 |
| 1-040 | 6.7 |
| 5-042 | 6.7 |
| 1-261 | 6.7 |
| 5-038 | 6.7 |
| 4-021 | 6.7 |
| 4-049 | 6.7 |
| 5-048 | 6.7 |
| 2-017 | 6.7 |
| 1-297 | 6.7 |
| 1-008 | 6.6 |
| 5-016 | 6.6 |
| 5-003 | 6.6 |
| 1-277 | 6.6 |
| 5-051 | 6.6 |
| 1-041 | 6.6 |
| 1-205 | 6.6 |
| 5-036 | 6.6 |
| 5-008 | 6.6 |
| 4-036 | 6.6 |
| 2-029 | 6.6 |
| 1-183 | 6.6 |
| 2-043 | 6.6 |
| 4-058 | 6.6 |

TABLE 8-continued

Pharmacological data for compounds according to the invention. All compounds were tested in presence of mGluR2 agonist, glutamate at a predetermined $EC_{25}$ concentration, to determine positive allosteric modulation (GTPγS-PAM). Values shown are averages of duplicate values of 11-concentration response curves, from at least one experiment. All compounds showed a $pEC_{50}$ value of more than 5.0, from 5.1 (weak activity) to 7.6 (very high activity). The error of determination of a $pEC_{50}$ value for a single experiment is estimated to be about 0.3 log-units.

| Co. Nr. | GTPgS-hR2 PAM $pEC_{50}$ |
|---|---|
| 1-197 | 6.6 |
| 4-059 | 6.6 |
| 3-004 | 6.6 |
| 1-068 | 6.6 |
| 1-258 | 6.5 |
| 1-112 | 6.5 |
| 1-180 | 6.5 |
| 1-266 | 6.5 |
| 5-028 | 6.5 |
| 1-142 | 6.5 |
| 1-030 | 6.5 |
| 1-278 | 6.5 |
| 5-027 | 6.5 |
| 1-111 | 6.5 |
| 5-040 | 6.5 |
| 1-203 | 6.5 |
| 1-022 | 6.5 |
| 3-008 | 6.5 |
| 2-002 | 6.5 |
| 4-047 | 6.5 |
| 1-006 | 6.5 |
| 1-058 | 6.5 |
| 1-191 | 6.5 |
| 4-032 | 6.4 |
| 1-012 | 6.4 |
| 1-157 | 6.4 |
| 1-007 | 6.4 |
| 1-279 | 6.4 |
| 1-105 | 6.4 |
| 4-012 | 6.4 |
| 4-038 | 6.4 |
| 5-037 | 6.4 |
| 1-237 | 6.4 |
| 4-040 | 6.4 |
| 1-221 | 6.4 |
| 1-162 | 6.4 |
| 4-033 | 6.4 |
| 5-025 | 6.4 |
| 5-034 | 6.4 |
| 1-190 | 6.4 |
| 1-247 | 6.4 |
| 1-005 | 6.4 |
| 1-073 | 6.4 |
| 1-064 | 6.4 |
| 1-120 | 6.3 |
| 2-011 | 6.3 |
| 1-026 | 6.3 |
| 1-027 | 6.3 |
| 1-158 | 6.3 |
| 1-159 | 6.3 |
| 1-192 | 6.3 |
| 1-253 | 6.3 |
| 1-167 | 6.3 |
| 5-013 | 6.3 |
| 1-171 | 6.3 |
| 1-291 | 6.3 |
| 1-094 | 6.3 |
| 1-230 | 6.3 |
| 4-018 | 6.3 |
| 1-121 | 6.3 |
| 1-156 | 6.3 |
| 1-154 | 6.3 |
| 4-043 | 6.3 |
| 5-047 | 6.3 |
| 1-227 | 6.3 |
| 4-051 | 6.3 |
| 1-169 | 6.3 |
| 2-040 | 6.3 |
| 1-066 | 6.3 |
| 2-045 | 6.3 |
| 4-005 | 6.3 |
| 4-006 | 6.3 |
| 4-009 | 6.3 |
| 1-155 | 6.3 |
| 1-095 | 6.2 |
| 1-113 | 6.2 |
| 1-021 | 6.2 |
| 1-136 | 6.2 |
| 1-284 | 6.2 |
| 1-126 | 6.2 |
| 1-119 | 6.2 |
| 1-106 | 6.2 |
| 1-160 | 6.2 |
| 1-233 | 6.2 |
| 2-042 | 6.2 |
| 1-116 | 6.2 |
| 2-053 | 6.2 |
| 1-211 | 6.2 |
| 2-016 | 6.2 |
| 1-161 | 6.2 |
| 1-003 | 6.2 |
| 1-036 | 6.2 |
| 2-005 | 6.2 |
| 1-057 | 6.2 |
| 1-273 | 6.2 |
| 1-071 | 6.2 |
| 4-052 | 6.2 |
| 1-070 | 6.2 |
| 1-019 | 6.1 |
| 1-239 | 6.1 |
| 1-214 | 6.1 |
| 1-085 | 6.1 |
| 1-170 | 6.1 |
| 5-017 | 6.1 |
| 1-282 | 6.1 |
| 1-283 | 6.1 |
| 2-028 | 6.1 |
| 2-013 | 6.1 |
| 1-138 | 6.1 |
| 2-025 | 6.1 |
| 1-255 | 6.1 |
| 1-032 | 6.1 |
| 1-245 | 6.1 |
| 1-090 | 6.1 |
| 1-186 | 6.1 |
| 1-038 | 6.1 |
| 2-020 | 6.1 |
| 2-014 | 6.1 |
| 1-035 | 6.1 |
| 2-039 | 6.1 |
| 5-023 | 6.1 |
| 1-114 | 6.0 |
| 1-210 | 6.0 |
| 1-017 | 6.0 |
| 1-263 | 6.0 |
| 1-135 | 6.0 |
| 1-137 | 6.0 |
| 1-099 | 6.0 |
| 2-035 | 6.0 |
| 5-043 | 6.0 |

TABLE 8-continued

Pharmacological data for compounds according to the invention. All compounds were tested in presence of mGluR2 agonist, glutamate at a predetermined $EC_{25}$ concentration, to determine positive allosteric modulation (GTPγS-PAM). Values shown are averages of duplicate values of 11-concentration response curves, from at least one experiment. All compounds showed a $pEC_{50}$ value of more than 5.0, from 5.1 (weak activity) to 7.6 (very high activity). The error of determination of a $pEC_{50}$ value for a single experiment is estimated to be about 0.3 log-units.

| Co. Nr. | GTPgS-hR2 PAM $pEC_{50}$ |
|---|---|
| 1-122 | 6.0 |
| 1-288 | 6.0 |
| 5-044 | 6.0 |
| 4-042 | 6.0 |
| 1-185 | 6.0 |
| 1-212 | 6.0 |
| 4-057 | 6.0 |
| 1-048 | 6.0 |
| 2-037 | 6.0 |
| 2-010 | 6.0 |
| 1-060 | 6.0 |
| 2-007 | 6.0 |
| 1-063 | 6.0 |
| 5-001 | 6.0 |
| 1-065 | 6.0 |
| 1-046 | 5.9 |
| 1-260 | 5.9 |
| 1-251 | 5.9 |
| 1-275 | 5.9 |
| 1-265 | 5.9 |
| 5-032 | 5.9 |
| 1-208 | 5.9 |
| 1-209 | 5.9 |
| 1-055 | 5.9 |
| 1-234 | 5.9 |
| 1-220 | 5.9 |
| 1-224 | 5.9 |
| 2-015 | 5.9 |
| 2-021 | 5.9 |
| 1-198 | 5.9 |
| 5-007 | 5.9 |
| 4-027 | 5.9 |
| 4-030 | 5.9 |
| 1-292 | 5.9 |
| 1-302 | 5.9 |
| 3-002 | 5.9 |
| 3-012 | 5.9 |
| 1-034 | 5.9 |
| 1-102 | 5.8 |
| 1-097 | 5.8 |
| 1-096 | 5.8 |
| 1-009 | 5.8 |
| 1-274 | 5.8 |
| 1-174 | 5.8 |
| 1-280 | 5.8 |
| 5-015 | 5.8 |
| 1-250 | 5.8 |
| 1-166 | 5.8 |
| 1-264 | 5.8 |
| 1-262 | 5.8 |
| 5-049 | 5.8 |
| 1-091 | 5.8 |
| 5-035 | 5.8 |
| 4-026 | 5.8 |
| 5-021 | 5.8 |
| 2-049 | 5.8 |
| 2-044 | 5.8 |
| 4-061 | 5.8 |
| 1-189 | 5.8 |
| 3-010 | 5.8 |
| 1-231 | 5.8 |
| 2-008 | 5.8 |
| 4-007 | 5.8 |
| 1-072 | 5.8 |
| 4-008 | 5.8 |
| 1-296 | 5.8 |
| 1-082 | 5.7 |
| 1-052 | 5.7 |
| 1-103 | 5.7 |
| 1-223 | 5.7 |
| 1-011 | 5.7 |
| 1-118 | 5.7 |
| 1-104 | 5.7 |
| 5-014 | 5.7 |
| 1-016 | 5.7 |
| 1-236 | 5.7 |
| 2-024 | 5.7 |
| 4-010 | 5.7 |
| 2-033 | 5.7 |
| 1-300 | 5.7 |
| 1-304 | 5.7 |
| 4-013 | 5.7 |
| 1-132 | 5.7 |
| 1-225 | 5.7 |
| 1-037 | 5.7 |
| 5-005 | 5.7 |
| 5-009 | 5.7 |
| 2-004 | 5.7 |
| 4-001 | 5.7 |
| 4-048 | 5.7 |
| 1-018 | 5.6 |
| 1-110 | 5.6 |
| 1-047 | 5.6 |
| 1-088 | 5.6 |
| 1-276 | 5.6 |
| 1-254 | 5.6 |
| 2-018 | 5.6 |
| 1-031 | 5.6 |
| 1-033 | 5.6 |
| 1-131 | 5.6 |
| 4-044 | 5.6 |
| 3-006 | 5.6 |
| 2-050 | 5.6 |
| 5-024 | 5.6 |
| 1-293 | 5.6 |
| 1-056 | 5.6 |
| 1-069 | 5.6 |
| 1-217 | 5.6 |
| 1-179 | 5.5 |
| 1-101 | 5.5 |
| 1-215 | 5.5 |
| 1-238 | 5.5 |
| 1-128 | 5.5 |
| 1-182 | 5.5 |
| 1-089 | 5.5 |
| 1-303 | 5.5 |
| 1-248 | 5.5 |
| 1-107 | 5.5 |
| 4-034 | 5.5 |
| 2-051 | 5.5 |
| 2-001 | 5.5 |
| 2-046 | 5.5 |
| 1-294 | 5.5 |
| 2-041 | 5.5 |
| 4-004 | 5.5 |
| 4-053 | 5.5 |
| 1-077 | 5.4 |
| 1-015 | 5.4 |
| 1-087 | 5.4 |
| 1-298 | 5.4 |

TABLE 8-continued

Pharmacological data for compounds according to the invention. All compounds were tested in presence of mGluR2 agonist, glutamate at a predetermined $EC_{25}$ concentration, to determine positive allosteric modulation (GTPγS-PAM). Values shown are averages of duplicate values of 11-concentration response curves, from at least one experiment. All compounds showed a $pEC_{50}$ value of more than 5.0, from 5.1 (weak activity) to 7.6 (very high activity). The error of determination of a $pEC_{50}$ value for a single experiment is estimated to be about 0.3 log-units.

| Co. Nr. | GTPgS-hR2 PAM $pEC_{50}$ |
|---|---|
| 1-201 | 5.4 |
| 1-246 | 5.4 |
| 1-184 | 5.4 |
| 1-286 | 5.4 |
| 2-034 | 5.4 |
| 1-249 | 5.4 |
| 1-139 | 5.4 |
| 1-177 | 5.4 |
| 1-242 | 5.4 |
| 2-055 | 5.4 |
| 1-306 | 5.4 |
| 5-045 | 5.4 |
| 5-006 | 5.4 |
| 3-013 | 5.4 |
| 2-052 | 5.4 |
| 1-295 | 5.4 |
| 1-078 | 5.4 |
| 4-002 | 5.4 |
| 1-076 | 5.4 |
| 4-003 | 5.4 |
| 1-079 | 5.3 |
| 1-059 | 5.3 |
| 1-176 | 5.3 |
| 1-053 | 5.3 |
| 5-004 | 5.3 |
| 1-125 | 5.3 |
| 1-109 | 5.3 |
| 1-193 | 5.3 |
| 4-023 | 5.3 |
| 2-047 | 5.3 |
| 2-054 | 5.3 |
| 4-056 | 5.3 |
| 2-038 | 5.3 |
| 1-074 | 5.3 |
| 1-075 | 5.3 |
| 4-063 | 5.3 |
| 1-081 | 5.2 |
| 1-252 | 5.2 |
| 1-168 | 5.2 |
| 1-108 | 5.2 |
| 5-011 | 5.2 |
| 2-019 | 5.2 |
| 1-173 | 5.2 |
| 5-030 | 5.2 |
| 5-031 | 5.2 |
| 1-244 | 5.2 |
| 4-024 | 5.2 |
| 3-007 | 5.2 |
| 2-027 | 5.2 |
| 1-061 | 5.2 |
| 2-009 | 5.2 |
| 5-002 | 5.2 |
| 1-062 | 5.2 |
| 1-084 | 5.1 |
| 1-050 | 5.1 |
| 5-010 | 5.1 |
| 1-127 | 5.1 |
| 1-098 | 5.1 |
| 1-181 | 5.1 |
| 1-281 | 5.1 |
| 1-222 | 5.1 |
| 1-235 | 5.1 |
| 5-029 | 5.1 |
| 1-129 | 5.1 |
| 1-229 | 5.1 |
| 1-213 | 5.1 |
| 3-011 | 5.1 |

E. Composition Examples

"Active ingredient" (a.i.) as used throughout these examples relates to a final compound of formula (I), the pharmaceutically acceptable acid or base addition salts thereof, the stereochemically isomeric forms thereof, the N-oxide form thereof, a quaternary ammonium salt thereof and prodrugs thereof.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol and water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:
1. A compound according to the general Formula (I),

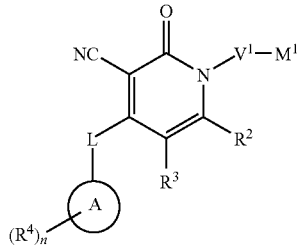

(I)

a pharmaceutically acceptable acid or base addition salt thereof, or a stereochemically isomeric form thereof, wherein
$V^1$ is selected from the group consisting of an unsubstituted bivalent saturated, straight or branched hydrocarbon radical having from 1 to 6 carbon atoms;
$M^1$ is selected from the group consisting of hydrogen; cyclo$C_{3-7}$alkyl; phenyl optionally substituted with $OCF_3$ or F; phenyloxy-; and tetrahydropyranyl;
L is selected from the group consisting of a covalent bond; —O—; —OCH$_2$—; NR$^7$—; wherein R$^7$, is selected from the group consisting of hydrogen and unsubstituted $C_{1-3}$alkyl;
$R^2$ and $R^3$ are hydrogen;
A is piperidinyl selected from the group consisting of

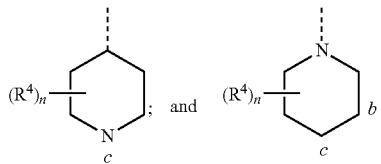

wherein n is an integer equal to 0, 1, or 2;
$R^4$ is, when present, at any of b, or c positions and is selected from the group consisting of $C_{1-6}$-alkyl; $C_{1-6}$-alkyloxy; $C_{1-6}$-alkyloxycarbonyl-; polyhalo$C_{1-3}$alkyl-; Het$^3$; Het$^3$-$C_{1-6}$-alkyl-; Het$^3$-oxy-; Het$^3$-oxy-$C_{1-6}$-alkyl-; Het$^3$-$C_{1-6}$-alkyloxy; —NR$^a$R$^b$; $C_{1-6}$-alkyl-NR$^a$R$^b$; wherein R$^a$ and R$^b$ are selected from the group consisting of hydrogen, $C_{1-6}$-alkyl, and $C_{3-7}$-cycloalkyl; and
Het$^3$ is selected from the group consisting of pyridinyl; pyrimidinyl; pyridazinyl; pyrrolyl; indolyl; morpholinyl; oxadiazolyl; benzoxazolyl; benzofuranyl; indolinyl; 1,2,3,4-tetrahydro-isoquinolinyl; phthalazinyl; and benzo[1,3]dioxolyl wherein each radical is optionally substituted with 1 or 2 substituents, each independently selected from the group consisting of halo, $C_{1-6}$alkyl, $C_{3-7}$-cycloalkyl, polyhalo$C_{1-3}$alkyl, cyano, mono($C_{1-6}$alkyl)amino, oxo, phenyl, morpholinyl, and $C_{1-3}$alkyloxy.

2. The compound according to claim 1, wherein $V^1$ is selected from the group consisting of CH$_2$—; —CH$_2$—CH$_2$—; —CH$_2$—CH$_2$—CH$_2$—; —CH$_2$—CH$_2$—CH$_2$—CH$_2$—; —CH$_2$—CH(CH$_3$)—CH$_2$—; —CH(CH$_3$)—CH$_2$—CH$_2$—CH$_2$—; —CH$_2$—CH(CH$_3$)—CH$_2$—CH$_2$—; and —CH$_2$—CH$_2$—CH(CH$_3$)—CH$_2$—.

3. The compound according to claim 1, wherein $V^1$-$M^1$ is selected from the group consisting of —CH$_2$—CH$_2$—CH$_2$—CH$_3$; —CH$_2$—CH(CH$_3$)—CH$_3$; —CH(CH$_3$)—CH$_2$—CH$_2$—CH$_3$; —CH$_2$—CH(CH$_3$—)CH$_2$—CH$_3$; —CH$_2$—CH$_2$—CH(CH$_3$)—CH$_3$; or $V^1$ is selected from the group consisting of —CH$_2$—; —CH$_2$—CH$_2$—; and —CH$_2$—CH$_2$—CH$_2$—; and $M^1$ is selected from the group of cyclopropyl; cyclopentyl; cyclohexyl; phenyl; and phenyloxy.

4. The compound according to claim 1, wherein:
$V^1$ is selected from the group consisting of a —CH$_2$—; —CH$_2$—CH$_2$—; —CH$_2$—CH$_2$—CH$_2$—; —CH$_2$—CH$_2$—CH$_2$—CH$_2$—; —CH$_2$—CH(CH$_3$)CH$_2$—; —CH(CH$_3$)—CH$_2$—CH$_2$—CH$_2$—; —CH$_2$—CH(CH$_3$)CH$_2$—CH$_2$—; and —CH$_2$—CH$_2$—CH(CH$_3$)—CH$_2$—;
$M^1$ is selected from the group consisting of hydrogen; cyclo$C_{3-7}$alkyl; phenyl; and phenyloxy; and
Het$^3$ is selected from the group consisting of pyridinyl; pyrimidinyl; pyridazinyl; morpholinyl; oxadiazolyl; benzoxazolyl; 1,2,3,4-tetrahydro-isoquinolinyl; indolyl; indolinyl; phthalazinyl; and benzo[1,3]dioxolyl; wherein each radical is optionally substituted with 1 or 2 substituents, each independently selected from the group consisting of halo, oxo, $C_{1-6}$alkyl, $C_{3-7}$cycloalkyl, polyhalo$C_{1-3}$alkyl, cyano, phenyl, morpholinyl, $C_{1-3}$alkyloxy; and mono(alkyl)amino.

5. The compound according to claim 1, wherein the compound exists as optical isomers, wherein said compound is either the racemic mixture or the individual optical isomer.

6. The compound as claimed in claim 1 wherein Het$^3$ is selected from the group consisting of pyridinyl; pyrimidinyl; morpholinyl; oxadiazolyl; benzofuranyl; indolyl; 1,2,3,4-tetrahydro-isoquinolinyl; wherein each radical is optionally substituted with 1 or 2 substituents, each independently selected from the group consisting of halo, $C_{1-6}$alkyl, polyhalo$C_{1-3}$alkyl, oxo, and phenyl.

7. A pharmaceutical composition comprising a therapeutically effective amount of a compound according to claim 1 and a pharmaceutically acceptable carrier and/or excipient.

* * * * *